United States Patent
Brown et al.

(10) Patent No.: US 11,535,833 B2
(45) Date of Patent: Dec. 27, 2022

(54) CARBOXYESTERASE BIOCATALYSTS

(71) Applicant: GlaxoSmithKline Intellectual Property Development Limited, Brentford (GB)

(72) Inventors: Kristin K. Brown, Collegeville, PA (US); Brent M. Dorr, Collegeville, PA (US); Douglas E. Fuerst, Collegeville, PA (US); Katherine Joyce Honicker, Collegeville, PA (US); Lydia Sanchez Jordan, Collegeville, PA (US); James Patrick Morrison, Collegeville, PA (US); Nikolay V. Plotnikov, Collegeville, PA (US); Markus Schober, Stevenage (GB); Rama Voladri, Redwood City, CA (US)

(73) Assignee: GLAXOSMITHKLINE INTELLECTUAL PROPERTY DEVELOPMENT LIMITED, Brentford (GB)

(*) Notice: Subject to any disclaimer, the term of this patent is extended or adjusted under 35 U.S.C. 154(b) by 39 days.

(21) Appl. No.: 16/771,279

(22) PCT Filed: Dec. 13, 2018

(86) PCT No.: PCT/IB2018/060042
§ 371 (c)(1),
(2) Date: Jun. 10, 2020

(87) PCT Pub. No.: WO2019/116311
PCT Pub. Date: Jun. 20, 2019

(65) Prior Publication Data
US 2021/0115417 A1 Apr. 22, 2021

Related U.S. Application Data

(60) Provisional application No. 62/598,181, filed on Dec. 13, 2017.

(51) Int. Cl.
| | | |
|---|---|---|
| C12N 9/04 | (2006.01) | |
| C12N 9/16 | (2006.01) | |
| C12N 9/18 | (2006.01) | |
| C12P 21/06 | (2006.01) | |
| C12P 17/16 | (2006.01) | |

(52) U.S. Cl.
CPC ............... *C12N 9/18* (2013.01); *C12P 17/16* (2013.01); *C12P 17/165* (2013.01); *C12Y 301/01001* (2013.01)

(58) Field of Classification Search
CPC ........ C12N 9/54; C12N 15/8213; C12N 9/16; C12N 15/113; C12N 9/18; C12Y 301/00; C12P 19/14
USPC ............ 435/196, 221, 320.1, 252.2
See application file for complete search history.

(56) References Cited

U.S. PATENT DOCUMENTS

| | | |
|---|---|---|
| 6,537,746 B2 | 3/2003 | Arnold et al. |
| 2002/0137171 A1 | 9/2002 | Short et al. |
| 2006/0195947 A1 | 8/2006 | Davis et al. |
| 2008/0248539 A1 | 10/2008 | Giver et al. |

FOREIGN PATENT DOCUMENTS

| | | |
|---|---|---|
| WO | WO 95/22625 | 8/1995 |
| WO | WO 97/00078 | 1/1997 |
| WO | WO 97/35966 | 10/1997 |
| WO | WO 98/27230 | 6/1998 |
| WO | WO 00/42651 | 7/2000 |
| WO | WO 01/75767 | 10/2001 |
| WO | WO 02/057411 | 7/2002 |
| WO | WO 2005/032496 A2 | 4/2005 |
| WO | WO 2006/096834 A2 | 9/2006 |
| WO | WO 2007/092314 A2 | 8/2007 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Altschul et al., "Basic local alignment search tool," J Mal. Biol., 1990, 215:403-410.
Altschul et al., "Gapped BLAST and PSI-BLAST: a new generation of protein database search programs," Nucleic Acids Res., 1977, 3389-3402.
Beaucage et al., "Deoxynucleoside phosphoramidites—a new class of key intermediates for deoxypolynucleotide synthesis," Tet Lett., 1981, 22:1859-69.
Black et al., "Creation of drug-specific herpes simplex virus type 1 thymidine kinase mutants for gene therapy," Proc Natl Acad Sci USA, 1996, 93:3525-3529.
Botstein et al., "Strategies and applications of in vitro mutagenesis," Science, 1985, 229: 1193-1201.
Caldwell et al., "Mutagenic PCR," PCRMethods Appl., 1994, 3:S136-S140.
Carter, "Site-directed mutagenesis," Biochem. J, 1986, 237:1-7.

(Continued)

*Primary Examiner* — Tekchand Saidha
*Assistant Examiner* — Mohammad Y Meah
(74) *Attorney, Agent, or Firm* — Fish & Richardson P.C.

(57) ABSTRACT

The present disclosure provides engineered carboxyesterase enzymes that have the ability to catalyze amide bond formation. Also provided are polynucleotides encoding the carboxyesterase enzymes, host cells capable of expressing the engineered carboxyesterase enzymes, and methods of using the engineered carboxyesterase enzymes to make commercially valuable amides. Also provided are amides that are made using the engineered carboxyesterase enzymes.

18 Claims, 19 Drawing Sheets
Specification includes a Sequence Listing.

(56) References Cited

OTHER PUBLICATIONS

Christians et al., "Directed evolution ofthymidine kinase for AZT phosphorylation using DNA family shuffling," Nature Biotech, 1999, 17:259-264.
Crameri et al., "DNA shuffling of a family of genes from diverse species accelerates directed evolution," Nature, 1998, 391:288-291.
Crameri et al., "Improved green fluorescent protein by molecular evolution using DNA shuffling," Nature Biotech, 1996, 14:315-319.
Crameri et al., "Molecular evolution of an arsenate detoxification pathway by DNA shuffling," Nature Biotech, 1997, 15:436-438.
Dale et al., "Oligonucleotide-directed random mutagenesis using the phosphorothioate method," Methods Mal. Biol., 1996, 57:369-74.
De Figueiredo et al., "Nonclassical Routes for Amide Bond Formation," Chemical Reviews, 2016, 12029-12122.
Eisenberg et al., "Analysis of membrane and surface protein sequences with the hydrophobic moment plot," J Mal. Biol., 1984, 179:125-142.
Gotor, "Non-conventional hydrolase chemistry: amide and carbamate bond formation catalyzed by lipases," Bioorg Med Chem, 1999, 7:2189-2197.
Henaut and Danchin, "Analysis and predictions from Escherichia coli sequences: *Escherichia coli* and *Salmonella*. Neidhardt FC edition," ASM Press, 1996, 2047-2066.
Henikoff and Henikoff, "Amino acid substitution matrices from protein blocks," Proc NatlAcad Sci USA, 1989, 89:10915.
International Preliminary Report on Patentability in International Appln. No. PCT/IB2018/060042, dated Jun. 16, 2020, 7 pages.
International Search Report and Written Opinion in International Appln. No. PCT/IB2018/060042, dated Mar. 15, 2019, 11 pages.
Kramer et al., "Point Mismatch Repair," Cell, 1984, 38:879-887.
Ling et al., "Approaches to DNA mutagenesis an overview," Anal. Biochem., 1997, 254(2):157-78.
Matthes, et al., "Simultaneous rapid chemical synthesis of over one hundred oligonucleotides on a microscale," EMBO J, 1984, 3:801-05.
Mcinerney, "GCUA: general codon usage analysis," Bioinformatics, 1998, 14:372-73.
Minshull et al., "Protein evolution by molecular breeding," Curr Opin Chem Biol, 1999, 3:284-290.
Nakamura, et al., "Codon usage tabulated from international DNA sequence databases: status for the year 2000," Nucl. Acids Res., 2000, 28:292.
Needleman and Wunsch, "A general method applicable to the search for similarities in the amino acid sequence of two proteins," J Mal. Biol., 1970, 48:443.

Pattabiraman and Bode, "Rethinking amide bond synthesis," Nature, 2011, 480:471-479.
Pearson and Lipman, "Improved tools for biological sequence comparison," Proc. Natl. Acad. Sci. USA, 1988, 85:2444.
Schneider et al., "Big Data from Pharmaceutical Patents: A Computational Analysis of Medicinal Chemists' Bread and Butter," J Med. Chem., 2016, 59:4385-4402.
Smith and Waterman, "Comparison of biosequences," Adv. Appl. Math., 1981, 2:482.
Smith, "In vitro mutagenesis," Ann. Rev. Genet., 1985, 19:423-462.
Stemmer, "DNA shuffling by random fragmentation and reassembly: in vitro recombination for molecular evolution," Proc Natl Acad Sci USA, 1994, 91:10747-10751.
Stemmer, "Rapid evolution of a protein in vitro by DNA shuffling," Nature, 1994, 370:389-391.
Stenico et al., "Codon usage in Caenorhabditis elegans: delineation of translational selection and mutational biases," Nucleic Acids Res., 1994, 22:2437-46.
Tiwari et al., "Prediction of probable genes by Fourier analysis of genomic sequences," Comput. Appl. Biosci., 1997, 13:263-270.
Uberbacher et al., "Discovering and understanding genes in human DNA sequence using GRAIL," Methods Enzymol., 1996, 266:259-281.
Van Pelt, "Pseudomonas stutzerilipase: a useful biocatalyst for aminolysis reactions," Green, Chem., 2011, 13:1791-1798.
Wada et al., "Codon usage tabulated from the GenBank genetic sequence data," Nucleic Acids Res., 1992, 20:2111-2118.
Wells et al., "Cassette mutagenesis: an efficient method for generation of multiple mutations at defined sites," Gene, 1985, 34:315-323.
Wright, "The 'effective number of codons' used in a gene," Gene, 1990, 87:23-29.
Zhang et al., 1997, "Directed evolution of an effective fructosidase from a galactosidase by DNA shuffling and screening," Proc Natl Acad Sci USA, 1997, 94:4504-4509.
Zhao et al., "Molecular evolution by staggered extension process (StEP) in vitro recombination," Nat. Biotechnol., 1998, 16:258-261.
DATABASE UniProt [Online] Mar. 15, 2017 (Mar. 15, 2017), "SubName: Full=Acetyl esterase {ECO:0000313:EMBL:SIS74246.1};",XP55560136, retrieved from EBI accession No. UNIPROT:A0A1N7LKA1 Database accession No. A0A1N7LKA1 sequence.
Anonymous: "Uni Prot:A0A1N7LKA1", Mar. 5, 2017 (Mar. 5, 2017), XP055560136, Retrieved from the Internet: URL:http://ibis.interal.epo.org/exam/dbfetch.jsp?id=UNIPROT:A0A1N7LKA1 [retrieved on Feb. 21, 2019] the whole document.

* cited by examiner

FIG. 1

**Pairwise alignment of all DNA sequences against the Polynucleotide Sequence Encoding the *E. coli* codon optimized for the Wild-Type Carboxyesterase Enzyme, *A. acidocaldarius* Esterase 2 (SEQ ID NO: 1)**

```
                     80         90        100        110        120        130        140
               ....|....|  ....|....|  ....|....|  ....|....|  ....|....|  ....|....|  ....|....|
SEQ1      71   ACTTAAGCGC  TCAACAGTTT  CGTTCACAGC  AATCACTGTT  TCCACCAGTT  AAGAAAGAAC  CGGTCGCAGA  140
SEQ3      71   ..........  ..........  ..........  ..........  ..........  ..........  ..........  140
SEQ5      71   ..........  ..........  ..........  ..........  ..........  ..........  ..........  140
SEQ7      71   ..........  ..........  ..........  ..........  ..........  ..........  ..........  140
SEQ9      71   ..........  ..........  ..........  ..........  ..........  ..........  ..........  140
SEQ11     71   ..........  ..........  ..........  ..........  ..........  ..........  ..........  140
SEQ13     71   ..........  ..........  ..........  ..........  ..........  ..........  ..........  140
SEQ15     71   ..........  ...G......  ..........  ..........  G.........  ..........  ..........  140
SEQ17     71   ..........  ...G......  ..........  ..........  ..........  ..........  ..........  140
SEQ19     71   ..........  ..........  ..........  ..........  G.........  ..........  ..........  140
SEQ21     71   ..........  ..........  ..........  ..........  C.........  ..........  ..........  140
SEQ23     71   ..........  ..........  ..........  ..CAC.....  ..........  ..........  ..........  140
SEQ25     71   ......C.G.  ........G.  ..........  ..........  ..........  ..........  ..........  140
SEQ27     71   ..........  ..........  ..........  .G........  ..........  ..........  ..........  140
SEQ29     71   ..........  ..........  ..........  ......G...  ..........  ..........  ..........  140
SEQ31     71   ..........  ..........  ..........  ......G...  ..........  ..........  ..........  140
SEQ33     71   ..........  ..........  ..........  ..........  ..........  ..........  ..........  140
SEQ35     71   ..........  ..........  ..........  ..CAC...AC  C.........  ..........  ..........  140
SEQ37     71   ..........  ..........  ..........  ..AGC.....  ..........  ..........  ..........  140
SEQ39     71   ..........  ..........  .........A  .CCAC.....  ..........  ..........  ..........  140
SEQ41     71   ..........  ..........  .........G  ..CAC.....  ..........  ..........  ..........  140
SEQ43     71   ..........  ..........  .........G  ..CAC.....  ..........  ..........  ......TG..  140
SEQ45     71   ..........  ..........  .........A  .CCAC.....  ..........  ..........  ......TG..  140
SEQ47     71   ..........  ..........  ..........  ..CAC.....  ..........  ..........  ..........  140
SEQ49     71   ..........  ..........  .........G  ..CAC.....  ..........  ..........  ......TG..  140
SEQ51     71   ..........  ..........  .........A  .CCAC.....  ..........  ..........  ..........  140
SEQ53     71   ..........  ..........  ..........  ..CAC.....  ..........  ..........  ..........  140
SEQ55     71   ..........  ..........  ..........  ..CAC.....  ..........  ..........  ..........  140
SEQ57     71   ..........  ........G.  ..........  ..CAC.....  ..........  ..........  ..........  140
SEQ59     71   ..........  ..........  .........G  ..CAC.....  ..........  ..........  ..........  140
SEQ61     71   ..........  ..........  ..........  ..CAC.....  ..........  ..........  ..........  140
SEQ63     71   ..........  ..........  ..........  ..CAC.....  ..........  ..........  ..........  140
SEQ65     71   ..........  ..........  ..........  ..CAC.....  ..........  ..........  ..........  140
SEQ67     71   ..........  ..........  ..........  ..CAC.....  ..........  ..........  ..........  140
SEQ69     71   ..........  ....G.T...  ..........  ..CAC.....  ..........  ..........  ..........  140
SEQ71     71   ..........  ..........  ......GGT.  ..CAC.....  ..........  ..........  ..........  140
SEQ73     71   ..........  .AGT......  ..........  ..CAC.....  ..........  ..........  ..........  140
SEQ75     71   ..........  ........G.  .........A  ..CAC.....  ..........  ..........  ..........  140
SEQ77     71   ..........  ..........  ..........  ..CACA.TGG  ..........  ..........  ..........  140
SEQ79     71   ..........  ..........  ..........  ..CACT..GG  ..........  ..........  ..........  140
SEQ81     71   ..........  .AGT......  ..........  ..CAC.....  ..........  ..........  ..........  140
SEQ83     71   ..........  .AGT......  ..........  ..CAT.....  ..........  ..........  ..........  140
SEQ85     71   ..........  .AGT......  ..........  ..CAC.....  ..........  ..........  ..........  140
SEQ87     71   ..........  ..........  ..........  ..CACA..GG  ..........  ..........  ..........  140
SEQ89     71   ..........  ......AG..  ......TG..  ..CAC.....  ..........  ..........  ..........  140
SEQ91     71   ..........  ......AG..  ......TG..  ..CAC.....  ..........  ..........  .....CGC..  140
SEQ93     71   ..........  ..........  ..........  ..CAC.....  ..........  ..........  ..........  140
SEQ95     71   ..........  ..........  ..........  ..CAC.....  ..........  ..........  .....AA...  140
SEQ97     71   ..........  ..........  ..........  ..CAC.....  ..........  ..........  .....AA...  140
SEQ99     71   ..........  .TGC......  ..........  ..CAC.....  .GA.......  ..........  ..........  140
SEQ101    71   ..........  ..........  ..........  ..AGC.....  ..........  ..........  ..........  140
SEQ103    71   ..........  ..........  ..........  ..AGC.....  ..........  ..........  ..........  140
SEQ105    71   ..........  .TGC......  ..........  ..CAC.....  ..........  ..........  ..........  140
SEQ107    71   ..........  .TGC......  ..........  ..CAC.....  .GA.......  ..........  ........T..  140
SEQ109    71   ..........  .TGC......  ..........  ..CAC.....  .GA.......  ..........  .....AA...  140
SEQ111    71   ..........  .TGC......  ..........  ..CACAC...  .TGG......  ..........  ..........  140
SEQ113    71   ..........  .TGC......  ..........  ..CACAC...  .TGG......  ..........  ..........  140
SEQ115    71   ..........  .TGC......  ..........  ..CACA....  .TGG......  ..........  .......C..  140
SEQ117    71   ..........  .TGC......  ..........  ..CACAC...  .TGG......  ..........  ..........  140
SEQ119    71   ..........  .TGC......  ..........  ..CAC.....  .GA.......  ..........  ..........  140
SEQ121    71   ..........  .TGC......  ..........  ..CACAC...  .TGG......  ..........  ..........  140
SEQ123    71   ..........  .TGC......  ..........  ..CACAC...  .TGG......  ..........  ..........  140
SEQ125    71   ..........  .TGC......  ..........  ..CACAC...  .TGG......  ..........  ..........  140
```

FIG. 1 CONT

```
                    150        160        170        180        190        200        210
               ....|....|  ....|....|  ....|....|  ....|....|  ....|....|  ....|....|  ....|....|
SEQ1       141 AGTTCGCGAA TTCGACATGG ATCTGCCGGG CCGTACCCTG AAAGTCCCTA TGTACCGTCC GGAAGGTGTT 210
SEQ3       141 .......... .......... .......... .......... .......... .......... .......... 210
SEQ5       141 .......... .......... .......... .......... .......... .......... .......... 210
SEQ7       141 .......... .......... .......... .......... .......... .......... .......... 210
SEQ9       141 .......... .......... .......... .......... .......... .......... .......... 210
SEQ11      141 .......... .......... .......... .......... .......... .......... .......... 210
SEQ13      141 .......... .......... .......... .......... .......... .......... .......... 210
SEQ15      141 .......... .......... .......... .......... .......... .......... .......... 210
SEQ17      141 .......... .......... .......... .......... .......... .......... .......... 210
SEQ19      141 .......... .......... .......... .......... .......... .......... .......... 210
SEQ21      141 .......... .......... .......... .......... .......... ......A... .......... 210
SEQ23      141 .......... .......... .......... .......... .......... ......C... .......... 210
SEQ25      141 .......... .......... .......... .....T.... .......... .......... .......... 210
SEQ27      141 .......... .......... .......AT G......... .......... .......... .......... 210
SEQ29      141 .......... .......... .......... .......... .......... .......... .......... 210
SEQ31      141 .......... .......... .......... .......... .......... .......... .......... 210
SEQ33      141 .......... .......... .......... .......... .......... .......... .......... 210
SEQ35      141 .......... .......... .......... .......... .......... ......C... .......... 210
SEQ37      141 .C.G...... .......... .......... .......... .......... ......C... .......... 210
SEQ39      141 .......... .......... .......... .......... .......... ......C... .......... 210
SEQ41      141 .......... .......... .......... .......... .......... ......C... .......... 210
SEQ43      141 .......... .......... .......... .......... .......... ......C... .......... 210
SEQ45      141 .......... .......... .......... .......... .......... ......C... .......... 210
SEQ47      141 .......... .......... .......... .......... .......... .....GTG.. .......... 210
SEQ49      141 .......... .......... .......... .......... .......... ......C... .......... 210
SEQ51      141 .......... .......... .......... .......... .......... ......C... .......... 210
SEQ53      141 .......... .......... .......... .......... .......... ......C... .......... 210
SEQ55      141 .......... .......... .......... .......... .......... ......C... .......... 210
SEQ57      141 .......... .......... .......... .......... .......... ......C... .......... 210
SEQ59      141 .......... .......... .......... .......... .......... ......C... .......... 210
SEQ61      141 .......... .......... .......... .......... .......... ......C... .......... 210
SEQ63      141 .......... .......... .......... .......... .......... ......C... .......... 210
SEQ65      141 .......... .......... .......... .......... .......... ......C... .......... 210
SEQ67      141 .......... .......... .......... .......... .......... ......C... .......... 210
SEQ69      141 .......... .......... .......... .......... .......... ......C... .......... 210
SEQ71      141 .......... .......... .......... .......... .......... ......C... .......... 210
SEQ73      141 .......... .......... .......... .......... .......... ......C... .......... 210
SEQ75      141 .......... .......... .......... .......... .......... ......C... .......... 210
SEQ77      141 .......... .......... .......... .......... .......... ......C... .......... 210
SEQ79      141 .......... .......... .......... .......... .......... ......C... .......... 210
SEQ81      141 .......... .......... .......... .......... .......... ......C... .......... 210
SEQ83      141 .......... .......... .......... .......... .......... ......C... .......... 210
SEQ85      141 .......... .......... .......... .......... .......... ......C... .......... 210
SEQ87      141 .......... .......... .......... .......... .......... ......C... .......... 210
SEQ89      141 .......... .......... .......... .......... .......... ......C... .......... 210
SEQ91      141 .......... .......... .......... .......... .......... .....ACG.. .......... 210
SEQ93      141 .......... .......... .......... .......... .......... ......C... .......... 210
SEQ95      141 .......... .......... .......... .......... .......... ......C... .......... 210
SEQ97      141 .......... .......... .......... .......... .......... ......C... .......... 210
SEQ99      141 .......... .......... .......... .......... .......... ......C... .......... 210
SEQ101     141 .......... .......... .......... .......... .......... .....TG... .......... 210
SEQ103     141 .......... .......... .......... .......... .......... .....TG... .......... 210
SEQ105     141 .......... ........C G......... .......... .......... ......C... .......... 210
SEQ107     141 .......... ........ C......... .......... .......... ......C... .......... 210
SEQ109     141 .......... ........ C......... .......... .......... ......C... .......... 210
SEQ111     141 .......... ........C .G........ .......... .......... .....ACG.. .......... 210
SEQ113     141 .......... .......... .......... .......... .......... ......C... .......... 210
SEQ115     141 .......... .......... .......... .......... .......... ......C... .......... 210
SEQ117     141 .......... .......... .......... .......... .......... ......C... .......... 210
SEQ119     141 .......... .......... .......... .......... .......... ......C... .......... 210
SEQ121     141 .......... .......... .......... .......... .......... ......C... .......... 210
SEQ123     141 .......... .......... .......... .......... .......... ......C... .......... 210
SEQ125     141 .......... .......... .......... .......... .......... ......C... .......... 210
```

FIG. 1 CONT

```
                        220         230         240         250         260         270         280
                   ....|....|  ....|....|  ....|....|  ....|....|  ....|....|  ....|....|  ....|....|
SEQ1       211  GAACCACCAT ATCCAGCACT GGTTTACTAC CATGGTGGCC GTTGGGTTGT TGGTGACCTG GAAACGCATG  280
SEQ3       211  .......... .......... .......... .......... .......... .......... ..........  280
SEQ5       211  .......... .......... .......... .......... .......... .......... ..........  280
SEQ7       211  .......... .......... .......... .......... .......... .......... ..........  280
SEQ9       211  .......... .......... .......... .......... .......... .......... ..........  280
SEQ11      211  .......... .......... .......... .......... .......... .......... ..........  280
SEQ13      211  .......... .......... .......... .......... .......... .......... ..........  280
SEQ15      211  .......... .......... .......... .......... .......... .......... ..........  280
SEQ17      211  .......... .......... .......... .......... .......... .......... ..........  280
SEQ19      211  .......... ....GG.... .......... .......... .......... .......... ..........  280
SEQ21      211  .......... ....G..... .......... .......... .......... .......... ..........  280
SEQ23      211  .......... .......... .......... .......... .......... .......... ..........  280
SEQ25      211  .......... .......... .......... .......... .......... .......... ..........  280
SEQ27      211  .......... .......... .......... .......... .......... .......... ..........  280
SEQ29      211  .......... .......... .......... .......... .......... .......... ..........  280
SEQ31      211  .......... .......... .......... .......... .......... .......... ..........  280
SEQ33      211  .......... .......... .......... .......... .......... .......... ..........  280
SEQ35      211  .......... .......... .......... .......... .......... .......... ..........  280
SEQ37      211  .......... .......... .......... .......... .......... .......... ..........  280
SEQ39      211  .......... .......... .......... .......... .........C G......... ..........  280
SEQ41      211  .......... .......... .......... .......... .........C G......... ..........  280
SEQ43      211  .......... .......... .......... .......... .........C G......... ..........  280
SEQ45      211  .......... .......... .......... .......... .........C G......... ..........  280
SEQ47      211  .......... .......... .......... .......... .......... .......... ..........  280
SEQ49      211  .......... .......... .......... .......... .........C G......... ..........  280
SEQ51      211  .......... .......... .......... .......... .........C G......... ..........  280
SEQ53      211  .......... .......... .......... .......... .........C G......... ..........  280
SEQ55      211  .......... .......... .......... .......... .........C G......... ..........  280
SEQ57      211  .......... .......... .......... .......... .........C G......... ..........  280
SEQ59      211  .......... .......... .......... .......... .........C G......... ..........  280
SEQ61      211  .......... .......... .......... .......... .........C G......... ..........  280
SEQ63      211  .......... .......... .......... .......... .........C G......... ..........  280
SEQ65      211  .......... .......... .......... .......... .........C G......... ..........  280
SEQ67      211  .......... .......... .......... .......... .........C G......... ..........  280
SEQ69      211  .......... .......... .......... .......... .........C G......... ..........  280
SEQ71      211  .......... .......... .......... .......... .........C G......... ..........  280
SEQ73      211  .......... .......... .......... .......... .........C G......... ..........  280
SEQ75      211  .......... .......... .......... .......... .........C G......... ..........  280
SEQ77      211  .......... .......... .......... .......... .........C G......... ..........  280
SEQ79      211  .......... .......... .......... .......... .........C G......... ..........  280
SEQ81      211  .......... .......... .......... .......... .........C G......... ..........  280
SEQ83      211  .......... .......... .......... .......... .........C G......... ..........  280
SEQ85      211  .......... .......... .......... .......... .........C G......... ..........  280
SEQ87      211  .......... .......... .......... .......... .........C G......... ..........  280
SEQ89      211  .......... ....GG.... .......... .......... .........C G......... ..........  280
SEQ91      211  .......... .......... .......... .......... .........C G......... ..........  280
SEQ93      211  .......... ....GG.... .......... .......... .........C G......... ..........  280
SEQ95      211  .......... .......... .......... .......... .........C G......... ..........  280
SEQ97      211  .......... .......... .......... .......... .........C G......... ..........  280
SEQ99      211  .......... .......... .......... .......... ....G.C....C G......... ..........  280
SEQ101     211  .......... .......... .......... .......... .....ACC.C G......... ..........  280
SEQ103     211  .......... .......... .......... .......... .....ACC.C G......... ..........  280
SEQ105     211  .......... ....GT.... .......... .......... .........C G......... ..........  280
SEQ107     211  .......... .......... .......... .......... ....G.C....C G......... ..........  280
SEQ109     211  .......... .......... .......... .......... ....G.C....C G......... ..........  280
SEQ111     211  .......... .......... .......... .......... ....G.C....C G......... ..........  280
SEQ113     211  .......... ....GC.... .......... .......... ....G.C....C G......... ..........  280
SEQ115     211  .......... ....GC.... .......... .......... ....G.C....C G......... ..........  280
SEQ117     211  .......... ....ATG... .......... .......... ....G.C....C G......... ..........  280
SEQ119     211  .......... .......... .......... .......... ....G.C....C G......... ..........  280
SEQ121     211  .......... ....GC.... .......... .......... ....G.C....C G......... ..........  280
SEQ123     211  .......... ....GC.... .......... .......... ....G.C....C G......... ..........  280
SEQ125     211  .......... ....GC.... .......... .......... ....G.C....C G......... ..........  280
```

FIG. 1 CONT

```
                 10         20         30         40         50         60         70
        ....|....|....|....|....|....|....|....|....|....|....|....|....|....|
SEQ1    1  ATGCCATTAG ATCCTGTGAT TCAACAAGTC CTCGATCAAC TGAACCGTAT GCCAGCCCCT GACTACAAGC  70
SEQ3    1  .......... .......... .......... .......... .......... .......... ..........  70
SEQ5    1  .......... .......... .......... .......... .......... .......... ..........  70
SEQ7    1  .......... .......... .......... .......... .......... .......... ..........  70
SEQ9    1  .......... .......... .......... .......... .......... .......... ..........  70
SEQ11   1  .......... .......... .......... .......... .......... .......... ..........  70
SEQ13   1  .......... .......... .......... .......... .......... ......A... ..........  70
SEQ15   1  .......... .......... .......... .......... .......... .......... ..........  70
SEQ17   1  .......... .......... .......... .......... .......... .......... ..........  70
SEQ19   1  .......... .......... .......... .......... .......... .......... ..........  70
SEQ21   1  .......... .......... .......... .......... .......... .......... ..........  70
SEQ23   1  .......... .......... .......... .......... .......... .......... ..........  70
SEQ25   1  .......... .......... .......... .......... .......... .......... ..........  70
SEQ27   1  .......... .......... .......... .......... .......... .......... ..........  70
SEQ29   1  .......... .......... .......... .......... .......... .......... ..........  70
SEQ31   1  .......... .......... .......... .......... .......... .......... ..........  70
SEQ33   1  .......... .......... .......... .......... .......... .......... ..........  70
SEQ35   1  .......... .......... ....T.T... .......... .......... .......... ..........  70
SEQ37   1  .......... .......... .......... .......... .......... .......... ..........  70
SEQ39   1  .......... .......... ....T.T... .......... .......... .....CGT.. ..........  70
SEQ41   1  .......... .......... ....T.T..G .......... .......... .......... ..........  70
SEQ43   1  .......... .......... ....T.T... .......... .......... .....CGT.. ..........  70
SEQ45   1  .......... .......... ....T.T... .......... .......... .......... ..........  70
SEQ47   1  .......... .......... .......... .......... .......... .......... ..........  70
SEQ49   1  .......... .......... ....T.T... .......... .......... .......... ..........  70
SEQ51   1  .......... .......... ....T.T... .......... .......... .......... ..........  70
SEQ53   1  .......... .......... ....T.T... .......... .......... .......... ..........  70
SEQ55   1  .......... .......... ....T.T... .......... .......... .......... ..........  70
SEQ57   1  .......... .......... ....T.T... .......... .......... .......... ..........  70
SEQ59   1  .......... .......... ....T.T... .......... .......... .......... ..........  70
SEQ61   1  .......... .......... ....T.T... .......... .......... .......... ..........  70
SEQ63   1  .......... .......... ....T.T... .......... .......... .......... ..........  70
SEQ65   1  .......... .......... ....T.T... .......... .......... .......AT. ..........  70
SEQ67   1  .......... .......... ....T.T... .......... .......... .......... ..........  70
SEQ69   1  .......... .......... ....T.T... .......... .......... .......... ..........  70
SEQ71   1  .......... .......... ....T.T... .......... .......... .......... ..........  70
SEQ73   1  .......... .......... ....T.T... .......... .......... .......... ..........  70
SEQ75   1  .......... .......... ....T.T..G .......... .......... .......... ..........  70
SEQ77   1  .......... .......... ....T.T..G .......... .......... .......... ..........  70
SEQ79   1  .......... .......... ....T.TA.G .......... .......... .......... ..........  70
SEQ81   1  .......... .......... ....T.T... .......... .......... .......... ..........  70
SEQ83   1  .......... .......... ....T.T... .......... .......... .......... ..........  70
SEQ85   1  .......... .......... ....T.T... .......... .......... .......... ..........  70
SEQ87   1  .......... .......... ....T.T... .......... .......... .......... ..........  70
SEQ89   1  .......... .......... ....T.T... .......... .......... ........C. ..........  70
SEQ91   1  .......... .......... ....T.T... .......... .......... .......AT. ..........  70
SEQ93   1  .......... .......... ....T.T... .......... .......... ......GG.. ..........  70
SEQ95   1  .......... .......... ....T.T... .......... .......... .......... ..........  70
SEQ97   1  .......... .......... ....T.T... .......... .......... .......... ..........  70
SEQ99   1  .......... .......... ....T.T... .......... .......... .......... ..........  70
SEQ101  1  .......... .......... ....T.T... .......... .......... .......... ..........  70
SEQ103  1  .......... .......... ....T.T... .......... .......... .......... ..........  70
SEQ105  1  .......... .......... ....T.T... .......... .......... .......... ..........  70
SEQ107  1  .......... ........C. ....T.T..G .......... .......... .......... ..........  70
SEQ109  1  .......... .......... ....T.T..G .......... .......... .......... ..........  70
SEQ111  1  .......... .......... ....T.T... .......... .......... .......... ..........  70
SEQ113  1  .......... .......... ....T.T... .......... .......... .......... ..........  70
SEQ115  1  .......... .......... ....T.T... .......... .......... ......GG.. ..........  70
SEQ117  1  .......... .......... ....T.T... .......... .......... .......... ..........  70
SEQ119  1  .......... .......... ....T.T... .......... .......... .......... ..........  70
SEQ121  1  .......... .......... ....T.T... .......... .......... .......... ..........  70
SEQ123  1  ...TTG.... .......... ....T.T... .......... .......... .......... ..........  70
SEQ125  1  .......... .......... ....T.T... .......... .......... .......... ..........  70
```

FIG. 1 CONT

```
                        290        300        310        320        330        340        350
                   ....|....|  ....|....|  ....|....|  ....|....|  ....|....|  ....|....|  ....|....|
SEQ1       281  ATCCGGTGTG  TCCTGTGTTG  GCGAAAGATG  GACGCGCAGT  GGTGTTTAGC  GTTGACTACC  GCCTGGCACC  350
SEQ3       281  ..........  ..........  ..........  ..........  ..........  ..........  ..........  350
SEQ5       281  ..........  ..........  ..........  ..........  ..........  ..........  ..........  350
SEQ7       281  ..........  ..........  ..........  ..........  ..........  ..........  ..........  350
SEQ9       281  ..........  ..........  ..........  ..........  ..........  ..........  ..........  350
SEQ11      281  ..........  ..........  ..........  ..........  ..........  ..........  ..........  350
SEQ13      281  ..........  ..........  ..........  ..........  ..........  ..........  ..........  350
SEQ15      281  ..........  ..........  ..........  ..........  ..........  ..........  ..........  350
SEQ17      281  ..........  ..........  ..........  ..........  ..........  ..........  ..........  350
SEQ19      281  ..........  ..........  ..........  ..........  ..........  ..........  ..........  350
SEQ21      281  ..........  ..........  ..........  ..........  ..........  ..........  ..........  350
SEQ23      281  ..........  ..........  ..........  ..........  ..........  ..........  ..........  350
SEQ25      281  ..........  ..........  ......TGG.  ..........  ..........  ..........  ..........  350
SEQ27      281  ..........  ..........  ......TGG.  ..........  ..........  ..........  ..........  350
SEQ29      281  ..........  ..........  ..........  ..........  ..........  ..........  ..........  350
SEQ31      281  ..........  ..........  ......TGG.  ..........  ..........  ..........  ..........  350
SEQ33      281  ..........  ..........  ......TGG.  ..........  ..........  ..........  ..........  350
SEQ35      281  ..........  ..........  ......TGG.  ..........  ..........  ..........  ..........  350
SEQ37      281  ..........  ..........  ..........  ..........  ..........  ..........  ..........  350
SEQ39      281  ..........  ..........  ..........  ..........  ..........  ..........  ..........  350
SEQ41      281  ..........  ..........  ..........  ..........  ..........  ..........  ..........  350
SEQ43      281  ..........  ..........  ..........  ..........  ..........  ..........  ..........  350
SEQ45      281  ..........  ..........  ..........  ..........  ..........  ..........  ..........  350
SEQ47      281  ..........  ..........  ..........  ..........  ..........  ..........  ..........  350
SEQ49      281  ..........  ..........  ..........  ..........  ..........  ..........  ..........  350
SEQ51      281  ..........  ..........  ..........  ..........  ..........  ..........  ..........  350
SEQ53      281  ..........  ..........  ..........  ..........  ..........  ..........  ..........  350
SEQ55      281  ..........  ..........  ..........  ..........  ..........  ..........  ..........  350
SEQ57      281  ..........  ..........  ..........  ..........  ..........  ..........  ..........  350
SEQ59      281  ..........  ..........  ..........  ..........  ..........  ..........  ..........  350
SEQ61      281  ..........  ..........  ..........  ..........  ..........  ..........  ..........  350
SEQ63      281  ..........  ..........  ..........  ..........  ..........  ..........  ..........  350
SEQ65      281  ..........  ..........  ..........  ..........  ..........  ..........  ..........  350
SEQ67      281  ..........  ..........  ..........  ..........  ..........  ..........  ..........  350
SEQ69      281  ..........  ..........  ..........  ..........  ..........  ..........  ..........  350
SEQ71      281  ..........  ..........  ..........  ..........  ..........  ..........  ..........  350
SEQ73      281  ..........  ..........  ..........  ..........  ..........  ..........  ..........  350
SEQ75      281  ..........  ..........  ..........  ..........  ..........  ..........  ..........  350
SEQ77      281  ..........  ..........  ..........  ..........  ..........  ..........  ..........  350
SEQ79      281  ..........  ..........  ..........  ..........  ..........  ..........  ..........  350
SEQ81      281  ..........  ..........  ..........  ..........  ..........  ..........  ..........  350
SEQ83      281  ..........  ..........  ..........  ..........  ..........  ..........  ..........  350
SEQ85      281  ..........  ..........  ..........  ..........  ..........  ..........  ..........  350
SEQ87      281  ..........  ..........  ..........  ..........  ..........  ..........  ..........  350
SEQ89      281  ..........  ..........  ......TGG.  ..........  ..........  ..........  ..........  350
SEQ91      281  ..........  ..........  ......TGG.  ..........  ..........  ..........  ..........  350
SEQ93      281  ..........  ..........  ..........  ..........  ..........  ..........  ..........  350
SEQ95      281  ..........  ..........  ..........  ..........  ..........  ..........  ..........  350
SEQ97      281  ..........  ..........  ..........  ..........  ..........  ..........  ..........  350
SEQ99      281  ..........  ..........  ..........  ..........  ..........  ..........  ..........  350
SEQ101     281  .....A....  ..........  ..........  ..........  ..........  ..........  ..........  350
SEQ103     281  .....A....  ..........  ..........  ..........  ..........  ..........  ..........  350
SEQ105     281  ..........  ..........  ..........  ..........  ..........  ..........  ..........  350
SEQ107     281  ..........  ..........  ..........  ..........  ..........  ..........  ..........  350
SEQ109     281  ..........  ..........  ..........  ..........  ..........  ..........  ..........  350
SEQ111     281  ..........  ..........  ..........  ..........  ..........  ..........  ..........  350
SEQ113     281  ..........  ..........  ..........  ..........  ..........  ..........  ..........  350
SEQ115     281  ..........  ..........  ..........  ..........  ..........  ..........  ..........  350
SEQ117     281  ..........  ..........  ..........  ..........  ..........  ..........  ..........  350
SEQ119     281  ..........  ..........  ..........  ..........  ..........  ..........  ..........  350
SEQ121     281  ..........  ..........  ..........  ..........  ..........  ..........  ..........  350
SEQ123     281  ..........  ..........  ..........  ..........  ..........  ..........  ..........  350
SEQ125     281  ..........  ..........  ..........  ..........  ..........  ..........  ..........  350
```

FIG. 1 CONT

```
               360        370        380        390        400        410        420
          ....|....|  ....|....|  ....|....|  ....|....|  ....|....|  ....|....|  ....|....|
SEQ1    351 AGAACACAAG TTTCCAGCGG CAGTTGAAGA CGCGTATGAT GCACTGCAAT GGATTGCAGA ACGTGCAGCC 420
SEQ3    351 .......... .......... .......... .......... .......... .......... .......... 420
SEQ5    351 .......... .......... .......... .......... .......... .......... .......... 420
SEQ7    351 .......... .......... .......... .......... .......... .......... .......... 420
SEQ9    351 .......... .......... .......... .......... .......... .......... .......... 420
SEQ11   351 .......... .......... .......... .......... .......... .......... .......... 420
SEQ13   351 .......... .......... .......... .......... .......... .......... .......... 420
SEQ15   351 .......... .......... .......... .......... .......... .......... .......... 420
SEQ17   351 .......... .......... .......... .......... .......... .......... .......... 420
SEQ19   351 .......... .......... .......... .......... .......... .......... .......... 420
SEQ21   351 .......... .......... .......... .......... .......... .......... .......... 420
SEQ23   351 .......... .......... .......... .......... .......... .......... .......... 420
SEQ25   351 .......... .......... .......... .......... .......... .......... .......... 420
SEQ27   351 .......... .......... .......... .......... .......... .......... .......... 420
SEQ29   351 .......... .......... .......... .......... .......... .......... .....C.... 420
SEQ31   351 .......... .......... .......... .......... .......... .......... .....C.... 420
SEQ33   351 .......... .......... .......... .......... .......... .......... .....C.... 420
SEQ35   351 .......... .......... .......... .......... .......... .......... .......... 420
SEQ37   351 .......... .......... .......... .......... .......... .......... .......... 420
SEQ39   351 .......... .......... .......... .......... .......... .......... .......... 420
SEQ41   351 .......... .......... .......... .......... .......... .......... .......... 420
SEQ43   351 .......... .......... .......... .......... .......... .......... .......... 420
SEQ45   351 .......... .......... .......... .......... .......... .......... .......... 420
SEQ47   351 .......... .......... .......... .......... .......... .......... .......... 420
SEQ49   351 .......... .......... .......... .......... .......... .......... ....CGT... 420
SEQ51   351 .......... .......... .......... .......... .......... .......... .......... 420
SEQ53   351 .......... .......... .......... .......... .......... .......... .......... 420
SEQ55   351 .......... .......... .......... .......... .......... .......... .......... 420
SEQ57   351 .......... .......... .......... .......... .......... .......... .......... 420
SEQ59   351 .......... .......... .......... .......... .......... .......... .......... 420
SEQ61   351 .......... .......... .......... .......... .......... .......... .......... 420
SEQ63   351 .......... .......... .......... .......... .......... .......... .......... 420
SEQ65   351 .......... .......... .......... .......... .......... .......... .......... 420
SEQ67   351 .......... .......... .......... .......... .......... .......... .......... 420
SEQ69   351 .......... .......... .......... .......... .......... .......... .......... 420
SEQ71   351 .......... .......... .......... .......... .......... .......... .......... 420
SEQ73   351 .......... .......... .......... .......... .......... .......... .......... 420
SEQ75   351 .......... .......... .......... .......... .......... .......... .......... 420
SEQ77   351 .......... .......... .......... .......... .......... .......... .......... 420
SEQ79   351 .......... .......... .......... .......... .......... .......... .......... 420
SEQ81   351 .......... .......... .......... .......... .......... .......... .......... 420
SEQ83   351 .......... .......... .......... .......... .......... .......... .......... 420
SEQ85   351 .......... .......... .......... .......... .......... .......... .......... 420
SEQ87   351 .......... .......... .......... .......... .......... .......... .......... 420
SEQ89   351 .......... .......... .......... .......... .......... .......... .......... 420
SEQ91   351 .......... .......... .......... .......... .......... .......... .......... 420
SEQ93   351 .......... .......... .......... .......... .......... .......... .......... 420
SEQ95   351 .......... .......... .......... .......... .......... .......... .......... 420
SEQ97   351 .......... .......... .......... .......... .......... .......... .......... 420
SEQ99   351 .......... .......... .......... .......... .......... .......... .......... 420
SEQ101  351 .......... .......... .......... .......... .......... .......... .......... 420
SEQ103  351 .......... .......... .......... .......... .......... .......... .......... 420
SEQ105  351 .......... .......... .......... .......... .......... .......... .......... 420
SEQ107  351 .......... .......... .......... .......... .......... .......... .......... 420
SEQ109  351 .......... .......... .......... .......... .......... .......... .......... 420
SEQ111  351 .......... .......... .......... .......... .......... .......... .......... 420
SEQ113  351 .......... .......... .......... .......... .......... .......... .......... 420
SEQ115  351 .......... .......... .......... .......... .......... .......... .......... 420
SEQ117  351 .......... .......... .......... .......... .......... .......... .......... 420
SEQ119  351 .......... .......... .......... .......... .......... .......... .......... 420
SEQ121  351 .......... .......... .......... .......... .......... .......... .......... 420
SEQ123  351 .......... .......... .......... .......... .......... .......... .......... 420
SEQ125  351 .......... .......... .......... .......... .......... .......... .......... 420
```

FIG. 1 CONT

```
                 430        440        450        460        470        480        490
                 ....|....|  ....|....|  ....|....|  ....|....|  ....|....|  ....|....|  ....|....|
SEQ1      421  GATTCCATC  TTGATCCAGC  ACGCATTGCA  GTGGCGGCC  ATTCAGCAGG  CGGCAACCTG  GCGGCCGTCA  490
SEQ3      421  .........  ..........  ..........  .........  ..........  ..........  ..........  490
SEQ5      421  .........  ..........  ..........  .........  ..........  ..........  ..........  490
SEQ7      421  .........  ..........  ..........  .........  ..........  ..........  ..........  490
SEQ9      421  .........  ..........  ..........  .........  ..........  ..........  ..........  490
SEQ11     421  .........  ..........  ..........  .........  ..........  ..........  ..........  490
SEQ13     421  .........  ..........  ..........  .........  ..........  ..........  ..........  490
SEQ15     421  .........  ..........  ..........  .........  ..........  ..........  ..........  490
SEQ17     421  .........  ..........  ..........  .........  ..........  ..........  ..........  490
SEQ19     421  .........  ..........  ..........  .........  ..........  ..........  ..........  490
SEQ21     421  .........  ..........  ..........  .........  ..........  ..........  ..........  490
SEQ23     421  .........  ..........  ..........  .........  ..........  ..........  ..........  490
SEQ25     421  .........  ..........  ..........  .........  ..........  ..........  ..........  490
SEQ27     421  .........  ..........  ..........  .........  ..........  ..........  ..........  490
SEQ29     421  .........  ..........  ..........  .........  ..........  ..........  ..........  490
SEQ31     421  .........  ..........  ..........  .........  ..........  ..........  ..........  490
SEQ33     421  .........  ..........  ..........  .........  ..........  ..........  ..........  490
SEQ35     421  .........  ..........  ..........  .........  ..........  ..........  ..........  490
SEQ37     421  .........  ..........  ..........  .........  ..........  ..........  ..........  490
SEQ39     421  .........  ..........  ..........  .........  ..........  ..........  ..........  490
SEQ41     421  .........  ..........  ..........  .........  ..........  ..........  ..........  490
SEQ43     421  .........  ..........  ..........  .........  ..........  ..........  ..........  490
SEQ45     421  .........  ..........  ..........  .........  ..........  ..........  ..........  490
SEQ47     421  .........  ..........  ..........  .........  ..........  ..........  ..........  490
SEQ49     421  .........  ..........  ..........  .........  ..........  ..........  ..........  490
SEQ51     421  .........  ..........  ..........  .........  ..........  ..........  ..........  490
SEQ53     421  .........  ..........  ..........  .........  ..........  ..........  ..........  490
SEQ55     421  .........  ..........  ..........  .........  ..........  ..........  ..........  490
SEQ57     421  .........  ..........  ..........  .........  ..........  ..........  ..........  490
SEQ59     421  .........  ..........  ..........  .........  ..........  ..........  ..........  490
SEQ61     421  .........  ..........  ..........  .........  ..........  ..........  ..........  490
SEQ63     421  .........  ..........  ..........  .........  ..........  ..........  ..........  490
SEQ65     421  .........  ..........  ..........  .........  ..........  ..........  ..........  490
SEQ67     421  .........  ..........  ..........  .........  ..........  ..........  ..........  490
SEQ69     421  .........  ..........  ..........  .........  ..........  ..........  ..........  490
SEQ71     421  .........  ..........  ..........  .........  ..........  ..........  ..........  490
SEQ73     421  .........  ..........  ..........  .........  ..........  ..........  ..........  490
SEQ75     421  .........  ..........  ..........  .........  ..........  ..........  ..........  490
SEQ77     421  .........  ..........  ..........  .........  ..........  ..........  ..........  490
SEQ79     421  .........  ..........  ..........  .........  ..........  ..........  ..........  490
SEQ81     421  .........  ..........  ..........  .........  ..........  ..........  ..........  490
SEQ83     421  .........  ..........  ..........  .........  .......G..  ..........  ..........  490
SEQ85     421  .........  ..........  ..........  .........  ..........  ..........  ..........  490
SEQ87     421  .........  ..........  ..........  .........  ..........  ..........  ..........  490
SEQ89     421  .........  ..........  ..........  .........  ..........  ..........  ..........  490
SEQ91     421  .........  ..........  ..........  .........  ..........  ..........  ..........  490
SEQ93     421  .........  ..........  ..........  .........  .......G..  ..........  ..........  490
SEQ95     421  .........  ..........  ..........  .........  ..........  .......ACC  ..........  490
SEQ97     421  .........  ..........  ..........  .........  ..........  .......ACC  ..........  490
SEQ99     421  .........  ..........  ..........  .........  ..........  ..........  ..........  490
SEQ101    421  .........  ..........  ..........  .........  ..........  .......C..  ..........  490
SEQ103    421  .........  ..........  ..........  .........  ..........  ..........  ..........  490
SEQ105    421  .........  ..........  ..........  .........  ..........  ..........  ..........  490
SEQ107    421  .........  ..........  ..........  .........  ..........  .........C  ..........  490
SEQ109    421  .........  ..........  ..........  .........  ..........  .........C  ..........  490
SEQ111    421  .........  ..........  ..........  .........  ..........  ..........  ..........  490
SEQ113    421  .........  ..........  ..........  .........  ..........  ..........  ..........  490
SEQ115    421  .........  ..........  ..........  .........  ..........  ..........  ..........  490
SEQ117    421  .........  ..........  ..........  .........  ..........  ..........  ..........  490
SEQ119    421  .........  ..........  ..........  .........  ..........  ..........  ..........  490
SEQ121    421  .........  ..........  ..........  .........  ..........  ..........  ..........  490
SEQ123    421  .........  ..........  ..........  .........  ..........  ..........  ..........  490
SEQ125    421  .........  ..........  ..........  .........  ..........  ..........  ..........  490
```

FIG. 1 CONT

```
              500        510        520        530        540        550        560
         ....|....|  ....|....|  ....|....|  ....|....|  ....|....|  ....|....|  ....|....|
SEQ1   491 CTAGTATTCT GGCGAAAGAA CGTGGTGGTC CAGCAATTGC GTTTCAACTG CTGATCTATC CCTCCACTGG 560
SEQ3   491 .......... .......... .......... .......... .......... .......... .......... 560
SEQ5   491 .......... .......... .......... .......... .......... .......... .......... 560
SEQ7   491 .......... .......... .......... .......... .......... .......... .......... 560
SEQ9   491 .......... .......... .......... .......... .......... .......... .......... 560
SEQ11  491 .......... .......... .......... .G........ .......... .......... .......... 560
SEQ13  491 .......... .......... .......... .......... .......... .......... ..ATG..... 560
SEQ15  491 .......... .......... .......... .......... .......... .......... ...TT..... 560
SEQ17  491 .......... .......... .......... .......... .......... .......... ...TT..... 560
SEQ19  491 .......... .......... .......... .......... .......... .......... ...TT..... 560
SEQ21  491 .......... .......... .......... .......... .......... .......... ...TT..... 560
SEQ23  491 .......... .......... .......... .......... .......... .......... ...TT..... 560
SEQ25  491 .......... .......... .......... .......... .......... .......... .......... 560
SEQ27  491 .......... .......... .......... .......... .......... .......... .......... 560
SEQ29  491 .......... .......... .......... .......... .......... .......... .......... 560
SEQ31  491 .......... .......... .......... .......... .......... .......... .......... 560
SEQ33  491 .......... .......... .......... .......... .......... .......... .......... 560
SEQ35  491 .......... .......... .......... .......... .......... .......... ...TT..... 560
SEQ37  491 .......... .......... .......... .......... .......... .......... ...TT..... 560
SEQ39  491 .......... .......... .......... .......... .......... .......... ...TT..... 560
SEQ41  491 .......... .......... .......... .......... .......... .......... ...TT..... 560
SEQ43  491 .......... .......... .......... .......... .......... .......... ...TT..... 560
SEQ45  491 .......... .......... .......... .......... .......... .......... ...TT..... 560
SEQ47  491 .......... .......... .......... .......... .......... .......... ...TT..... 560
SEQ49  491 .......... .......... .......... .......... .......... .......... ...TT..... 560
SEQ51  491 .......... .......... .......... .......... .......... .......... ...TT..... 560
SEQ53  491 .......... .......... .......... .......... .......... .......... ...TT..... 560
SEQ55  491 .......... .......... .......... .......... .......... .......... ...TT..... 560
SEQ57  491 .......... .......... .......... .......... .......... .......... ...TT..... 560
SEQ59  491 .......... .......... .......... .......... .......... .......... ...TT..... 560
SEQ61  491 .......... .......... .......... .......... .......... .......... ...TT..... 560
SEQ63  491 .......... .......... .......... .......... .......... .......... ...TT..... 560
SEQ65  491 .......... .......... .......... .......... .......... .......... ...TT..... 560
SEQ67  491 .......... .......... .......... .......... .......... .......... ...TT..... 560
SEQ69  491 .......... .......... .......... .......... .......... .......... ...TT..... 560
SEQ71  491 .......... .......... .......... .......... .......... .......... ...TT..... 560
SEQ73  491 .......... .......... .......... .......... .......... .......... ...TT..... 560
SEQ75  491 .......... .......... .......... .......... .......... .......... ...TT..... 560
SEQ77  491 .......... .......... .......... .......... .......... .......... ...TT..... 560
SEQ79  491 .......... .......... .......... .......... .......... .......... ...TT..... 560
SEQ81  491 .......... .......... .......... .......... .......... .......... ...TT..... 560
SEQ83  491 .......... .......... .......... .......... .......... .......... ...TT..... 560
SEQ85  491 .......... .......... .......... .......... .......... .......... ...TT..... 560
SEQ87  491 .......... .......... .......... .......... .......... .......... ...TT..... 560
SEQ89  491 .......... .......... .......... .......... .......... .......... ...TT..... 560
SEQ91  491 .......... .......... .......... .......... .......... .......... ...TT..... 560
SEQ93  491 .......... .......... .......... .......... .......... .......... ...TT..... 560
SEQ95  491 .......... .......... .......... .......... .......... .......... ...TT..... 560
SEQ97  491 .......... .......... .......... .......... .......... .......... ...TT..... 560
SEQ99  491 .......... .......... .......... .......... .......... .......... ...TT..... 560
SEQ101 491 .......... .......... .......... .......... .......... ......C.G. ...TT..... 560
SEQ103 491 .......... .......... .......... .......... .......... .......... ...TT..... 560
SEQ105 491 .......... .......... .......... .......... ......G... .......... ...TT..... 560
SEQ107 491 .......... .......... .......... .......... .......... .......... ...TT..... 560
SEQ109 491 .......... .......... .......... .......... .......... .......... ...TT..... 560
SEQ111 491 .......... .......... .......... .......... .......... .......... ...TT..... 560
SEQ113 491 .......... .......... .......... .......... .......... .......... ...TT..... 560
SEQ115 491 .......... .......... .......... .......... .......... .......... ...TT..... 560
SEQ117 491 .......... .......... .......... .......... .......... .......... ...TT..... 560
SEQ119 491 .......... .......... .......... .......... .......... .......... ...TT..... 560
SEQ121 491 .......... .......... .......... .......... .......... .......... ...TT..... 560
SEQ123 491 .......... .......... .......... .......... .......... .......... ...TT..... 560
SEQ125 491 .......... .......... .......... .......... .......G.. .AA....... ...TT..... 560
```

FIG. 1 CONT

```
              570        580        590        600        610        620        630
              ....|....| ....|....| ....|....| ....|....| ....|....| ....|....| ....|....|
SEQ1    561   TTATGATCCA GCACATCCAC CAGCAAGTAT CGAAGAGAAT GCGGAGGGTT ACCTGTTAAC CGGAGGCATG  630
SEQ3    561   .......... .......... .......... .CTT...... .......... .......... ..........  630
SEQ5    561   .......... .......... .......... .ATT...... .......... .......... ..........  630
SEQ7    561   .......... .......... .......... .T.T...... .......... .......... ..........  630
SEQ9    561   .......... .......... .......... .TTT...... .......... .......... ..........  630
SEQ11   561   .......... .......... .......... .ATG...... .......... .......... ..........  630
SEQ13   561   .......... .......... .......... .CTT...... .......... ........GA G.........  630
SEQ15   561   .......... .......... .......... .CTT...... .......... ........GA GCAT......  630
SEQ17   561   .......... .......... .......... .CTT...... .......... .......... ..........  630
SEQ19   561   .......... .......... .......... .CTT...... .......... .......... GCAT......  630
SEQ21   561   .......... .......... .......... .CTT...... .......... ........GA GCAT......  630
SEQ23   561   .......... .......... .......... .CTT...... .......... .......... ..........  630
SEQ25   561   .......... .......... .......... .ATT...... .......... .......... ..........  630
SEQ27   561   .......... .......... .......... .CTT...... .......... .......... .CAT......  630
SEQ29   561   .......... .......... .......... .CTT...... .......... .......... ..........  630
SEQ31   561   .......... .......... .......... .ATT...... .......... .......... ...T......  630
SEQ33   561   .......... .......... .......... .CTT...... .......... .......... ...T......  630
SEQ35   561   .......... .......... .......... .CTT...... .......... .......... ..........  630
SEQ37   561   .......... .......... .......... .CTT...... .......... .......... ..........  630
SEQ39   561   .......... .......... .......... .CTT...... .......... .......... ..........  630
SEQ41   561   .......... .......... .......... .CTT...... .......... .......... ..........  630
SEQ43   561   .......... .......... .......... .CTT...... .......... .......... ..........  630
SEQ45   561   .......... .......... .......... .CTT...... .......... .......... ..........  630
SEQ47   561   .......TAT .......... .......... .CTT...... .......... ........GA A.........  630
SEQ49   561   .......... .......... .......... .CTT...... .......... .......... ..........  630
SEQ51   561   .......... .......... .......... .CTT...... .......... .......... ..........  630
SEQ53   561   .......... .......... .......... .CTT...... .......... .......... ..........  630
SEQ55   561   .......... .......... .......... .CTT...... .......... .......... ..........  630
SEQ57   561   .......... .......... .......... .CTT...... .......... .......... ..........  630
SEQ59   561   .......... .......... .......... .CTT...... .......... .......... ..........  630
SEQ61   561   ..T....... .......... .......... .CTT...... .......... .......... ..........  630
SEQ63   561   .......... .......... .......... .CTT...... .......... .......... ..........  630
SEQ65   561   .......... .......... .......... .CTT...... .......... .......... ..........  630
SEQ67   561   .......... .......... .......... .CTT...... .......... .......... ..........  630
SEQ69   561   .......... .......... .......... .CTT...... .......... .......... ..........  630
SEQ71   561   .......... .......... .......... .CTT...... .......... .......... ..........  630
SEQ73   561   .......... .......... .......... .CTT...... .......... .......... ..........  630
SEQ75   561   .......... .......... ........C. TCTT...... .......... .......... ..........  630
SEQ77   561   .......... .......... .......... .CTT...... .......... .......... ..........  630
SEQ79   561   .......... .......... .......... .CTT...... .......... .......... ..........  630
SEQ81   561   ...C...... .......... .......... TCTT...... .......... .......... ..........  630
SEQ83   561   ...C...... .......... ........C. TCTT...... .......... .......... ..........  630
SEQ85   561   .......... .......... ........C. TCTT...... .......... .......... ..........  630
SEQ87   561   .......... .......... .......... .CTT...... .......... .......... ..........  630
SEQ89   561   561 A..... .......... .......... .CTT...... .......... .......... ..........  630
SEQ91   561   A......... .......... .......... .CTT...... .......... .......... ..........  630
SEQ93   561   .......... .......... .......... .CTT...... .......... .......... ..........  630
SEQ95   561   .......... .......... .......... .CTT...... .......... .......... ..........  630
SEQ97   561   .......... .......... .......... .CTT...... .......... .......... ..........  630
SEQ99   561   .......... .......... .......... .CTT...... .......... .......... ..........  630
SEQ101  561   ..T....... .......... .......... .CTT...... .......... ..T.T..... ..........  630
SEQ103  561   .......... .......... .......... .CTT...... .......... ..T.T..... ..........  630
SEQ105  561   .......... .......... .......... .CTT...... .......... ..T.T..... ..........  630
SEQ107  561   .......... .......... .......... .CTG...... .......... .......... ..........  630
SEQ109  561   .......... .......... .......... .CTT...... .......... .......... ..........  630
SEQ111  561   .......... .......... .......... .CTT...... .......... .......... ..........  630
SEQ113  561   .......... .......... .......... .CTT...... .......... .......... ..........  630
SEQ115  561   .......... .......... .......... .CTT...... .......... .......... ..........  630
SEQ117  561   .......... .......... .......... .CTT...... .......... .......... ..........  630
SEQ119  561   .......... .......... .......... .CTT...... .......... .......... ..........  630
SEQ121  561   .......... .......... .......... .CTT...... .......... .......... ..........  630
SEQ123  561   .......... .......... .......... .CTT...... .......... .......... ..........  630
SEQ125  561   .......... .......... .......... .CTT...... .......... .......... ..........  630
```

FIG. 1 CONT

```
                    640        650        660        670        680        690        700
                 ....|....|  ....|....|  ....|....|  ....|....|  ....|....|  ....|....|  ....|....|
SEQ1      631  ATGCTGTGGT  TTCGTGACCA  GTACCTGAAC  AGCCTTGAGG  AACTGACTCA  CCCATGGTTT  AGTCCAGTGC  700
SEQ3      631  ..........  ..........  ..........  ..........  ..........  ..........  ..........  700
SEQ5      631  ..........  ..........  ..........  ..........  ..........  ..........  ..........  700
SEQ7      631  ..........  ..........  ..........  ..........  ..........  ..........  ..........  700
SEQ9      631  ..........  ..........  ..........  ..........  ..........  ..........  ..........  700
SEQ11     631  ..........  ..........  ..........  ..........  ..........  ..........  ..........  700
SEQ13     631  ..........  ..........  ..........  ..........  ..........  ..........  ..........  700
SEQ15     631  ..........  ..........  ..........  ..........  ..........  ..........  ..........  700
SEQ17     631  ..........  ..........  ..........  ..........  ..........  ..........  ..........  700
SEQ19     631  ..........  ..........  ..........  ..........  ..........  ..........  ..........  700
SEQ21     631  ..........  ..........  ..........  ..........  ..........  ..........  ..........  700
SEQ23     631  ..........  ..........  ..........  ..........  ..........  ..........  ..........  700
SEQ25     631  ..........  ..........  ..........  ..........  ..........  ..........  ..........  700
SEQ27     631  ..........  ..........  ..........  ..........  ..........  ..........  ..........  700
SEQ29     631  ..........  ..........  ..........  ..........  ..........  ..........  ..........  700
SEQ31     631  ..........  ..........  ..........  ..........  ..........  ..........  ..........  700
SEQ33     631  ..........  ..........  ..........  ..........  ..........  ..........  ..........  700
SEQ35     631  ..........  ..........  ..........  ..........  ..........  ..........  ..........  700
SEQ37     631  ..........  .....A....  ..........  ..........  ..........  ..........  ..........  700
SEQ39     631  ..........  ..........  ..........  ..........  ..........  ..........  ..........  700
SEQ41     631  ..........  ..........  ..........  ..........  ..........  ..........  ..........  700
SEQ43     631  ..........  ..........  ..........  ..........  ..........  ..........  ..........  700
SEQ45     631  ..........  ..........  ..........  ..........  ..........  ..........  ..........  700
SEQ47     631  ..........  ..........  ..........  ..........  ..........  ..........  ..........  700
SEQ49     631  ..........  ..........  ..........  ..........  ..........  ..........  ..........  700
SEQ51     631  ..........  ..........  ..........  ..........  ..........  ..........  ..........  700
SEQ53     631  ..........  ..........  ..........  ..........  ..........  ..........  ..........  700
SEQ55     631  ..........  ..........  ..........  ..........  ..........  ..........  ..........  700
SEQ57     631  ..........  ..........  ..........  ..........  ..........  ..........  ..........  700
SEQ59     631  ..........  ..........  ..........  ..........  ..........  ..........  ..........  700
SEQ61     631  ..........  ..........  ..........  ..........  ..........  ..........  ..........  700
SEQ63     631  ..........  .....ATT..  ..........  ..........  ..........  ..........  ..........  700
SEQ65     631  ..........  ..........  ..........  ..........  ..........  ..........  ..........  700
SEQ67     631  ..........  .....A.T..  ..........  ..........  ..........  ..........  ..........  700
SEQ69     631  ..........  ..........  ..........  ..........  ..........  ..........  ..........  700
SEQ71     631  ..........  ..........  ..........  ..........  ..........  ..........  ..........  700
SEQ73     631  ..........  ..........  ..........  ..........  ..........  ..........  ..........  700
SEQ75     631  ..........  .....A.T..  ..........  ..........  ..........  ..........  ..........  700
SEQ77     631  ..........  .....A.T..  ..........  ..........  ..........  ..........  ..........  700
SEQ79     631  ..........  .....A.T..  ..........  ..........  ..........  ..........  ..........  700
SEQ81     631  ..........  .....A.T..  ..........  ..........  ..........  ..........  ..........  700
SEQ83     631  ..........  .....A.T..  ..........  ..........  ..........  ..........  ..........  700
SEQ85     631  ..........  .....A.T..  ..........  ..........  ..........  ..........  ..........  700
SEQ87     631  ..........  .....A.T..  ..........  ..........  ..........  ..........  ..........  700
SEQ89     631  ..........  .....A.T..  ..........  ..........  ..........  ..........  ..........  700
SEQ91     631  ..........  .....A.T..  ..........  ..........  ..........  ..........  ..........  700
SEQ93     631  ..........  .....A.T..  ..........  ..........  ..........  ..........  ..........  700
SEQ95     631  ..........  .....A.T..  ..........  ..........  ..........  ..........  ..........  700
SEQ97     631  ..........  .....A.T..  ..........  ..........  ..........  ..........  ..........  700
SEQ99     631  ..........  .....A.T..  ..........  ..........  ..........  ..........  ..........  700
SEQ101    631  ...GAT....  .....A.T..  ..........  ..........  ..........  ..........  ..........  700
SEQ103    631  ..........  .....A.T..  ..........  ..........  ..........  ..........  ..........  700
SEQ105    631  ..........  .....A.T..  ..........  ..........  ..........  ..........  ..........  700
SEQ107    631  ..........  .....A.T..  ..........  ..........  ..........  ..........  ..........  700
SEQ109    631  ..........  .....A.T..  ..........  ..........  ..........  ..........  ..........  700
SEQ111    631  ..........  .....A.T..  ..........  ..........  ..........  ..........  ..........  700
SEQ113    631  ..........  .....A.T..  ..........  ..........  ..........  ..........  ..........  700
SEQ115    631  ..........  .....A.T..  ..........  ..........  ..........  ..........  ..........  700
SEQ117    631  ..........  .....A.T..  ..........  ..........  ..........  ..........  ..........  700
SEQ119    631  ..........  .....A.T..  ..........  ..........  ..........  ..........  ..........  700
SEQ121    631  ..........  .....A.T..  ..........  ..........  ..........  ..........  ..........  700
SEQ123    631  ..........  .....A.T..  ..........  ..........  ..........  ..........  ..........  700
SEQ125    631  ..........  .....A.T..  ..........  ..........  ..........  ..........  ..........  700
```

FIG. 1 CONT

|         |     | 710        | 720        | 730        | 740        | 750        | 760        | 770        |     |
|---------|-----|------------|------------|------------|------------|------------|------------|------------|-----|
| SEQ1    | 701 | TGTACCCGGA | TCTTAGCGGT | TTACCACCGG | CGTACATTGC | AACCGCACAG | TACGATCCCC | TGCGCGATGT | 770 |
| SEQ3    | 701 | .......... | .......... | .......... | .......... | .......... | .......... | .......... | 770 |
| SEQ5    | 701 | .......... | .......... | .......... | .......... | .......... | .......... | .......... | 770 |
| SEQ7    | 701 | .......... | .......... | .......... | .......... | .......... | .......... | .......... | 770 |
| SEQ9    | 701 | .......... | .......... | .......... | .......... | .......... | .......... | .......... | 770 |
| SEQ11   | 701 | .......... | .......... | .......... | .......... | .......... | .......... | .......... | 770 |
| SEQ13   | 701 | .......... | .......... | .......... | .......... | .......... | .......... | .......... | 770 |
| SEQ15   | 701 | .......... | .......... | .......... | .......... | .......... | .......... | .......... | 770 |
| SEQ17   | 701 | .......... | .......... | .......... | .......... | .......... | .......... | .......... | 770 |
| SEQ19   | 701 | .......... | .......... | .......... | .......... | .......... | .......... | .......... | 770 |
| SEQ21   | 701 | .......... | .......... | .......... | .......... | .......... | .......... | .......... | 770 |
| SEQ23   | 701 | .......... | .......... | .......... | .......... | .......... | .......... | .......... | 770 |
| SEQ25   | 701 | .......... | .......... | .......... | .......... | .......... | .......... | .......... | 770 |
| SEQ27   | 701 | .......... | .......... | .......... | .......... | .......... | .......... | .......... | 770 |
| SEQ29   | 701 | .......... | .......... | .......... | .......... | .......... | .......... | .......... | 770 |
| SEQ31   | 701 | .......... | .......... | .......... | .......... | .......... | .......... | .......... | 770 |
| SEQ33   | 701 | .......... | .......... | .......... | .......... | .......... | .......... | .......... | 770 |
| SEQ35   | 701 | .......... | .......... | .......... | .......... | .......... | .......... | .......... | 770 |
| SEQ37   | 701 | .......... | .......... | .......... | .......... | .......... | .......... | .......... | 770 |
| SEQ39   | 701 | .......... | .......... | .......... | .......... | .......... | .......... | .......... | 770 |
| SEQ41   | 701 | .......... | .......... | .......... | .......... | .......... | .......... | .......... | 770 |
| SEQ43   | 701 | .......... | .......... | .......... | .......... | .......... | .......... | .......... | 770 |
| SEQ45   | 701 | .......... | .......... | .......... | .......... | .......... | .......... | .......... | 770 |
| SEQ47   | 701 | .......... | .......... | .......... | .......... | .......... | .......... | .......... | 770 |
| SEQ49   | 701 | .......... | .......... | .......... | .......... | .......... | .......... | .......... | 770 |
| SEQ51   | 701 | .......... | .......... | .......... | .......... | .......... | .......... | .......... | 770 |
| SEQ53   | 701 | .......... | .......... | .......... | .......... | .......... | .......... | .......... | 770 |
| SEQ55   | 701 | .......... | .......... | .......... | .......... | .......... | .......... | .......... | 770 |
| SEQ57   | 701 | .......... | .......... | .......... | .......... | .......... | .......... | .......... | 770 |
| SEQ59   | 701 | .......... | .......... | .......... | .......... | .......... | .......... | .......... | 770 |
| SEQ61   | 701 | .......... | .......... | .......... | .......... | .......... | .......... | .......... | 770 |
| SEQ63   | 701 | .......... | .......... | .......... | .......... | .......... | .......... | .......... | 770 |
| SEQ65   | 701 | .......... | .......... | .......... | .......... | .......... | .......... | .......... | 770 |
| SEQ67   | 701 | .......... | .......... | .......... | .......... | .......... | .......... | .......... | 770 |
| SEQ69   | 701 | .......... | .......... | .......... | .......... | .......... | .......... | .......... | 770 |
| SEQ71   | 701 | .......... | .......... | .......... | .......... | .......... | .......... | .......... | 770 |
| SEQ73   | 701 | .......... | .......... | .......... | .......... | .......... | .......... | .......... | 770 |
| SEQ75   | 701 | .......... | .......... | .......... | .......... | .......... | .......... | .......... | 770 |
| SEQ77   | 701 | .......... | .......... | .......... | .......... | .......... | .......... | .......... | 770 |
| SEQ79   | 701 | .......... | .......... | .......... | .......... | .......... | .......... | .......... | 770 |
| SEQ81   | 701 | .......... | .......... | .......... | .......... | .......... | .......... | .......... | 770 |
| SEQ83   | 701 | .......... | .......... | .......... | .......... | .......... | .......... | .......... | 770 |
| SEQ85   | 701 | .......... | .......... | .......... | .......... | .......... | .......... | .......... | 770 |
| SEQ87   | 701 | .......... | .......... | .......... | .......... | .......... | .......... | .......... | 770 |
| SEQ89   | 701 | .......... | .......... | .......... | .......... | .......... | .......... | .......... | 770 |
| SEQ91   | 701 | .......... | .......... | .......... | .......... | .......... | .......... | .......... | 770 |
| SEQ93   | 701 | .......... | .......... | .......... | .......... | .......... | .......... | .......... | 770 |
| SEQ95   | 701 | .......... | .......... | .......... | .......... | .......... | .......... | .......... | 770 |
| SEQ97   | 701 | .......... | .......... | .......... | .......... | .......... | .......... | .......... | 770 |
| SEQ99   | 701 | .......... | .......... | .......... | .......... | .......... | .......... | .......... | 770 |
| SEQ101  | 701 | .......... | .......... | .......... | .......... | .......... | .......... | ..AA...... | 770 |
| SEQ103  | 701 | .......... | .......... | .......... | .......... | ....TGG... | .......... | .......... | 770 |
| SEQ105  | 701 | .......... | .......... | .......... | .......... | .GTG...... | .......... | .......... | 770 |
| SEQ107  | 701 | .......... | .......... | .......... | .......... | .......... | .......... | .......... | 770 |
| SEQ109  | 701 | .......... | .......... | .......... | .......... | .......... | .......... | .......... | 770 |
| SEQ111  | 701 | .......... | .......... | .......... | .......... | .......... | .......... | .......... | 770 |
| SEQ113  | 701 | .......... | .......... | .......... | .......... | .......... | .......... | .......... | 770 |
| SEQ115  | 701 | .......... | .......... | .......... | .......... | .......... | .......... | .......... | 770 |
| SEQ117  | 701 | .......... | .......... | .......... | .......... | .......... | .......... | .......... | 770 |
| SEQ119  | 701 | .......... | .......... | .......... | .......... | .......... | .......... | .......... | 770 |
| SEQ121  | 701 | .......... | .......... | .......... | .......... | .......... | .......... | .......... | 770 |
| SEQ123  | 701 | .......... | .......... | .......... | .......... | .......... | .......... | .......... | 770 |
| SEQ125  | 701 | .......... | .......... | .......... | .......... | .......... | .......... | .......... | 770 |

FIG. 1 CONT

```
                  780        790        800        810        820        830        840
                  ....|....|  ....|....|  ....|....|  ....|....|  ....|....|  ....|....|  ....|....|
SEQ1      771  CGGCAAACTT TACGCTGAAG CCCTGAACAA AGCGGGCGTT AAGGTGGAGA TCGAGAACTT CGAGGATCTG  840
SEQ3      771  .......... .......... .......... .......... .......... .......... ..........  840
SEQ5      771  .......... .......... .......... .......... .......... .......... ..........  840
SEQ7      771  .......... .......... .......... .......... .......... .......... ..........  840
SEQ9      771  .......... .......... .......... .......... .......... .......... ..........  840
SEQ11     771  .......... .......... .......... .......... .......... .......... ..........  840
SEQ13     771  .......... .......... .......... .......... .......... .......... ..........  840
SEQ15     771  .......... .......... .......... .......... .......... .......... ..........  840
SEQ17     771  .......... .......... .......... .......... .......... .......... ..........  840
SEQ19     771  .......... .......... .......... .......... .......... .......... ..........  840
SEQ21     771  .......... .......... .......... .......... .......... .......... ..........  840
SEQ23     771  .......... .......... .......... .......... .......... .......... ..........  840
SEQ25     771  .......... .......... .......... .......... .......... .......... ..........  840
SEQ27     771  .......... .......... .......... ........A. .......... .......... ..........  840
SEQ29     771  .......... .......... .......... ........A. .......... .......... ..........  840
SEQ31     771  .......... .......... .......... ........A. .......... .......... ..........  840
SEQ33     771  .......... .......... .......... ......G.T. .......... .......... ..........  840
SEQ35     771  .......... .......... .......... .......... .......... .......... ..........  840
SEQ37     771  .......... .......... .......... .......... .......... .......... ..........  840
SEQ39     771  .......... .......... .......... ......G.T. .......... .......... ..........  840
SEQ41     771  .......... .......... .......... ......G.T. .......... .......... ..........  840
SEQ43     771  .......... .......... .......... ......G.T. .......... ....C..... ..........  840
SEQ45     771  .......... .......... .......... .......... .......... ....C..... ..........  840
SEQ47     771  .......... .....ACC.. .......... .......... .......... .......... ..........  840
SEQ49     771  .......... .......... .......... .......... .......... .......... ..........  840
SEQ51     771  .......... .......... .......... .......... .......... .......... ..........  840
SEQ53     771  .......... .......... .......... .......... .......... .......... ..........  840
SEQ55     771  .......... .......... .......... .......... .......... .......... ..........  840
SEQ57     771  .......... .......... .......... .......... .......... .......... ..........  840
SEQ59     771  .......... .......... .......... .......... .......... .......... ..........  840
SEQ61     771  .......... .......... .......... .......... .......... .......... ..........  840
SEQ63     771  .......... .......... .......... .......... .......... .......... ..........  840
SEQ65     771  .......... .......... .......... .......... .......... .......... ..........  840
SEQ67     771  .......... .......... .......... .......... .......... .......... ..........  840
SEQ69     771  .......... .......... .......... .......... .......... .......... ..........  840
SEQ71     771  .......... .......... .......... .......... .......... .......... ..........  840
SEQ73     771  .......... .......... .......... .......... .......... .......... ..........  840
SEQ75     771  .......... .......... .......... .......... .......... .......... ..........  840
SEQ77     771  .......... .......... .......... .......... .......... .......... .......AC.  840
SEQ79     771  .......... .......... .......... .......... .......... .......... ........A.  840
SEQ81     771  ...T...... .......... .......... .......... .......... .......... ..........  840
SEQ83     771  ...T...... .......... ......C... .......... .......... .......... ..........  840
SEQ85     771  ...T...... .......... .......... .......... .......... .......... ..........  840
SEQ87     771  .......... .......... .......... .......... .......... .......... ........A.  840
SEQ89     771  .......... .......... .......... ........A. .......... .......... ..........  840
SEQ91     771  .......... .....AC... .......... ........A. .......... .......... ..........  840
SEQ93     771  .......... .......... .......... .......... .......... .......... ..........  840
SEQ95     771  .......... .......... .......... .......... .......... .......... ..........  840
SEQ97     771  .......... .......... .......... .......... .......... .......... ..........  840
SEQ99     771  .......... .......... .......... .......... .......... .......... ..........  840
SEQ101    771  .......... .......... .......... .......C.G .......... .......... ..........  840
SEQ103    771  .......... .......... .......... .......... .......... .......... ..........  840
SEQ105    771  .......... .......... .......... .......... .......... .......... ..........  840
SEQ107    771  .......... .......... .......... .......... .......... .......... ..........  840
SEQ109    771  .......... .......... .......... .......... .......... .......... ..........  840
SEQ111    771  .......... .......... .......... .......... .......... .......... ..........  840
SEQ113    771  .......... .......... .......... .......... .......... .......... ..........  840
SEQ115    771  .......... .......... .......... .......... .......... .......... ..........  840
SEQ117    771  .......... .......... .......... .......... .......... .......... ..........  840
SEQ119    771  .......... .......... .......... .......... .......... .......... ..........  840
SEQ121    771  .......... .......... .......... .......... .......... .......... ..........  840
SEQ123    771  .......... .......... .......... .......... .......... .......... ..........  840
SEQ125    771  .......... .......... .......... .......... .......... .......... ..........  840
```

FIG. 1 CONT

```
                   850        860        870        880        890        900        910
              ....|....|  ....|....|  ....|....|  ....|....|  ....|....|  ....|....|  ....|....|
SEQ1     841  ATTCATGGCT  TCGCGCAGTT  CTATTCTCTG  AGCCCAGGCC  CAACCAAAGC  ACTGGTACGT  ATTGCCGACA  910
SEQ3     841  ..........  ..........  ..........  ..........  ..........  ..........  ..........  910
SEQ5     841  ..........  ..........  ..........  ..........  ..........  ..........  ..........  910
SEQ7     841  ..........  ..........  ..........  ..........  ..........  ..........  ..........  910
SEQ9     841  ..........  ..........  ..........  ..........  ..........  ..........  ..........  910
SEQ11    841  ..........  ..........  ..........  ..........  ..........  ..........  ..........  910
SEQ13    841  ..........  ..........  ..........  ..........  ..........  .....GTC..  ..........  910
SEQ15    841  ..........  .......A..  T.........  ..........  ..........  ..........  ..........  910
SEQ17    841  ..........  ..........  ..........  ..........  ..........  .......G..  ..........  910
SEQ19    841  ..........  ..........  ..........  ..........  ..........  .....CTC..  ..........  910
SEQ21    841  ..........  ..........  ..........  ..........  ..........  .......G..  ..........  910
SEQ23    841  ..........  ..........  ..........  ..........  ..........  ..........  ..........  910
SEQ25    841  ..........  .....GG...  ..........  ..........  ..........  ..........  ..........  910
SEQ27    841  ..........  .....GG...  ..........  ..........  ..........  .......G..  ..........  910
SEQ29    841  ..........  .....GG...  ..........  ..........  ..........  ..........  ..........  910
SEQ31    841  ..........  .....GG...  ..........  ..........  ..........  ..........  ..........  910
SEQ33    841  ..........  .....GG...  ..........  ..........  ..........  ..........  ..........  910
SEQ35    841  ..........  ..........  ..........  ..........  ..........  ..........  ..........  910
SEQ37    841  ..........  ..........  ..........  ..........  ..........  ..........  ..........  910
SEQ39    841  ..........  ..........  ..........  ..........  ..........  .....CGT..  ..........  910
SEQ41    841  ..........  ..........  ..........  ..........  ..........  ..........  ..........  910
SEQ43    841  ..........  ..........  ..........  ..........  ..........  .....CGT..  ..........  910
SEQ45    841  ..........  ..........  ..........  ..........  ..........  .....CGT..  ..........  910
SEQ47    841  ..........  ..........  ..........  ..........  ..........  ..........  ..........  910
SEQ49    841  ..........  ..........  ..........  ..........  ..........  ..........  ..........  910
SEQ51    841  ..........  ..........  ..........  ..........  ..........  .....CGT..  ..........  910
SEQ53    841  ..........  ..........  ..........  ..........  ..........  ..........  ..........  910
SEQ55    841  ..........  .....AGT..  ..........  ..........  ..........  ..........  ..........  910
SEQ57    841  ..........  ..........  ..........  ..........  ..........  ..........  ..........  910
SEQ59    841  ..........  ..........  ..........  ..........  ..........  ..........  ..........  910
SEQ61    841  ..........  ..........  ..........  ..........  ..........  ..........  ..........  910
SEQ63    841  ..........  ..........  ..........  ..........  ..........  ..........  ..........  910
SEQ65    841  ..........  ..........  ..........  ..........  ..........  ..........  ..........  910
SEQ67    841  ..........  ..........  ..........  ..........  ..........  ..........  ..........  910
SEQ69    841  ..........  ..........  ..........  ..........  ..........  ..........  ..........  910
SEQ71    841  ..........  ..........  ..........  ..........  ..........  ..........  ..........  910
SEQ73    841  ..........  ..........  ..........  ..........  ..........  ..........  ..........  910
SEQ75    841  ..........  ..........  ..........  ..........  ..........  ..........  ..........  910
SEQ77    841  ..........  ..........  T......A.T  ..........  ..........  ..........  ..........  910
SEQ79    841  ..........  ..........  ..........  ..........  ..........  ..........  ..........  910
SEQ81    841  ..........  ..........  ..........  ..........  ..........  ..........  ..........  910
SEQ83    841  ..........  ..........  ..........  ..........  ..........  ..........  ..........  910
SEQ85    841  ..........  ..........  ..........  ..........  ..........  ..........  ..........  910
SEQ87    841  ..........  ..........  .......A.T  ..........  ..........  ..........  ..........  910
SEQ89    841  ..........  ..........  ..........  ..........  ..........  ..........  ..........  910
SEQ91    841  ..........  ..........  ..........  ..........  ..........  ..........  ..........  910
SEQ93    841  ..........  ..........  .......A.T  ..........  ..........  ..........  ..........  910
SEQ95    841  ..........  .....A.C..  ..........  ..........  ..........  ..........  ..........  910
SEQ97    841  ..........  .....AGC..  ..........  ..........  ..........  ..........  ..........  910
SEQ99    841  ..........  ..........  ..........  ..........  ..........  ..........  ..........  910
SEQ101   841  ..........  .....AGC..  ..........  ..........  ..........  ..........  ..........  910
SEQ103   841  ..........  .....AGC..  ..........  ..........  ..........  ..........  ..........  910
SEQ105   841  ..........  ..........  ..........  ..........  ..........  ..........  ..........  910
SEQ107   841  ..........  ..........  ..........  ..........  ..........  ..........  ..........  910
SEQ109   841  ..........  ..........  ..........  ..........  ..........  ..........  ..........  910
SEQ111   841  ..........  ..........  ..........  ..........  ..........  ..........  ..........  910
SEQ113   841  ..........  ..........  ..........  ..........  ..........  ..........  ..........  910
SEQ115   841  ..........  ..........  ..........  ..........  ..........  ..........  ..........  910
SEQ117   841  ..........  ..........  ..........  ..........  ..........  ..........  ..........  910
SEQ119   841  ..........  ....A.....  ..........  ..........  ..........  ..........  ..........  910
SEQ121   841  ..........  .....TGT..  ..........  ..........  ..........  ..........  ..........  910
SEQ123   841  ..........  ..........  ..........  ..........  ..........  ..........  ..........  910
SEQ125   841  ..........  ..........  ..........  ..........  ..........  ..........  ..........  910
```

FIG. 1 CONT

```
                       920        930
                 ....|....| ....|....|
SEQ1      911   AACTGCGCGA TGCGTTGGCG   930
SEQ3      911   .......... ..........   930
SEQ5      911   .......... ..........   930
SEQ7      911   .......... ..........   930
SEQ9      911   .......... ..........   930
SEQ11     911   .......... ..........   930
SEQ13     911   .......... ..........   930
SEQ15     911   .......... ..........   930
SEQ17     911   .......... ..........   930
SEQ19     911   .......... ..........   930
SEQ21     911   .......... ..........   930
SEQ23     911   .......... ..........   930
SEQ25     911   .......... ..........   930
SEQ27     911   .......... ..........   930
SEQ29     911   .......... ..........   930
SEQ31     911   .......... ..........   930
SEQ33     911   .......... ..........   930
SEQ35     911   .......... ..........   930
SEQ37     911   .......... ..........   930
SEQ39     911   .......... ..........   930
SEQ41     911   .......... ..........   930
SEQ43     911   .......... ..........   930
SEQ45     911   .......... ..........   930
SEQ47     911   .......... ..........   930
SEQ49     911   .......... ..........   930
SEQ51     911   .......... ..........   930
SEQ53     911   .......... ..........   930
SEQ55     911   .......... ..........   930
SEQ57     911   .......... ..........   930
SEQ59     911   .......... ..........   930
SEQ61     911   .......... ..........   930
SEQ63     911   .......... ..........   930
SEQ65     911   .......... ..........   930
SEQ67     911   .......... ..........   930
SEQ69     911   .......... ..........   930
SEQ71     911   .......... ..........   930
SEQ73     911   .......... ..........   930
SEQ75     911   .......... ..........   930
SEQ77     911   .......... ..........   930
SEQ79     911   .......... ..........   930
SEQ81     911   .......... ..........   930
SEQ83     911   .......... ..........   930
SEQ85     911   .......... ..........   930
SEQ87     911   .......... ..........   930
SEQ89     911   .......... ..........   930
SEQ91     911   .......... ..........   930
SEQ93     911   .......... ..........   930
SEQ95     911   .......... ..........   930
SEQ97     911   .......... ..........   930
SEQ99     911   .......... ..........   930
SEQ101    911   .......... ..........   930
SEQ103    911   .......... ..........   930
SEQ105    911   .......... ..........   930
SEQ107    911   .......... ..........   930
SEQ109    911   .......... ..........   930
SEQ111    911   .......... ..........   930
SEQ113    911   .......... ..........   930
SEQ115    911   .......... ..........   930
SEQ117    911   .......... ..........   930
SEQ119    911   .......... ..........   930
SEQ121    911   .......... ..........   930
SEQ123    911   .......... ..........   930
SEQ125    911   .......... ..........   930
```

FIG. 2

Pairwise Alignments of all Amino Acid Sequences against the Amino Acid of Wild-Type
Carboxyesterase Enzyme, *A. acidocaldarius* Esterase 2 (SEQ ID NO: 2)

```
                    10         20         30         40         50         60         70
              ....|....| ....|....| ....|....| ....|....| ....|....| ....|....| ....|....|
SEQ2     1    MPLDPVIQQV LDQLNRMPAP DYKHLSAQQF RSQQSLPPPV KKEPVAEVRE PDMDLPGRTL KVRMYRPEGV  70
SEQ4     1    .......... .......... .......... .......... .......... .......... ..........  70
SEQ6     1    .......... .......... .......... .......... .......... .......... ..........  70
SEQ8     1    .......... .......... .......... .......... .......... .......... ..........  70
SEQ10    1    .......... .......... .......... .......... .......... .......... ..........  70
SEQ12    1    .......... .......... .......... .......... .......... .......... ..........  70
SEQ14    1    .......... .......... .......... .......... .......... .......... ..........  70
SEQ16    1    .......... .......... .......... ......L... .......... .......... ..........  70
SEQ18    1    .......... .......... .......... .......... .......... .......... ..........  70
SEQ20    1    .......... .......... .......... ......L... .......... .......... ..........  70
SEQ22    1    .......... .......... .......... .......... .......... .......... ..........  70
SEQ24    1    .......... .......... .......... ....H..... .......... .......... ..........  70
SEQ26    1    .......... .......... .....P..L. .......... .......... .......... ..........  70
SEQ28    1    .......... .......... .......... .......... .......... .....M.... ..........  70
SEQ30    1    .......... .......... .......... .......... .......... .......... ..........  70
SEQ32    1    .......... .......... .......... .......... .......... .......... ..........  70
SEQ34    1    .......... .......... .......... .......... .......... .......... ..........  70
SEQ36    1    ........Y. .......... .......... ....H.T... .......... .......... ..........  70
SEQ38    1    .......... .......... .......... .......... ......L... .......... ..........  70
SEQ40    1    ........Y. .........R. .......... ...NH..... .......... .......... ..........  70
SEQ42    1    ........Y. .......... .......... ...EH..... .......... .......... ..........  70
SEQ44    1    ........Y. .........R. .......... ...EH..... .....V.... .......... ..........  70
SEQ46    1    ........Y. .......... .......... ...NH..... .....V.... .......... ..........  70
SEQ48    1    ........Y. .......... .......... ....H..... .......... .......... ......V...  70
SEQ50    1    ........Y. .......... .......... ...EH..... .....V.... .......... ..........  70
SEQ52    1    ........Y. .......... .......... ...NH..... .......... .......... ..........  70
SEQ54    1    ........Y. .......... .......... ....H..... .......... .......... ..........  70
SEQ56    1    ........Y. .......... .......... ....H..... .......... .......... ..........  70
SEQ58    1    ........Y. .......... ........V. ....H..... .......... .......... ..........  70
SEQ60    1    ........Y. .......... .......... ...EH..... .......... .......... ..........  70
SEQ62    1    ........Y. .......... .......... ....H..... .......... .......... ..........  70
SEQ64    1    ........Y. .......... .......... ....H..... .......... .......... ..........  70
SEQ66    1    ........Y. ..........I .......... ....H..... .......... .......... ..........  70
SEQ68    1    ........Y. .......... .......... ....H..... .......... .......... ..........  70
SEQ70    1    ........Y. .......... ........D. ....H..... .......... .......... ..........  70
SEQ72    1    ........Y. .......... .......... ...G.H.... .......... .......... ..........  70
SEQ74    1    ........Y. .......... ........S. ....H..... .......... .......... ..........  70
SEQ76    1    ........Y. .......... ........V. ....H..... .......... .......... ..........  70
SEQ78    1    ........Y. .......... .......... ....HIG... .......... .......... ..........  70
SEQ80    1    ........YM .......... .......... ....H.G... .......... .......... ..........  70
SEQ82    1    ........Y. .......... ........S. ....H..... .......... .......... ..........  70
SEQ84    1    ........Y. .......... ........S. ....H..... .......... .......... ..........  70
SEQ86    1    ........Y. .......... ........S. ....H..... .......... .......... ..........  70
SEQ88    1    ........Y. .......... .......... ....HMG... .......... .......... ..........  70
SEQ90    1    ........Y. .......... ........V. ..W.H..... .......... .......... ..........  70
SEQ92    1    ........Y. ..........I ........V. ..W.H..... .....R.... .......... ......T...  70
SEQ94    1    ........Y. .......... ...W...... ....H..... .......... .......... ..........  70
SEQ96    1    ........Y. .......... .......... ....H..... .....K.... .......... ..........  70
SEQ98    1    ........Y. .......... .......... ....H..... .....K.... .......... ..........  70
SEQ100   1    ........Y. .......... ........C. ....H..E.. .......... .......... ..........  70
SEQ102   1    ........Y. .......... .......... .......... .......... .......... ......L...  70
SEQ104   1    ........Y. .......... .......... .......... .......... .......... ......L...  70
SEQ106   1    ........Y. .......... ........C. ....H..... .......... ....R..... ..........  70
SEQ108   1    .....L..Y. .......... ........C. ....H..E.. .......... .......... ..........  70
SEQ110   1    ........Y. .......... ........C. ....H..E.. .....K.... .......... ..........  70
SEQ112   1    ........Y. .......... ........C. ....HT.W.. .......... ....Q..... ......T...  70
SEQ114   1    ........Y. .......... ........C. ....HT.W.. .......... .......... ..........  70
SEQ116   1    ........Y. .......... ...W....C. ....HM.W.. .......... .......... ..........  70
SEQ118   1    ........Y. .......... ........C. ....HT.W.. .......... .......... ..........  70
SEQ120   1    ........Y. .......... ........C. ....H..E.. .......... .......... ..........  70
SEQ122   1    ........Y. .......... ........C. ....HT.W.. .......... .......... ..........  70
SEQ124   1    .L......Y. .......... ........C. ....HT.W.. .......... .......... ..........  70
SEQ126   1    ........Y. .......... ........C. ....HT.W.. .......... .......... ..........  70
```

FIG. 2 CONT

```
                  80         90        100        110        120        130        140
               ....|....|  ....|....|  ....|....|  ....|....|  ....|....|  ....|....|  ....|....|
SEQ2     71    EPPYPALVYY  HGGGWVVGDL  ETHDPVCRVL  ARDGRAVVFS  VDYRLAPEHK  PPAAVEDAYD  ALQWIAERAA   140
SEQ4     71    ..........  ..........  ..........  ..........  ..........  ..........  ..........   140
SEQ6     71    ..........  ..........  ..........  ..........  ..........  ..........  ..........   140
SEQ8     71    ..........  ..........  ..........  ..........  ..........  ..........  ..........   140
SEQ10    71    ..........  ..........  ..........  ..........  ..........  ..........  ..........   140
SEQ12    71    ..........  ..........  ..........  ..........  ..........  ..........  ..........   140
SEQ14    71    ..........  ..........  ..........  ..........  ..........  ..........  ..........   140
SEQ16    71    ..........  ..........  ..........  ..........  ..........  ..........  ..........   140
SEQ18    71    ..........  ..........  ..........  ..........  ..........  ..........  ..........   140
SEQ20    71    ....R.....  ..........  ..........  ..........  ..........  ..........  ..........   140
SEQ22    71    ..........  ..........  ..........  ..........  ..........  ..........  ..........   140
SEQ24    71    ..........  ..........  ..........  ..........  ..........  ..........  ..........   140
SEQ26    71    ..........  ..........  ..........  ..W.......  ..........  ..........  ..........   140
SEQ28    71    ..........  ..........  ..........  ..W.......  ..........  ..........  ..........   140
SEQ30    71    ..........  ..........  ..........  ..........  ..........  ..........  ..........   140
SEQ32    71    ..........  ..........  ..........  ..W.......  ..........  ..........  ..........   140
SEQ34    71    ..........  ..........  ..........  ..W.......  ..........  ..........  ..........   140
SEQ36    71    ..........  ..........  ..........  ..W.......  ..........  ..........  ..........   140
SEQ38    71    ..........  ..........  ..........  ..........  ..........  ..........  ..........   140
SEQ40    71    ..........  .....A....  ..........  ..........  ..........  ..........  ..........   140
SEQ42    71    ..........  .....A....  ..........  ..........  ..........  ..........  ..........   140
SEQ44    71    ..........  .....A....  ..........  ..........  ..........  ..........  ..........   140
SEQ46    71    ..........  .....A....  ..........  ..........  ..........  ..........  ..........   140
SEQ48    71    ..........  .....A....  ..........  ..........  ..........  ..........  ..........   140
SEQ50    71    ..........  .....A....  ..........  ..........  ..........  ..........  ........R.   140
SEQ52    71    ..........  .....A....  ..........  ..........  ..........  ..........  ..........   140
SEQ54    71    ..........  .....A....  ..........  ..........  ..........  ..........  ..........   140
SEQ56    71    ..........  .....A....  ..........  ..........  ..........  ..........  ..........   140
SEQ58    71    ..........  .....A....  ..........  ..........  ..........  ..........  ..........   140
SEQ60    71    ..........  .....A....  ..........  ..........  ..........  ..........  ..........   140
SEQ62    71    ..........  .....A....  ..........  ..........  ..........  ..........  ..........   140
SEQ64    71    ..........  .....A....  ..........  ..........  ..........  ..........  ..........   140
SEQ66    71    ..........  .....A....  ..........  ..........  ..........  ..........  ..........   140
SEQ68    71    ..........  .....A....  ..........  ..........  ..........  ..........  ..........   140
SEQ70    71    ..........  .....A....  ..........  ..........  ..........  ..........  ..........   140
SEQ72    71    ..........  .....A....  ..........  ..........  ..........  ..........  ..........   140
SEQ74    71    ..........  .....A....  ..........  ..........  ..........  ..........  ..........   140
SEQ76    71    ..........  .....A....  ..........  ..........  ..........  ..........  ..........   140
SEQ78    71    ..........  .....A....  ..........  ..........  ..........  ..........  ..........   140
SEQ80    71    ..........  .....A....  ..........  ..........  ..........  ..........  ..........   140
SEQ82    71    ..........  .....A....  ..........  ..........  ..........  ..........  ..........   140
SEQ84    71    ..........  .....A....  ..........  ..........  ..........  ..........  ..........   140
SEQ86    71    ..........  .....A....  ..........  ..........  ..........  ..........  ..........   140
SEQ88    71    ..........  .....A....  ..........  ..........  ..........  ..........  ..........   140
SEQ90    71    ....R.....  .....A....  ..........  ..W.......  ..........  ..........  ..........   140
SEQ92    71    ..........  .....A....  ..........  ..W.......  ..........  ..........  ..........   140
SEQ94    71    ....R.....  .....A....  ..........  ..........  ..........  ..........  ..........   140
SEQ96    71    ..........  .....A....  ..........  ..........  ..........  ..........  ..........   140
SEQ98    71    ..........  .....A....  ..........  ..........  ..........  ..........  ..........   140
SEQ100   71    ..........  ....G.A...  ..........  ..........  ..........  ..........  ..........   140
SEQ102   71    ..........  .....TA...  .....M....  ..........  ..........  ..........  ..........   140
SEQ104   71    ..........  .....TA...  .....M....  ..........  ..........  ..........  ..........   140
SEQ106   71    ....R.....  .....A....  ..........  ..........  ..........  ..........  ..........   140
SEQ108   71    ..........  ....G.A...  ..........  ..........  ..........  ..........  ..........   140
SEQ110   71    ..........  ....G.A...  ..........  ..........  ..........  ..........  ..........   140
SEQ112   71    ..........  ....G.A...  ..........  ..........  ..........  ..........  ..........   140
SEQ114   71    ....R.....  ....G.A...  ..........  ..........  ..........  ..........  ..........   140
SEQ116   71    ....R.....  ....G.A...  ..........  ..........  ..........  ..........  ..........   140
SEQ118   71    ....M.....  ....G.A...  ..........  ..........  ..........  ..........  ..........   140
SEQ120   71    ..........  ....G.A...  ..........  ..........  ..........  ..........  ..........   140
SEQ122   71    ....R.....  ....G.A...  ..........  ..........  ..........  ..........  ..........   140
SEQ124   71    ....R.....  ....G.A...  ..........  ..........  ..........  ..........  ..........   140
SEQ126   71    ....R.....  ....G.A...  ..........  ..........  ..........  ..........  ..........   140
```

FIG. 2 CONT

```
              150        160        170        180        190        200        210
         ....|....|  ....|....|  ....|....|  ....|....|  ....|....|  ....|....|  ....|....|
SEQ2   141 DPHLDPARIA  VGGDSAGGNL  AAVTSILAKE  RGGPAIAFQL  LIYPSTGYDP  AHPPASIEEN  AEGYLLTGGM 210
SEQ4   141 ..........  ..........  ..........  ..........  ..........  .......L..  .......... 210
SEQ6   141 ..........  ..........  ..........  ..........  ..........  ........I.  .......... 210
SEQ8   141 ..........  ..........  ..........  ..........  ..........  ........Y.  .......... 210
SEQ10  141 ..........  ..........  ..........  ..........  ..........  ........F.  .......... 210
SEQ12  141 ..........  ..........  ..........  ..........  ..........  .......M..  .......... 210
SEQ14  141 ..........  ..........  ..........  ..........  ....M.....  .......L..  ......E... 210
SEQ16  141 ..........  ..........  ..........  ..........  ....F.....  .......L..  ......EH.. 210
SEQ18  141 ..........  ..........  ..........  ..........  ....F.....  .......L..  .......... 210
SEQ20  141 ..........  ..........  ..........  ..........  ....F.....  .......L..  ........H. 210
SEQ22  141 ..........  ..........  ..........  ..........  ....F.....  .......L..  ......EH.. 210
SEQ24  141 ..........  ..........  ..........  ..........  ....F.....  .......L..  .......... 210
SEQ26  141 ..........  ..........  ..........  ..........  ..........  ........I.  .......... 210
SEQ28  141 ..........  ..........  ..........  ..........  ..........  .......L..  ........H. 210
SEQ30  141 ..........  ..........  ..........  ..........  ..........  .......L..  .......... 210
SEQ32  141 ..........  ..........  ..........  ..........  ..........  ........I.  .......... 210
SEQ34  141 ..........  ..........  ..........  ..........  ..........  .......L..  .......... 210
SEQ36  141 ..........  ..........  ..........  ..........  ....F.....  .......L..  .......... 210
SEQ38  141 ..........  ..........  ..........  ..........  ....F.....  .......L..  .......... 210
SEQ40  141 ..........  ..........  ..........  ..........  ....F.....  .......L..  .......... 210
SEQ42  141 ..........  ..........  ..........  ..........  ....F.....  .......L..  .......... 210
SEQ44  141 ..........  ..........  ..........  ..........  ....F.....  .......L..  .......... 210
SEQ46  141 ..........  ..........  ..........  ..........  ....F.....  .......L..  .......... 210
SEQ48  141 ..........  ..........  ..........  ..........  ....F...Y.  .......L..  ......E... 210
SEQ50  141 ..........  ..........  ..........  ..........  ....F.....  .......L..  .......... 210
SEQ52  141 ..........  ..........  ..........  ..........  ....F.....  .......L..  .......... 210
SEQ54  141 ..........  ..........  ..........  ..........  ....F.....  .......L..  .......... 210
SEQ56  141 ..........  ..........  ..........  ..........  ....F.....  .......L..  .......... 210
SEQ58  141 ..........  ..........  ..........  ..........  ....F.....  .......L..  .......... 210
SEQ60  141 ..........  ..........  ..........  ..........  ....F.....  .......L..  .......... 210
SEQ62  141 ..........  ..........  ..........  ..........  ....F..F..  .......L..  .......... 210
SEQ64  141 ..........  ..........  ..........  ..........  ....F.....  .......L..  .......... 210
SEQ66  141 ..........  ..........  ..........  ..........  ....F.....  .......L..  .......... 210
SEQ68  141 ..........  ..........  ..........  ..........  ....F.....  .......L..  .......... 210
SEQ70  141 ..........  ..........  ..........  ..........  ....F.....  .......L..  .......... 210
SEQ72  141 ..........  ..........  ..........  ..........  ....F.....  .......L..  .......... 210
SEQ74  141 ..........  ..........  ..........  ..........  ....F.....  .......L..  .......... 210
SEQ76  141 ..........  ..........  ..........  ..........  ....F.....  ......LL..  .......... 210
SEQ78  141 ..........  ..........  ..........  ..........  ....F.....  .......L..  .......... 210
SEQ80  141 ..........  ..........  ..........  ..........  ....F.....  .......L..  .......... 210
SEQ82  141 ..........  ..........  ..........  ..........  ....F.....  .......L..  .......... 210
SEQ84  141 ..........  ..........  ..........  ..........  ....F.....  ......LL..  .......... 210
SEQ86  141 ..........  ..........  ..........  ..........  ....F.....  ......LL..  .......... 210
SEQ88  141 ..........  ..........  ..........  ..........  ....F.....  .......L..  .......... 210
SEQ90  141 ..........  ..........  ..........  ..........  ....F.....  .......L..  .......... 210
SEQ92  141 ..........  ..........  ..........  ..........  ....F.....  .......L..  .......... 210
SEQ94  141 ..........  ..........  ..........  ..........  ....F.....  .......L..  .......... 210
SEQ96  141 ..........  .......T..  ..........  ..........  ....F.....  .......L..  .......... 210
SEQ98  141 ..........  .......T..  ..........  ..........  ....F.....  .......L..  .......... 210
SEQ100 141 ..........  ..........  ..........  ..........  ....F.....  .......L..  .......... 210
SEQ102 141 ..........  .....P....  ..........  ..Q.F..F..  ..........  .......L..  ....F..... 210
SEQ104 141 ..........  ..........  ..........  ..........  ....F.....  .......L..  ....F..... 210
SEQ106 141 ..........  ..........  ..........  .....M....  ....F.....  .......L..  ....F..... 210
SEQ108 141 ..........  ..........  ..........  ..........  ....F.....  .......L..  .......... 210
SEQ110 141 ..........  ..........  ..........  ..........  ....F.....  .......L..  .......... 210
SEQ112 141 ..........  ..........  ..........  ..........  ....F.....  .......L..  .......... 210
SEQ114 141 ..........  ..........  ..........  ..........  ....F.....  .......L..  .......... 210
SEQ116 141 ..........  ..........  ..........  ..........  ....F.....  .......L..  .......... 210
SEQ118 141 ..........  ..........  ..........  ..........  ....F.....  .......L..  .......... 210
SEQ120 141 ..........  ..........  ..........  ..........  ....F.....  .......L..  .......... 210
SEQ122 141 ..........  ..........  ..........  ..........  ....F.....  .......L..  .......... 210
SEQ124 141 ..........  ..........  ..........  ..........  ....F.....  .......L..  .......... 210
SEQ126 141 ..........  ..........  ..........  ......Q...  ....F.....  .......L..  .......... 210
```

FIG. 2 CONT

```
              220        230        240        250        260        270        280
         ....|....|  ....|....|  ....|....|  ....|....|  ....|....|  ....|....|  ....|....|
SEQ2   211 MLWFRDQYLN  SLEELTHPWF  SPVLYPDLSG  LPPAYIATAQ  YDPLRDVGKL  YAEALNKAGV  KVEIENFEDL 280
SEQ4   211 ..........  ..........  ..........  ..........  ..........  ..........  .......... 280
SEQ6   211 ..........  ..........  ..........  ..........  ..........  ..........  .......... 280
SEQ8   211 ..........  ..........  ..........  ..........  ..........  ..........  .......... 280
SEQ10  211 ..........  ..........  ..........  ..........  ..........  ..........  .......... 280
SEQ12  211 ..........  ..........  ..........  ..........  ..........  ..........  .......... 280
SEQ14  211 ..........  ..........  ..........  ..........  ..........  ..........  .......... 280
SEQ16  211 ..........  ..........  ..........  ..........  ..........  ..........  .......... 280
SEQ18  211 ..........  ..........  ..........  ..........  ..........  ..........  .......... 280
SEQ20  211 ..........  ..........  ..........  ..........  ..........  ..........  .......... 280
SEQ22  211 ..........  ..........  ..........  ..........  ..........  ..........  .......... 280
SEQ24  211 ..........  ..........  ..........  ..........  ..........  ..........  .......... 280
SEQ26  211 ..........  ..........  ..........  ..........  ..........  ..........  .......... 280
SEQ28  211 ..........  ..........  ..........  ..........  ..........  ..........  .......... 280
SEQ30  211 ..........  ..........  ..........  ..........  ..........  ..........  .......... 280
SEQ32  211 ..........  ..........  ..........  ..........  ..........  ..........  .......... 280
SEQ34  211 ..........  ..........  ..........  ..........  ..........  .D........  .......... 280
SEQ36  211 ..........  ..........  ..........  ..........  ..........  ..........  .......... 280
SEQ38  211 .....N....  ..........  ..........  ..........  ..........  ..........  .......... 280
SEQ40  211 ..........  ..........  ..........  ..........  ..........  .D........  .......... 280
SEQ42  211 ..........  ..........  ..........  ..........  ..........  .D........  .......... 280
SEQ44  211 ..........  ..........  ..........  ..........  ..........  .D......Q.  .......... 280
SEQ46  211 ..........  ..........  ..........  ..........  ..........  ........Q.  .......... 280
SEQ48  211 ..........  ..........  ..........  ..........  ..T.......  ..........  .......... 280
SEQ50  211 ..........  ..........  ..........  ..........  ..........  ..........  .......... 280
SEQ52  211 ..........  ..........  ..........  ..........  ..........  ..........  .......... 280
SEQ54  211 ..........  ..........  ..........  ..........  ..........  ..........  .......... 280
SEQ56  211 ..........  ..........  ..........  ..........  ..........  ..........  .......... 280
SEQ58  211 ..........  ..........  ..........  ..........  ..........  ..........  .......... 280
SEQ60  211 ..........  ..........  ..........  ..........  ..........  ..........  .......... 280
SEQ62  211 ..........  ..........  ..........  ..........  ..........  ..........  .......... 280
SEQ64  211 .....I....  ..........  ..........  ..........  ..........  ..........  .......... 280
SEQ66  211 ..........  ..........  ..........  ..........  ..........  ..........  .......... 280
SEQ68  211 .....N....  ..........  ..........  ..........  ..........  ..........  .......... 280
SEQ70  211 ..........  ..........  ..........  ..........  ..........  ..........  .......... 280
SEQ72  211 ..........  ..........  ..........  ..........  ..........  ..........  .......... 280
SEQ74  211 ..........  ..........  ..........  ..........  ..........  ..........  .......... 280
SEQ76  211 .....N....  ..........  ..........  ..........  ..........  ..........  .......... 280
SEQ78  211 .....N....  ..........  ..........  ..........  ..........  ..........  .........T 280
SEQ80  211 .....N....  ..........  ..........  ..........  ..........  ..........  .......... 280
SEQ82  211 .....N....  ..........  ..........  ..........  ..........  ..........  .......... 280
SEQ84  211 .....N....  ..........  ..........  ..........  ......T...  ..........  .......... 280
SEQ86  211 .....N....  ..........  ..........  ..........  ..........  ..........  .......... 280
SEQ88  211 .....N....  ..........  ..........  ..........  ..........  ..........  .........M 280
SEQ90  211 .....N....  ..........  ..........  ..........  ..........  ..........  .......... 280
SEQ92  211 .....N....  ..........  ..........  ..........  ......R...  ..........  .......... 280
SEQ94  211 .....N....  ..........  ..........  ..........  ..........  ..........  .......... 280
SEQ96  211 .....N....  ..........  ..........  ..........  ..........  ..........  .......... 280
SEQ98  211 .....N....  ..........  ..........  ..........  ..........  ..........  .......... 280
SEQ100 211 .....N....  ..........  ..........  ..........  ..........  ..........  .......... 280
SEQ102 211 .D...N....  ..........  ..........  .....N....  ..........  .L........  .......... 280
SEQ104 211 .....N....  ..........  ..........  ......W...  ..........  ..........  .......... 280
SEQ106 211 .....N....  ..........  ..........  ......V...  ..........  ..........  .......... 280
SEQ108 211 .....N....  ..........  ..........  ..........  ..........  ..........  .......... 280
SEQ110 211 .....N....  ..........  ..........  ..........  ..........  ..........  .......... 280
SEQ112 211 .....N....  ..........  ..........  ..........  ..........  ..........  .......... 280
SEQ114 211 .....N....  ..........  ..........  ..........  ..........  ..........  .......... 280
SEQ116 211 .....N....  ..........  ..........  ..........  ..........  ..........  .......... 280
SEQ118 211 .....N....  ..........  ..........  ..........  ..........  ..........  .......... 280
SEQ120 211 .....N....  ..........  ..........  ..........  ..........  ..........  .......... 280
SEQ122 211 .....N....  ..........  ..........  ..........  ..........  ..........  .......... 280
SEQ124 211 .....N....  ..........  ..........  ..........  ..........  ..........  .......... 280
SEQ126 211 .....N....  ..........  ..........  ..........  ..........  ..........  .......... 280
```

FIG. 2 CONT

```
                    290         300         310
               ....|....| ....|....| ....|....|
SEQ2      281  IHGFAQFYSL SPGATKALVR IAEKLRDALA  310
SEQ4      281  .......... .......... ..........  310
SEQ6      281  .......... .......... ..........  310
SEQ8      281  .......... .......... ..........  310
SEQ10     281  .......... .......... ..........  310
SEQ12     281  .......... .......... ..........  310
SEQ14     281  .......... .....V.... ..........  310
SEQ16     281  .......... .......... ..........  310
SEQ18     281  .......... .......... ..........  310
SEQ20     281  .......... .....L.... ..........  310
SEQ22     281  .......... .......... ..........  310
SEQ24     281  .......... .......... ..........  310
SEQ26     281  .....G.... .......... ..........  310
SEQ28     281  .....G.... .....R.... ..........  310
SEQ30     281  .....G.... .......... ..........  310
SEQ32     281  .....G.... .......... ..........  310
SEQ34     281  .....G.... .......... ..........  310
SEQ36     281  .......... .......... ..........  310
SEQ38     281  .......... .......... ..........  310
SEQ40     281  .......... .....R.... ..........  310
SEQ42     281  .......... .......... ..........  310
SEQ44     281  .......... .....R.... ..........  310
SEQ46     281  .......... .....R.... ..........  310
SEQ48     281  .......... .......... ..........  310
SEQ50     281  .......... .......... ..........  310
SEQ52     281  .......... .....R.... ..........  310
SEQ54     281  .......... .......... ..........  310
SEQ56     281  .....S.... .......... ..........  310
SEQ58     281  .......... .......... ..........  310
SEQ60     281  .......... .......... ..........  310
SEQ62     281  .......... .......... ..........  310
SEQ64     281  .......... .......... ..........  310
SEQ66     281  .......... .......... ..........  310
SEQ68     281  .......... .......... ..........  310
SEQ70     281  .......... .......... ..........  310
SEQ72     281  .......... .......... ..........  310
SEQ74     281  .......... .......... ..........  310
SEQ76     281  .......... .......... ..........  310
SEQ78     281  ........I. .......... ..........  310
SEQ80     281  .......... .......... ..........  310
SEQ82     281  .......... .......... ..........  310
SEQ84     281  .......... .......... ..........  310
SEQ86     281  .......... .......... ..........  310
SEQ88     281  ........I. .......... ..........  310
SEQ90     281  .......... .......... ..........  310
SEQ92     281  .......... .......... ..........  310
SEQ94     281  ........I. .......... ..........  310
SEQ96     281  .....N.... .......... ..........  310
SEQ98     281  .....S.... .......... ..........  310
SEQ100    281  .......... .......... ..........  310
SEQ102    281  .....S.... .......... ..........  310
SEQ104    281  .....S.... .......... ..........  310
SEQ106    281  .......... .......... ..........  310
SEQ108    281  .......... .......... ..........  310
SEQ110    281  .......... .......... ..........  310
SEQ112    281  .......... .......... ..........  310
SEQ114    281  .......... .......... ..........  310
SEQ116    281  .......... .......... ..........  310
SEQ118    281  .......... .......... ..........  310
SEQ120    281  .......... .......... ..........  310
SEQ122    281  .....C.... .......... ..........  310
SEQ124    281  .......... .......... ..........  310
SEQ126    281  .......... .......... ..........  310
```

CARBOXYESTERASE BIOCATALYSTS

The material in the ASCII text file named 26368-0103US1_SL.txt created on Oct. 26, 2020 and having a size of 272,589 bytes is incorporated herein by reference in its entirety.

FIELD OF THE INVENTION

The present disclosure relates to improved carboxyesterase biocatalysts and methods of using the biocatalysts to make amides.

BACKGROUND OF THE INVENTION

Amide bond formation is one of the most frequently encountered reactions in organic synthesis and amides are commonly found in active pharmaceutical ingredients, biologically active molecules, synthetic polymers, peptides and proteins. A study by the Novartis Institute for BioMedical Research found that amide-bond formation and related acylation chemistries accounted for 21.3% of all chemical reactions performed in the synthesis of pharmaceuticals over the last 40 years (Schneider, et al., *J. Med. Chem.* 59, 4385-4402, 2016). Traditional methods of amide synthesis use carboxylic acid and amine substrates and require stoichiometric coupling reagents. As the reaction proceeds via a highly reactive activated intermediate, undesirable side reactions can occur leading to the formation of unwanted by-products, such as ureas. The poor atom economy and the significant amount of (metal-containing and frequently toxic) waste generated results in the process of amide formation being costly. Other drawbacks of traditional methods of amide synthesis include a lack of enantioselectivity and chemoselectivity, the use of explosive or toxic coupling reagents, and the requirement to protect other functional groups present in the reactants.

Chemical catalytic approaches have been developed that remove the requirement for stoichiometric coupling reagents and hence improve atom economy and reduce the amount of waste generated (reviewed in Pattabiraman and Bode, *Nature*, 480, 471-479, 2011 and de Figueiredo, et al., *Chemical Reviews*, 12029-12122, 2016). Boronic acid catalysis represents the oldest approach to chemical amidation, in which transient carboxylic acid activation by an aryl boronate enables the catalytic formation of amide. However, these methods suffer from very poor solvent tolerance, in addition to limited substrate scope and the frequent need for high temperatures, which limits their broader use. More recent studies include the use of metal catalyzed amidation, in which metal salts serve as Lewis acids for the transient activation of carboxylic acids to support amidation. To date, these studies suffer from many of the same shortcomings as boronate catalysis, requiring high temperature, catalyst loadings, and limited solvent scope and substrate tolerance. Redox-based methods employing either N-heterocyclic carbenes (NHCs) or metal catalysts have also been explored, enabling the oxidative conversion of alcohols, aldehydes, ketones or nitriles into their corresponding amides. Unfortunately, both metal and NHC catalysts are expensive, themselves are quite toxic, frequently require hazardous co-solvents, and typically suffer from poor functional group tolerance.

Lipases have been used as biocatalysts to generate amide bonds in organic solvents, by directly activating and then coupling an ester starting material to an amine. Advantageously, these enzymes are typically highly enantioselective and thermally tolerant (for a review, see Gotor, *Bioorg Med Chem*, 7, 2189-2197, 1999). However, most of the currently studied lipases appear to have a narrow substrate specificity and furthermore, must be used in dry organic solvents to prevent unwanted hydrolysis. This specificity issue is especially pronounced in the synthesis of tertiary amides, where very few enzymes have been shown to have even marginal activities (studied in van Pelt, *Green, Chem.* 13, 1791-1798, 2011).

To overcome such limitations, typically, a process of directed evolution is employed in which enzyme variants are expressed and studied in a high-throughput fashion. However, these enzymes are frequently derived from *Pseudomonas* or *Bacillus* strains, and cannot be readily expressed in lab strains for which robust genetic manipulation techniques exist, such as *E. coli* or *S. cerevisiae*. In addition, the requirement for dry solvents and molecular sieves makes directed evolution extremely challenging, due both to the high water content of cell lysates and to the technical challenge of drying hundreds of reactions in parallel.

BRIEF DESCRIPTION OF THE FIGURES

FIG. 1 shows a sequence alignment of the polynucleotide sequence encoding the *E. coli* codon optimized for wild-type carboxyesterase enzyme, *A. acidocaldarius* Esterase 2 (SEQ ID NO: 1) against each of the polynucleotide sequences that encode the engineered carboxyesterases referred to below in Table 3 and shown in the below Sequence Listing (SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, and 125). All of these disclosed polynucleotide sequences are from 95-99% identical to each other.

FIG. 2 shows a sequence alignment of the polypeptide sequence derived from the wild-type carboxyesterase enzyme, *A. acidocaldarius* Esterase 2 (SEQ ID NO: 2) against each of the engineered polypeptide carboxyesterase sequences referred to below in Table 3 and shown in the below Sequence Listing (SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, and 126). All of these disclosed polypeptide sequences are from 95-99% identical to each other.

SUMMARY OF THE INVENTION

In light of the prior art limitations, we have developed a series of mutants from the highly thermo-tolerant wild-type carboxyesterase enzyme, *A. acidocaldarius* Esterase 2 (SEQ ID NO: 2), wherein such mutated enzymes possess in excess of 785,000-fold improved amidation activity relative to the wild-type enzyme. Owing to this dramatically altered activity, these mutant enzymes possess substantial tolerance to water and alcohols, enabling the direct synthesis, at scale, of amides from simple ester and amine precursors. This strategy of direct synthesis shortens amide syntheses by 1-2 steps of chemistry, reduces organic solvent usage, and removes the use of stoichiometric activating agents, collectively representing a dramatic improvement in the chemical state of the art.

The present disclosure provides polypeptides, polynucleotides encoding the polypeptides and methods of using the polypeptides, in particular, for the biocatalytic conversion of ethyl oxazole-5-carboxylate (the "ester substrate") to (4-isopropylpiperazin-1-yl)(oxazol-5-yl)methanone (a "product") in the presence of 1-isopropylpiperazine (an "amine substrate").

The present disclosure also provides polypeptides, polynucleotides encoding the polypeptides and methods of using the polypeptides, in particular, for the biocatalytic conversion of ethyl oxazole-5-carboxylate (the "ester substrate") ester substrate to ((2S,6R)-2,6-dimethylmorpholino)(oxazol-5-yl)methanone (another product) in the presence of cis-2,6-dimethylmorpholine, an amine substrate. The products are starting materials for pharmaceuticals that are of interest in the development for the treatment of chronic obstructive pulmonary disease (COPD). Specifically, the products may be used to synthesize phosphoinositide 3-kinase 8 inhibitors (PI3Kδ inhibitors), which are a class of drugs used to treat inflammation, autoimmune diseases, and cancer. The compositions of the invention may also be used as starting materials for other types of pharmaceuticals, as well.

While the wild-type polypeptide, carboxyesterase enzyme, *A. acidocaldarius* Esterase 2 (SEQ ID NO: 2) only acts on the ester substrate with very low efficiency (<1% of substrate converted into product), as evidenced in Table 3, the engineered carboxyesterases (E.C. 3.1.1) of the present disclosure are capable of carrying out the facile conversion of the ester substrate to the products in the presence of an amine substrate. Thus, in one aspect, the present disclosure relates to improved carboxyesterases capable of converting ethyl oxazole-5-carboxylate, the ester substrate, to (4-isopropylpiperazin-1-yl)(oxazol-5-yl)methanone, a product, in the presence of 1-isopropylpiperazine the "amine substrate", to levels measurable by about 0.1% conversion by an analysis technique, such as HPLC-UV absorbance.

In some embodiments, the improved carboxyesterase polypeptide comprises an amino acid sequence that is at least 80%, 85%, 86%, 87%, 88%, 89%, 90%, 91%, 92%, 93%, 94%, 95%, 96%, 97%, 98%, 99%, or more identical to the amino acid sequence set forth in SEQ ID NO: 4, or a functional fragment thereof, and wherein the improved carboxyesterase amino acid sequence includes the feature that: the residue corresponding to X198 is chosen from: a non-polar residue, an aromatic residue, and an aliphatic residue. Guidance for the choice of various amino acid residues that can be present at the specified residue positions are provided in the detailed description that follows, as well as in the claims.

In some embodiments, the improved carboxyesterase polypeptide comprises an amino acid sequence that corresponds to the amino acid sequences set forth in SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 92, 94, 96, 98, 100, 102, 104, 106, 108, 110, 112, 114, 116, 118, 120, 122, 124, or 126.

In some embodiments, the improved carboxyesterase polypeptide consists of an amino acid sequence as set forth in SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 92, 94, 96, 98, 100, 102, 104, 106, 108, 110, 112, 114, 116, 118, 120, 122, 124, or 126.

In some embodiments, the present disclosure provides a carboxyesterase polypeptide comprising the amino acid sequence set forth in SEQ ID NO: 122. In another embodiment, the present disclosure provides a polynucleotide sequence that encodes the carboxyesterase polypeptide sequence set forth in SEQ ID NO: 122. In yet another embodiment, the present disclosure provides a polynucleotide that encodes a carboxyesterase polypeptide, wherein the polynucleotide comprises the polynucleotide sequence set forth in SEQ ID NO: 121. In yet another embodiment, the polynucleotide encoding a carboxyesterase polypeptide consists of the polynucleotide sequence set forth in SEQ ID NO: 121.

In another aspect, the improved carboxyesterase polypeptides can be used in a process for preparing an amide, wherein components are combined containing: (a) an ester of the form $R_1$—$COOR_2$, wherein $R_1$ is chosen from: an $sp^3$ carbon with 0 to 3 alkyl substituents; and an aromatic ring, and $R_2$ is chosen from: a methyl group; an ethyl group; and 1-6 carbon alkyl chains; (b) an amine substrate; (c) an improved carboxyesterase polypeptide comprising an amino acid sequence that is at least 80%, 85%, 86%, 87%, 88%, 89%, 90%, 91%, 92%, 93%, 94%, 95%, 96%, 97%, 98%, 99%, or more, identical to the amino acid sequence set forth in SEQ ID NO: 4, or a functional fragment thereof, wherein the carboxyesterase polypeptide amino acid sequence includes the feature that: the residue corresponding to X198 in SEQ ID NO: 4 is chosen from: a non-polar residue, an aromatic residue, and an aliphatic residue; and (d)olvent.

DETAILED DESCRIPTION OF THE INVENTION

The present disclosure provides highly efficient biocatalysts capable of mediating transformations involving amidation of certain amide group acceptors, e.g., the synthesis of the compound of formula III. The biocatalysts are engineered amidated polypeptides that can convert the substrate of formula I, ethyl oxazole-5-carboxylate (the "ester substrate"), to the product of formula III, (4-isopropylpiperazin-1-yl)(oxazol-5-yl)methanone, (a "product") in the presence of an amine substrate of formula II (1-isopropylpiperazine), as follows:

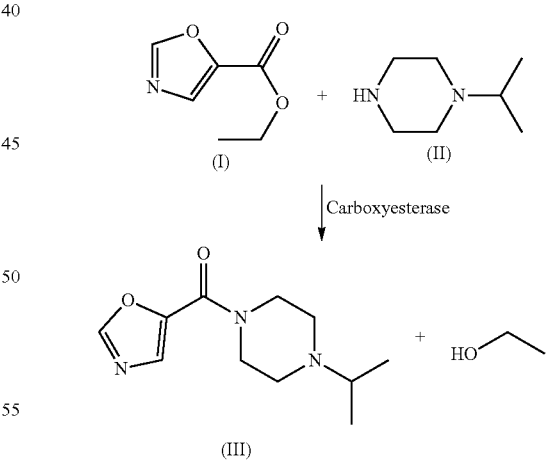

In certain embodiments, the engineered carboxyesterases are derived from the naturally occurring carboxyesterase from *A. acidocaldarius* Esterase 2, which is a carboxyesterase enzyme that catalyzes the hydrolysis of an ester through the formation and resolution of an acyl-enzyme intermediate amine. The carboxyesterase of SEQ ID NO: 4 differs from the naturally occurring enzyme derived from wild-type carboxyesterase, *A. acidocaldarius* Esterase 2 (SEQ ID NO: 2) in having a substitution of glutamate (E) at residue position X198 with leucine (L) and has measurable activity for the ester substrate, ethyl oxazole-5-carboxylate (formula I). The carboxyesterase of SEQ ID NO: 4 has been engineered to mediate the efficient conversion of the ester substrate of formula I. to the product of formula III. in the presence of an amine substrate, such as 1-isopropylpiperazine (formula II). The conversion can be carried out under mild conditions (30° C. with high % conversion), making the process applicable to high volume production of the amides of formula III. and formula V.

Abbreviations and Definitions

For the purposes of the descriptions herein, the abbreviations used for the genetically encoded amino acids are conventional and are as follows in Table 1:

TABLE 1

| AMINO ACID | THREE-LETTER | ONE-LETTER |
|---|---|---|
| ALANINE | ALA | A |
| ARGININE | ARG | R |
| ASPARAGINE | ASN | N |
| ASPARTATE | ASP | D |
| CYSTEINE | CYS | C |
| GLUTAMATE | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

When the three-letter abbreviations are used, unless specifically preceded by an "L" or a "D" or clear from the context in which the abbreviation is used, the amino acid may be in either the L- or D-configuration about α-carbon (Cα). For example, whereas "Ala" designates alanine without specifying the configuration about the α carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When peptide sequences are presented as a string of one-letter or three-letter abbreviations (or mixtures thereof), the sequences are presented in the N→C direction in accordance with convention.

The technical and scientific terms used in the descriptions herein will have the meanings commonly understood by one of ordinary skill in the art, unless specifically defined otherwise. Accordingly, the following terms are intended to have the following meanings.

All U.S patents and published U.S. patent applications, including all sequences disclosed within such patents and patent applications, referred to herein are expressly incorporated by reference.

"Acid side-product" or "hydrolysis side-product" refers to the carboxylic acid resulting from the reaction of an ester substrate with water as the result of a carboxyesterase enzyme. Acid side-products are molecules of the general formula (3) in which $R_3$ is —H. $R_1$ is described above.

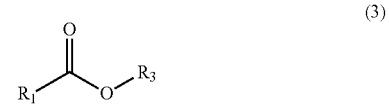

(3)

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically, encoded acidic amino acids include L-Glu (E) and L-Asp (D).

"Alkyl" is intended to include alkyl groups of the designated length in either a straight or branched configuration. Exemplary alkyl groups are methyl, ethyl, propyl, isopropyl, butyl, sec-butyl, tert-butyl, pentyl, isopentyl, hexyl, isohexyl, and the like. The alkyl groups are unsubstituted or substituted with one to three groups independently chosen from: halogen, hydroxy, carboxy, aminocarbonyl, amino, $C_{1-4}$alkoxy, and $C_{1-4}$ alkylthio.

"Amide" is intended to mean a functional group containing a carbonyl group linked to a nitrogen atom. An amide also refers to any compound containing the amide functional group. Amides are derived from a carboxylic acid and an amine.

"Amidate or "Amidation" is intended to mean the formation of an amide functional group from a carbonyl-containing compound, typically resulting from the reaction of a carboxylic acid and amine functionality, but also formed here from an ester and amine functionality.

"Amine" is intended to mean a functional group containing a sp3-hybridized nitrogen atom. An amine also refers to any compound containing the amine functional group.

"Amine substrate" refers to an amino compound that is capable of displacing the alcohol side-chain of an ester substrate under the action of a carboxyesterase, thereby generating an amide product. Amine substrates are molecules of the general formula (5), in which each of $R_3$ and $R_4$, when taken independently, is an alkyl, or an aryl group which is unsubstituted or substituted with at least one enzymatically non-inhibiting groups. The groups $R_3$ and $R_4$, when taken together, may form a ring that is unsubstituted, substituted, or fused to other rings. Typical amine substrates that can be used with the invention include, but are not limited to, cyclic piperazinyl or morpholino moieties, as well as primary or aromatic amines. In the context of the present disclosure, an amine substrate includes, among others, the compounds of formula II, 1-isopropylpiperazine, and of formula IV, cis-2,6-dimethylmorpholine.

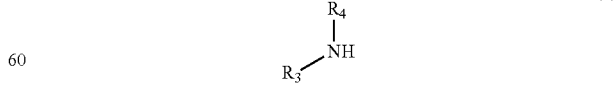

(5)

"Amino acid" or "residue" as used in context of the polypeptides disclosed herein refers to the specific monomer at a sequence position (e.g., P5 indicates that the "amino acid" or "residue" at position 5 of SEQ ID NO: 2 is a proline.)

"Amino acid difference" or "residue difference" refers to a change in the residue at a specified position of a polypeptide sequence when compared to a reference sequence. The polypeptide sequence position at which a particular amino acid or amino acid change ("residue difference") is present is sometimes described herein as "Xn", or "position n", where n refers to the residue position with respect to the reference sequence.

For example, a residue difference at position X8, where the reference sequence has a serine, refers to a change of the residue at position X8 to any residue other than serine. As disclosed herein, an enzyme can include one or more residue differences relative to a reference sequence, where multiple residue differences typically are indicated by a list of the specified positions where changes are made relative to the reference sequence (e.g., "one or more residue differences as compared to SEQ ID NO: 4 at the following residue positions: X27, X30, X35, X37, X57, X75, X103, X185, X207, X208, X271, X286, or X296.").

A specific substitution mutation, which is a replacement of the specific residue in a reference sequence with a different specified residue may be denoted by the conventional notation "X(number)Y", where X is the single letter identifier of the residue in the reference sequence, "number" is the residue position in the reference sequence, and Y is the single letter identifier of the residue substitution in the engineered sequence.

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Aryl" is intended to mean an aromatic group, including phenyl and naphthyl. "Aryl" is unsubstituted or substituted with one to five substituents independently selected from fluoro, hydroxy, trifluoromethyl, amino, $C_{1-4}$ alkyl, and $C_{1-4}$ alkoxy.

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Carboxyesterase" is used to refer to a polypeptide having an enzymatic capability of interconverting the sidechain of an ester substrate (1) with that of a donor compound (2), converting the ester substrate (1) into its corresponding ester product (3) and the free alcohol form of the ester side-chain (4).

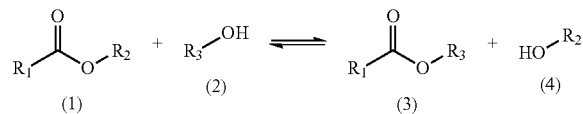

"Codon-optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the carboxyesterase enzymes may be codon-optimized for optimal production from the host organism selected for expression.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. Table 2 below shows exemplary conservative substitutions.

TABLE 2

| Residue | Possible Conservative Mutations |
|---|---|
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| P | none |
| N, Q, S, T | Other polar |
| H, Y, W, F | Other aromatic (H, Y, W, F) |
| C | None |

"Constrained amino acid or residue" refers to an amino acid or residue that has a constrained geometry. Herein, constrained residues include L-Pro (P) and L-His (H). Histidine has a constrained geometry because it has a relatively small imidazole ring. Proline has a constrained geometry, because it also has a five-membered ring.

"Control sequence" is defined herein to include all components, which are necessary or advantageous for the expression of a polynucleotide and/or polypeptide of the present disclosure. Each control sequence may be native or foreign to the polynucleotide of interest. Such control sequences include, but are not limited to, a leader, polyadenylation sequence, propeptide sequence, promoter, signal peptide sequence, and transcription terminator.

"Conversion" refers to the enzymatic transformation of a substrate to the corresponding product.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence of the non-reference sequence. For example, a given amino acid sequence, such as that of an engineered carboxyesterase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Cysteine" or L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Deletion" refers to modification of the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, up to 20% of the total number of amino acids, or up to 30% of the total number of amino acids making up the polypeptide while retaining enzymatic activity and/or retaining the improved properties of an engineered carboxyesterase enzyme. Deletions can be directed to the internal portions and/or terminal portions of the polypeptide. In various embodiments, the deletion can comprise a continuous segment or can be discontinuous.

"Derived from" as used herein in the context of engineered enzymes identifies the originating enzyme, and/or the gene encoding such enzyme, upon which the engineering was based. For example, the engineered carboxyesterase enzyme of SEQ ID NO: 4 was obtained by mutating the carboxyesterase of SEQ ID NO: 2. Thus, this engineered carboxyesterase enzyme of SEQ ID NO: 4 is "derived from" the polypeptide of SEQ ID NO: 2

An "engineered carboxyesterase", as used herein, refers to a carboxyesterase-type protein which has been systematically modified, through the insertion of new amino acids into its reference sequence, the deletion of amino acids present in its reference sequence, or the mutation of amino acids in its reference sequence into alternate amino acids, either through a process of random mutagenesis followed by selection of mutants having a particular property or through the intentional introduction of particular amino acid changes into the protein sequence.

"Ester" is intended to mean a functional group containing a carbonyl group linked to an oxygen atom which is in turn linked to a carbon atom. An ester also refers to any compound containing the ester functional group. Esters are derived from a carboxylic acid and an alcohol.

An "ester substrate" specifically refers to compounds of formula (1) containing an ester, which reacts with an engineered carboxyesterase. In the contact of the present disclosure, an ester substrate includes, among others, the compound of formula I, ethyl oxazole-5-carboxylate.

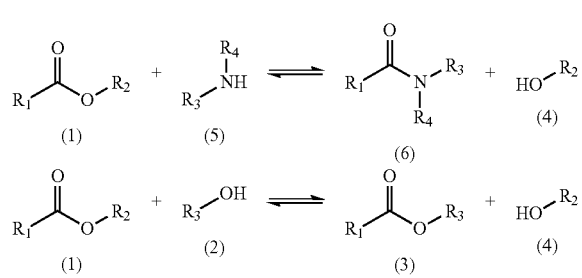

"Fragment", as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99%, or more, of the full-length carboxyesterase polypeptide, for example, the polypeptide of SEQ ID NO: 4.

A "functional fragment" or a "biologically active fragment", used interchangeably, herein refers to a polypeptide that has an amino-terminal and/or carboxy-terminal deletion(s) and/or internal deletions, but where the remaining amino acid sequence is identical to the corresponding positions in the sequence to which it is being compared (e.g., a full-length engineered T. fusca enzyme of the present invention). and that retains substantially all of the activity of the full-length polypeptide.

"Halogen" is intended to include the halogen atoms, fluorine, chlorine, bromine, and iodine. "Heterologous" polynucleotide refers to any polynucleotide that is introduced into a host cell by laboratory techniques, and includes polynucleotides that are removed from a host cell, subjected to laboratory manipulation, and then reintroduced into a host cell.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably, about 75% identity, about 85% identity to the target DNA, or with greater than about 90% identity to target-polynucleotide. Exemplary moderately stringent conditions are conditions equivalent to hybridization in 50% formamide, 5×Denhart's solution, 5× saline-sodium phosphate-EDTA (SSPE), 0.2% sodium dodecyl sulfate (SDS) at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5×Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Hydrophilic amino acid or residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R). "Hydrophobic amino acid or residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically, encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

"Improved enzyme property" refers to any enzyme property made better or more desirable for a particular purpose as compared to that property found in a reference enzyme. For the engineered carboxyesterase polypeptides described herein, the comparison is generally made to the wild-type carboxyesterase enzyme, although in some embodiments, the reference carboxyesterase can be another improved engineered carboxyesterase. Enzyme properties for which improvement can be made include, but are not limited to, enzymatic activity (which can be expressed in terms of percent conversion of the substrate in a period of time), thermal stability, solvent stability, pH activity profile, coenzyme requirements, refractoriness to inhibitors (e.g., product inhibition), stereospecificity, and suppression of acid side-product production.

"Increased enzymatic activity" or "increased activity" refers to an improved property of an engineered enzyme, which can be represented by an increase in specific activity (e.g., product produced/time/weight protein) or an increase in percent conversion of the substrate to the product (e.g., percent conversion of starting amount of substrate to product in a specified time period using a specified amount of carboxyesterase), as compared to a reference enzyme.

Exemplary methods to determine enzyme activity are provided in the Examples. Any property relating to enzyme activity may be affected, including the classical enzyme properties of $K_m$, $V_{max}$ or $k_{cat}$, changes in which can lead to increased enzymatic activity.

Improvements in enzyme activity can be from about 1.5 times the enzymatic activity of the corresponding wild-type or engineered enzyme, to as much as 2 times, 5 times, 10 times, 20 times, 25 times, 50 times, 75 times, 100 times, 1000 times, 10,000 times, 100,000 times, 500,000 times, 785,000 times or more enzymatic activity than the naturally occurring enzyme (e.g., a carboxyesterase) or another engineered enzyme from which the enzymes exhibiting increased activity were derived. In specific embodiments, the engineered carboxyesterase enzymes of the present disclosure exhibit improved enzymatic activity in the range of 1.5 to 50 times, 1.5 to 100 times or greater than that of the parent carboxyesterase enzyme (i.e., the wild-type or engineered carboxyesterase from which they were derived). It is understood by the skilled artisan that the activity of any enzyme is diffusion limited such that the catalytic turnover rate cannot exceed the diffusion rate of the substrate, including any required coenzymes. The theoretical maximum of the diffusion limit is generally about 10 to 109 ($M^{-1}$ $s^{-1}$). Hence, any improvements in the enzyme activity of the carboxyesterase will have an upper limit related to the diffusion rate of the substrates acted on by the carboxyesterase enzyme. Carboxyesterase activity can be measured by any one of standard assays used for measuring carboxyesterases, such as change in substrate or product concentration, or change in concentration of the amine substrate. Comparisons of enzyme activities are made using a defined preparation of enzyme, a defined assay under a set condition, and one or more defined substrates, as further described in detail herein. Generally, when enzymes in cell lysates are compared, the numbers of cells and the amount of protein assayed are determined as well as use of identical expression systems and identical host cells to minimize variations in amount of enzyme produced by the host cells and present in the lysates.

"Insertion" refers to modification of the polypeptide by addition of one or more amino acids to the reference polypeptide. In some embodiments, the improved engineered carboxyesterase enzymes comprise insertions of one or more amino acids to the naturally occurring carboxyesterase polypeptide as well as insertions of one or more amino acids to other improved carboxyesterase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved carboxyesterase enzymes may be present within a cell, present in the cellular medium, or prepared in various forms, such as lysates or isolated preparations. As such, in some embodiments, the improved carboxyesterase enzyme can be an isolated polypeptide.

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects: (a) the structure of the peptide backbone in the area of the substitution (e.g., proline for glycine); (b) the charge or hydrophobicity; or (c) the bulk of the side chain.

"Non-polar amino acid" or "Non-polar residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Percent conversion" refers to the percent of the substrate that is converted to the product within a period of time under specified conditions. Thus, for example, the "enzymatic activity" or "activity" of a carboxyesterase polypeptide can be expressed as "percent conversion" of the substrate to the product.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see, e.g., Altschul, et al., 1990, *J. Mol. Biol.* 215: 403-410 and Altschul, et al., 1977, *Nucleic Acids Res.* 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul, et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Nat Acad Sci USA* 89:10915).

Numerous other algorithms are available that function similarly to BLAST in providing percent identity for two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Nat. Acad. Sci. USA* 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel, et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"pH stable" refers to a polypeptide that maintains similar activity (more than e.g., 60% to 80%) after exposure to low or high pH (e.g., 4.5-6 or 8-12) for a period of time (e.g., 0.5-24 hrs) compared to the untreated enzyme.

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Preferred, optimal, high codon usage bias codons" refers, interchangeably, to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, *Bioinformatics* 14:372-73; Stenico, et al., 1994, *Nucleic Acids Res.* 222437-46; Wright, F., 1990, *Gene* 87:23-29). Codon usage tables are available for a growing list of organisms (see for, example, Wada, et al., 1992, *Nucleic Acids Res.* 20:2111-2118; Nakamura, et al., 2000, *Nucl. Acids Res.* 28:292; Duret, et al., supra; Henaut and Danchin, "*Escherichia coli* and *Salmonella*," 1996, Neidhardt, et al., Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (EST), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, *Methods Enzymol.* 266:259-281; Tiwari, et al., 1997, *Comput. Appl. Biosci.* 13:263-270).

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Reference sequence" refers to a defined sequence to which another (e.g., altered) sequence is compared. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Because two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a comparison window to identify and compare local regions of sequence similarity.

The term, "reference sequence", is not intended to be limited to wild-type sequences, and can include engineered or altered sequences. For example, in some embodiments, a "reference sequence" can be a previously engineered or altered amino acid sequence. For instance, a "reference sequence based on SEQ ID NO: 2 having a glycine residue at position X12" refers to a reference sequence corresponding to SEQ ID NO: 2 with a glycine residue at X12 (the un-altered version of SEQ ID NO: 2 has an aspartate at X12).

"Small amino acid" or "small residue" refers to an amino acid or residue having a side chain that is composed of a total of three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Solvent stable" or "solvent stability" refers to a polypeptide that maintains similar activity (more than, e.g., 60% to 80%) after exposure to varying concentrations (e.g., 5-99%) of a solvent, (e.g., isopropyl alcohol, dimethylsulfoxide, tetrahydrofuran, 2-methyltetrahydrofuran, acetone, toluene, butylacetate, methyl tert-butylether, acetonitrile, etc.) for a period of time (e.g., 0.5-24 hrs) compared to the untreated enzyme.

"Substantial identity" refers to a polynucleotide or polypeptide sequence that has at least 80, 81, 82, 83, 84, 85, 86, 87, 88, 89, 90, 91, 91, 93, 94, 95, 96, 97, 98, 99, or more percent sequence identity, as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure carboxyesterase composition will comprise about 60% or more, about 70% or more, about 80% or more, about 90% or more, about 95% or more, about 96% or more, about 97% or more, about 98% or more or about 99% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species and elemental ion species are not considered to be macromolecular species. In some embodiments, the isolated improved carboxyesterase polypeptide is a substantially pure polypeptide composition.

"Substrate", as used herein refers to a carboxyesterase-reactive compound, consisting of a compound containing an ester (1), an amine (5), or an alcohol (2). In the context of the present disclosure, a substrate for the carboxyesterase includes, among others, the compound of formula I and the compound of formula II, as further described herein.

"Thermostable" or "thermal stability" are used interchangeably to refer to a polypeptide that is resistant to inactivation when exposed to a set of temperature conditions (e.g., 40-80° C.) for a period of time (e.g., 0.5-24 hrs) compared to the untreated enzyme, thus retaining a certain level of residual activity (more than 60% to 80% for example) after exposure to elevated temperatures.

As used herein, "solvent stable" refers to the ability of a polypeptide to maintain similar activity (e.g., more than e.g., 60% to 80%) after exposure to varying concentrations (e.g., 5-99%) of solvent (e.g., isopropyl alcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

DETAILED DESCRIPTION OF THE EMBODIMENTS OF THE INVENTION

In the embodiments herein, the engineered carboxyesterases are improved in their capability of converting ester substrate, ethyl oxazole-5-carboxylate to the product, (4-isopropylpiperazin-1-yl)(oxazol-5-yl)methanone, in the presence of an amine substrate, 1-isopropylpiperazine, as compared to the wild-type carboxyesterase enzyme *A. acidocaldarius* Esterase 2 (SEQ ID NO: 2). Carboxyesterases, including those described herein, are free-standing enzymes which lack chemical cofactors, and which are water-soluble enzymes which may be formulated as dissolved enzyme, as enzyme immobilized to a resin, or as lyophilized powder in the presence of one or more salts.

In some embodiments, the improvement in enzyme activity is with respect to another engineered carboxyesterase, such as the polypeptide of SEQ ID NO: 4. The improved activity on the ester substrate can be manifested by an increase in the amount of substrate converted to product (e.g., percent conversion) by the engineered enzyme relative to a reference enzyme (e.g., the wild-type, SEQ ID NO: 2) under defined conditions. The improved activity can include an increased rate of product formation resulting in an increase in conversion of ester substrate to the product in the presence of an amine substrate in a defined time under a defined condition. The increase in activity (e.g., increased percent conversion and/or conversion rate) may also be characterized by conversion of substrate to the same amount of product with a lower amount of enzyme. The amount of product can be assessed by a variety of techniques, for example, separation of the reaction mixture (e.g., by chromatography) and detection of the separated product by UV absorbance or tandem mass spectroscopy (MS/MS) (see, e.g., Example 4). An exemplary defined reaction condition for comparison to the activity of SEQ ID NO: 2 is about 40 g/L ethyl oxazole-5-carboxylate (the ester substrate), 44 g/L 1-isopropylpiperazine (the amine substrate), and 20 g/L of a carboxyesterase polypeptide corresponding to an amino acid sequence chosen from: SEQ ID NOs: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 92, or 94, 96, 98, 100, 102, 104, 106, 108, 110, 112, 114, 116, 118, 120, 122, 124, or 126, wherein the enzyme is prepared in the presence of sodium sulfate and run in the presence of about 10 g/L to about 20 g/L water in methyl isobutyl ketone (MIBK), as given below in the description of reaction conditions for the carboxyesterases listed in Table 3. Defined reaction conditions for comparison to certain engineered carboxyesterases are also provided in the description for the carboxyesterases listed on Table 3, and in the corresponding descriptions in Example 7. In some embodiments, the engineered carboxyestereases have at least 1.5 times, 2 times, 3 times, 4 times, 5 times, 6 times, 7 times, 8 times, 9 times, 10 times, 15 times, 20 times, 30 times, 40 times, 50 times, 75 times, 100 times, 150 times, 200 times, 300 times, 400 times, 500 times, 1000 times, 1,500 times, 2,000 times, 10,000 times, 100,000 times, 500,000 times, 785,000 times, or greater than the activity of the polypeptide of SEQ ID NO: 2 under the defined reaction conditions.

In some embodiments, the improved enzymatic activity is also associated with other improvements in enzyme property. In some embodiments, the improvement in enzyme property is with respect to thermal stability, such as at 60° C. or higher.

In some embodiments, the improved enzymatic activity is associated with improvements in solvent stability, such as when run in 98% (volume/volume) in Methyl IsoButyl Ketone (MIBK) or tert-Butyl Methyl Ether (TBME).

In some embodiments, the engineered carboxyesterase polypeptides of the present disclosure are capable of converting the ester substrate, ethyl oxazole-5-carboxylate, to the product, (4-isopropylpiperazin-1-yl)(oxazol-5-yl)methanone with an activity that is greater than the activity of the polypeptide of SEQ ID NO: 2 in the presence of an amine substrate, for instance, 1-isopropylpiperazine, and comprises an amino acid sequence that is at least 80%, 85%, 86%, 87%, 88%, 89%, 90%, 91%, 92%, 93%, 94%, 95%, 96%, 97%, 98%, 99%, or more, identical to the reference sequence of SEQ ID NO: 2, or a functional fragment thereof.

In some embodiments, the engineered carboxyesterase polypeptides of the present disclosure are capable of converting the ester substrate, ethyl oxazole-5-carboxylate to the product, (4-isopropylpiperazin-1-yl)(oxazol-5-yl)methanone in the presence of an amine substrate, such as 1-isopropylpiperazine, with an activity that is greater than the polypeptide of SEQ ID NO: 2, and comprises an amino acid sequence that is at least 80%, 85%, 86%, 87%, 88%, 89%, 90%, 91%, 92%, 93%, 94%, 95%, 96%, 97%, 98%, 99% or more identical to a reference sequence listed in Table 3, for example, SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 92, 94, 96, 98, 100, 102, 104, 106, 108, 110, 112, 114, 116, 118, 120, 122, 124, or 126, or a functional fragment thereof, as further described below.

In some embodiments, the engineered carboxyesterase polypeptides comprise an amino acid sequence that has one or more residue differences as compared to a carboxyesterase reference sequence. The residue differences can be non-conservative substitutions, conservative substitutions, or a combination of non-conservative and conservative substitutions. With respect to the residue differences and the descriptions of residue positions, the carboxyesterases provided herein can be described in reference to the amino acid sequence of the naturally occurring carboxyesterases of $A.$ $acidocaldarius$ Esterase 2 (SEQ ID NO: 2), the carboxyesterase of SEQ ID NO: 2, or an engineered carboxyesterase, such as the polypeptide of SEQ ID NO: 4. For the descriptions herein, the amino acid residue position in the reference sequence is determined in the carboxyesterase beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue.

In some embodiments, the residue differences can occur at one or more of the following residue positions: X2, X7, X9, X10, X19, X20, X22, X27, X28, X29, X30, X33, X34, X35, X36, X37, X38, X46, X48, X54, X57, X66, X75, X85, X86, X87, X96, X103, X139, X160, X176, X181, X183, X185, X188, X190, X197, X198, X205, X207, X208, X212, X216, X248, X249, X255, X263, X266, X270, X271, X278, X280, X286, X290 and X296. In some embodiments, the residue differences or combinations thereof, are associated with improved enzyme properties. In some embodiments, the carboxyesterase polypeptides can have, additionally, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-22, 1-24, 1-26, 1-28, 1-30, 1-35, 1-40, 1-45, 1-50, 1-55, 1-60, or 1-62 residue differences at residue positions other than those specific positions denoted by "Xn" listed above. In some embodiments, the number of differences can be 1, 2, 3, 4, 5, 6, 7, 8, 9, 10, 11, 12, 13, 14, 15, 16, 17, 18, 19, 20, 22, 24, 26, 28, 30, 35, 40, 45, 50, 55, 60, or 62 residue differences at the other amino acid residue positions. In some embodiments, the residue differences at other residue positions comprise substitutions with conservative amino acid residues.

In the embodiments herein, the residue differences as compared to SEQ ID NO: 2 at residue positions affecting substrate binding on the carboxyesterase allows accommodation of the ester substrate of structural formula (I), further described below, in particular, the ester substrate, ethyl oxazole-5-carboxylate. Without being bound by theory, at least two regions, a first substrate binding region and a second substrate binding region, interact with different structural elements of the ester substrate. The first binding region comprises residue X85, X185, X214, X215 and X254, the second binding region comprises residue positions X30, X33, X34, X37, X82, X205, X210, X283, X286 and X287 while positions X83, X84, X155. X156, X206, X214 and X282 overlap the two sites. These residues were determined by X-ray crystallography. Accordingly, the carboxyesterase polypeptides herein have one or more residue differences at residue positions comprising X30, X33, X34, X37, X85, X185, X205, and X286. In some embodiments, the carboxyesterase polypeptides herein have at least two or more, or three or more residue differences at the specified residue positions associated with substrate binding.

In other embodiments, the improved carboxyesterase polypeptide comprises an amino acid sequence that is at least 80% identical to the amino acid sequence set forth in SEQ ID NO: 4, wherein the improved carboxyesterase amino acid sequence includes the feature that: the residue corresponding to X198 is chosen from: a non-polar residue, an aromatic residue, and an aliphatic residue. In yet other embodiments, the improved carboxyesterase polypeptides include the following feature: X198 is chosen from: F, L, I, Y, and M. In some embodiments, the improved carboxyesterase polypeptide can comprise an amino acid sequence comprising one or more residue differences as compared to the sequence of SEQ ID NO:4 at the following residue positions corresponding to: X27, X30, X35, X37, X57, X66, X75, X103, X207, X208, X271 X286, and X296. Guidance for the choice of various amino acid residues that can be present at the specified residue positions are provided in the detailed description that follows.

In other embodiments, the improved carboxyesterase polypeptide comprises an amino acid sequence that is at least 80% identical to the amino acid sequence set forth in SEQ ID NO: 4, wherein the amino acid sequence includes at least one feature chosen from: the residue corresponding to X27 is a constrained residue; the residue corresponding to X30 is an aliphatic residue; the residue corresponding to X35 is chosen from a basic residue and a polar residue; the residue corresponding to X37 is chosen from an aliphatic residue and a polar residue; the residue corresponding to X57 is a non-polar residue; the residue corresponding to X75 is chosen from a basic residue and a polar residue; the residue corresponding to X103 is chosen from anon-polar and an aromatic residue; the residue corresponding to X185 is chosen from an aliphatic residue, a non-polar residue, and an aromatic residue; the residue corresponding to X207 is chosen from an acidic residue and a polar residue; the residue corresponding to X208 is chosen from an aliphatic residue, a basic residue, and a polar residue; the residue corresponding to X271 is chosen from an acidic residue and a polar residue; the residue corresponding to X286 is chosen from an aliphatic residue, a polar residue and a small residue; and the residue corresponding to X296 is chosen from an aliphatic residue and a basic residue.

In yet other embodiments, the improved carboxyesterase polypeptide comprises an amino acid sequence that is at least 80% identical to the amino acid sequence set forth in SEQ ID NO: 4, wherein the amino acid sequence includes at least one feature chosen from: X27 is P; X30 is chosen from I, L, and V; X35 is H; X37 is chosen from I, L, T, and V; X57 is M; X75 is R; X103 is chosen from F, M, and W; X185 is chosen from F, I, and M; X207 is E; X208 is chosen from R, L and H; X271 is D; X286 is chosen from M, V, and G; and X296 is chosen from V, L, and R. In some embodiments, the improved carboxyesterase polypeptides comprise an amino acid sequence including the following features: X35 is chosen from a basic residue and a polar residue; and X185 is chosen from a polar residue and an aliphatic residue. In alternative embodiments, the improved carboxyesterase polypeptide comprises an amino acid sequence that includes the following features: X35 is H; and X185 is chosen from F, I, and M.

In some embodiments, the improved carboxyesterase polypeptide comprises a residue difference as compared to the amino acid sequence set forth in SEQ ID NO: 24, at least one residue position chosen from: X9, X19, X34, X35, X37, X46, X48, X66, X87, X103, X139, X190, X207, X216, X263, X271, X278 and X296. In other embodiments, the improved carboxyesterase polypeptide comprises an amino acid sequence that includes at least one of the following features: the residue corresponding to X9 is an aromatic residue; the residue corresponding to X19 is chosen from a basic residue and a polar residue; the residue corresponding to X34 is chosen from a constrained residue, an acidic residue, and a polar residue; the residue corresponding to X35 is chosen from a polar residue; the residue corresponding to X46 is an aliphatic residue; the residue corresponding to X48 is an aliphatic residue; the residue corresponding to X66 is an aliphatic residue; the residue corresponding to X87 is chosen from an aliphatic residue and a small residue; the residue corresponding to X103 is chosen from an aromatic residue; the residue corresponding to X139 is a basic residue; the residue corresponding to X190 is an aromatic residue; the residue corresponding to X207 is a basic residue; the residue corresponding to X216 is chosen form an aromatic residue, a basic residue, and a polar residue; the residue corresponding to X263 is chosen from an aliphatic residue, and a polar residue; the residue corresponding to X271 is chosen from an acidic residue and a polar residue; the residue corresponding to X278 is chosen from an aliphatic residue and an aromatic residue, and the residue corresponding to X296 is chosen from an aliphatic residue and an basic residue.

In yet other embodiments, the improved carboxyesterase polypeptide comprises an amino acid sequence that is at least 80% identical to the amino acid sequence set forth in SEQ ID NO: 24, wherein the amino acid sequence includes at least one feature chosen from: X9 is Y; X19 is R; X34 is chosen from E, N or P; X35 is S, X37 is T; X46 is chosen from I, L or V; X48 is L; X66 is V; X87 is A; X103 is chosen from W or F; X139 is R; X190 is Y; X207 is E; X216 is chosen from N and W; X263 is chosen from T and A; X271 is D; X278 is chosen from W and L; and X296 is chosen from V, L, and R. In yet other embodiments, the improved carboxyesterase polypeptide comprises an amino acid sequence that includes the following features: X9 is aromatic residue and X87 is an aliphatic residue. In alternative embodiments, the improved carboxyesterase polypeptide comprises an amino acid sequence that includes the following features: X9 is Y; and X87 is A.

In other embodiments, the improved carboxyesterase polypeptide comprises an amino acid sequence that comprises a residue difference as compared to the amino acid sequence set forth in SEQ ID NO: 54, at least one residue position chosen from: X20, X28, X29, X30, X33, X34, X188, X216 and X286. In alternative embodiments, the improved carboxyesterase polypeptide comprises an amino acid sequence that includes at least one feature chosen from: X20 is chosen from an aliphatic residue and basic residue; the residue corresponding to X28 is chosen from an acidic residue, a polar residue, and a constrained residue; the residue corresponding to X29 is chosen from an acidic residue and a polar residue; the residue corresponding to X30 is an aliphatic residue; the residue corresponding to X33 is an aromatic residue; the residue corresponding to X34 is a small residue; the residue corresponding to X188 is chosen from a small residue and an aromatic residue; the residue corresponding to X216 is a polar residue, and the residue corresponding to X286 is chosen from an aliphatic residue, small residue, non-polar residue and a polar residue.

In some embodiments, the improved carboxyesterase polypeptide comprises the amino acid sequence set forth in SEQ ID NO: 54, wherein the amino acid sequence includes at least one specific mutations chosen from: X20 is chosen from I and R; X28 is chosen from D, P, and S; X29 is D; X30 is V; X33 is W; X34 is G; X188 is chosen from G and F; X216 is N and X286 is chosen from S, M, V, G and A. In alternative embodiments, the improved carboxyesterase polypeptide comprises an amino acid sequence that includes the following feature: X216 is a polar residue. In still other embodiments, the improved carboxyesterase polypeptide comprises an amino acid sequence that includes the following feature: X216 is N.

In other embodiments, the improved carboxyesterase polypeptide comprises an amino acid sequence that comprises a residue difference as compared to the amino acid sequence set forth in SEQ ID NO: 68 at one residue position chosen from: X10, X20, X22, X28, X30, X33, X36, X37, X46, X66, X75, X103, X197, X263, X266, X280, and X290. In another embodiment, the improved carboxyesterase polypeptide comprises an amino acid sequence that includes at least one feature chosen from: the residue corresponding to X10 is an aliphatic residue; the residue corresponding to X20 is chosen from an aliphatic residue and basic residue; the residue corresponding to X22 is an aromatic residue; the residue corresponding to X28 is chosen from an acidic residue, a polar residue, and a constrained residue; the residue corresponding to X30 is an aliphatic residue; the residue corresponding to X33 is an aromatic residue; the residue corresponding to X36 is an aliphatic or aromatic residue; the residue corresponding to X37 is an aromatic or small residue; the residue corresponding to X46 is a basic residue; the residue corresponding to X66 is a polar residue; the residue corresponding to X75 is a basic residue; the residue corresponding to X103 is an aromatic residue; the residue corresponding to X197 is an aliphatic residue; the residue corresponding to X263 is a basic residue; the residue corresponding to X266 is a polar residue; the residue corresponding to X280 is chosen from an aliphatic residue and a polar residue; and the residue corresponding to X290 is chosen from an aliphatic residue and an aromatic residue.

In yet other embodiments, the improved carboxyesterase polypeptide comprises an amino acid sequence that is at least 80% identical to the amino acid sequence set forth in SEQ ID NO: 68, wherein the amino acid sequence includes at least one feature chosen from: X10 is chosen from L and M; X20 is chosen from I and R; X22 is W; X28 is chosen from D, P, and S; X30 is V; X33 is W; X36 is chosen from F, I, and M; X37 is chosen from G and Y; X46 is R; X66 is T; X75 is R; X103 is W; X197 is L; X263 is R; X266 is T; X280 is chosen from M and T; and X290 is chosen from W and I. In an alternative embodiment, the improved carboxyesterase polypeptide comprises an amino acid sequence that includes at least one feature chosen from: X30 is an aliphatic residue, X33 is an aromatic residue, X75 is a basic residue, and X103 is an aromatic residue. In yet another embodiment, the improved carboxyesterase polypeptide comprises an amino acid sequence that includes the following features: X30 is V; X33 is W; X75 is R; and X103 is W.

In other embodiments, the improved carboxyesterase polypeptide comprises an amino acid sequence that comprises a residue difference as compared to the amino acid sequence set forth in SEQ ID NO: 68 at one residue position chosen from: X28, X38, X46, X54, X66, X75, X85, X86, X96, X160, X176, X183, X188, X205, X212, X248, X249, X255, X270, and X286. In another embodiment, the improved carboxyesterase polypeptide comprises an amino acid sequence that includes at least one feature chosen from: the residue corresponding to X28 is chosen from an acidic residue, a polar residue, a small residue and a constrained residue; the residue corresponding to X38 is chosen from an aliphatic residue and basic residue; the residue corresponding to X46 is chosen from an acidic residue and basic residue; the residue corresponding to X54 is chosen from an acidic residue and a polar residue; the residue corresponding to X66 is a polar residue; the residue corresponding to X75 is a basic residue; the residue corresponding to X85 is chosen from an aromatic or basic residue and small residue; the residue corresponding to X86 is a polar residue; the residue corresponding to X96 is chosen from a nonpolar residue and aliphatic residue; the residue corresponding to X160 is chosen from a polar residue and a constrained residue; the residue corresponding to X176 is chosen from an aliphatic residue, an aromatic or basic residue and a nonpolar residue; the residue corresponding to X183 is a nonpolar residue; the residue corresponding to X188 is chosen from an aromatic and a small residue; the residue corresponding to X205 is an aromatic residue; the residue corresponding to X212 is an acidic residue; the residue corresponding to X248 is an aliphatic residue; the residue corresponding to X249 is an aromatic residue; the residue corresponding to X255 is a polar residue; the residue corresponding to X270 is chosen from an aliphatic residue and a polar residue; and the residue corresponding to X286 is chosen from an aliphatic residue, a non-polar residue, a small residue and a polar residue.

In yet other embodiments, the improved carboxyesterase polypeptide comprises an amino acid sequence that is at least 80% identical to the amino acid sequence set forth in SEQ ID NO: 68, wherein the amino acid sequence includes at least one feature chosen from: X28 is chosen from C, D, S, H, P, G and R; X38 is chosen from E and L; X46 is chosen from K, R and Q; X54 is chosen from R, Q, and S: X66 is chosen from L, T and V; X75 is R; X85 is chosen from G and H; X86 is T; X96 is chosen from M and L; X160 is chosen from T and P; X176 is chosen from M, L and H; X183 is Q; X188 is chosen from G and F; X205 is F; X212 is D; X248 is V; X249 is W; X255 is N; X270 chosen from is N and L; and X286 is chosen from M, V, G, N and S. In an alternative embodiment, the improved carboxyesterase polypeptide comprises an amino acid sequence that includes at least one feature chosen from: X28 is a polar residue, X38 is a basic residue, and X85 is a small residue. In yet another embodiment, the improved carboxyesterase polypeptide comprises an amino acid sequence that includes the following features: X28 is C; X38 is E; and X85 is G.

In other embodiments, the improved carboxyesterase polypeptide comprises an amino acid sequence that comprises a residue difference as compared to the amino acid sequence set forth in SEQ ID NO: 100 at one residue position chosen from: X7, X22, X36, X38, X46, X54, X66, and X75. In another embodiment, the improved carboxyesterase polypeptide comprises an amino acid sequence that includes at least one feature chosen from: the residue corresponding to X7 is an aliphatic residue; the residue corresponding to X22 is chosen from an aliphatic residue and aromatic residue; the residue corresponding to X36 is chosen from a polar residue and a non-polar residue; the residue corresponding to X38 is an aromatic residue; the residue corresponding to X46 is chosen from a polar residue and a basic residue; the residue corresponding to X54 is chosen from a polar residue and a basic residue; the residue corresponding to X66 is a polar residue; and the residue corresponding to X75 is chosen from a basic residue and a non-polar residue.

In yet other embodiments, the improved carboxyesterase polypeptide comprises an amino acid sequence that is at least 80% identical to the amino acid sequence set forth in SEQ ID NO: 100, wherein the amino acid sequence includes at least one feature chosen from: X7 is L; X22 is chosen from W and L; X36 is chosen from T and M; X38 is W; X46 is chosen from K and Q; X54 is chosen from S, Q, and K; X66 is chosen from G and T; and X75 is chosen from M and R. In an alternative embodiment, the improved carboxyesterase polypeptide comprises an amino acid sequence that includes at least one feature chosen from: X36 is a polar residue, X38 is an aromatic residue, and X75 is a basic residue. In yet another embodiment, the improved carboxyesterase polypeptide comprises an amino acid sequence that includes the following features: X36 is T; X38 is W; and X75 is R.

In other embodiments, the improved carboxyesterase polypeptide comprises an amino acid sequence that comprises a residue difference as compared to the amino acid sequence set forth in SEQ ID NO: 114 at one residue position chosen from: X2, X181, and X286. In another embodiment, the improved carboxyesterase polypeptide comprises an amino acid sequence that includes at least one feature chosen from: the residue corresponding to X2 is chosen from an aliphatic residue, a basic residue, a polar residue and an aromatic residue; the residue corresponding to X181 is a basic residue; and the residue corresponding to X286 is chosen from a polar residue and a non-polar residue.

In yet other embodiments, the improved carboxyesterase polypeptide comprises an amino acid sequence that is at least 80% identical to the amino acid sequence set forth in SEQ ID NO: 114, wherein the amino acid sequence includes at least one feature chosen from: X2 is chosen from L, Q, R, and H; X181 is Q; and X286 is chosen from C and S. In an alternative embodiment, the improved carboxyesterase polypeptide comprises an amino acid sequence that includes at least one feature chosen from: X286 is a non-polar residue. In yet another embodiment, the improved carboxyesterase polypeptide comprises an amino acid sequence that includes the following feature: X286 is C.

In some embodiments, the improved carboxyesterase polypeptide comprises an amino acid sequence that corresponds to the amino acid sequences set forth in SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 92, 94, 96, 98, 100, 102, 104, 106, 108, 110, 112, 114, 116, 118, 120, 122, 124, or 126.

In a further aspect, the present disclosure provides polynucleotides encoding each of the above-described improved engineered carboxyesterase polypeptides. In some embodiments, the polynucleotides can be part of an expression vector having one or more control sequences for the expression of the carboxyesterase polypeptide. In an alternative embodiment, the polynucleotide corresponds to any one of the nucleotide sequences set forth in SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 91, 93, 95, 97, 99, 101, 103, 105, 107, 109, 111, 113, 115, 117, 119, 121, 123, or 125.

In another aspect, the present disclosure provides host cells comprising the polynucleotides encoding the engineered carboxyesterases or expression vectors capable of expressing the engineered carboxyesterases. In some embodiments, the host cell can be a bacterial host cell, such as *E. coli*. The host cells can be used for the expression and isolation of the engineered carboxyesterase enzymes described herein, or, alternatively, they can be used directly for the conversion of the ester substrate to product. In some embodiments, the engineered amides, in the form of whole cells, crude extracts, isolated polypeptides, or purified polypeptides, can be used individually, or as a combination of different engineered amides.

The skilled person will appreciate that, upon production of an enzyme, in particular, depending upon the cell line used and the particular amino acid sequence of the enzyme, post-translational modifications may occur. For example, such post-translational modifications may include the cleavage of certain leader sequences, the addition of various sugar moieties in various glycosylation and phosphorylation patterns, deamidation, oxidation, disulfide bond scrambling, isomerisation, C-terminal lysine clipping, and N-terminal glutamine cyclisation. The present invention encompasses the use of engineered carboxyesterase enzymes that have been subjected to, or may have undergone, one or more post-translational modifications. Thus, the engineered carboxyesterases of the invention may include one which has undergone a post-translational modification, such as described herein.

Deamidation is an enzymatic reaction primarily converting asparagine (N) to iso-aspartic acid (iso-aspartate) and aspartic acid (aspartate) (D) at approximately 3:1 ratio. This deamidation reaction is, therefore, related to isomerization of aspartate (D) to iso-aspartate. The deamidation of asparagine and the isomerisation of aspartate, both involve the intermediate succinimide. To a much lesser degree, deamidation can occur with glutamine residues in a similar manner.

Oxidation can occur during production and storage (i.e., in the presence of oxidizing conditions) and results in a covalent modification of a protein, induced either directly by reactive oxygen species, or indirectly by reaction with secondary by-products of oxidative stress. Oxidation happens primarily with methionine residues, but may occur at tryptophan and free cysteine residues.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

N-terminal glutamine (Q) and glutamate (glutamic acid) (E) in the engineered carboxyesterases are likely to form pyroglutamate (pGlu) via cyclization. Most pGlu formation happens in manufacturing, but it can be formed non-enzymatically, depending upon pH and temperature of processing and storage conditions.

C-terminal lysine clipping is an enzymatic reaction catalyzed by carboxypeptidases, and is commonly observed in enzymes. Variants of this process include removal of lysine from the enzymes from the recombinant host cell.

In the present invention, the post-translational modifications and changes in primary amino acid sequence described above are not known to result in significant changes in the activity of the engineered carboxyesterase enzymes.

Table 3 below provides exemplary engineered carboxyesterase polypeptides, with each row listing two SEQ ID NOs, the odd number referring to the nucleotide sequence encoding the amino acid sequence provided by the even number. The residue differences are based on comparison to reference sequence of SEQ ID NO: 2, a carboxyesterase corresponding to the wild-type *A. acidocaldarius* Esterase 2, referenced in Example 6. In the Activity column, the levels of increasing activity (i.e., "+" "++" "+++" etc.) were defined as follows: "−" indicates less than 1% conversion of substrate to product but not greater than 0.9% conversion (175 μL lysate, 100 mM ester, 100 mM isopropylpiperazine, 2% water in TBME); "+" indicates at least 1.1 to 80 times the activity of SEQ ID NO: 2, but not greater than the activity of SEQ ID NO: 4 (175 μL lysate, 100 mM ester, 100 mM isopropylpiperazine, 2% water in TBME); "++" indicates at least 1.1 to 11 times the activity of SEQ ID NO: 4, but not greater than the activity of SEQ ID NO: 18 (150 μL lysate, 200 mM ester, 200 mM isopropyl piperazine, 2% water in MIBK); "+++" indicates at least 1.1 to 5 times the activity of SEQ ID NO: 18 but not greater than the activity of SEQ ID NO: 54 (120 μL lysate, 300 mM ester, 300 mM isopropyl piperazine, 20% water in MIBK); "++++" indicates at least 1.5 to 2 times the activity of SEQ ID NO:54, but not greater than the activity of SEQ ID NO:68 (90 μL lysate, 300 mM ester, 300 mM isopropyl piperazine, 2% water in MIBK); "+++++" indicates at least 1.1 to 2.0 times the activity SEQ ID NO: 68 (50 μL lysate, 300 mM ester, 300 mM isopropyl piperazine, 2% water in MIBK); "$", indicates at least 1.1 to 2 times the activity of SEQ ID NO: 68, but not greater than the activity of SEQ ID NO: 100 (50 μL lysate, 354 mM ester, 425 mM isopropyl piperazine, 2% water in MIBK); "$$" indicates at least 1.1 to 5 times the activity of SEQ ID NO: 100, but not greater than the activity of SEQ ID NO: 114 (50 μL lysate, 354 mM ester, 425 mM isopropyl piperazine, 2% water in MIBK); "$$$" indicates at least 1.1 to 2 times the activity of SEQ ID NO: 114 (50 μL lysate, 354 mM ester, 354 mM isopropyl piperazine, 2% water in MIBK). In each case, activity was determined using a variable quantity of lysate loaded into a multi-well lyophilization and activity screen, then reacted with the noted concentration of substrate and in the noted solvent system in 200 μL volume over 16 hours, as described in Example 5.

TABLE 3

| SEQ ID NO | Mutations relative to SEQ ID NO: 2 | Number of Residue Differences | Activity |
| --- | --- | --- | --- |
| 1/2 | | | − |
| 3/4 | E198L; | 1 | + |
| 5/6 | E198I; | 1 | + |
| 7/8 | E198Y; | 1 | + |
| 9/10 | E198F; | 1 | + |
| 11/12 | E198M; | 1 | + |
| 13/14 | S185M; E198L; T207E; K296V; | 4 | ++ |
| 15/16 | F37L; S185F; E198L; T207E; G208H; | 5 | ++ |
| 17/18 | S185F; E198L; | 2 | ++ |
| 19/20 | F37L; P75R; S185F; E198L; G208H; K296L; | 6 | ++ |
| 21/22 | S185F; E198L; T207E; G208H; | 4 | ++ |
| 23/24 | S35H; S185F; E198L; | 3 | ++ |
| 25/26 | A27P; F30L; D103W; E198I; Q286G; | 5 | ++ |
| 27/28 | G57M; D103W; E198L; G208H; Q286G; K296R; | 6 | ++ |
| 29/30 | E198L; Q286G; | 2 | ++ |
| 31/32 | D103W; E198I; Q286G; | 3 | ++ |
| 33/34 | D103W; E198L; K271D; Q286G; | 4 | ++ |
| 35/36 | Q9Y; S35H; F37T; D103W; S185F; E198L; | 6 | +++ |
| 37/38 | V48L; S185F; E198L; D216N; | 4 | +++ |
| 39/40 | Q9Y; A19R; Q34N; S35H; V87A; S185F; E198L; K271D; K296R; | 9 | +++ |
| 41/42 | Q9Y; Q34E; S35H; V87A; S185F; E198L; K271D; | 7 | +++ |

TABLE 3-continued

| SEQ ID NO | Mutations relative to SEQ ID NO: 2 | Number of Residue Differences | Activity |
| --- | --- | --- | --- |
| 43/44 | Q9Y; A19R; Q34E; S35H; A46V; V87A; S185F; E198L; K271D; E278Q; K296R; | 11 | +++ |
| 45/46 | Q9Y; Q34N; S35H; A46V; V87A; S185F; E198L; E278Q; K296R; | 9 | +++ |
| 47/48 | S35H; R66V; S185F; P190Y; E198L; T207E; E263T; | 7 | +++ |
| 49/50 | Q9Y; Q34E; S35H; A46V; V87A; A139R; S185F; E198L; | 8 | +++ |
| 51/52 | Q9Y; Q34N; S35H; V87A; S185F; E198L; K296R; | 7 | +++ |
| 53/54 | Q9Y; S35H; V87A; S185F; E198L; | 5 | +++ |
| 55/56 | Q9Y; S35H; V87A; S185F; E198L; Q286S; | 6 | ++++ |
| 57/58 | Q9Y; F30V; S35H; V87A; S185F; E198L; | 6 | ++++ |
| 59/60 | Q9Y; Q34E; S35H; V87A; S185F; E198L; | 6 | ++++ |
| 61/62 | Q9Y; S35H; V87A; S185F; Y188F; E198L; | 6 | ++++ |
| 63/64 | Q9Y; Q34G; S35H; V87A; S185F; E198L; | 6 | ++++ |
| 65/66 | Q9Y; P20I; S35H; V87A; S185F; E198L; | 6 | ++++ |
| 67/68 | Q9Y; S35H; V87A; S185F; E198L; D216N; | 6 | ++++ |
| 69/70 | Q9Y; Q29D; S35H; V87A; S185F; E198L; | 6 | ++++ |
| 71/72 | Q9Y; Q33G; S35H; V87A; S185F; E198L; | 6 | ++++ |
| 73/74 | Q9Y; Q28S; S35H; V87A; S185F; E198L; | 6 | ++++ |
| 75/76 | Q9Y; F30V; S35H; V87A; S185F; I197L; E198L; D216N; | 8 | +++++ |
| 77/78 | Q9Y; S35H; L36I; F37G; V87A; S185F; E198L; D216N; L280T; L290I; | 10 | +++++ |
| 79/80 | Q9Y; V10M; S35H; F37G; V87A; S185F; E198L; D216N; | 8 | +++++ |
| 81/82 | Q9Y; Q28S; S35H; V87A; S185F; E198L; D216N; | 7 | +++++ |
| 83/84 | Q9Y; Q28S; S35H; V87A; S185F; I197L; E198L; D216N; N266T; | 9 | +++++ |
| 85/86 | Q9Y; Q28S; S35H; V87A; S185F; I197L; E198L; D216N; | 8 | +++++ |
| 87/88 | Q9Y; S35H; L36M; F37G; V87A; S185F; E198L; D216N; L280M; L290I | 10 | +++++ |
| 89/90 | Q9Y; F30V; Q33W; S35H; P75R; V87A; D103W; S185F; E198L; D216N; | 10 | +++++ |
| 91/92 | Q9Y; P20I; F30V; Q33W; S35H; A46R; R66T; V87A; D103W; S185F; E198L; D216N; E263R; | 13 | +++++ |
| 93/94 | Q9Y; Y22W; S35H; P75R; V87A; S185F; E198L; D216N; L290I; | 9 | +++++ |
| 95/96 | Q9Y; S35H; A46K; V87A; L160T; S185F; E198L; D216N; Q286N; | 9 | $ |
| 97/98 | Q9Y; S35H; A46K; V87A; L160T; S185F; E198L; D216N; Q286S; | 9 | $ |
| 99/100 | Q9Y; Q28C; S35H; P38E; W85G; V87A; S185F; E198L; D216N; | 9 | $ |
| 101/102 | Q9Y; R66L; V86T; V87A; V96M; L160P; Y183Q; S185F; Y188F; E198L; L205F; L212D; D216N; R255N; V270L; Q286S; | 16 | $ |
| 103/104 | Q9Y; R66L; V86T; V87A; V96M; S185F; E198L; L205F; D216N; A249W; Q286S; | 11 | $ |
| 105/106 | Q9Y; Q28C; S35H; D54R; P75R; V87A; I176M; S185F; E198L; L205F; D216N; T248V; | 12 | $ |
| 107/108 | I7L; Q9Y; Q28C; S35H; P38E; W85G; V87A; S185F; E198L; D216N; | 10 | $$ |

TABLE 3-continued

| SEQ ID NO | Mutations relative to SEQ ID NO: 2 | Number of Residue Differences | Activity |
|---|---|---|---|
| 109/110 | Q9Y; Q28C; S35H; P38E; A46K; W85G; V87A; S185F; E198L; D216N; | 10 | $$ |
| 111/112 | Q9Y; Q28C; S35H; L36T; P38W; D54Q; R66T; W85G; V87A; S185F; E198L; D216N; | 12 | $$ |
| 113/114 | Q9Y; Q28C; S35H; L36T; P38W; P75R; W85G; V87A; S185F; E198L; D216N; | 11 | $$ |
| 115/116 | Q9Y; Y22W; Q28C; S35H; L36M; P38W; P75R; W85G; V87A; S185F; E198L; D216N; | 12 | $$ |
| 117/118 | Q9Y; Q28C; S35H; L36T; P38W; P75M; W85G; V87A; S185F; E198L; D216N; | 11 | $$ |
| 119/120 | Q9Y; Q28C; S35H; P38E; W85G; V87A; S185F; E198L; D216N; | 9 | $$ |
| 121/122 | Q9Y; Q28C; S35H; L36T; P38W; P75R; W85G; V87A; S185F; E198L; D216N; Q286C; | 12 | $$$ |
| 123/124 | P2L; Q9Y; Q28C; S35H; L36T; P38W; P75R; W85G; V87A; S185F; E198L; D216N; | 12 | $$$ |
| 125/126 | Q9Y; Q28C; S35H; L36T; P38W; P75R; W85G; V87A; L181Q; S185F; E198L; D216N; | 12 | $$$ |

As noted above, in some embodiments, the improved carboxyesterase polypeptide comprises an amino acid sequence that is at least about 80%, 85%, 86%, 87%, 88%, 89%, 90%, 91%, 92%, 93%, 94%, 95%, 96%, 97%, 98%, 99% or more identical to a reference sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126. In some embodiments, the improved carboxyesterase polypeptides can have 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-22, 1-24, 1-26, 1-28, 1-30, 1-35, 1-40, 1-45, 1-50, 1-55, 1-60, or 1-62 residue differences as compared to the carboxyesterase represented by SEQ ID NO: 2. In some embodiments, the number of residue differences can be 1, 2, 3, 4, 5, 6, 7, 8, 9, 10, 11, 12, 13, 14, 15, 16, 17, 18, 19, 20, 22, 24, 26, 28, 30, 35, 40, 45, 50, 55, 60, or 62 differences as compared to SEQ ID NO: 2.

In some embodiments, the improved carboxyesterase polypeptide comprises an amino acid sequence that is at least about 80%, 85%, 86%, 87%, 88%, 89%, 90%, 91%, 92%, 93%, 94%, 95%, 96%, 97%, 8%, or 99% identical to a reference sequence based on SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126, with the proviso that the improved carboxyesterase amino acid sequence comprises any one of the set of residue differences contained in any one of the polypeptide sequences listed in Table 3, as compared to SEQ ID NO: 2. In some embodiments, the improved carboxyesterase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, 1-60, or 1-62 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35, 40, 45, 50, 55, or 62 residue differences at other residue positions.

In some embodiments, the residue differences at other residue positions comprise substitutions with conservative amino acid residues.

In some embodiments, the improved carboxyesterase polypeptides capable of converting the ester substrate, ethyl oxazole-5-carboxylate in the presence of an amine substrate to levels of product detectable by HPLC-UV at 230 nm in water-saturated MIBK comprises an amino acid sequence chosen from the sequence of SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126.

In some embodiments, the engineered carboxyesterase polypeptide is capable of converting the ester substrate to product with as 2 times, 5 times, 10 times, 20 times, 25 times, 50 times, 75 times, 100 times, 1000 times, 10,000 times, 100,000 times, 500,000 times, 785,000 times or greater activity than the polypeptide of SEQ ID NO: 2. In some embodiments, the engineered carboxyesterase polypeptide is capable of converting the ester substrate to product with 50 to 100 times or greater activity than the polypeptide of SEQ ID NO: 2 and comprises an amino acid sequence corresponding to SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126.

In some embodiments, the engineered carboxyesterase polypeptide is capable of converting the ester substrate to product with about 1.1 to 5 times or greater activity than the polypeptide of SEQ ID NO: 24. In some embodiments, the engineered carboxyesterase polypeptide is capable of converting the ester substrate to product with about 1.1 to 5 times or greater activity than the polypeptide of SEQ ID NO: 24 and comprises an amino acid sequence corresponding to the sequence of SEQ ID NO: 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126.

In some embodiments, the engineered carboxyesterase polypeptide is capable of converting the ester substrate to product with about 1.1 to 5-times or greater activity than the polypeptide of SEQ ID NO: 54. In some embodiments, the engineered carboxyesterase polypeptide is capable of converting the ester substrate to product with about 1.1 to 5-times or greater activity than the polypeptide of SEQ ID NO: 54 and comprises a sequence corresponding to the sequence of SEQ ID NO: 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126.

In some embodiments, the engineered carboxyesterase polypeptide is capable of converting the ester substrate to product with about 1.1 to 6 times or greater activity than the polypeptide of SEQ ID NO: 68. In some embodiments, the engineered carboxyesterase polypeptide is capable of converting the ester substrate to product with about 1.1 to 5 times or greater activity than the polypeptide of SEQ ID NO:68 and comprises an amino acid sequence corresponding to the sequence of SEQ ID NO: 76, 78, 80, 82, 84, 86, 88, 90, 92, 94, 96, 98, 100, 102, 104, 106, 108, 110, 112, 114, 116, 118, 120, 122, 124, or 126.

In some embodiments, the engineered carboxyesterase polypeptide is capable of converting the ester substrate to product with about 1.1 to 5 times or greater activity than the polypeptide of SEQ ID NO: 100. In some embodiments, the engineered carboxyesterase polypeptide is capable of converting the ester substrate to product with about 1.7 times or greater activity than the polypeptide of SEQ ID NO:100 and comprises an amino acid sequence corresponding to the sequence of SEQ ID NO: 108, 110, 112, 114, 116, 118, 120, 122, 124, or 126.

In some embodiments, the engineered carboxyesterase polypeptide is capable of converting the ester substrate to product with about 1.1 to 2 times greater activity than the polypeptide of SEQ ID NO: 114. In some embodiments, the engineered carboxyesterase polypeptide is capable of converting the ester substrate to product with about 1.1 to 5 times or greater activity than the polypeptide of SEQ ID NO: 114 and comprises an amino acid sequence corresponding to the sequence of SEQ ID NO: 122, 124, or 126.

In some embodiments, the improved engineered carboxyesterase polypeptides can comprise deletions at specific amino acid residues of the engineered carboxyesterase polypeptides described herein. Thus, for each and every embodiment of the carboxyesterase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 5% of the total number of amino acids, up to 10% of the total number of amino acids, up to 20% of the total number of amino acids, or up to 30% of the total number of amino acids of the carboxyesterase polypeptides, as long as the functional activity of the carboxyesterase activity is maintained. In some embodiments, the deletions can comprise up to 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, 1-50, 1-55, 1-60, or 1-62 amino acid residues. In some embodiments, the number of deletions can be up to 1, 2, 3, 4, 5, 6, 7, 8, 9, 10, 11, 12, 14, 15, 16, 18, 20, 22, 24, 26, 30, 35, 40, 45, 50, 55, 60, or 62 amino acids. As described herein, the carboxyesterase polypeptides of the disclosure can be in the form of fusion polypeptides in which the carboxyesterase polypeptides are fused to other polypeptides, such as, by way of example and not limitation, antibody tags (e.g., myc epitope), purification sequences (e.g., His tags for binding to metals), and cell localization signals (e.g., secretion signals). Thus, the carboxyesterase polypeptides can be used with or without fusions to other polypeptides.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); α-aminoisobutyric acid (Aib); ε-aminohexanoic acid (Aha); 6-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (lnAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, *CRC Practical Handbook of Biochemistry and Molecular Biology*, CRC Press, Boca Raton, Fla., at pp. 3-70 and the references cited therein). These amino acids may be in either the L- or D-configuration.

Those of skill in the art will recognize that amino acids or residues bearing side chain protecting groups may also be comprised in the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(6-benzylester), Gln(xanthyl), Asn(N-δ-xanthyl), His(bom), His (benzyl), His(tos), Lys(finoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above, the various modifications introduced into the naturally occurring polypeptide to generate an engineered carboxyesterase enzyme can be targeted to affect a specific property of the enzyme, such as activity, specificity to its substrate, and thermostability, etc.

In another aspect, the present disclosure provides polynucleotides encoding the improved carboxyesterase polypeptides. The polynucleotides may be operatively linked to one or more heterologous regulatory sequences that control gene expression to create a recombinant polynucleotide capable of expressing the carboxyesterase polypeptide. Expression constructs containing a heterologous polynucleotide encoding the engineered carboxyesterase can be introduced into appropriate host cells to express the corresponding carboxyesterase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved carboxyesterase polypeptides disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based upon the possible codon choices, and all such variations are to be considered specifically disclosed for any polypeptide disclosed herein, including the amino acid sequences presented in Table 3.

In some embodiments, the polynucleotides can be selected and/or engineered to comprise codons that are selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. Since not all codons need to be replaced to optimize the codon usage of the carboxyesterase (e.g., because the natural sequence can have preferred codons and because use of preferred codons may not be required for all amino acid residues), codon-optimized polynucleotides encoding the carboxyesterase polypeptides may contain preferred codons at about 40%, 50%, 60%, 70%, 80%, or greater than 90% of codon positions of the full-length coding region.

In some embodiments, the polynucleotide encodes a carboxyesterase polypeptide comprising an amino acid sequence that is at least 80%, 85%, 86%, 87%, 88%, 89%, 90%, 91%, 92%, 93%, 94%, 95%, 96%, 97%, 98%, 99% or more identical to the reference sequence of SEQ ID NO:4, or a functional fragment thereof, wherein the polypeptide is capable of converting the ester substrate, in the presence of an amine substrate with an activity that is improved as compared to the activity of the carboxyesterase of SEQ ID NO: 2 derived from *A. acidocaldarius* Esterase 2.

In some embodiments, the polynucleotide encodes a carboxyesterase polypeptide comprising an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid sequence corresponding to SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126, or a functional fragment thereof, wherein the polypeptide has at least one improved properties in converting the ester substrate, ethyl oxazole-5-carboxylate to the product, (4-isopropylpiperazin-1-yl)(oxazol-5-yl)methanone in the presence of an amine substrate, 1-isopropylpiperazine. In some embodiments, the encoded carboxyesterase polypeptide has an activity that is equal to or greater than the activity of the polypeptide of SEQ ID NO: 2.

In some embodiments, the polynucleotide encodes a carboxyesterase polypeptide comprising an amino acid sequence that is at least about 80%, 85%, 86%, 87%, 88%, 89%, 90%, 91%, 92%, 93%, 94%, 95%, 96%, 97%, 98%, or 99% identical to a reference sequence based on SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126, or a functional fragment thereof, with the proviso that the improved carboxyesterase amino acid sequence comprises any one of the set of residue differences contained in any one of the polypeptide sequences listed in Table 3, as compared to SEQ ID NO: 2.

In some embodiments, the polynucleotides encoding the improved carboxyesterase polypeptides are selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, or 125.

In some embodiments, the polynucleotides are capable of hybridizing under highly stringent conditions to a polynucleotide comprising SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, or 125, or a complement thereof, where the highly stringently hybridizing polynucleotides encode a carboxyesterase polypeptide capable of converting to product in the presence of an amine substrate with an activity that is equal to or greater than the polypeptide of SEQ ID NO:2.

In some embodiments, the polynucleotides encode the polypeptides described herein, but have about 80% or more sequence identity, about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered carboxyesterase described herein. In some embodiments, the reference polynucleotide is selected from SEQ ID NO: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, or 125.

In some embodiments, the carboxyesterase polypeptide comprises the amino acid sequence set forth in SEQ ID NO: 122. In another embodiment, the present disclosure provides a polynucleotide sequence that encodes the carboxyesterase polypeptide sequence set forth in SEQ ID NO: 122. In yet another embodiment, the present disclosure provides a polynucleotide that encodes a carboxyesterase polypeptide, wherein the polynucleotide comprises the polynucleotide sequence set forth in SEQ ID NO: 121. In yet another embodiment, the carboxyesterase polypeptide consists of the polypeptide sequence set forth in SEQ ID NO: 122. In another embodiment, the carboxyesterase polypeptide consists of residues 2-310 of SEQ ID NO: 122.

The improved carboxyesterases and polynucleotides encoding such polypeptides can be prepared using methods commonly used by those skilled in the art. As noted above, the naturally-occurring amino acid sequence and corresponding polynucleotide encoding the wild-type carboxyesterase enzyme, *A. acidocaldarius* Esterase 2, from which the parent sequence, SEQ ID NO: 2 was derived, is available in WO02/057411 (see SEQ ID NO: 10). In some embodiments, the parent polynucleotide sequence is codon-optimized to enhance expression of the carboxyesterase in a specified host cell. The engineered carboxyesterases can be obtained by subjecting the polynucleotide encoding the naturally occurring carboxyesterase to mutagenesis and/or directed evolution methods. An exemplary directed evolution technique is mutagenesis and/or DNA shuffling, as described in Stemmer, 1994, *Proc Natl Acad Sci USA* 91:10747-10751; WO 95/22625; WO 97/0078; WO 97/35966; WO 98/27230; WO 00/42651; WO 01/75767; and U.S. Pat. No. 6,537,746.

Other directed evolution procedures that can be used include, among others, staggered extension process (StEP), in vitro recombination (Zhao, et al., 1998, *Nat. Biotechnol.* 16:258-261), mutagenic PCR (Caldwell, et al., 1994, *PCR Methods Appl.* 3:S136-S140), and cassette mutagenesis (Black, et al., 1996, *Proc Natl Acad Sci USA* 93:3525-3529). Mutagenesis and directed evolution techniques useful for the purposes herein are also described in the following references: Ling, et al. 1997, "Approaches to DNA mutagenesis: an overview," *Anal. Biochem.* 254(2):157-78; Dale, et al., 1996, "Oligonucleotide-directed random mutagenesis using the phosphorothioate method," *Methods Mol. Biol.* 57:369-74; Smith, 1985, "In vitro mutagenesis," *Ann. Rev. Genet.* 19:423-462; Botstein, et al., 1985, "Strategies and applications of in vitro mutagenesis," *Science* 229:1193-1201; Carter, 1986, "Site-directed mutagenesis," *Biochem. J.* 237: 1-7; Kramer, et al., 1984, "Point Mismatch Repair," *Cell* 38:879-887; Wells, et al., 1985, "Cassette mutagenesis: an efficient method for generation of multiple mutations at defined sites," *Gene* 34:315-323; Minshull, et al., 1999, "Protein evolution by molecular breeding," *Curr Opin Chem Biol* 3:284-290; Christians, et al., 1999, "Directed evolution of thymidine kinase for AZT phosphorylation using DNA family shuffling," *Nature Biotech* 17:259-264; Crameri, et al., 1998, "DNA shuffling of a family of genes from diverse species accelerates directed evolution," *Nature* 391:288-291; Crameri, et al., 1997, "Molecular evolution of an arsenate detoxification pathway by DNA shuffling," *Nature Biotech* 15:436-438; Zhang, et al., 1997, "Directed evolution of an effective fructosidase from a galactosidase by DNA shuffling and screening," *Proc Natl Acad Sci USA* 94:45-4-4509; Crameri, et al., 1996, "Improved green fluorescent protein by molecular evolution using DNA shuffling,' *Nature Biotech* 14:315-319; and Stemmer, 1994, "Rapid evolution of a protein in vitro by DNA shuffling," *Nature* 370:389-391.

In some embodiments, the clones obtained following mutagenesis treatment are screened for carboxyesterases having a desired improved enzyme property. Measuring carboxyesterase enzyme activity from the expression libraries can be performed using standard techniques, such as separation of the product (e.g., by HPLC) and detection of the product by measuring UV absorbance of the separated substrate and products and/or by detection using tandem mass spectroscopy (e.g., MS/MS). Exemplary assays are described in Example 4 below. The rate of increase in desired product per unit time indicates the relative (enzymatic) activity of the carboxyesterase polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Clones containing a polynucleotide encoding the desired carboxyesterases are then isolated, sequenced to identify the nucleotide sequence changes (if any), and used to express the enzyme in a host cell.

In other embodiments, which are well known in the art, enzymes may be diversified genetically while maintaining their target activities, such as by the technique of neutral drift.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage, et al., 1981, *Tet Lett* 22:1859-69, or the method described by Matthes, et al., 1984, *EMBO J* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, The Great American Gene Company, Ramona, Calif., ExpressGen Inc, Chicago, Ill., Operon Technologies Inc, Alameda, Calif., and many others.

The engineered carboxyesterase enzymes expressed in a host cell can be recovered from the cells and/or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic BTM from Sigma-Aldrich of St. Louis, Mo.

Chromatographic techniques for isolation of the carboxyesterase polypeptide include, among others, reverse phase chromatography high performance liquid chromatography, ion exchange chromatography, gel electrophoresis, and affinity chromatography. Conditions for purifying a particular enzyme will depend, in part, upon factors such as net charge, hydrophobicity, hydrophilicity, molecular weight, molecular shape, etc., and will be apparent to those having skill in the art. In some embodiments, the engineered carboxyesterases can be expressed as fusion proteins with purification tags, such as His-tags having affinity for metals, or antibody tags for binding to antibodies, e.g., myc epitope tag.

In some embodiments, affinity techniques may be used to isolate the improved carboxyesterase enzymes. For affinity chromatography purification, any antibody that specifically binds the carboxyesterase polypeptide may be used. For the production of antibodies, various host animals, including but not limited to rabbits, mice, rats, etc., may be immunized by injection with an engineered polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels, such as aluminum hydroxide, surface active substances, such as lysolecithin, pluronic polyols, polyanions, peptides, oil emulsions, keyhole limpet hemocyanin, dinitrophenol, and potentially useful human adjuvants, such as BCG (bacilli Calmette Guerin) and *Corynebacterium parvum*.

In a further aspect, the improved carboxyesterase polypeptides described herein can be used in a process for amidation of certain amide group acceptors (e.g., an ester substrate) in the presence of an amine substrate.

In some embodiments, the improved carboxyesterases can be used in a process for preparing an amide, wherein components are combined containing:

(a) an ester of the form $R_1$—$COOR_2$, wherein $R_1$ is chosen from: an $sp^3$ carbon with 0 to 3 alkyl substituents; and an aromatic ring, and $R_2$ is chosen from: a methyl group; an ethyl group; and 1-6 carbon alkyl chains;

(b) an amine substrate;

(c) an improved carboxyesterase polypeptide, and;

(d) a solvent.

In one embodiment, the solvent is an organic solvent that contains up to 3 molar equivalents of water, relative to the ester substrate, in an amount of from about 0.5% (vol/vol) to about 3% (vol/vol).

In some embodiments of the process, the improved carboxyesterases are chosen from: SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, and 126.

In other embodiments, the improved carboxyesterase polypeptides can be used in a process for preparing an amide molecule, wherein components are combined containing: (a) an ester substrate of the form $R_1$—$COOR_2$, wherein $R_1$ is chosen from: an $sp^3$ carbon with 0 to 3 alkyl substituents; and an aromatic ring, and $R_2$ is chosen from: a methyl group; an ethyl group and a 1-6 carbon alkyl chain; (b) an amine substrate; (c) an improved carboxyesterase polypeptide described above; and (d) a solvent that In another embodiment of this process, an organic solvent is used. In one embodiment, the organic solvent is chosen from: toluene; 2-methyltetrahydrofuran; tetrahydrofuran; dimethylacetamide; methyl isobutyl ketone (MIBK); dichloromethane; tert-butyl methyl ether; cyclopentyl methyl ether; methyl cyclohexane; dichloromethane; acetonitrile; methyl ethyl ketone; isopropyl acetate; ethanol; isopropanol; ethyl acetate; heptane; xathane; and 2-methyltetrahydrofuran (2-Me-THF); and water. In yet another embodiment, the organic solvent contains up to 3 molar equivalents of water relative to the ester substrate in an amount of from about 0.5% (vol/vol) to about 3% (vol/vol). In another embodiment of this process, the carboxyesterase polypeptide in step (c) is prepared in the presence of a salt to stabilize its physical form during the reaction. In yet another embodiment, salt is added as an additional reaction component. In one embodiment of this process, the ester is ethyl oxazole-5-carboxylate that has the formula:

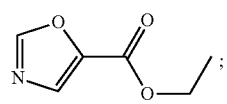

the amine substrate is 1-isopropylpiperazine that has the formula:

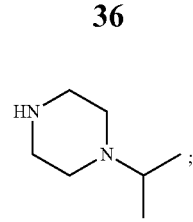

and the amide is (4-isopropylpiperazin-1-yl)(oxazol-5-yl)methanone that has the formula:

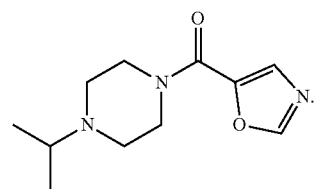

In yet another embodiment of this process, the ester is ethyl oxazole-5-carboxylate that has the formula:

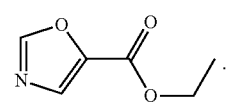

and the amine substrate is cis-2,6-dimethylmorpholine that has the formula:

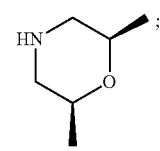

and the amide is ((2S,6R)-2,6-dimethylmorpholino)(oxazol-5-yl)methanone that has the formula:

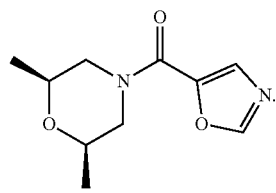

In another embodiment, this reaction in this process comprises: about 50 g/L ethyl oxazole-5-carboxylate, 44 g/L 1-isopropylpiperazine, and about 25 g/L of a carboxyesterase polypeptide corresponding to an amino acid sequence of: SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108 110, 112, 114, 116, 118, 120, 122, 124, or 126, wherein the carboxyesterase is prepared in the presence of sodium sulfate and run in the presence of about 10 g/L to about 20 g/L water in MIBK.

In some embodiments, the invention is an amide that is made by these processes using the improved carboxyesterases. In another embodiment, the invention is an amide, 4-isopropylpiperazin-1-yl)(oxazol-5-yl)methanone, that has the formula:

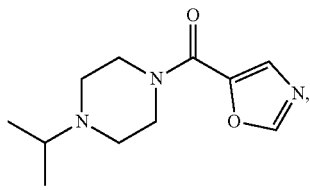

III wherein the amide of formula III. is made by the above-described processes.

In an alternative embodiment, the invention is an amide, ((2S,6R)-2,6-dimethylmorpholino)(oxazol-5-yl)methanone, that has the formula:

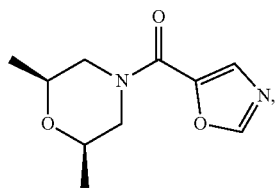

V wherein the amide of formula V. is made by the above-described processes.

The compounds of formula I (Astatech, AS-23210), formula II (Oakwood Products Inc, OAK-008910), and formula IV (Oakwood Products Inc, OAK-091224), were acquired from commercial providers.

In some embodiments, the process comprises contacting or incubating the ester substrate, ethyl oxazole-5-carboxylate, with an improved carboxyesterase in the presence of an amine substrate under suitable reaction conditions to convert the ester substrate to the product, (4-isopropylpiperazin-1-yl)(oxazol-5-yl)methanone, with from about 50 to about 785,000 times or greater conversion rate and/or activity than that of SEQ ID NO: 2. Exemplary polypeptides comprise an amino acid sequence corresponding to SEQ ID NO: 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, or 126.

In some embodiments of the processes above, the reaction solvent for carrying out the process is chosen from methyl isobutyl ketone (MIBK), toluene, tert-butyl methyl ether (TBME) or 2-methyl tetrahydrofuran (2-Me-THF).

In some embodiments of the above processes, the enzyme preparation for the reaction includes a salt chosen from one of potassium phosphate (KPi), potassium sulfate, or sodium sulfate.

In some embodiments, the reaction condition for carrying out the process can comprise a temperature of about 15° C. to a temperature of about 30° C. In one embodiment, the amine substrate used in the process can be a chiral amine or an achiral amine. An achiral amine substrate has the advantage of not being limited in its reaction to a specific stereoisomer, thus requiring less of the amine substrate.

Various suitable amine substrates can be used, including, by way of example and not limited to, 1-isopropylpiperazine and cis-2,6-dimethylmorpholine. In some embodiments, other amine substrates may be used, including, among others, α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-aspartic acid, L-lysine, L-ornithine, β-alanine, taurine, n-octylamine, cyclohexylamine, 1,4-butanediamine, 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (S) single isomers where possible.

In some embodiments, the process for converting ester substrate, ethyl oxazole-5-carboxylate, comprises contacting the ester substrate at about 36 mL/L with about 20 g/L of a carboxyesterase described herein in MIBK and a temperature of about 30° C. in the presence of 43 mL/L 1-isopropylpiperazine, wherein at least 80%, 85%, 90%, 92%, 94%, 96%, or 98% or more of the ester substrate is converted to product in 24 hrs. In some embodiments, the carboxyesterase polypeptide capable of carrying out the foregoing reaction comprises an amino acid sequence corresponding to SEQ ID NO: 122.

In some embodiments, the processes above can further comprise the step of isolating the compound of structural formula III, or the compound of structural formula V., from the reaction solvent.

Also provided herein are compositions of the carboxyesterases and substrates/products. In some embodiments, the compositions can comprise the compound of formula III., or the compound V., and an improved carboxyesterase of the disclosure.

Any one or more of the improved engineered carboxyesterases can be part of the composition.

EXAMPLES

Various features and embodiments of the disclosure are illustrated in the following representative examples, which are intended to be illustrative, and not limiting.

Example 1: *A. acidocaldarius* Esterase 2 Wild-Type Carboxyesterase Gene Acquisition and Construction of Expression Vectors Carboxyesterase (CE) encoding genes were designed for expression in *E. coli* based on the reported amino acid sequence of the carboxyesterase, *A. acidocaldarius* Esterase 2 (SEQ ID NO: 2), and a codon optimization algorithm described in Example 1 of application US 2008/0248539. Oligonucleotides were synthesized separately and then joined using oligonucleotides, generally composed of 42 nucleotides. The gene was then cloned into the expression vector pCK110900 (depicted as FIG. 3 in US application 2006/195947, both of which are incorporated herein by reference in their entireties and for all purposes) under the control of a lac promoter. This expression vector also contains the P15a origin of replication and the chloramphenicol resistance gene. Resulting plasmids were transformed into *E. coli* W3110 using standard methods. The codon-optimized gene and the encoded polypeptide are listed, respectively, as SEQ ID NOs: 1 and 2 in Table 3 and the below Sequence Listing.

Likewise, the genes encoding the engineered carboxyesterases of the present disclosure listed in Table 3 (SEQ ID NOs: 3-94) were cloned into vector pCK110900 for expression in *E. coli* W3110.

Example 2: Production of Carboxyesterase Powders—Shake Flask Procedure

A single microbial colony of *E. coli* containing a plasmid encoding a carboxyesterase of interest was inoculated into 50 mL Luria Bertoni broth containing 30 μg/mL chloramphenicol and 1% glucose. Cells were grown overnight (at least 16 hrs) in an incubator at 30° C. with shaking at 250 rpm. The culture was diluted into 1000 mL of Terrific broth containing 30 μg/mL chloramphenicol to give an approximate OD600 of 0.2 and allowed to grow at 30° C. with shaking at 250 rpm. Expression of the carboxyesterase gene was induced by addition of isopropyl RD-thiogalactoside (IPTG) to a final concentration of 1 mM when the OD600 of the culture is 0.6 to 0.8 and incubation was then continued overnight (at least 16 hrs). Cells were harvested by centrifugation (3738 RCF, 20 min, 4° C.) and the supernatant discarded. Pellets were frozen for 2 hours at −80° C. Pellets were then thawed and resuspended to 3 mL sodium sulfate buffer (consisting of 15 g/L anhydrous sodium sulfate in water) per gram of final pellet mass (e.g., 10 g frozen pellet suspended in 30 mL sodium sulfate buffer). Cell debris was removed by centrifugation (15,777 RCF, 40 min, 4° C.). The clear lysate supernatant was collected, pooled, and lyophilized to provide a dry powder of crude carboxyesterase enzyme.

Example 3: Production of Carboxyesterase Powders—Fermentation Procedure

An aliquot of frozen working stock (*E. coli* containing plasmid with the carboxyesterase gene of interest) was removed from the freezer and allowed to thaw at room temperature. 300 μL of this working stock was inoculated into a primary seed stage of 250 ml M9YE broth (1.0 g/L ammonium chloride, 0.5 g/L of sodium chloride, 6.0 g/L of disodium monohydrogen phosphate, 3.0 g/L of potassium dihydrogen phosphate, 2.0 g/L of Tastone-154 yeast extract, 1 L/L de-ionized water) containing 30 g/ml chloramphenicol and 1% glucose in 1 L flasks and allowed to grow at 26° C. with shaking at 220 rpm. When the OD600 of the culture was 0.5 to 1.0, the flasks were removed from the incubator and immediately used to inoculate a secondary seed stage.

A secondary seed stage was carried out in bench scale 5 L fermenters using 4 L of growth medium (0.88 g/L ammonium sulfate, 0.98 g/L of sodium citrate; 12.5 g/L of dipotassium hydrogen phosphate trihydrate, 6.25 g/L of potassium dihydrogen phosphate, 3.3 g/L of Springer 0251 yeast extract, 0.083 g/L ferric ammonium citrate, 0.5 mL/L antifoam and 8.3 ml/L of a trace element solution containing 2 g/L of calcium chloride dihydrate, 2.2 g/L of zinc sulfate heptahydrate, 0.5 g/L manganese sulfate monohydrate, 1 g/L cuprous sulfate heptahydrate, 0.1 g/L ammonium molybdate tetrahydrate and 0.02 g/L sodium tetraborate) sterilized at 120° C. for 40 minutes. Fermenters were inoculated with 2 ml OD 0.5-1.0 primary seed and incubated at 30° C., 300 rpm and 0.5 vvm aeration. When the OD600 of the culture was 0.5-1.0 OD600 the secondary seed was immediately transferred to a final stage fermentation.

The final stage fermentation was carried out at bench scale in 10 L fermenters using 6 L of growth medium (0.88 g/L ammonium sulfate, 0.98 g/L of sodium citrate; 12.5 g/L of dipotassium hydrogen phosphate trihydrate, 6.25 g/L of potassium dihydrogen phosphate, 3.3 g/L of Springer 0251 yeast extract, 0.083 g/L ferric ammonium citrate, 0.5 mL/L antifoam and 8.3 ml/L of a trace element solution containing 2 g/L of calcium chloride dihydrate, 2.2 g/L of zinc sulfate heptahydrate, 0.5 g/L manganese sulfate monohydrate, 1 g/L cuprous sulfate heptahydrate, 0.1 g/L ammonium molybdate tetrahydrate and 0.02 g/L sodium tetraborate) sterilized at 121 C for 40 minutes and supplemented post sterilization with 20 g/L glucose monohydrate, 0.48 g/L ammonium chloride and 0.204 g/L magnesium sulphate heptahydrate. Fermenters were inoculated with 500 ml OD600 0.5-1.0 secondary seed and incubated at 30 C and 1.6 vvm aeration. Dissolved oxygen was controlled at 30% by variable speed agitation of 300-950 rpm. The pH was maintained at 7.0 by addition of 20% v/v ammonium hydroxide. Growth of the culture was maintained by addition of a feed solution containing 500 g/L glucose monohydrate, 12 g/L ammonium chloride and 5.1 g/L magnesium sulfate heptahydrate.

After the culture reached an OD600 of 80+/−10, expression of carboxyesterase was induced by addition of isopropyl-β-D-thiogalactoside (IPTG) to a final concentration of 1 mM and fermentation was continued for another 24 hours. The culture was then chilled to 8° C. and maintained at that temperature until harvested. Cells were collected by centrifugation at 5000 G for 40 minutes in a Sorvall RC12BP centrifuge at 4° C. Harvested cell pellets were then frozen at −80° C. and stored until downstream processing and recovery, as described below.

Pellets were frozen for 2 hours at −80° C. Pellets were then thawed and resuspended to 3 mL sodium sulfate buffer (consisting of 15 g/L anhydrous sodium sulfate in water) per gram of final pellet mass (e.g., 10 g frozen pellet suspended in 30 mL sodium sulfate buffer). After resuspension, cells were filtered through 200 um mesh before passing twice through the microfluidizer at 12000 psig. Cell debris was removed by centrifugation (15,777 RCF, 40 min, 4° C.). The clear lysate supernatant was collected, pooled, and lyophilized to provide a dry powder of crude carboxyesterase enzyme. The carboxyesterase powder was stored at −80° C.

Example 4: High-Throughput Analytical Methods for Identification of Variants of the *A. acidocaldarius* Esterase 2 Capable of Converting Ester Substrate to Amide Under Aqueous Conditions UPLC method to determine conversion of ester substrate I to amide III: Enzymatic conversion of the ester substrate of formula I. (commercially available, CAS number 118994-89-1) to the amide of formula III was determined using an Agilent 1290 UPLC equipped with an Agilent Zorbax RRHD Eclipse Plus Phenyl-Hexyl column (3.0×50 mm, 1.8 μm) using a gradient of 5 mM NH$_4$Ac in Water (mobile phase A) and Acetonitrile (mobile phase B) at a flow rate of 2 mL/min at a column temperature of 60° C. Beginning from a 99.9:0.1 ratio of A:B, the method followed a 0.25 minute hold, followed by a 0.05 minute gradient to 80:20 A:B, followed by a 0.5 minute gradient to 60:40 A:B, then a 0.1 minute purge gradient to 0:100 A:B, a 0.2 minute hold at 0:100 A:B, and a 0.1 minute gradient to 99.9:0.1 A:B, and finally a 0.3 minute hold at 99.9:0.1 A:B. Compound elution was monitored at 210 and 230 nm, with ester eluting at 0.56 min, amide eluting at 0.52 min, and the acid by-product of the reaction eluting as a narrow peak near the solvent front, at 0.14 min.

UPLC method to determine conversion of ester substrate of formula I. to the amide of formula III.: Enzymatic conversion of the ester substrate of formula I. to the amide of formula III. was determined using an Agilent 1290 UPLC equipped with an Agilent Zorbax SB-C18 RRHD column (3.0×50 mm, 1.8 m) using a gradient of 0.05% TFA in Water (mobile phase A) and 0.05% TFA in Acetonitrile (mobile phase B) at a flow rate of 2 mL/min at a column temperature of 60° C. Beginning from a 99.9:0.10 ratio of A:B, the method followed a 0.25 minute hold, followed by a 0.0.25 minute gradient to 80:20 A:B, followed by a 0.1 minute gradient to 100:0 A:B, followed by a 0.1 minute hold, followed by a 0.1 minute gradient to 99.9:0.1 A:B, followed by a 0.2 minute hold. Compound elution was monitored at 210 and 230 nm, with ester eluting at 0.53 min, amide at 0.23 min, and the acid by-product of the reaction eluting as a narrow peak near the solvent front, at 0.2 min with a 1 uL injection volume.

UPLC method to determine conversion of ester substrate of formula I. to the amide of formula V.: Enzymatic conversion of the ester substrate of formula I. to the amide of formula V. was determined using an Agilent 1290 UPLC equipped with an Agilent Zorbax SB-C18 column (3.0×50 mm, 1.8 m) using a gradient of 0.05% TFA in Water (mobile phase A) and 0.05% TFA in Acetonitrile (mobile phase B) at a flow rate of 1.5 mL/min at a column temperature of 60° C. Beginning from a 80:20 ratio of A:B, the method followed a 0.9 minute hold, followed by a 0.1 minute gradient to 0:100 A:B, followed by a 0.1 minute gradient to 80:20 A:B, followed by a 0.4 minute hold. Compound elution was monitored at 210 and 230 nm, with ester eluting at 0.5 min, amide at 0.39 min, and the acid by-product of the reaction eluting as a narrow peak near the solvent front, at 0.14 min.

Example 5: High-Throughput Screening for Identification of Variants of the *A. Acidocaldarius* Esterase 2 Capable of Converting Ester Substrate to Amide The gene encoding *A. acidocaldarius* Esterase 2 (SEQ ID NO: 2), constructed as described in Example 1, was mutagenized using methods described below and the population of altered DNA molecules was used to transform a suitable *E. coli* host strain. Antibiotic resistant transformants were selected and processed to identify those expressing a carboxyesterase with an improved ability to amidate the ester substrate of formula I. to the compound of formulas (III) and (V) in the presence of either amine substrates of formulas (II) or (IV), respectively. Cell selection, growth, induced expression of carboxyesterase variant enzymes and collection of cell pellets were as described below.

Recombinant *E. coli* colonies carrying a gene encoding carboxyesterase were picked using a Q-PIX molecular devices robotic colony picker (Genetix USA, Inc., Boston, Mass.) into 96-well shallow well microtiter plates containing in each well 180 μL LB Broth, 1% glucose and 30 μg/mL chloramphenicol (CAM). Cells were grown overnight at 30° C. with shaking at 200 rpm. A 20 μL aliquot of this culture was then transferred into 96-deep well plates containing 380 μL TB broth and 30 μg/mL CAM. After incubation of the deep-well plates at 30° C. with shaking at 250 rpm for 2-3 hrs, recombinant gene expression within the cultured cells was induced by addition of IPTG to a final concentration of 1 mM. The plates were then incubated at 30° C. with shaking at 250 rpm for 18 hrs.

Cells were pelleted by centrifugation (3738 RCF, 10 min, 4° C.), resuspended in 200 μL lysis buffer and lysed by shaking at room temperature for 2 hours. In the case of lyophilized screening conditions, the lysis buffer contained 100 mM sodium sulfate (14.2 g/L), 1 mg/mL lysozyme, 500 μg/mL polymyxin B sulfate (PMBS), and 12.5 U/mL Benzonase. In the case of aqueous screening conditions, the lysis buffer consisted of 10 mM Potassium Phosphate, pH 7.0, 1 mg/mL lysozyme, and 500 μg/mL PMBS. After sealing the plates with air-permeable nylon seals, they were shaken vigorously for 2 hours at room temperature. Cell debris was pelleted by centrifugation (3738 RCF, 10 min., 4° C.) and the clear supernatant assayed directly or stored at 4° C. until use.

For screening in semi-aqueous conditions, with early-stage engineered carboxyesterases, a 120 μL aliquot of substrate solution (720 mL/L DMSO, 90 mL/L 200-proof ethanol, 19.67 mL/L isopropyl-piperazine, 23.5 mL/L ester substrate and 8.5 mL/L 6N HCl) was added to each well of a Costar deep well plate, followed by addition of 80 μL of the recovered lysate supernatant using a Biomek FX robotic instrument (Beckman Coulter, Fullerton, Calif.). A solution resulted that comprised 100 mM ester substrate, 100 mM isopropyl-piperazine, 45% DMSO, 5% EtOH at a final pH of 9.0. The plates were heat-sealed with aluminum/polypropylene laminate heat seal tape at 165° C. for 4 seconds and then shaken overnight (at least 16 hours) at 50° C. Reactions were quenched by the addition of 200 μL of Acetonitrile by a Biomex FX. Plates were resealed, shaken for 5 min, and then centrifuged at 3738 RCF for 10 min. A 20 μL sample of substrate was transferred to a shallow well polypropylene plate (Costar #3365) containing 180 μL of 75% Acetonitrile in water, sealed, shaken for 10 min and then analyzed as described in Example 4.

For screening in organic conditions, with early-stage engineered carboxyesterases, a 150 μL aliquot of recovered lysate supernatant was added to an aluminum 96 well rack (F158359, Unchained Labs, Pleasanton, Calif.) loaded with 1 mL glass vial inserts (S11168, Unchained Labs, Pleasanton, Calif.). This apparatus was then subjected to lyophilization, gently warmed to room temperature, and charged with 4 μL of distilled water using a Multidrop Combi Reagent Dispenser (Thermo Scientific, Waltham, Mass.) followed by 200 μL of organic substrate solution (10.93 mL/L isopropyl-piperazine, 23.5 mL/L ester substrate) in tert-butyl methyl ether (tBME). The plates were then sealed by the use of a Teflon sheet (S11690-2, Unchained Labs, Pleasanton, Calif.) layered beneath two rubber gaskets (S13086, Unchained Labs, Pleasanton, Calif.) and a metal rack lid (F158424, Unchained Labs, Pleasanton, Calif.), attached by seven screws (C151943-050, Unchained Labs, Pleasanton, Calif.). These constructs were then incubated, with shaking, at 50° C. overnight (at least 16 hours). Reactions were quenched by the addition of 200 μL of isopropyl alcohol by a Biomek FX, then sealed, shaken for 10 min, and centrifuged at 235 RCF for 2 minutes to settle residual solids. A 200 μL sample was then transferred to a Costar deep well plate containing 200 μL isopropanol in each well, heat-sealed with aluminum/ polypropylene laminate heat seal tape at 165° C. for 4 seconds, shaken for 10 min and then centrifuged at 3738 RCF for 10 min. A 40 μL sample of substrate was transferred to a shallow well polypropylene plate (Costar #3365) containing 160 μL of Isopropanol, sealed, shaken for 10 min and then analyzed as described in Example 4.

For screening in organic conditions, with late-stage engineered carboxyesterases, a 120 μL aliquot of recovered lysate supernatant was added to an aluminum 96 well rack (F158359, Unchained Labs, Pleasanton, Calif.) loaded with 1 mL glass vial inserts (S11168, Unchained Labs, Pleasanton, Calif.). This apparatus was then subjected to lyophilization, gently warmed to room temperature, and charged with 200 μL of organic substrate solution (53.2 mL/L isopropylpiperazine, 43 mL/L ester substrate) in methyl isobutyl ester (MIBK) followed by 4 μL of distilled water using a Multidrop Combi Reagent Dispenser (Thermo Scientific, Waltham, Mass.). The plates were then sealed by the use of a Teflon sheet (S11690-2, Unchained Labs, Pleasanton, Calif.) layered beneath one rubber gaskets (S13086, Unchained Labs, Pleasanton, Calif.) and a metal rack lid (F158424, Unchained Labs, Pleasanton, Calif.), attached by five screws (C151943-050, Unchained Labs, Pleasanton, Calif.). These constructs were then incubated, with shaking, at 15° C. overnight (at least 16 hours). Reactions were removed from the incubator, and were centrifuged at 235 RCF. A 20 μL sample of supernatant was transferred to a shallow well polypropylene plate (Costar #3365) containing 180 μL isopropanol (with 5 g/L naphthalene) in each well, heat-sealed with aluminum/polypropylene laminate heat seal tape at 165° C. for 4 seconds, shaken for 10 min and then centrifuged at 3738 RCF for 10 min. A 10 μL sample of substrate was transferred to a shallow well polypropylene plate (Costar #3365) containing 190 μL of Isopropanol, sealed, shaken for 10 min and then analyzed as described in Example 4.

Example 6: Amidation in Methyl Isobutyl Ester (MIBK) of Ester Substrate, Formula I. And Amine Substrate, Formula II., by Engineered Carboxyesterases Derived from *A. acidocaldarius* Esterase 2

Improved early-stage carboxyesterases described in Table 3 were evaluated at preparative scale in MIBK as follows. 10 mg of lyophilized enzyme powder was added to a 1.5 mL HPLC vial, along with 15 μL of distilled water. Subsequently, 485 μL of a substrate solution (42.93 mL isopropyl piperazine/L MIBK, 36.4 mL ester/L MIBK) was added, and the vials sealed. The reaction was shaken on an Eppendorf Thermomixer C heated vial shaker at 50° C. and 850 rpm for 16 hours. Reactions were quenched by the addition of 500 μL of isopropanol. A 50 μL sample was then transferred into a shallow well polypropylene plate (Costar #3365) containing 150 μL of Isopropanol, shaken for 10 minutes and then centrifuged at 3738 RCF for 10 min. A 10 μL sample of substrate was transferred to a shallow well polypropylene plate (Costar #3365) containing 190 μL of Isopropanol, sealed, shaken for 10 min and then analyzed, as described in Example 4.

Improved late-stage carboxyesterases described in Table 3 were evaluated at preparative scale in MIBK as follows. 11.25 mg of lyophilized enzyme powder was added to a 1.5 mL HPLC vial, Subsequently, 750 μL of a substrate solution (53.2 mL isopropyl piperazine/L MIBK, 43 mL ester/L MIBK) was added, along with 15 μL of distilled water, and the vials sealed. The reaction was shaken on an Eppendorf Thermomixer C heated vial shaker at 15° C. and 850 rpm for 16 hours. Reactions were quenched by removal of 20 uL as described in late-stage engineered carboxyesterase screening in Example 5 Table 3 provides the SEQ ID NO: corresponding to the carboxyesterase variants there were tested in this fashion, as well as the number of amino acid residue differences from the *A. acidocaldarius* Esterase 2 wild-type carboxyesterase (SEQ ID NO: 2).

Example 7: Amidation in Methyl Isobutyl Ester (MIBK) of Ester Substrate I and Amine Substrate II by Engineered Carboxyesterases Derived from *A. acidocaldarius* Esterase The following example illustrates a gram scale process used to increase conversion of ester substrate, ethyl oxazole-2-carboxylate, the compound of formula I. and amine substrate, 1-isopropyl piperazine, the compound of formula II. This process takes advantage of improved liquid mixing at large scale to increase the conversion of substrate to product. Routine monitoring enables the capture and isolation of greater than 70% overall yield of product.

The large scale reaction process contains the following reaction components:

| | |
|---|---|
| ETHYL OXAZOLE 2-CARBOXYLATE: | 20 G (98%) (141.7 MMOLE) |
| 1-ISOPROPYL PIPERAZINE: | 23.62 G (184.2 MMOLE) |
| CARBOXYESTERASE (SEQ ID NO: 90): | 14 G |
| MIBK: | 400 ML |
| WATER: | 11 ML |

Process. To a 2 L CLR reactor fitted with overhead stirrer was added 340 mL of MIBK and set to stir at ambient temperature. 11 mL of water was then added, followed by gentle heating to 30° C. 14 g of carboxyesterase was charged, followed by a 20 mL MIBK wash. 23.62 g of 1-Isopropyl Piperazine was then charged, followed by a 20 mL MIBK wash. Finally, 20 g of ethyl oxazole 2-carboxylate was added, followed by a final 20 mL MIBK wash. After 16 hours, the conversion exceeded 90%.

Residual solids were filtered and washed with 80 mL MIBK to isolate any adsorbed material. Washes were then pooled and washed with 20 mL of 10% w/w sodium chloride, stirred and separated. The organic phase was collected and concentrated to 60 mL under vacuum, then cooled to 15° C., at which point crystallization began to occur. 70 mL n-heptane was charged over the course of 10 minutes, crystallization allowed to proceed to completion over the course of 2 hours, and then the crystalline material collected by filtration. Crystalline product was washed twice with 80 mL of 1:4 MIBK:n-heptane, and dried at 50° C. under vacuum.

This process resulted in an overall yield (w/w) of 66% as assessed by mass of product.

Example 8: Amidation in Methyl Isobutyl Ester (MIBK) of Ester Substrate I and Amine Substrate IV by Engineered Carboxyesterases Derived from *A. acidocaldarius* Esterase Vial-scale reactions were performed to produce the amide of formula V. using engineered carboxyesterases. 25 mg of lyophilized enzyme powder was added to a 1.5 mL HPLC vial, along with 10 μL of distilled water. Subsequently, 490 μL of a substrate solution (26.72 mL (2S,6R)-2,6-dimethylmorpholine/L MIBK, 24.27 mL ester/L MIBK) was added, and the vials sealed. The reaction was shaken on an Eppendorf Thermomixer C heated vial shaker at 50° C. and 800 rpm for 16 hours. A 100 µL aliquot of each reaction solution was added to a shallow well polypropylene plate (Costar #3365) containing 100 µL of isopropanol, sealed, shaken for 10 minutes and then centrifuged at 3738 RCF for 10 minutes. A 10 µL aliquot of the supernatant was then diluted in 190 µL of acetonitrile containing 25% water in a shallow well polypropylene plate (Costar #3365), sealed, and then shaken at 850 rpm for 5 minutes. Reactions were analyzed as described in Example 4. In all observed cases, enzyme activity closely matched that of the reactions described in Example 6 and in Table 3.

While various specific embodiments have been illustrated and described, it will be appreciated that various changes can be made without departing from the spirit and scope of the invention(s).

```
                              SEQUENCE LISTING

>S00032511
SEQ ID NO: 1
TYPE: DNA, ORGANISM: ALICYCLOBACILLUS
ACIDOCALDARIUSATGCCATTAGATCCTGTGATTCAACAAGTCCTCGATCAACTGAACCGTATGCCAGCCCCT
GACTACAAGCACTTAAGCGCTCAACAGTTTCGTTCACAGCAATCACTGTTTCCACCAGTTAAGAAAGAACCGGT
CGCAGAAGTTCGCGAATTCGACATGGATCTGCCGGGCCGTACCCTGAAAGTCCGTATGTACCGTCCGGAAGGTG
TTGAACCACCATATCCAGCACTGGTTTACTACCATGGTGGCGGTTGGGTTGTTGGTGACCTGGAAACGCATGAT
CCGGTGTGTCGTGTGTTGGCGAAAGATGGACGCGCAGTGGTGTTTAGCGTTGACTACCGTCTGGCACCAGAACA
CAAGTTTCCAGCGGCAGTTGAAGACGCGTATGATGCACTGCAATGGATTGCAGAACGTGCAGCCGATTTCCATC
TTGATCCAGCACGCATTGCAGTTGGCGGCGATTCAGCAGGCGGCAACCTGGCGGCCGTGACTAGTATTCTGGCG
AAAGAACGTGGTGGTCCAGCAATTGCGTTTCAACTGCTGATCTATCCCTCCACTGGTTATGATCCAGCACATCC
ACCAGCAAGTATCGAAGAGAATGCGGAGGGTTACCTGTTAACCGGAGGCATGATGCTGTGGTTTCGTGACCAGT
ACCTGAACAGCCTTGAGGAACTGACTCACCCATGGTTTAGTCCAGTGCTGTACCCGGATCTTAGCGGTTTACCA
CCGGCGTACATTGCAACCGCACAGTACGATCCCCTGCGCGATGTCGGCAAACTTTACGCTGAAGCCCTGAACAA
AGCGGGCGTTAAGGTGGAGATCGAGAACTTCGAGGATCTGATTCATGGCTTCGCGCAGTTCTATTCTCTGAGCC
CAGGCGCAACCAAAGCACTGGTACGTATTGCCGAGAAACTGCGCGATGCGTTGGCG

>S00039799
SEQ ID NO: 3
TYPE: DNA, ORGANISM: ARTIFICIAL
SEQUENCEATGCCATTAGATCCTGTGATTCAACAAGTCCTCGATCAACTGAACCGTATGCCAGCCCCTGACTAC
AAGCACTTAAGCGCTCAACAGTTTCGTTCACAGCAATCACTGTTTCCACCAGTTAAGAAAGAACCGGTCGCAGA
AGTTCGCGAATTCGACATGGATCTGCCGGGCCGTACCCTGAAAGTCCGTATGTACCGTCCGGAAGGTGTTGAAC
CACCATATCCAGCACTGGTTTACTACCATGGTGGCGGTTGGGTTGTTGGTGACCTGGAAACGCATGATCCGGTG
TGTCGTGTGTTGGCGAAAGATGGACGCGCAGTGGTGTTTAGCGTTGACTACCGTCTGGCACCAGAACACAAGTT
TCCAGCGGCAGTTGAAGACGCGTATGATGCACTGCAATGGATTGCAGAACGTGCAGCCGATTTCCATCTTGATC
CAGCACGCATTGCAGTTGGCGGCGATTCAGCAGGCGGCAACCTGGCGGCCGTGACTAGTATTCTGGCGAAAGAA
CGTGGTGGTCCAGCAATTGCGTTTCAACTGCTGATCTATCCCTCCACTGGTTATGATCCAGCACATCCACCAGC
AAGTATCCTTGAGAATGCGGAGGGTTACCTGTTAACCGGAGGCATGATGCTGTGGTTTCGTGACCAGTACCTGA
ACAGCCTTGAGGAACTGACTCACCCATGGTTTAGTCCAGTGCTGTACCCGGATCTTAGCGGTTTACCACCGGCG
TACATTGCAACCGCACAGTACGATCCCCTGCGCGATGTCGGCAAACTTTACGCTGAAGCCCTGAACAAAGCGGG
CGTTAAGGTGGAGATCGAGAACTTCGAGGATCTGATTCATGGCTTCGCGCAGTTCTATTCTCTGAGCCCAGGCG
CAACCAAAGCACTGGTACGTATTGCCGAGAAACTGCGCGATGCGTTGGCG

>S00039972
SEQ ID NO: 5
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTTCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCCACTGGTTATGATCCAGCACATCCACCAGCAAGTATCA
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00039989
SEQ ID NO: 7
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTTCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCACAAGTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCCACTGGTTATGATCCAGCACATCCACCAGCAAGTATCT
ATGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG
```

SEQUENCE LISTING

>S00040129
SEQ ID NO: 9
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTTCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCCACTGGTTATGATCCAGCACATCCACCAGCAAGTATCT
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00040188
SEQ ID NO: 11
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTTCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCCACTGGTTATGATCCAGCACATCCACCAGCAAGTATCA
TGGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00044917
SEQ ID NO: 13
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAGCAGTTTCGTTCACAGCAATCACTGTTGCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAGAGCATGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAATTTTATTCTCTGAGCCCAGGCGCAACCAAA
GCACTGGTACGTATTGCCGAGAAACTGCGCGATGCGTTGGCG

>S00044931
SEQ ID NO: 15
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAGCAGTTTCGTTCACAGCAATCACTGTTTCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAG
GCACTGGTACGTATTGCCGAGAAACTGCGCGATGCGTTGGCG

>S00044943
SEQ ID NO: 17
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTGCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CGGGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG

```
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACGCATGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCCTC
GCACTGGTACGTATTGCCGAGAAACTGCGCGATGCGTTGGCG

>S00045046
SEQ ID NO: 19
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTCCCACCAGTTAAGAAAGAACCGGTCGCAGAAGTTCGCG
AATTCGACATGGATCTGCCGGGCCGTACCCTGAAAGTCCGTATGTACCGACCGGAAGGTGTTGAACCACCATAT
CCGGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAGAGCATGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAG
GCACTGGTACGTATTGCCGAGAAACTGCGCGATGCGTTGGCG

>S00045575
SEQ ID NO: 21
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00047040
SEQ ID NO: 23
TYPE: DNA, ORGANISM: ARTIFICIAL
ATGCCATTAGATCCTGTGATTCAACAAGTCCTCGATCAACTGAACCGTATGCCAGCCACCTGACTACAAGCACTT
AAGCGCTCAACAGTTTCGTTCACAGCAATCACTGTTTCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCATGACTGGTTATGATCCAGCACATCCACCAGCAAGTATCC
TTGAGAATGCGGAGGGTTACCTGTTAGAGGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCGTC
GCACTGGTACGTATTGCCGAGAAACTGCGCGATGCGTTGGCG

>S00048311
SEQ ID NO: 25
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCCCGCAACAGTTGCGTTCACAGCAATCACTGTTTCCACCAGTTAAGAAAGAACCGGTCGCAGAAGTTCGCG
AATTCGACATGGATCTGCCGGGTCGTACCCTGAAAGTCCGTATGTACCGTCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAATGGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCACTGGTTATGATCCAGCACATCCACCAGCAAGTATCA
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGGGGTTCTATTCTCTGAGCCCAGGCGCAACCAAA
GCACTGGTACGTATTGCCGAGAAACTGCGCGATGCGTTGGCG
```

SEQUENCE LISTING

>S00048430
SEQ ID NO: 27
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAGTCACTGTTTCCACCAGTTAAGAAAGAACCGGTCGCAGAAGTTCGCG
AATTCGACATGGATCTGCCGATGCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAATGGGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCCACTGGTTATGATCCAGCACATCCACCAGCAAGTATCC
TTGAGAATGCGGAGGGTTACCTGTTAACCCATGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAAG
TGGAGATCGAGAACTTCGAGGATCTGATTCATGGCTTCGCGGGGTTCTATTCTCTGAGCCCAGGCGCAACCAGA
GCACTGGTACGTATTGCCGAGAAACTGCGCGATGCGTTGGCG

>S00048441
SEQ ID NO: 29
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTTCCGCCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCCGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCCACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAAG
TGGAGATCGAGAACTTCGAGGATCTGATTCATGGCTTCGCGGGGTTCTATTCTCTGAGCCCAGGCGCAACCAAA
GCACTGGTACGTATTGCCGAGAAACTGCGCGATGCGTTGGCG

>S00048480
SEQ ID NO: 31
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTTCCGCCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAATGGGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCCGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCCACTGGTTATGATCCAGCACATCCACCAGCAAGTATCA
TTGAGAATGCGGAGGGTTACCTGTTAACCGGTGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAAG
TGGAGATCGAGAACTTCGAGGATCTGATTCATGGCTTCGCGGGGTTCTATTCTCTGAGCCCAGGCGCAACCAAA
GCACTGGTACGTATTGCCGAGAAACTGCGCGATGCGTTGGCG

>S00048593
SEQ ID NO: 33
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAATCACTGTTTCCACCAGTTAAGAAAGAACCGGTCGCAGAAGTTCGCG
AATTCGACATGGATCTGCCGGGCCGTACCCTGAAAGTCCGTATGTACCGTCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAATGGGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCCGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTCCACTGGTTATGATCCAGCACATCCACCAGCAAGTATCC
TTGAGAATGCGGAGGGTTACCTGTTAACCGGTGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTGATG
TGGAGATCGAGAACTTCGAGGATCTGATTCATGGCTTCGCGGGGTTCTATTCTCTGAGCCCAGGCGCAACCAAA
GCACTGGTACGTATTGCCGAGAAACTGCGCGATGCGTTGGCG

>S00052854
SEQ ID NO: 35
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACCTGACCCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAATGGGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC

SEQUENCE LISTING

```
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00053124
SEQ ID NO: 37
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAAAGCCTGTTTCCACCAGTTAAGAAAGAACCGGTCGCAGAACTGCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGTTGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00053286
SEQ ID NO: 39
TYPE: DNA, ORGANISM: ARTIFICIAL
ATGCCATTAGATCCTGTGATTCAATATGTCCTCGATCAACTGAACCGTATGCCACGTCCTGACTACAAGCACTT
AAGCGCTCAACAGTTTCGTTCACAGAACCACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTGATG
TGGAGATCGAGAACTTCGAGGATCTGATTCATGGCTTCGCGCAGTTCTATTCTCTGAGCCCAGGCGCAACCCGT
GCACTGGTACGTATTGCCGAGAAACTGCGCGATGCGTTGGCG

>S00053297
SEQ ID NO: 41
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGGAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTGATG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00053319
SEQ ID NO: 43
TYPE: DNA, ORGANISM: ARTIFICIAL
ATGCCATTAGATCCTGTGATTCAATATGTCCTCGATCAACTGAACCGTATGCCACGTCCTGACTACAAGCACTT
AAGCGCTCAACAGTTTCGTTCACAGGAACACCTGTTTCCACCAGTTAAGAAAGAACCGGTCGTGGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTGATG
TGGAGATCGAGAACTTCCAGGATCTGATTCATGGCTTCGCGCAGTTCTATTCTCTGAGCCCAGGCGCAACCCGT
GCACTGGTACGTATTGCCGAGAAACTGCGCGATGCGTTGGCG
```

SEQUENCE LISTING

>S00053506
SEQ ID NO: 45
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGAACCACCTGTTTCCACCAGTTAAGAAAGAACCGGTCGTGGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCCAGGATCTGATTCATGGCTTCGCGCAGTTCTATTCTCTGAGCCCAGGCGCAACCCGT
GCACTGGTACGTATTGCCGAGAAACTGCGCGATGCGTTGGCG

>S00054201
SEQ ID NO: 47
TYPE: DNA, ORGANISM: ARTIFICIAL
ATGCCATTAGATCCTGTGATTCAACAAGTCCTCGATCAACTGAACCGTATGCCAGCCCCTGACTACAAGCACTT
AAGCGCTCAACAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACGTGCCGGAAGGTGTTGAACCACCATAT
CCAGCACTGGTTTACTACCATGGTGGCGGTTGGGTTGTTGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATTATGCACATCCACCAGCAAGTATCC
TTGAGAATGCGGAGGGTTACCTGTTAGAAGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTACCGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00054685
SEQ ID NO: 49
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGGAACACCTGTTTCCACCAGTTAAGAAAGAACCGGTCGTGGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTCGTGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00054833
SEQ ID NO: 51
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGAACCACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCCGT
GCACTGGTACGTATTGCCGAGAAACTGCGCGATGCGTTGGCG

>S00054853
SEQ ID NO: 53
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC

ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00058614
SEQ ID NO: 55
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGAGTTTCTATTCTCTGAGCCCAGGCGCAACCAAA
GCACTGGTACGTATTGCCGAGAAACTGCGCGATGCGTTGGCG

>S00059197
SEQ ID NO: 57
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGGTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00059305
SEQ ID NO: 59
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGGAACACCTGTTTCCACCAGTTAAGAAAGAACCGGTCGCAGAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00059320
SEQ ID NO: 61
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACCTGTTTCCACCAGTTAAGAAAGAACCGGTCGCAGAAGTTCGCG
AATTCGACATGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTTTGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

```
>S00059754
SEQ ID NO: 63
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTATTCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00059759
SEQ ID NO: 65
TYPE: DNA, ORGANISM: ARTIFICIAL
ATGCCATTAGATCCTGTGATTCAATATGTCCTCGATCAACTGAACCGTATGCCAGCCATTGACTACAAGCACTT
AAGCGCTCAACAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00059902
SEQ ID NO: 67
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00060141
SEQ ID NO: 69
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAAGATTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00060676
SEQ ID NO: 71
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCAGGTCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
```

ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00060772
SEQ ID NO: 73
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTAGTCAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTGACCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00066575
SEQ ID NO: 75
TYPE: DNA, ORGANISM: ARTIFICIAL
ATGCCATTAGATCCTGTGATTCAATATGTGCTCGATCAACTGAACCGTATGCCAGCCCCTGACTACAAGCACTT
AAGCGCTCAACAGGTTCGTTCACAACAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTCTTC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00067402
SEQ ID NO: 77
TYPE: DNA, ORGANISM: ARTIFICIAL
ATGCCATTAGATCCTGTGATTCAATATGTGCTCGATCAACTGAACCGTATGCCAGCCCCTGACTACAAGCACTT
AAGCGCTCAACAGTTTCGTTCACAGCAACACATTGGTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATACGATTCATGGCTTCGCGCAGTTTTATTCTATTAGCCCAGGCGCAACCAAA
GCACTGGTACGTATTGCCGAGAAACTGCGCGATGCGTTGGCG

>S00067403
SEQ ID NO: 79
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACATGGGTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATATGATTCATGGCTTCGCGCAGTTCTATTCTATTAGCCCAGGCGCAACCAAA
GCACTGGTACGTATTGCCGAGAAACTGCGCGATGCGTTGGCG

SEQUENCE LISTING

>S00067700
SEQ ID NO: 81
TYPE: DNA, ORGANISM: ARTIFICIAL
ATGCCATTAGATCCTGTGATTCAATATATGCTCGATCAACTGAACCGTATGCCAGCCCCTGACTACAAGCACTT
AAGCGCTCAACAGTTTCGTTCACAGCAACACTTGGGTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTAATTCATGGCTTCGCGCAGTTCTATTCTCTGAGCCCAGGCGCAACCAAA
GCACTGGTACGTATTGCCGAGAAACTGCGCGATGCGTTGGCG

>S00068003
SEQ ID NO: 83
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTAGTCAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTACGATCCAGCACATCCACCAGCAAGTATTC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGTAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00068079
SEQ ID NO: 85
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTAGTCAGTTTCGTTCACAGCAACATCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCGGGCGGCAACCTGGCGGCCGTGACTAGTATTCTGGCGAAAGAACGTGGTGG
TCCAGCAATTGCGTTTCAACTGCTGATCTATCCCTTTACTGGTTACGATCCAGCACATCCACCAGCAAGTCTTC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGTAAACTTTACGCTGAAGCCCTGACCAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00068124
SEQ ID NO: 87
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTAGTCAGTTTCGTTCACAGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTCTTC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGTAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00068512
SEQ ID NO: 89
TYPE: DNA, ORGANISM: ARTIFICIAL
ATGCCATTAGATCCTGTGATTCAATATGTCCTCGATCAACTGAACCGTATGCCAGCCCCCGACTACAAGCACTT
AAGCGCTCAACAAGTTCGTTCATGGCAACACCTGTTTCCACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CGGGCACTGGTTTACTACCATGGTGGCGGTTGGGTTGCGGGTGACCTGGAAACGCATGATCCGGTGTGTCGTGT
GTTGGCGAAATGGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC

ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGATATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAAG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00068639
SEQ ID NO: 91
TYPE: DNA, ORGANISM: ARTIFICIAL
ATGCCATTAGATCCTGTGATTCAATATGTCCTCGATCAACTGAACCGTATGCCAGCCATTGACTACAAGCACTT
AAGCGCTCAACAAGTTCGTTCATGGCAACACCTGTTTCCACCAGTTAAGAAGAACCGGTCCGCGAAGTTCGCG
AATTCGACATGGATCTGCCGGGCCGTACCCTGAAAGTCCGTATGTACACGCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAATGGGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGATATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTAGAGCCCTGAACAAAGCGGGCGTTAAAG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00068752
SEQ ID NO: 93
TYPE: DNA, ORGANISM: ARTIFICIAL
ATGCCATTAGATCCTGTGATTCAATATGTCCTCGATCAACTGAACCGTATGCCAGCCCCTGACTGGAAGCACTT
AAGCGCTCAACAGTTTCGTTCACAGCAACACCTGTTTCCACCAGTTAAGAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CGGGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCGGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTATTAGCCCAGGCGCAACCAAA
GCACTGGTACGTATTGCCGAGAAACTGCGCGATGCGTTGGCG

>S00176502
SEQ ID NO: 95
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACCTGTTTCCACCAGTTAAGAAGAACCGGTCAAAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACACCGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGAACTTCTATTCTCTGAGCCCAGGCGCAACCAAA
GCACTGGTACGTATTGCCGAGAAACTGCGCGATGCGTTGGCG

>S00176595
SEQ ID NO: 97
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAACACCTGTTTCCACCAGTTAAGAAGAACCGGTCAAAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACACCGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGAGCTTCTATTCTCTGAGCCCAGGCGCAACCAAA
GCACTGGTACGTATTGCCGAGAAACTGCGCGATGCGTTGGCG

SEQUENCE LISTING

\>S00176980
SEQ ID NO: 99
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTTGCCAGTTTCGTTCACAGCAACACCTGTTTGAACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

\>S00177019
SEQ ID NO: 101
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAAAGCCTGTTTCCACCAGTTAAGAAAGAACCGGTCGCAGAAGTTCGCG
AATTCGACATGGATCTGCCGGGCCGTACCCTGAAAGTCCGTATGTACCTGCCGGAAGGTGTTGAACCACCATAT
CCAGCACTGGTTTACTACCATGGTGGCGGTTGGACCGCGGGTGACCTGGAAACGCATGATCCGATGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCCGGCGGCCGTGACTAGTATTCTGGCGAAAGAACGTGGTGG
TCCAGCAATTGCGTTTCAACTGCTGATCCAGCCCTTTACTGGTTTTGATCCAGCACATCCACCAGCAAGTATCC
TTGAGAATGCGGAGGGTTACTTTTTAACCGGAGGCATGATGGATTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGAACGATGTCGGCAAACTTTACGCTGAAGCCCTGAACAAAGCGGGCCTGAAGG
TGGAGATCGAGAACTTCGAGGATCTGATTCATGGCTTCGCGAGCTTCTATTCTCTGAGCCCAGGCGCAACCAAA
GCACTGGTACGTATTGCCGAGAAACTGCGCGATGCGTTGGCG

\>S00177053
SEQ ID NO: 103
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTCAACAGTTTCGTTCACAGCAAAGCCTGTTTCCACCAGTTAAGAAAGAACCGGTCGCAGAAGTTCGCG
AATTCGACATGGATCTGCCGGGCCGTACCCTGAAAGTCCGTATGTACCTGCCGGAAGGTGTTGAACCACCATAT
CCAGCACTGGTTTACTACCATGGTGGCGGTTGGACCGCGGGTGACCTGGAAACGCATGATCCGATGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACTTTTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCTGGCAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGAGCTTCTATTCTCTGAGCCCAGGCGCAACCAAA
GCACTGGTACGTATTGCCGAGAAACTGCGCGATGCGTTGGCG

\>S00177175
SEQ ID NO: 105
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTTGCCAGTTTCGTTCACAGCAACACCTGTTTCCACCAGTTAAGAAAGAACCGGTCGCAGAAGTTCGCG
AATTCGACATGCGTCTGCCGGGCCGTACCCTGAAAGTCCGTATGTACCGCCCGGAAGGTGTTGAACCACCATAT
CGTGCACTGGTTTACTACCATGGTGGCGGTTGGGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATGGCGTTTCAACTGCTGATCTATCCCTTTACTGGTTATGATCCAGCACATCCACCAGCAAGTATCC
TTGAGAATGCGGAGGGTTACTTTTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AGTGGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

\>S00187023
SEQ ID NO: 107
TYPE: DNA, ORGANISM: ARTIFICIAL
ATGCCATTAGATCCTGTGCTTCAATATGTGCTCGATCAACTGAACCGTATGCCAGCCCCTGACTACAAGCACTT
AAGCGCTTGCCAGTTTCGTTCACAGCAACACCTGTTTGAACCAGTTAAGAAAGAACCGGTCGCTGAAGTTCGCG
AATTCGACATGGACCTGCCGGGCCGTACCCTGAAAGTCCGTATGTACCGCCCGGAAGGTGTTGAACCACCATAT
CCAGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC

```
ATTGCAGTTGGCGGCGATTCAGCAGGCGGCAACCTCGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TGGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00187052
SEQ ID NO: 109
TYPE: DNA, ORGANISM: ARTIFICIAL
ATGCCATTAGATCCTGTGATTCAATATGTGCTCGATCAACTGAACCGTATGCCAGCCCCTGACTACAAGCACTT
AAGCGCTTGCCAGTTTCGTTCACAGCAACACCTGTTTGAACCAGTTAAGAAAGAACCGGTCAAAGAAGTTCGCG
AATTCGACATGGACCTGCCGGGCCGTACCCTGAAAGTCCGTATGTACCGCCCGGAAGGTGTTGAACCACCATAT
CCAGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTCGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TGGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00187266
SEQ ID NO: 111
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTTGCCAGTTTCGTTCACAGCAACACACGTTTTGGCCAGTTAAGAAAGAACCGGTCGCAGAAGTTCGCG
AATTCGACATGCAGCTGCCGGGCCGTACCCTGAAAGTCCGTATGTACACGCCGGAAGGTGTTGAACCACCATAT
CCAGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00187283
SEQ ID NO: 113
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTTGCCAGTTTCGTTCACAGCAACACACGTTTTGGCCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CGCGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00187324
SEQ ID NO: 115
TYPE: DNA, ORGANISM: ARTIFICIAL
ATGCCATTAGATCCTGTGATTCAATATGTCCTCGATCAACTGAACCGTATGCCAGCCCCTGACTGGAAGCACTT
AAGCGCTTGCCAGTTTCGTTCACAGCAACACATGTTTTGGCCAGTTAAGAAAGAACCGGTCGCCGAAGTTCGCG
AATTCGACATGGATCTGCCGGGCCGTACCCTGAAAGTCCGTATGTACCGCCCGGAAGGTGTTGAACCACCATAT
CGCGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG
```

SEQUENCE LISTING

>S00187421
SEQ ID NO: 117
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTTGCCAGTTTCGTTCACAGCAACACACGTTTTGGCCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
ATGGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00188542
SEQ ID NO: 119
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTTGCCAGTTTCGTTCACAGCAACACCTGTTTGAACCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CCAGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCACAGTTCTATTCTCTGAGCCCAGGCGCAACCAAA
GCACTGGTACGTATTGCCGAGAAACTGCGCGATGCGTTGGCG

>S00207145
SEQ ID NO: 121
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTTGCCAGTTTCGTTCACAGCAACACACGTTTTGGCCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CGCGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGTGTTTCTATTCTCTGAGCCCAGGCGCAACCAAA
GCACTGGTACGTATTGCCGAGAAACTGCGCGATGCGTTGGCG

>S00208699
SEQ ID NO: 123
TYPE: DNA, ORGANISM: ARTIFICIAL
ATGTTGTTAGATCCTGTGATTCAATATGTCCTCGATCAACTGAACCGTATGCCAGCCCCTGACTACAAGCACTT
AAGCGCTTGCCAGTTTCGTTCACAGCAACACACGTTTTGGCCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CGCGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCTGATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00209368
SEQ ID NO: 125
TYPE: DNA, ORGANISM: ARTIFICIAL
ATGCCATTAGATCCTGTGATTCAATATGTCCTCGATCAACTGAACCGTATGCCAGCCCCTGACTACAAGCACTT
AAGCGCTTGCCAGTTTCGTTCACAGCAACACACGTTTTGGCCAGTTAAGAAAGAACCGGTCGCAGAAGTTCGCG
AATTCGACATGGATCTGCCGGGCCGTACCCTGAAAGTCCGTATGTACCGCCCGGAAGGTGTTGAACCACCATAT
CGCGCACTGGTTTACTACCATGGTGGCGGTGGCGTTGCGGGTGACCTGGAAACGCATGATCCGGTGTGTCGTGT
GTTGGCGAAAGATGGACGCGCAGTGGTGTTTAGCGTTGACTACCGTCTGGCACCAGAACACAAGTTTCCAGCGG
CAGTTGAAGACGCGTATGATGCACTGCAATGGATTGCAGAACGTGCAGCCGATTTCCATCTTGATCCAGCACGC

SEQUENCE LISTING

```
ATTGCAGTTGGCGGCGATTCAGCAGGCGGCAACCTGGCGGCCGTGACTAGTATTCTGGCGAAAGAACGTGGTGG
TCCAGCAATTGCGTTTCAACTGCAAATCTATCCCTTTACTGGTTATGATCCAGCACATCCACCAGCAAGTATCC
TTGAGAATGCGGAGGGTTACCTGTTAACCGGAGGCATGATGCTGTGGTTTCGTAATCAGTACCTGAACAGCCTT
GAGGAACTGACTCACCCATGGTTTAGTCCAGTGCTGTACCCGGATCTTAGCGGTTTACCACCGGCGTACATTGC
AACCGCACAGTACGATCCCCTGCGCGATGTCGGCAAACTTTACGCTGAAGCCCTGAACAAAGCGGGCGTTAAGG
TGGAGATCGAGAACTTCGAGGATCTGATTCATGGCTTCGCGCAGTTCTATTCTCTGAGCCCAGGCGCAACCAAA
GCACTGGTACGTATTGCCGAGAAACTGCGCGATGCGTTGGCG

>S00032511
SEQ ID NO: 2
TYPE: PROTEIN, ORGANISM: ALICYCLOBACILLUS ACIDOCALDARIUS
MPLDPVIQQVLDQLNRMPAPDYKHLSAQQFRSQQSLFPPVKKEPVAEVREFDMDLPGRTLKVRMYRPEGVEPPY
PALVYYHGGGWVVGDLETHDPVCRVLAKDGRAVVESVDYRLAPEHKEPAAVEDAYDALQWIAERAADFHLDPAR
IAVGGDSAGGNLAAVTSILAKERGGPAIAFQLLIYPSTGYDPAHPPASIEENAEGYLLTGGMMLWFRDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00039799
SEQ ID NO: 4
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
PALVYYHGGGWVVGDLETHDPVCRVLAKDGRAVVESVDYRLAPEHKFPAAVEDAYDALQWIAERAADFHLDPAR
IAVGGDSAGGNLAAVTSILAKERGGPAIAFQLLIYPSTGYDPAHPPASILENAEGYLLTGGMMLWFRDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00039972
SEQ ID NO: 6
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
PALVYYHGGGWVVGDLETHDPVCRVLAKDGRAVVESVDYRLAPEHKFPAAVEDAYDALQWIAERAADFHLDPAR
IAVGGDSAGGNLAAVTSILAKERGGPAIAFQLLIYPSTGYDPAHPPASIIENAEGYLLTGGMMLWFRDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00039989
SEQ ID NO: 8
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
PALVYYHGGGWVVGDLETHDPVCRVLAKDGRAVVESVDYRLAPEHKFPAAVEDAYDALQWIAERAADFHLDPAR
IAVGGDSAGGNLAAVTSILAKERGGPAIAFQLLIYPSTGYDPAHPPASIYENAEGYLLTGGMMLWFRDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00040129
SEQ ID NO: 10
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPSTGYDPAHPPASIFENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00040188
SEQ ID NO: 12
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
RALVYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPSTGYDPAHPPASIMENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00044917
SEQ ID NO: 14
TYPE: PRT, ORGANISM: ARTIFICIAL SEQUENCE
MPLDPVIQQVLDQLNRMPAPDYKHLSAQQFRSQQSLLPPVKKEPVAEVREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLEHGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00044931
SEQ ID NO: 16
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
```

EELTHPWFSPVLYPDLSGLPPAYIATAQYDPLRDVGKLYAEALNKAGVKVEIENFEDLIHGFAQFYSLSPGATK
ALVRIAEKLRDALA

>S00044943
SEQ ID NO: 18
TYPE: PRT, ORGANISM: ARTIFICIAL SEQUENCE
MPLDPVIQQVLDQLNRMPAPDYKHLSAQQFRSQQSLLPPVKKEPVAEVREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTHGMMLWERDQYLNSL
EELTHPWFSPVLYPDLSGLPPAYIATAQYDPLRDVGKLYAEALNKAGVKVEIENFEDLIHGFAQFYSLSPGATL
ALVRIAEKLRDALA

>S00045046
SEQ ID NO: 20
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLEHGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00045575
SEQ ID NO: 22
TYPE: PRT, ORGANISM: ARTIFICIAL SEQUENCE
MPLDPVIQQVLDQLNRMPAPDYKHLSAQQFRSQQHLFPPVKKEPVAEVREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00047040
SEQ ID NO: 24
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPMTGYDPAHPPASILENAEGYLLEGGMMLWERDQYLNSL
EELTHPWFSPVLYPDLSGLPPAYIATAQYDPLRDVGKLYAEALNKAGVKVEIENFEDLIHGFAQFYSLSPGATV
ALVRIAEKLRDALA

>S00048311
SEQ ID NO: 26
TYPE: PRT, ORGANISM: ARTIFICIAL SEQUENCE
MPLDPVIQQVLDQLNRMPAPDYKHLSPQQLRSQQSLFPPVKKEPVAEVREFDMDLPGRTLKVRMYRPEGVEPPY
RALVYYHGGGWVVGDLETHDPVCRVLAKWGRAVVESVDYRLAPEHKEPAAVEDAYDALQWIAERAADFHLDPAR
LAVGGDSAGGNLAAVTSILAKERGGPAIAFQLLIYPSTGYDPAHPPASIIENAEGYLLTGGMMLWERDQYLNSL
EELTHPWFSPVLYPDLSGLPPAYIATAQYDPLRDVGKLYAEALNKAGVKVEIENFEDLIHGFAGFYSLSPGATK
ALVRIAEKLRDALA

>S00048430
SEQ ID NO: 28
TYPE: PRT, ORGANISM: ARTIFICIAL SEQUENCE
MPLDPVIQQVLDQLNRMPAPDYKHLSAQQFRSQQSLFPPVKKEPVAEVREFDMDLPMRTLKVRMYRPEGVEPPY
RALVYYHGGGWVVGDLETHDPVCRVLAKWGRAVVESVDYRLAPEHKEPAAVEDAYDALQWIAERAADFHLDPAR
LAVGGDSAGGNLAAVTSILAKERGGPAIAFQLLIYPSTGYDPAHPPASILENAEGYLLTHGMMLWERDQYLNSL
EELTHPWFSPVLYPDLSGLPPAYIATAQYDPLRDVGKLYAEALNKAGVKVEIENFEDLIHGFAGFYSLSPGATR
ALVRIAEKLRDALA

>S00048441
SEQ ID NO: 30
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPSTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAGFYSLSPGATK
ALVRIAEKLRDALA

>S00048480
SEQ ID NO: 32
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
RALVYYHGGGWVVGDLETHDPVCRVLAKWGRAVVESVDYRLAPEHKEPAAVEDAYDALQWIAERAADFHLDPAR
LAVGGDSAGGNLAAVTSILAKERGGPAIAFQLLIYPSTGYDPAHPPASIIENAEGYLLTGGMMLWERDQYLNSL
EELTHPWFSPVLYPDLSGLPPAYIATAQYDPLRDVGKLYAEALNKAGVKVEIENFEDLIHGFAGFYSLSPGATK
ALVRIAEKLRDALA

SEQUENCE LISTING

```
>S00048593
SEQ ID NO: 34
TYPE: PRT, ORGANISM: ARTIFICIAL SEQUENCE
MPLDPVIQQVLDQLNRMPAPDYKHLSAQQFRSQQSLFPPVKKEPVAEVREFDMDLPGRTLKVRMYRPEGVEPPY
RALVYYHGGGWVVGDLETHDPVCRVLAKWGRAVVESVDYRLAPEHKEPAAVEDAYDALQWIAERAADFHLDPAR
LAVGGDSAGGNLAAVTSILAKERGGPAIAFQLLIYPSTGYDPAHPPASILENAEGYLLTGGMMLWERDQYLNSL
EELTHPWFSPVLYPDLSGLPPAYIATAQYDPLRDVGKLYAEALNKAGVDVEIENFEDLIHGFAGFYSLSPGATK
ALVRIAEKLRDALA

>S00052854
SEQ ID NO: 36
TYPE: PRT, ORGANISM: ARTIFICIAL SEQUENCE
MPLDPVIQYVLDQLNRMPAPDYKHLSAQQFRSQQHLTPPVKKEPVAEVREFDMDLPGRTLKVRMYRPEGVEPPY
RALVYYHGGGWVVGDLETHDPVCRVLAKWGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00053124
SEQ ID NO: 38
TYPE: PRT, ORGANISM: ARTIFICIAL SEQUENCE
MPLDPVIQQVLDQLNRMPAPDYKHLSAQQFRSQQSLFPPVKKEPVAELREFDMDLPGRTLKVRMYRPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00053286
SEQ ID NO: 40
TYPE: PRT, ORGANISM: ARTIFICIAL SEQUENCE
MPLDPVIQYVLDQLNRMPRPDYKHLSAQQFRSQNHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVDVEIENFEDLIHGFAQFYSLSPGATR
ALVRIAEKLRDALA

>S00053297
SEQ ID NO: 42
TYPE: PRT, ORGANISM: ARTIFICIAL SEQUENCE
MPLDPVIQYVLDQLNRMPAPDYKHLSAQQFRSQEHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVDVEIENFEDLIHGFAQFYSLSPGATK
ALVRIAEKLRDALA

>S00053319
SEQ ID NO: 44
TYPE: PRT, ORGANISM: ARTIFICIAL SEQUENCE
MPLDPVIQYVLDQLNRMPRPDYKHLSAQQFRSQEHLFPPVKKEPVVEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVDVEIENFQDLIHGFAQFYSLSPGATR
ALVRIAEKLRDALA

>S00053506
SEQ ID NO: 46
TYPE: PRT, ORGANISM: ARTIFICIAL SEQUENCE
MPLDPVIQYVLDQLNRMPAPDYKHLSAQQFRSQNHLFPPVKKEPVVEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFQDLIHGFAQFYSLSPGATR
ALVRIAEKLRDALA

>S00054201
SEQ ID NO: 48
TYPE: PRT, ORGANISM: ARTIFICIAL SEQUENCE
MPLDPVIQQVLDQLNRMPAPDYKHLSAQQFRSQQHLFPPVKKEPVAEVREFDMDLPGRTLKVRMYVPEGVEPPY
RALVYYHGGGWVVGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDYAHPPASILENAEGYLLEGGMMLWERDQYLNSL
EELTHPWFSPVLYPDLSGLPPAYIATAQYDPLRDVGKLYATALNKAGVKVEIENFEDLIHGFAQFYSLSPGATK
ALVRIAEKLRDALA

>S00054685
SEQ ID NO: 50
TYPE: PRT, ORGANISM: ARTIFICIAL SEQUENCE
MPLDPVIQYVLDQLNRMPAPDYKHLSAQQFRSQEHLFPPVKKEPVVEVREFDMDLPGRTLKVRMYRPEGVEPPY
RALVYYHGGGWVAGDLETHDPVCRVLAKDGRAVVESVDYRLAPEHKEPAAVEDAYDALQWIAERRADFHLDPAR
```

SEQUENCE LISTING

```
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00054833
SEQ ID NO: 52
TYPE: PRT, ORGANISM: ARTIFICIAL SEQUENCE
MPLDPVIQYVLDQLNRMPAPDYKHLSAQQFRSQNHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATR
ALVRIAEKLRDALA

>S00054853
SEQ ID NO: 54
TYPE: PRT, ORGANISM: ARTIFICIAL SEQUENCE
MPLDPVIQYVLDQLNRMPAPDYKHLSAQQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00058614
SEQ ID NO: 56
TYPE: PRT, ORGANISM: ARTIFICIAL SEQUENCE
MPLDPVIQYVLDQLNRMPAPDYKHLSAQQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFASFYSLSPGATK
ALVRIAEKLRDALA

>S00059197
SEQ ID NO: 58
TYPE: PRT, ORGANISM: ARTIFICIAL SEQUENCE
MPLDPVIQYVLDQLNRMPAPDYKHLSAQQVRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00059305
SEQ ID NO: 60
TYPE: PRT, ORGANISM: ARTIFICIAL SEQUENCE
MPLDPVIQYVLDQLNRMPAPDYKHLSAQQFRSQEHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00059320
SEQ ID NO: 62
TYPE: PRT, ORGANISM: ARTIFICIAL SEQUENCE
MPLDPVIQYVLDQLNRMPAPDYKHLSAQQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGFDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00059754
SEQ ID NO: 64
TYPE: PRT, ORGANISM: ARTIFICIAL SEQUENCE
MPLDPVIQYVLDQLNRMPAPDYKHLSAQQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWFRIQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00059759
SEQ ID NO: 66
TYPE: PRT, ORGANISM: ARTIFICIAL SEQUENCE
MPLDPVIQYVLDQLNRMPAIDYKHLSAQQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA
```

SEQUENCE LISTING

>S00059902
SEQ ID NO: 68
TYPE: PRT, ORGANISM: ARTIFICIAL SEQUENCE
MPLDPVIQYVLDQLNRMPAPDYKHLSAQQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00060141
SEQ ID NO: 70
TYPE: PRT, ORGANISM: ARTIFICIAL SEQUENCE
MPLDPVIQYVLDQLNRMPAPDYKHLSAQDFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00060676
SEQ ID NO: 72
TYPE: PRT, ORGANISM: ARTIFICIAL SEQUENCE
MPLDPVIQYVLDQLNRMPAPDYKHLSAQQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00060772
SEQ ID NO: 74
TYPE: PRT, ORGANISM: ARTIFICIAL SEQUENCE
MPLDPVIQYVLDQLNRMPAPDYKHLSASQFRSQQHLEPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERDQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00066575
SEQ ID NO: 76
TYPE: PRT, ORGANISM: ARTIFICIAL SEQUENCE
MPLDPVIQYVLDQLNRMPAPDYKHLSAQQVRSQQHLEPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASLLENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00067402
SEQ ID NO: 78
TYPE: PRT, ORGANISM: ARTIFICIAL SEQUENCE
MPLDPVIQYVLDQLNRMPAPDYKHLSAQQFRSQQHIGPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDTIHGFAQFYSISPGATK
ALVRIAEKLRDALA

>S00067403
SEQ ID NO: 80
TYPE: PRT, ORGANISM: ARTIFICIAL SEQUENCE
MPLDPVIQYVLDQLNRMPAPDYKHLSAQQFRSQQHMGPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDMIHGFAQFYSISPGATK
ALVRIAEKLRDALA

>S00067700
SEQ ID NO: 82
TYPE: PRT, ORGANISM: ARTIFICIAL SEQUENCE
MPLDPVIQYMLDQLNRMPAPDYKHLSAQQFRSQQHLGPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00068003
SEQ ID NO: 84
TYPE: PRT, ORGANISM: ARTIFICIAL SEQUENCE
MPLDPVIQYVLDQLNRMPAPDYKHLSASQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR

SEQUENCE LISTING

```
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00068079
SEQ ID NO: 86
TYPE: PRT, ORGANISM: ARTIFICIAL SEQUENCE
MPLDPVIQYVLDQLNRMPAPDYKHLSASQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASLLENAEGYLLTGGMMLWERNQYLNSL
EELTHPWFSPVLYPDLSGLPPAYIATAQYDPLRDVGKLYAEALTKAGVKVEIENFEDLIHGFAQFYSLSPGATK
ALVRIAEKLRDALA

>S00068124
SEQ ID NO: 88
TYPE: PRT, ORGANISM: ARTIFICIAL SEQUENCE
MPLDPVIQYVLDQLNRMPAPDYKHLSASQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASLLENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00068512
SEQ ID NO: 90
TYPE: PRT, ORGANISM: ARTIFICIAL SEQUENCE
MPLDPVIQYVLDQLNRMPAPDYKHLSAQQVRSWQHLFPPVKKEPVAEVREFDMDLPGRTLKVRMYRPEGVEPPY
RALVYYHGGGWVAGDLETHDPVCRVLAKWGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00068639
SEQ ID NO: 92
TYPE: PRT, ORGANISM: ARTIFICIAL SEQUENCE
MPLDPVIQYVLDQLNRMPAIDYKHLSAQQVRSWQHLFPPVKKEPVREVREFDMDLPGRTLKVRMYTPEGVEPPY
RALVYYHGGGWVAGDLETHDPVCRVLAKWGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYARALNKAGVKVEIENFEDLIHGFAQFYSLSPGATK
ALVRIAEKLRDALA

>S00068752
SEQ ID NO: 94
TYPE: PRT, ORGANISM: ARTIFICIAL SEQUENCE
MPLDPVIQYVLDQLNRMPAPDWKHLSAQQFRSQQHLFPPVKKEPVAEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSISPGATK
ALVRIAEKLRDALA

>S00176502
SEQ ID NO: 96
TYPE: PRT, ORGANISM: ARTIFICIAL SEQUENCE
MPLDPVIQYVLDQLNRMPAPDYKHLSAQQFRSQQHLFPPVKKEPVKEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNTAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFANFYSLSPGATK
ALVRIAEKLRDALA

>S00176595
SEQ ID NO: 98
TYPE: PRT, ORGANISM: ARTIFICIAL SEQUENCE
MPLDPVIQYVLDQLNRMPAPDYKHLSAQQFRSQQHLEPPVKKEPVKEVREFDMDLPGRTLKVRMYRPEGVEPPY
RALVYYHGGGWVAGDLETHDPVCRVLAKDGRAVVESVDYRLAPEHKEPAAVEDAYDALQWIAERAADFHLDPAR
LAVGGDSAGGNTAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFASFYSLSPGATK
ALVRIAEKLRDALA

>S00176980
SEQ ID NO: 100
TYPE: PRT, ORGANISM: ARTIFICIAL SEQUENCE
MPLDPVIQYVLDQLNRMPAPDYKHLSACQFRSQQHLFEPVKKEPVAEVREFDMDLPGRTLKVRMYRPEGVEPPY
RALVYYHGGGGVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA
```

SEQUENCE LISTING

```
>S00177019
SEQ ID NO: 102
TYPE: PRT, ORGANISM: ARTIFICIAL SEQUENCE
MPLDPVIQYVLDQLNRMPAPDYKHLSAQQFRSQQSLEPPVKKEPVAEVREFDMDLPGRTLKVRMYLPEGVEPPY
RALVYYHGGGWTAGDLETHDPMCRVLAKDGRAVVESVDYRLAPEHKEPAAVEDAYDALQWIAERAADFHLDPAR
LAVGGDSAGGNPAAVTSILAKERGGPAIAFQLLIQPFTGFDPAHPPASILENAEGYFLTGGMMDWERNQYLNSL
EELTHPWFSPVLYPDLSGLPPAYIATAQYDPLNDVGKLYAEALNKAGLKVEIENFEDLIHGFASFYSLSPGATK
ALVRIAEKLRDALA

>S00177053
SEQ ID NO: 104
TYPE: PRT, ORGANISM: ARTIFICIAL SEQUENCE
MPLDPVIQYVLDQLNRMPAPDYKHLSAQQFRSQQSLEPPVKKEPVAEVREFDMDLPGRTLKVRMYLPEGVEPPY
RALVYYHGGGWTAGDLETHDPMCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYFLTGGMMLWERNQYLNSL
EELTHPWFSPVLYPDLSGLPPAYIATWQYDPLRDVGKLYAEALNKAGVKVEIENFEDLIHGFASFYSLSPGATK
ALVRIAEKLRDALA

>S00177175
SEQ ID NO: 106
TYPE: PRT, ORGANISM: ARTIFICIAL SEQUENCE
MPLDPVIQYVLDQLNRMPAPDYKHLSACQFRSQQHLFPPVKKEPVAEVREFDMRLPGRTLKVRMYRPEGVEPPY
RALVYYHGGGWVAGDLETHDPVCRVLAKDGRAVVESVDYRLAPEHKEPAVEDAYDALQWIAERAADFHLDPAR
LAVGGDSAGGNLAAVTSILAKERGGPAMAFQLLIYPFTGYDPAHPPASILENAEGYFLTGGMMLWERNQYLNSL
EELTHPWFSPVLYPDLSGLPPAYIAVAQYDPLRDVGKLYAEALNKAGVKVEIENFEDLIHGFAQFYSLSPGATK
ALVRIAEKLRDALA

>S00187023
SEQ ID NO: 108
TYPE: PRT, ORGANISM: ARTIFICIAL SEQUENCE
MPLDPVLQYVLDQLNRMPAPDYKHLSACQFRSQQHLFEPVKKEPVAEVREFDMDLPGRTLKVRMYRPEGVEPPY
RALVYYHGGGVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00187052
SEQ ID NO: 110
TYPE: PRT, ORGANISM: ARTIFICIAL SEQUENCE
MPLDPVIQYVLDQLNRMPAPDYKHLSACQFRSQQHLFEPVKKEPVKEVREFDMDLPGRTLKVRMYRPEGVEPPY
RALVYYHGGGVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00187266
SEQ ID NO: 112
TYPE: PRT, ORGANISM: ARTIFICIAL SEQUENCE
MPLDPVIQYVLDQLNRMPAPDYKHLSACQFRSQQHTFWPVKKEPVAEVREFDMQLPGRTLKVRMYTPEGVEPPY
RALVYYHGGGGVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00187283
SEQ ID NO: 114
TYPE: PRT, ORGANISM: ARTIFICIAL SEQUENCE
MPLDPVIQYVLDQLNRMPAPDYKHLSACQFRSQQHTFWPVKKEPVAEVREFDMDLPGRTLKVRMYRPEGVEPPY
RALVYYHGGGGVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00187324
SEQ ID NO: 116
TYPE: PRT, ORGANISM: ARTIFICIAL SEQUENCE
MPLDPVIQYVLDQLNRMPAPDWKHLSACQFRSQQHMEWPVKKEPVAEVREFDMDLPGRTLKVRMYRPEGVEPPY
RALVYYHGGGGVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00187421
SEQ ID NO: 118
TYPE: PRT, ORGANISM: ARTIFICIAL SEQUENCE
MPLDPVIQYVLDQLNRMPAPDYKHLSACQFRSQQHTFWPVKKEPVAEVREFDMDLPGRTLKVRMYRPEGVEPPY
MALVYYHGGGGVAGDLETHDPVCRVLAKDGRAVVESVDYRLAPEHKEPAAVEDAYDALQWIAERAADFHLDPAR
```

SEQUENCE LISTING

```
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00188542
SEQ ID NO: 120
TYPE: PRT, ORGANISM: ARTIFICIAL SEQUENCE
MPLDPVIQYVLDQLNRMPAPDYKHLSACQFRSQQHLFEPVKKEPVAEVREFDMDLPGRTLKVRMYRPEGVEPPY
RALVYYHGGGGVAGDLETHDPVCRVLAKDGRAVVESVDYRLAPEHKEPAAVEDAYDALQWIAERAADFHLDPAR
LAVGGDSAGGNLAAVTSILAKERGGPAIAFQLLIYPFTGYDPAHPPASILENAEGYLLTGGMMLWERNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00207145
SEQ ID NO: 122
TYPE: PRT, ORGANISM: ARTIFICIAL SEQUENCE
MPLDPVIQYVLDQLNRMPAPDYKHLSACQFRSQQHTFWPVKKEPVAEVREFDMDLPGRTLKVRMYRPEGVEPPY
RALVYYHGGGGVAGDLETHDPVCRVLAKDGRAVVFSVDYRLAPEHKEPAAVEDAYDALQWIAERAADFHLDPAR
IAVGGDSAGGNLAAVTSILAKERGGPAIAFQLLIYPFTGYDPAHPPASILENAEGYLLTGGMMLWFRNQYLNSL
EELTHPWFSPVLYPDLSGLPPAYIATAQYDPLRDVGKLYAEALNKAGVKVEIENFEDLIHGFACFYSLSPGATK
ALVRIAEKLRDALA

>S00208699
SEQ ID NO: 124
TYPE: PRT, ORGANISM: ARTIFICIAL SEQUENCE
MLLDPVIQYVLDQLNRMPAPDYKHLSACQFRSQQHTFWPVKKEPVAEVREFDMDLPGRTLKVRMYRPEGVEPPY
RALVYYHGGGGVAGDLETHDPVCRVLAKDGRAVVFSVDYRLAPEHKEPAAVEDAYDALQWIAERAADFHLDPAR
IAVGGDSAGGNLAAVTSILAKERGGPAIAFQLLIYPFTGYDPAHPPASILENAEGYLLTGGMMLWFRNQYLNSL
EELTHPWFSPVLYPDLSGLPPAYIATAQYDPLRDVGKLYAEALNKAGVKVEIENFEDLIHGFAQFYSLSPGATK
ALVRIAEKLRDALA

>S00209368
SEQ ID NO: 126
TYPE: PRT, ORGANISM: ARTIFICIAL SEQUENCE
MPLDPVIQYVLDQLNRMPAPDYKHLSACQFRSQQHTFWPVKKEPVAEVREFDMDLPGRTLKVRMY
RPEGVEPPYRALVYYHGGGGVAGDLETHDPVCRVLAKDGRAVVFSVDYRLAPEHKFPAAVEDAYD
ALQWIAERAADFHLDPARIAVGGDSAGGNLAAVTSILAKERGGPAIAFQLQIYPFTGYDPAHPPASIL
ENAEGYLLTGGMMLWFRNQYLNSLEELTHPWFSPVLYPDLSGLPPAYIATAQYDPLRDVGKLYAEA
LNKAGVKVEIENFEDLIHGFAQFYSLSPGATKALVRIAEKLRDALA
```

We claim:

1. A carboxyesterase polypeptide having carboxyesterase activity and comprising an amino acid sequence that is at least 93%, or more identical to the amino acid sequence set forth in SEQ ID NO: 4, wherein the residue corresponding to X198 in SEQ ID NO: 4 is a leucine (L) residue.

2. The carboxyesterase polypeptide of claim 1, wherein the amino acid sequence of the carboxyesterase polypeptide further comprises a residue difference as compared to the amino acid sequence set forth in SEQ ID NO: 4 in at least one residue position selected from the group consisting of: X27, X30, X35, X37, X57, X75, X103, X185, X207, X208, X271, X286, and X296.

3. The carboxyesterase polypeptide of claim 1, wherein the amino acid sequence of the carboxyesterase polypeptide further comprises
an aliphatic residue or an aromatic residue at the residue corresponding to X103.

4. The carboxyesterase polypeptide of claim 1, wherein the amino acid sequence of the carboxyesterase polypeptide further includes at least one feature selected from the group consisting of: X27 is P; X30 is I, L, or V; X35 is H; X37 is I, L, T, or V; X57 is M; X75 is R; X103 is F, M, or W; X185 is F, I, or M; X207 is E; X208 is R, L, or H; X271 is D; X286 is M, V, or G; and X296 is V, L, or R.

5. The carboxyesterase polypeptide of claim 1, wherein the carboxyesterase polypeptide comprises the amino acid sequence set forth in SEQ ID NO: 4.

6. A process for preparing an amide, wherein components are combined containing:
(a) an ester substrate of the form R1-COOR2, wherein R1 is chosen from: an sp3 carbon with 0 to 3 alkyl substituents; and an aromatic ring, and R2 is chosen from: a methyl group; an ethyl group; and 1-6 carbon alkyl chains;
(b) an amine substrate;
(c) a carboxyesterase polypeptide comprising an amino acid sequence that is at least 93% identical to the amino acid sequence set forth in SEQ ID NO: 4, wherein the residue corresponding to X198 in SEQ ID NO: 4 is a L residue; and
(d) a solvent.

7. The process of claim 6, wherein the carboxyesterase polypeptide in step (c) is prepared in the presence of a salt.

8. The process of claim 7, wherein the salt is chosen from: sodium sulfate; potassium sulfate; lithium sulfate; sodium phosphate; and potassium phosphate.

9. The process of claim 6, wherein the solvent is an organic solvent chosen from: toluene; 2-methyltetrahydrofuran; tetrahydrofuran;
dimethylacetamide; methyl isobutyl ketone (MIBK); dichloromethane; tert-butyl methyl ether;
cyclopentyl methyl ether; methyl cyclohexane; dichloromethane; acetonitrile; methyl ethyl ketone; isopropyl acetate; ethanol; isopropanol; ethyl acetate; heptane; xathane; and 2-methyltetrahydrofuran (2-Me-THF); and water.

10. The process of claim 9, wherein the organic solvent contains up to 3 molar equivalents of water relative to the ester substrate in an amount of from about 0.5% (vol/vol) to about 3% (vol/vol).

11. The process of claim 6, wherein the ester substrate is ethyl oxazole 5-carboxylate that has the formula:

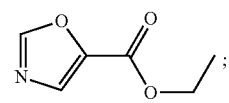

the amine substrate is 1-isopropy 1piperazine that has the formula:

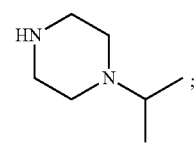

and the amide is (4-isopropylpiperazin-1-yl)(oxazol-5y1) methanone that has the formula:

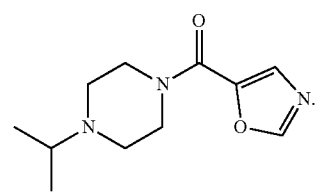

12. The process of claim 6, wherein the ester substrate is ethyl oxazole-5-carboxylate that has the formula:

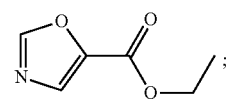

the amine substrate is cis-2,6-dimethylmorpholine that has the formula:

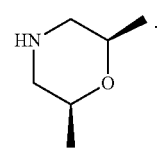

and the amide is ((2S,6R)-2,6-dimethylmorpholino)(oxazol-5-yl)methanone that has the formula:

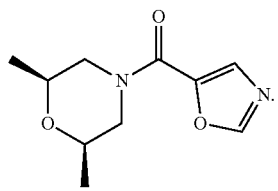

13. The process of claim 6, wherein the reaction comprises: about 40 g/L ethyl oxazole-5-carboxylate, about 44 g/L 1-isopropylpiperazine, and about 20 g/L of a carboxyesterase polypeptide comprises the amino acid sequence set forth in the SEQ ID NO: 4, wherein the carboxyesterase polypeptide is prepared in the presence of sodium sulfate and run in the presence of from about 10 g/L to about 20 g/L water in MIBK.

14. The carboxyesterase polypeptide of claim 3, wherein X103 is an aromatic residue.

15. The carboxyesterase polypeptide of claim 14, wherein X103 is a tryptophan (W) residue.

16. The carboxyesterase polypeptide of claim 1, wherein the amino acid sequence of the carboxyesterase polypeptide further comprises a non-polar residue, an aliphatic residue, or an aromatic residue at the residue corresponding to X185.

17. The carboxyesterase polypeptide of claim 16, wherein X185 is an aromatic residue.

18. The carboxyesterase polypeptide of claim 17, wherein X185 is a phenylalanine (F) residue.

* * * * *

UNITED STATES PATENT AND TRADEMARK OFFICE
CERTIFICATE OF CORRECTION

PATENT NO. : 11,535,833 B2
APPLICATION NO. : 16/771279
DATED : December 27, 2022
INVENTOR(S) : Kristin K Brown et al.

It is certified that error appears in the above-identified patent and that said Letters Patent is hereby corrected as shown below:

On the Title Page

Item (56), Line 20, delete "PCRMethods" and insert -- PCR Methods --, therefore.

In the Claims

In Claim 11, Column 274, Line 18, delete "1-isopropy 1piperazine" and insert -- 1-isopropylpiperazine --, therefore.

In Claim 11, Column 274, Line 30, delete "(oxazol-5y1)" and insert -- (oxazol-5-yl) --, therefore.

In Claim 12, Column 274, Line 59, delete "." and insert -- ; --, therefore.

Signed and Sealed this
Twenty-eighth Day of February, 2023

Katherine Kelly Vidal
*Director of the United States Patent and Trademark Office*

SEQUENCE LISTING

<160> NUMBER OF SEQ ID NOS: 126

<210> SEQ ID NO 1
<211> LENGTH: 930
<212> TYPE: DNA
<213> ORGANISM: Alicyclobacillus acidocaldarius

<400> SEQUENCE: 1

```
atgccattag atcctgtgat tcaacaagtc ctcgatcaac tgaaccgtat gccagcccct      60
gactacaagc acttaagcgc tcaacagttt cgttcacagc aatcactgtt tccaccagtt     120
aagaaagaac cggtcgcaga agttcgcgaa ttcgacatgg atctgccggg ccgtaccctg     180
aaagtccgta tgtaccgtcc ggaaggtgtt gaaccaccat atccagcact ggtttactac     240
catggtggcg gttggttgt tggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctccactgg ttatgatcca gcacatccac cagcaagtat cgaagagaat     600
gcggagggtt acctgttaac cggaggcatg atgctgtggt tcgtgaccg gtacctgaac     660
```

-continued

```
agccttgagg aactgactca cccatggttt agtccagtgc tgtacccgga tcttagcggt      720
ttaccaccgg cgtacattgc aaccgcacag tacgatcccc tgcgcgatgt cggcaaactt      780
tacgctgaag ccctgaacaa gcgggcgttt aaggtggaga tcgagaactt cgaggatctg      840
attcatggct tcgcgcagtt ctattctctg agcccaggcg caaccaaagc actggtacgt      900
attgccgaga aactgcgcga tgcgttggcg                                       930
```

<210> SEQ ID NO 2
<211> LENGTH: 310
<212> TYPE: PRT
<213> ORGANISM: Alicyclobacillus acidocaldarius

<400> SEQUENCE: 2

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Val Lys Lys Glu Pro Val Ala Glu Val
        35                  40                  45

Arg Glu Phe Asp Met Asp Leu Pro Gly Arg Thr Leu Lys Val Arg Met
50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Ser Thr Gly Tyr Asp Pro Ala His
            180                 185                 190

Pro Pro Ala Ser Ile Glu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
290                 295                 300

Leu Arg Asp Ala Leu Ala
305                 310
```

<210> SEQ ID NO 3
<211> LENGTH: 930
<212> TYPE: DNA
<213> ORGANISM: Artificial Sequence
<220> FEATURE:
<223> OTHER INFORMATION: Description of Artificial Sequence: Synthetic
polynucleotide sequence encoding a codon optimized
carboxyesterase enzyme

<400> SEQUENCE: 3

```
atgccattag atcctgtgat tcaacaagtc ctcgatcaac tgaaccgtat gccagcccct     60
gactacaagc acttaagcgc tcaacagttt cgttcacagc aatcactgtt tccaccagtt    120
aagaaagaac cggtcgcaga agttcgcgaa ttcgacatgg atctgccggg ccgtaccctg    180
aaagtccgta tgtaccgtcc ggaaggtgtt gaaccaccat atccagcact ggtttactac    240
catggtggcg gttgggttgt tggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttgcggcg attcagcagg cggcaacctg    480
gcggccgtga ctagtattct ggcgaaagaa cgtggtggtc cagcaattgc gtttcaactg    540
ctgatctatc cctccactgg ttatgatcca gcacatccac cagcaagtat ccttgagaat    600
gcggagggtt acctgttaac cggaggcatg atgctgtggt tcgtgacca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct cgcgcagtt ctattctctg agcccaggcg caaccaaagc actggtacgt    900
attgccgaga aactgcgcga tgcgttggcg                                    930
```

<210> SEQ ID NO 4
<211> LENGTH: 310
<212> TYPE: PRT
<213> ORGANISM: Artificial Sequence
<220> FEATURE:
<223> OTHER INFORMATION: Description of Artificial Sequence: Synthetic
polypeptide sequence of a codon optimized
carboxyesterase enzyme

<400> SEQUENCE: 4

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125
```

Tyr Asp Ala Leu Gln Trp Ile Ala Glu Arg Ala Ala Asp Phe His Leu
                130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Ser Thr Gly Tyr Asp Pro Ala His
                180                 185                 190

Pro Pro Ala Ser Ile Leu Glu Asn Ala Glu Gly Tyr Leu Leu Thr Gly
                195                 200                 205

Gly Met Met Leu Trp Phe Arg Asp Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
                260                 265                 270

Glu Ile Glu Asn Phe Glu Asp Leu Ile His Gly Phe Ala Gln Phe Tyr
                275                 280                 285

Ser Leu Ser Pro Gly Ala Thr Lys Ala Leu Val Arg Ile Ala Glu Lys
                290                 295                 300

Leu Arg Asp Ala Leu Ala
305                 310

<210> SEQ ID NO 5
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 5
atgccattag atcctgtgat tcaacaagtc ctcgatcaac tgaaccgtat gccagcccct       60
gactacaagc acttaagcgc tcaacagttt cgttcacagc aatcactgtt tccaccagtt      120
aagaaagaac cggtcgcaga agttcgcgaa ttcgacatgg atctgccggg ccgtaccctg      180
aaagtccgta tgtaccgtcc ggaaggtgtt gaaccaccat atccagcact ggtttactac      240
catggtggcg gttgggttgt tggtgacctg gaaacgcatg atccggtgtg tcgtgtgttg      300
gcgaaagatg gacgcgcagt ggtgtttagc gttgactacc gtctggcacc agaacacaag      360
tttccagcgg cagttgaaga cgcgtatgat gcactgcaat ggattgcaga acgtgcagcc      420
gatttccatc ttgatccagc acgcattgca gttggcggcg attcagcagg cggcaacctg      480
gcggccgtga ctagtattct ggcgaaagaa cgtggtggtc cagcaattgc gtttcaactg      540
ctgatctatc cctccactgg ttatgatcca gcacatccac cagcaagtat cattgagaat      600
gcggagggtt acctgttaac cggaggcatg atgctgtggt tcgtgaccag tacctgaac       660 agccttgagg aactgactca cccatggttt agtccagtgc tgtacccgga tcttagcggt      720
ttaccaccgg cgtacattgc aaccgcacag tacgatcccc tgcgcgatgt cggcaaactt      780
tacgctgaag ccctgaacaa agcgggcgtt aaggtggaga tcgagaactt cgaggatctg      840
attcatggct cgcgcagttt ctattctctg agcccaggcg caaccaaagc actggtacgt      900
attgccgaga aactgcgcga tgcgttggcg                                       930

<210> SEQ ID NO 6
<211> LENGTH: 310
<212> TYPE: PRT
<213> ORGANISM: Artificial Sequence
<220> FEATURE:
<223> OTHER INFORMATION: Description of Artificial Sequence: Synthetic
    polypeptide sequence of a codon optimized
    carboxyesterase enzyme

<400> SEQUENCE: 6

Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Ser Thr Gly Tyr Asp Pro Ala His
            180                 185                 190

Pro Pro Ala Ser Ile Ile Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 7
<211> LENGTH: 930
<212> TYPE: DNA
<213> ORGANISM: Artificial Sequence
<220> FEATURE:

<223> OTHER INFORMATION: Description of Artificial Sequence: Synthetic
polynucleotide sequence encoding a codon optimized
carboxyesterase enzyme

<400> SEQUENCE: 7

```
atgccattag atcctgtgat tcaacaagtc ctcgatcaac tgaaccgtat gccagcccct      60
gactacaagc acttaagcgc tcaacagttt cgttcacagc aatcactgtt tccaccagtt     120
aagaaagaac cggtcgcaga agttcgcgaa ttcgacatgg atctgccggg ccgtaccctg     180
aaagtccgta tgtaccgtcc ggaaggtgtt gaaccaccat atccagcact ggtttactac     240
catggtggcg gttgggttgt tggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc agcaattgc gtttcaactg      540
ctgatctatc cctccactgg ttatgatcca gcacatccac cagcaagtat ctatgagaat     600
gcggagggtt acctgttaac cggaggcatg atgctgtggt tcgtgacca gtacctgaac      660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa gcgggcgtt aaggtggaga tcgagaactt cgaggatctg      840
attcatggct tcgcgcagtt ctattctctg agcccaggcg caaccaaagc actggtacgt     900
attgccgaga aactgcgcga tgcgttggcg                                      930
```

<210> SEQ ID NO 8
<211> LENGTH: 310
<212> TYPE: PRT
<213> ORGANISM: Artificial Sequence
<220> FEATURE:
<223> OTHER INFORMATION: Description of Artificial Sequence: Synthetic
polypeptide sequence of a codon optimized
carboxyesterase enzyme

<400> SEQUENCE: 8

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160
```

Ala Ala Val Thr Ser Ile Leu Ala Lys Glu Arg Gly Gly Pro Ala Ile
            165                 170                 175

Ala Phe Gln Leu Leu Ile Tyr Pro Ser Thr Gly Tyr Asp Pro Ala His
        180                 185                 190

Pro Pro Ala Ser Ile Tyr Glu Asn Ala Glu Gly Tyr Leu Leu Thr Gly
        195                 200                 205

Gly Met Met Leu Trp Phe Arg Asp Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 9
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 9
atgccattag atcctgtgat tcaacaagtc ctcgatcaac tgaaccgtat gccagcccct      60
gactacaagc acttaagcgc tcaacagttt cgttcacagc aatcactgtt tccaccagtt    120
aagaaagaac cggtcgcaga agttcgcgaa ttcgacatgg atctgccggg ccgtaccctg    180
aaagtccgta tgtaccgtcc ggaaggtgtt gaaccaccat atccagcact ggtttactac    240
catggtggcg ttgggttgt tggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc cctccactgg ttatgatcca gcacatccac cagcaagtat ctttgagaat    600
gcggagggtt acctgttaac cggaggcatg atgctgtggt tcgtgacca gtacctgaac    660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                      930

<210> SEQ ID NO 10
<211> LENGTH: 310
<212> TYPE: PRT

<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 10

```
Met Pro Leu Asp Pro Val Ile Gln Gln Val Leu Asp Gln Leu Asn Arg
1               5                   10                  15
Met Pro Ala Pro Asp Tyr Lys His Leu Ser Ala Gln Gln Phe Arg Ser
            20                  25                  30
Gln Gln Ser Leu Phe Pro Pro Val Lys Lys Glu Pro Val Ala Glu Val
        35                  40                  45
Arg Glu Phe Asp Met Asp Leu Pro Gly Arg Thr Leu Lys Val Arg Met
    50                  55                  60
Tyr Arg Pro Glu Gly Val Glu Pro Pro Tyr Pro Ala Leu Val Tyr Tyr
65                  70                  75                  80
His Gly Gly Gly Trp Val Val Gly Asp Leu Glu Thr His Asp Pro Val
                85                  90                  95
Cys Arg Val Leu Ala Lys Asp Gly Arg Ala Val Val Phe Ser Val Asp
            100                 105                 110
Tyr Arg Leu Ala Pro Glu His Lys Phe Pro Ala Ala Val Glu Asp Ala
        115                 120                 125
Tyr Asp Ala Leu Gln Trp Ile Ala Glu Arg Ala Ala Asp Phe His Leu
    130                 135                 140
Asp Pro Ala Arg Ile Ala Val Gly Gly Asp Ser Ala Gly Gly Asn Leu
145                 150                 155                 160
Ala Ala Val Thr Ser Ile Leu Ala Lys Glu Arg Gly Gly Pro Ala Ile
                165                 170                 175
Ala Phe Gln Leu Leu Ile Tyr Pro Ser Thr Gly Tyr Asp Pro Ala His
            180                 185                 190
Pro Pro Ala Ser Ile Phe Glu Asn Ala Glu Gly Tyr Leu Leu Thr Gly
        195                 200                 205
Gly Met Met Leu Trp Phe Arg Asp Gln Tyr Leu Asn Ser Leu Glu Glu
    210                 215                 220
Leu Thr His Pro Trp Phe Ser Pro Val Leu Tyr Pro Asp Leu Ser Gly
225                 230                 235                 240
Leu Pro Pro Ala Tyr Ile Ala Thr Ala Gln Tyr Asp Pro Leu Arg Asp
                245                 250                 255
Val Gly Lys Leu Tyr Ala Glu Ala Leu Asn Lys Ala Gly Val Lys Val
            260                 265                 270
Glu Ile Glu Asn Phe Glu Asp Leu Ile His Gly Phe Ala Gln Phe Tyr
        275                 280                 285
Ser Leu Ser Pro Gly Ala Thr Lys Ala Leu Val Arg Ile Ala Glu Lys
    290                 295                 300
Leu Arg Asp Ala Leu Ala
305                 310
```

<210> SEQ ID NO 11
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 11

```
atgccattag atcctgtgat tcaacaagtc ctcgatcaac tgaaccgtat gccagcccct    60
gactacaagc acttaagcgc tcaacagttt cgttcacagc aatcactgtt tccaccagtt   120
aagaaagaac cggtcgcaga agttcgcgaa ttcgacatgg atctgccggg ccgtaccctg   180
aaagtccgta tgtaccgtcc ggaaggtgtt gaaccaccat atccagcact ggtttactac   240
catggtggcg gttgggttgt tggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc cggcaattgc gtttcaactg   540
ctgatctatc cctccactgg ttatgatcca gcacatccac cagcaagtat catggagaat   600
gcggagggtt acctgttaac cggaggcatg atgctgtggt tcgtgacca gtacctgaac    660
agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctgaag ccctgaacaa agcgggcgtt aaggtggaga tcgagaactt cgaggatctg   840
attcatggct tcgcgcagtt ctattctctg agcccaggcg caaccaaagc actggtacgt   900
attgccgaga aactgcgcga tgcgttggcg                                    930
```

<210> SEQ ID NO 12
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 12

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Ser Thr Gly Tyr Asp Pro Ala His
```

```
                    180             185              190
Pro Pro Ala Ser Ile Met Glu Asn Ala Glu Gly Tyr Leu Leu Thr Gly
            195                 200                 205

Gly Met Met Leu Trp Phe Arg Asp Gln Tyr Leu Asn Ser Leu Glu Glu
        210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
        290                 295                 300

Leu Arg Asp Ala Leu Ala
305                 310

<210> SEQ ID NO 13
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 13
atgccattag atcctgtgat tcaacaagtc ctcgatcaac tgaaccgtat gccagcccct      60
gactacaagc acttaagcgc tcagcagttt cgttcacagc aatcactgtt gccaccagtt    120
aagaaagaac cggtcgcaga agttcgcgaa ttcgacatgg atctgccggg ccgtaccctg    180
aaagtccgta tgtaccgtcc ggaaggtgtt gaaccaccat atccagcact ggtttactac    240
catggtggcg gttgggttgt tggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc agcaattgc gtttcaactg    540 ctgatctatc cctttactgg ttatgatcca gcacatccac cagcaagtat ccttgagaat    600
gcggagggtt acctgttaga gcatggcatg atgctgtggt tcgtgacca gtacctgaac    660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcaatt ttattctctg agcccaggcg caaccaaagc actggtacgt    900
attgccgaga aactgcgcga tgcgttggcg                                      930

<210> SEQ ID NO 14
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme
```

<400> SEQUENCE: 14

Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Leu Pro Pro Val Lys Lys Glu Pro Val Ala Glu Val
        35                  40                  45

Arg Glu Phe Asp Met Asp Leu Pro Gly Arg Thr Leu Lys Val Arg Met
50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Glu His
        195                 200                 205

Gly Met Met Leu Trp Phe Arg Asp Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
290                 295                 300

Leu Arg Asp Ala Leu Ala
305                 310

<210> SEQ ID NO 15
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 15
atgccattag atcctgtgat tcaacaagtc ctcgatcaac tgaaccgtat gccagcccct    60
gactacaagc acttaagcgc tcagcagttt cgttcacagc aatcactgtt tccaccagtt   120

```
aagaaagaac cggtcgcaga agttcgcgaa ttcgacatgg atctgccggg ccgtacccctg    180 aaagtccgta tgtaccgtcc ggaaggtgtt gaaccaccat atccagcact ggtttactac    240
catggtggcg gttgggttgt tggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc cctttactgg ttatgatcca gcacatccac cagcaagtat ccttgagaat    600
gcggagggtt acctgttaac cggaggcatg atgctgtggt tcgtgacca gtacctgaac    660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaggc actggtacgt    900
attgccgaga aactgcgcga tgcgttggcg                                     930
```

<210> SEQ ID NO 16
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 16

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205
```

```
Gly Met Met Leu Trp Phe Arg Asp Gln Tyr Leu Asn Ser Leu Glu Glu
            210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
                275                 280                 285

Ser Leu Ser Pro Gly Ala Thr Lys Ala Leu Val Arg Ile Ala Glu Lys
290                 295                 300

Leu Arg Asp Ala Leu Ala
305                 310

<210> SEQ ID NO 17
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 17
atgccattag atcctgtgat tcaacaagtc ctcgatcaac tgaaccgtat gccagcccct    60
gactacaagc acttaagcgc tcaacagttt cgttcacagc aatcactgtt gccaccagtt   120
aagaaagaac cggtcgcaga agttcgcgaa ttcgacatgg atctgccggg ccgtaccctg   180
aaagtccgta tgtaccgtcc ggaaggtgtt gaaccaccat atcgggcact ggtttactac   240
catggtggcg gttgggttgt tggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc agcaattgc gtttcaactg   540 ctgatctatc cctttactgg ttatgatcca gcacatccac cagcaagtat ccttgagaat   600
gcggagggtt acctgttaac gcatggcatg atgctgtggt tcgtgacca gtacctgaac   660 agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctgaag ccctgaacaa agcgggcgtt aaggtggaga tcgagaactt cgaggatctg   840
attcatggct cgcgcagtt ctattctctg agcccaggcg caaccctcgc actggtacgt    900
attgccgaga aactgcgcga tgcgttggcg                                    930

<210> SEQ ID NO 18
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 18

Met Pro Leu Asp Pro Val Ile Gln Gln Val Leu Asp Gln Leu Asn Arg
1               5                   10                  15
```

Met Pro Ala Pro Asp Tyr Lys His Leu Ser Ala Gln Gln Phe Arg Ser
            20                  25                  30

Gln Gln Ser Leu Leu Pro Pro Val Lys Lys Glu Pro Val Ala Glu Val
        35                  40                  45

Arg Glu Phe Asp Met Asp Leu Pro Gly Arg Thr Leu Lys Val Arg Met
50                  55                  60

Tyr Arg Pro Glu Gly Val Glu Pro Pro Tyr Arg Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr His
        195                 200                 205

Gly Met Met Leu Trp Phe Arg Asp Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Leu Ala Leu Val Arg Ile Ala Glu Lys
290                 295                 300

Leu Arg Asp Ala Leu Ala
305                 310

<210> SEQ ID NO 19
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 19
atgccattag atcctgtgat tcaacaagtc ctcgatcaac tgaaccgtat gccagcccct     60
gactacaagc acttaagcgc tcaacagttt cgttcacagc aatcactgtt cccaccagtt    120
aagaaagaac cggtcgcaga agttcgcgaa ttcgacatgg atctgccggg ccgtaccctg    180
aaagtccgta tgtaccgacc ggaaggtgtt gaaccaccat atccggcact ggtttactac    240
catggtggcg gttgggttgt tggtgacctg gaaacgcatg atccggtgtg tcgtgtgttg    300

```
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc cctttactgg ttatgatcca gcacatccac cagcaagtat ccttgagaat    600
gcggagggtt acctgttaga gcatggcatg atgctgtggt tcgtgacca gtacctgaac     660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaggc actggtacgt    900
attgccgaga aactgcgcga tgcgttggcg                                      930

<210> SEQ ID NO 20
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 20

Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Glu His
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240
```

```
Leu Pro Pro Ala Tyr Ile Ala Thr Ala Gln Tyr Asp Pro Leu Arg Asp
            245                 250                 255

Val Gly Lys Leu Tyr Ala Glu Ala Leu Asn Lys Ala Gly Val Lys Val
        260                 265                 270

Glu Ile Glu Asn Phe Glu Asp Leu Ile His Gly Phe Ala Gln Phe Tyr
    275                 280                 285

Ser Leu Ser Pro Gly Ala Thr Lys Ala Leu Val Arg Ile Ala Glu Lys
    290                 295                 300

Leu Arg Asp Ala Leu Ala
305                 310
```

<210> SEQ ID NO 21
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 21

```
atgccattag atcctgtgat tcaacaagtc ctcgatcaac tgaaccgtat gccagcccct     60
gactacaagc acttaagcgc tcaacagttt cgttcacagc aacacctgtt tccaccagtt    120
aagaaagaac cggtcgcaga agttcgcgaa ttcgacatgg atctgccggg ccgtaccctg    180
aaagtccgta tgtaccgccc ggaaggtgtt gaaccaccat atccagcact ggtttactac    240
catggtggcg gttgggttgt tggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga gcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc agcaattgc gtttcaactg    540 ctgatctatc cctttactgg ttatgatcca gcacatccac cagcaagtat ccttgagaat    600
gcggagggtt acctgttaac cggaggcatg atgctgtggt tcgtgacca gtacctgaac    660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct cgcgcagtt ctattctctg agcccaggcg caaccaaagc actggtacgt    900
attgccgaga aactgcgcga tgcgttggcg                                     930
```

<210> SEQ ID NO 22
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 22

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Pro Val Lys Lys Glu Pro Val Ala Glu Val
```

```
                35                  40                  45
Arg Glu Phe Asp Met Asp Leu Pro Gly Arg Thr Leu Lys Val Arg Met
 50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
                180                 185                 190

Pro Pro Ala Ser Ile Leu Glu Asn Ala Glu Gly Tyr Leu Leu Thr Gly
            195                 200                 205

Gly Met Met Leu Trp Phe Arg Asp Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
                260                 265                 270

Glu Ile Glu Asn Phe Glu Asp Leu Ile His Gly Phe Ala Gln Phe Tyr
            275                 280                 285

Ser Leu Ser Pro Gly Ala Thr Lys Ala Leu Val Arg Ile Ala Glu Lys
            290                 295                 300

Leu Arg Asp Ala Leu Ala
305                 310

<210> SEQ ID NO 23
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 23
atgccattag atcctgtgat tcaacaagtc ctcgatcaac tgaaccgtat gccagcacct      60
gactacaagc acttaagcgc tcaacagttt cgttcacagc aatcactgtt tccaccagtt     120
aagaaagaac cggtcgcaga agttcgcgaa ttcgacatgg atctgccggg ccgtaccctg     180
aaagtccgta tgtaccgtcc ggaaggtgtt gaaccaccat atccagcact ggtttactac     240
catggtggcg gttgggttgt tggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
```

```
gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc ccatgactgg ttatgatcca gcacatccac cagcaagtat ccttgagaat    600
gcggagggtt acctgttaga gggaggcatg atgctgtggt tcgtgacca gtacctgaac     660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccgtcgc actggtacgt    900
attgccgaga aactgcgcga tgcgttggcg                                     930
```

<210> SEQ ID NO 24
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 24

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Met Thr Gly Tyr Asp Pro Ala His
            180                 185                 190

Pro Pro Ala Ser Ile Leu Glu Asn Ala Glu Gly Tyr Leu Leu Glu Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
```

```
                260                 265                 270
Glu Ile Glu Asn Phe Glu Asp Leu Ile His Gly Phe Ala Gln Phe Tyr
                275                 280                 285

Ser Leu Ser Pro Gly Ala Thr Val Ala Leu Val Arg Ile Ala Glu Lys
            290                 295                 300

Leu Arg Asp Ala Leu Ala
305                 310

<210> SEQ ID NO 25
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 25
atgccattag atcctgtgat caacaagtc ctcgatcaac tgaaccgtat gccagcccct    60
gactacaagc acttaagccc gcaacagttg cgttcacagc aatcactgtt ccaccagtt   120 aagaaagaac cggtcgcaga agttcgcgaa ttcgacatgg atctgccggg tcgtaccctg   180
aaagtccgta tgtaccgtcc ggaaggtgtt gaaccaccat atccagcact ggtttactac   240
catggtggcg gttgggttgt tggtgacctg gaaacgcatg atccggtgtg tcgtgtgttg   300
gcgaaatggg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc cagcaattgc gtttcaactg   540
ctgatctatc cctccactgg ttatgatcca gcacatccac cagcaagtat cattgagaat   600
gcggagggtt acctgttaac cggaggcatg atgctgtggt tcgtgacca gtacctgaac    660 agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctgaag ccctgaacaa gcgggcgtt aaggtggaga tcgagaactt cgaggatctg   840
attcatggct cgcggggtt ctattctctg agcccaggcg caaccaaagc actggtacgt   900
attgccgaga aactgcgcga tgcgttggcg                                   930

<210> SEQ ID NO 26
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 26

Met Pro Leu Asp Pro Val Ile Gln Gln Val Leu Asp Gln Leu Asn Arg
1               5                   10                  15

Met Pro Ala Pro Asp Tyr Lys His Leu Ser Pro Gln Gln Leu Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60
```

```
Tyr Arg Pro Glu Gly Val Glu Pro Pro Tyr Pro Ala Leu Val Tyr Tyr
 65                  70                  75                  80

His Gly Gly Gly Trp Val Val Gly Asp Leu Glu Thr His Asp Pro Val
                 85                  90                  95

Cys Arg Val Leu Ala Lys Trp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Ser Thr Gly Tyr Asp Pro Ala His
            180                 185                 190

Pro Pro Ala Ser Ile Ile Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gly Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 27
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 27
atgccattag atcctgtgat tcaacaagtc ctcgatcaac tgaaccgtat gccagcccct      60
gactacaagc acttaagcgc tcaacagttt cgttcacagc agtcactgtt tccaccagtt     120
aagaaagaac cggtcgcaga agttcgcgaa ttcgacatgg atctgccgat gcgtaccctg     180
aaagtccgta tgtaccgtcc ggaaggtgtt gaaccaccat atccagcact ggtttactac     240
catggtggcg gttgggttgt tggtgacctg gaaacgcatg atccggtgtg tcgtgtgttg     300
gcgaaatggg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctccactgg ttatgatcca gcacatccac cagcaagtat ccttgagaat     600
```

```
gcggagggtt acctgttaac ccatggcatg atgctgtggt ttcgtgacca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaagtggaga tcgagaactt cgaggatctg    840
attcatggct tcgcggggtt ctattctctg agcccaggcg caaccagagc actggtacgt    900
attgccgaga aactgcgcga tgcgttggcg                                      930
```

<210> SEQ ID NO 28
<211> LENGTH: 310
<212> TYPE: PRT
<213> ORGANISM: Artificial Sequence
<220> FEATURE:
<223> OTHER INFORMATION: Description of Artificial Sequence: Synthetic
    polypeptide sequence of a codon optimized
    carboxyesterase enzyme

<400> SEQUENCE: 28

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Val Lys Lys Glu Pro Val Ala Glu Val
        35                  40                  45

Arg Glu Phe Asp Met Asp Leu Pro Met Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Trp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Ser Thr Gly Tyr Asp Pro Ala His
            180                 185                 190

Pro Pro Ala Ser Ile Leu Glu Asn Ala Glu Gly Tyr Leu Leu Thr His
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gly Phe Tyr
        275                 280                 285
```

Ser Leu Ser Pro Gly Ala Thr Arg Ala Leu Val Arg Ile Ala Glu Lys
    290                 295                 300

Leu Arg Asp Ala Leu Ala
305                 310

<210> SEQ ID NO 29
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 29

```
atgccattag atcctgtgat tcaacaagtc ctcgatcaac tgaaccgtat gccagcccct      60
gactacaagc acttaagcgc tcaacagttt cgttcacagc aatcactgtt tccgccagtt     120
aagaaagaac cggtcgcaga agttcgcgaa ttcgacatgg atctgccggg ccgtaccctg     180
aaagtccgta tgtaccgtcc ggaaggtgtt gaaccaccat atccagcact ggtttactac     240
catggtggcg gttgggttgt tggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgccgcc     420
gatttccatc ttgatccagc acgcattgca gttggcggcg attcagcagg cggcaacctg     480
gcggccgtga ctagtattct ggcgaaagaa cgtggtggtc agcaattgc gtttcaactg     540
ctgatctatc cctccactgg ttatgatcca gcacatccac cagcaagtat ccttgagaat     600
gcggagggtt acctgttaac cggaggcatg atgctgtggt tcgtgacca gtacctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaagtggaga tcgagaactt cgaggatctg     840
attcatggct cgcggggtt ctattctctg agcccaggcg caaccaaagc actggtacgt     900
attgccgaga aactgcgcga tgcgttggcg                                       930
```

<210> SEQ ID NO 30
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 30

Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
        130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Ser Thr Gly Tyr Asp Pro Ala His
            180                 185                 190

Pro Pro Ala Ser Ile Leu Glu Asn Ala Glu Gly Tyr Leu Leu Thr Gly
            195                 200                 205

Gly Met Met Leu Trp Phe Arg Asp Gln Tyr Leu Asn Ser Leu Glu Glu
        210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gly Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 31
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 31
atgccattag atcctgtgat tcaacaagtc ctcgatcaac tgaaccgtat gccagcccct     60
gactacaagc acttaagcgc tcaacagttt cgttcacagc aatcactgtt tccgccagtt    120
aagaaagaac cggtcgcaga agttcgcgaa ttcgacatgg atctgccggg ccgtaccctg    180
aaagtccgta tgtaccgtcc ggaaggtgtt gaaccaccat atccagcact ggtttactac    240
catggtggcg gttgggttgt tggtgacctg gaaacgcatg atccggtgtg tcgtgtgttg    300
gcgaaatggg gacgcgcagt ggtgtttagc gttgactacc gtctggcacc agaacacaag    360
tttccagcgg cagttgaaga cgcgtatgat gcactgcaat ggattgcaga acgtgccgcc    420
gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc cctccactgg ttatgatcca gcacatccac cagcaagtat cattgagaat    600
gcggagggtt acctgttaac cggtggcatg atgctgtggt tcgtgaccca gtacctgaac    660
agccttgagg aactgactca cccatggttt agtccagtgc tgtacccgga tcttagcggt    720

```
ttaccaccgg cgtacattgc aaccgcacag tacgatcccc tgcgcgatgt cggcaaactt    780
tacgctgaag ccctgaacaa agcgggcgtt aaagtggaga tcgagaactt cgaggatctg    840
attcatggct tcgcggggtt ctattctctg agcccaggcg caaccaaagc actggtacgt    900
attgccgaga aactgcgcga tgcgttggcg                                     930
```

<210> SEQ ID NO 32
<211> LENGTH: 310
<212> TYPE: PRT
<213> ORGANISM: Artificial Sequence
<220> FEATURE:
<223> OTHER INFORMATION: Description of Artificial Sequence: Synthetic
    polypeptide sequence of a codon optimized
    carboxyesterase enzyme

<400> SEQUENCE: 32

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Trp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Pro Ala Ile
                165                 170                 175

Ala Phe Gln Leu Leu Ile Tyr Pro Ser Thr Gly Tyr Pro Ala His
            180                 185                 190

Pro Pro Ala Ser Ile Ile Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gly Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310
```

<210> SEQ ID NO 33
<211> LENGTH: 930
<212> TYPE: DNA
<213> ORGANISM: Artificial Sequence
<220> FEATURE:
<223> OTHER INFORMATION: Description of Artificial Sequence: Synthetic
polynucleotide sequence encoding a codon optimized
carboxyesterase enzyme

<400> SEQUENCE: 33

```
atgccattag atcctgtgat tcaacaagtc ctcgatcaac tgaaccgtat gccagcccct    60
gactacaagc acttaagcgc tcaacagttt cgttcacagc aatcactgtt tccaccagtt   120
aagaaagaac cggtcgcaga agttcgcgaa ttcgacatgg atctgccggg ccgtaccctg   180
aaagtccgta tgtaccgtcc ggaaggtgtt gaaccaccat atccagcact ggtttactac   240
catggtggcg gttgggttgt tggtgacctg gaaacgcatg atccggtgtg tcgtgtgttg   300
gcgaaatggg gacgcgcagt ggtgtttagc gttgactacc gtctggcacc agaacacaag   360
tttccagcgg cagttgaaga cgcgtatgat gcactgcaat ggattgcaga cgtgccgcc    420
gatttccatc ttgatccagc acgcattgca gttggcggcg attcagcagg cggcaacctg   480
gcggccgtga ctagtattct ggcgaaagaa cgtggtggtc agcaattgc gtttcaactg    540
ctgatctatc cctccactgg ttatgatcca gcacatccac cagcaagtat ccttgagaat   600
gcggagggtt acctgttaac cggtggcatg atgctgtggt ttcgtgacca gtacctgaac   660
agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctgaag ccctgaacaa agcgggcgtt gatgtggaga tcgagaactt cgaggatctg   840
attcatggct cgcgggggtt ctattctctg agcccaggcg caaccaaagc actggtacgt   900
attgccgaga aactgcgcga tgcgttggcg                                    930
```

<210> SEQ ID NO 34
<211> LENGTH: 310
<212> TYPE: PRT
<213> ORGANISM: Artificial Sequence
<220> FEATURE:
<223> OTHER INFORMATION: Description of Artificial Sequence: Synthetic
polypeptide sequence of a codon optimized
carboxyesterase enzyme

<400> SEQUENCE: 34

Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Gly Asp Leu Glu Thr His Asp Pro Val
                85                  90                  95

Cys Arg Val Leu Ala Lys Trp Gly Arg Ala Val Val Phe Ser Val Asp
            100                 105                 110

Tyr Arg Leu Ala Pro Glu His Lys Phe Pro Ala Ala Val Glu Asp Ala

```
            115                 120                 125
Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Ser Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Asp Val
            260                 265                 270

Glu Ile Glu Asn Phe Glu Asp Leu Ile His Gly Phe Ala Gly Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 35
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 35
atgccattag atcctgtgat tcaatatgtc ctcgatcaac tgaaccgtat gccagcccct      60
gactacaagc acttaagcgc tcaacagttt cgttcacagc aacacctgac cccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgt tggtgacctg gaaacgcatg atccggtgtg tcgtgtgttg     300
gcgaaatggg gacgcgcagt ggtgtttagc gttgactacc gtctggcacc agaacacaag     360
tttccagcgg cagttgaaga cgcgtatgat gcactgcaat ggattgcaga cgtgcagcc     420 gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt tcgtgacca gtacctgaac      660 agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct tcgcgcagtt ctattctctg agcccaggcg caaccaaagc actggtacgt     900
```
attgccgaga aactgcgcga tgcgttggcg                                           930

<210> SEQ ID NO 36
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 36

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Thr Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Trp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 37
<211> LENGTH: 930
<212> TYPE: DNA

<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 37

```
atgccattag atcctgtgat tcaacaagtc ctcgatcaac tgaaccgtat gccagcccct      60
gactacaagc acttaagcgc tcaacagttt cgttcacagc aaagcctgtt tccaccagtt     120
aagaaagaac cggtcgcaga actgcgcgaa ttcgacatgg atctgccggg ccgtaccctg     180
aaagtccgta tgtaccgccc ggaaggtgtt gaaccaccat atccagcact ggtttactac     240
catggtggcg gttgggttgt tggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttgcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt tcgtaaccaa gtacctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct tcgcgcagtt ctattctctg agcccaggcg caaccaaagc actggtacgt     900
attgccgaga aactgcgcga tgcgttggcg                                      930
```

<210> SEQ ID NO 38
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 38

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Leu
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
        130                 135                 140
```

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 39
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 39
atgccattag atcctgtgat tcaatatgtc ctcgatcaac tgaaccgtat gccacgtcct      60
gactacaagc acttaagcgc tcaacagttt cgttcacaga accacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga gcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt tcgtgacca gtacctgaac     660 agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt gatgtggaga tcgagaactt cgaggatctg     840
attcatggct tcgcgcagtt ctattctctg agcccaggcg caacccgtgc actggtacgt     900
attgccgaga aactgcgcga tgcgttggcg                                      930

<210> SEQ ID NO 40

```
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 40

Met Pro Leu Asp Pro Val Ile Gln Tyr Val Leu Asp Gln Leu Asn Arg
1               5                   10                  15

Met Pro Arg Pro Asp Tyr Lys His Leu Ser Ala Gln Gln Phe Arg Ser
            20                  25                  30

Gln Asn His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Asp Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Arg Ala Leu Val Arg Ile Ala Glu Lys
    290                 295                 300

Leu Arg Asp Ala Leu Ala
305                 310

<210> SEQ ID NO 41
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme
```

<400> SEQUENCE: 41

```
atgccattag atcctgtgat tcaatatgtc ctcgatcaac tgaaccgtat gccagcccct      60
gactacaagc acttaagcgc tcaacagttt cgttcacagg aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt tcgtgacca gtacctgaac      660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt gatgtggaga tcgagaactt cgaggatctg     840
attcatggct tcgcgcagtt ctattctctg agcccaggcg caaccaaagc actggtacgt     900
attgccgaga aactgcgcga tgcgttggcg                                      930
```

<210> SEQ ID NO 42
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 42

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Glu His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175
```

```
Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
            245                 250                 255

Val Gly Lys Leu Tyr Ala Glu Ala Leu Asn Lys Ala Gly Val Asp Val
            260                 265                 270

Glu Ile Glu Asn Phe Glu Asp Leu Ile His Gly Phe Ala Gln Phe Tyr
            275                 280                 285

Ser Leu Ser Pro Gly Ala Thr Lys Ala Leu Val Arg Ile Ala Glu Lys
            290                 295                 300

Leu Arg Asp Ala Leu Ala
305                 310

<210> SEQ ID NO 43
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 43
atgccattag atcctgtgat tcaatatgtc ctcgatcaac tgaaccgtat gccacgtcct      60
gactacaagc acttaagcgc tcaacagttt cgttcacagg aacacctgtt tccaccagtt     120
aagaaagaac cggtcgtgga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc agcaattgc gtttcaactg     540 ctgatctatc cctttactgg ttatgatcca gcacatccac cagcaagtat ccttgagaat     600
gcggagggtt acctgttaac cggaggcatg atgctgtggt ttcgtgacca gtacctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt gatgtggaga tcgagaactt ccaggatctg     840
attcatggct cgcgcagtt ctattctctg agcccaggcg caacccgtgc actggtacgt     900
attgccgaga aactgcgcga tgcgttggcg                                     930

<210> SEQ ID NO 44
<211> LENGTH: 310
<212> TYPE: PRT
<213> ORGANISM: Artificial Sequence
<220> FEATURE:
<223> OTHER INFORMATION: Description of Artificial Sequence: Synthetic
``` polypeptide sequence of a codon optimized
carboxyesterase enzyme

<400> SEQUENCE: 44

```
Met Pro Leu Asp Pro Val Ile Gln Tyr Val Leu Asp Gln Leu Asn Arg
1               5                   10                  15

Met Pro Arg Pro Asp Tyr Lys His Leu Ser Ala Gln Gln Phe Arg Ser
            20                  25                  30

Gln Glu His Leu Phe Pro Pro Val Lys Lys Glu Pro Val Val Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
            195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Asp Val
            260                 265                 270

Glu Ile Glu Asn Phe Gln Asp Leu Ile His Gly Phe Ala Gln Phe Tyr
    275                 280                 285

Ser Leu Ser Pro Gly Ala Thr Arg Ala Leu Val Arg Ile Ala Glu Lys
290                 295                 300

Leu Arg Asp Ala Leu Ala
305                 310
```

<210> SEQ ID NO 45
<211> LENGTH: 930
<212> TYPE: DNA
<213> ORGANISM: Artificial Sequence
<220> FEATURE:
<223> OTHER INFORMATION: Description of Artificial Sequence: Synthetic polynucleotide sequence encoding a codon optimized carboxyesterase enzyme

<400> SEQUENCE: 45
atgccattag atcctgtgat tcaatatgtc ctcgatcaac tgaaccgtat gccagcccct    60

```
gactacaagc acttaagcgc tcaacagttt cgttcacaga accacctgtt tccaccagtt    120
aagaaagaac cggtcgtgga agttcgcgaa ttcgacatgg atctgccggg ccgtaccctg    180
aaagtccgta tgtaccgccc ggaaggtgtt gaaccaccat atccagcact ggtttactac    240
catggtggcg gttgggttgc gggtgaccty gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc cctttactgg ttatgatcca gcacatccac cagcaagtat ccttgagaat    600
gcggagggtt acctgttaac cggaggcatg atgctgtggt tcgtgacca gtacctgaac    660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa gcgggcgtt aaggtggaga tcgagaactt ccaggatctg    840
attcatggct cgcgcagtt ctattctctg agcccaggcg caacccgtgc actggtacgt    900
attgccgaga aactgcgcga tgcgttggcg                                       930
```

<210> SEQ ID NO 46
<211> LENGTH: 310
<212> TYPE: PRT
<213> ORGANISM: Artificial Sequence
<220> FEATURE:
<223> OTHER INFORMATION: Description of Artificial Sequence: Synthetic
    polypeptide sequence of a codon optimized
    carboxyesterase enzyme

<400> SEQUENCE: 46

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Asn His Leu Phe Pro Pro Val Lys Lys Glu Pro Val Val Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
```

```
              195                 200                 205
Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Gln Asp Leu Ile His Gly Phe Ala Gln Phe Tyr
        275                 280                 285

Ser Leu Ser Pro Gly Ala Thr Arg Ala Leu Val Arg Ile Ala Glu Lys
    290                 295                 300

Leu Arg Asp Ala Leu Ala
305                 310
```

<210> SEQ ID NO 47
<211> LENGTH: 930
<212> TYPE: DNA
<213> ORGANISM: Artificial Sequence
<220> FEATURE:
<223> OTHER INFORMATION: Description of Artificial Sequence: Synthetic polynucleotide sequence encoding a codon optimized carboxyesterase enzyme

<400> SEQUENCE: 47

```
atgccattag atcctgtgat tcaacaagtc ctcgatcaac tgaaccgtat gccagcccct    60
gactacaagc acttaagcgc tcaacagttt cgttcacagc aacacctgtt tccaccagtt   120
aagaaagaac cggtcgcaga agttcgcgaa ttcgacatgg atctgccggg ccgtaccctg   180
aaagtccgta tgtacgtgcc ggaaggtgtt gaaccaccat atccagcact ggtttactac   240
catggtggcg gttgggttgt tggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttgcggcg attcagcagg cggcaacctg   480
gcggccgtga ctagtattct ggcgaaagaa cgtggtggtc agcaattgc gtttcaactg   540
ctgatctatc cctttactgg ttatgattat gcacatccac cagcaagtat ccttgagaat   600
gcggagggtt acctgttaga aggaggcatg atgctgtggt tcgtgacca gtacctgaac   660
agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctaccg ccctgaacaa agcgggcgtt aaggtggaga tcgagaactt cgaggatctg   840
attcatggct tcgcgcagtt ctattctctg agcccaggcg caaccaaagc actggtacgt   900
attgccgaga aactgcgcga tgcgttggcg                                    930
```

<210> SEQ ID NO 48
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 48

```
Met Pro Leu Asp Pro Val Ile Gln Gln Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
50                  55                  60

Tyr Val Pro Glu Gly Val Glu Pro Pro Tyr Pro Ala Leu Val Tyr Tyr
65                  70                  75                  80

His Gly Gly Gly Trp Val Val Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Tyr Ala His
            180                 185                 190

Pro Pro Ala Ser Ile Leu Glu Asn Ala Glu Gly Tyr Leu Leu Glu Gly
        195                 200                 205

Gly Met Met Leu Trp Phe Arg Asp Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Thr Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
290                 295                 300

Leu Arg Asp Ala Leu Ala
305             310

<210> SEQ ID NO 49
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 49
atgccattag atcctgtgat tcaatatgtc ctcgatcaac tgaaccgtat gccagcccct   60
gactacaagc acttaagcgc tcaacagttt cgttcacagg aacacctgtt tccaccagtt  120
aagaaagaac cggtcgtgga agttcgcgaa ttcgacatgg atctgccggg ccgtaccctg  180
aaagtccgta tgtaccgccc ggaaggtgtt gaaccaccat atccagcact ggtttactac  240
```

-continued

```
catggtggcg gttgggttgc gggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtcgtgcc    420
gatttccatc ttgatccagc acgcattgca gttggcggcg attcagcagg cggcaacctg    480
gcggccgtga ctagtattct ggcgaaagaa cgtggtggtc agcaattgc gtttcaactg     540 ctgatctatc cctttactgg ttatgatcca gcacatccac cagcaagtat ccttgagaat    600
gcggagggtt acctgttaac cggaggcatg atgctgtggt tcgtgacca gtacctgaac     660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                      930
```

<210> SEQ ID NO 50
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 50

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Glu His Leu Phe Pro Pro Val Lys Lys Glu Pro Val Val Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Arg Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220
```

```
Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 51
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 51
atgccattag atcctgtgat tcaatatgtc ctcgatcaac tgaaccgtat gccagcccct      60
gactacaagc acttaagcgc tcaacagttt cgttcacaga accacctgtt tccaccagtt    120
aagaaagaac cggtcgcaga agttcgcgaa ttcgacatgg atctgccggg ccgtaccctg    180
aaagtccgta tgtaccgccc ggaaggtgtt gaaccaccat atccagcact ggtttactac    240
catggtggcg gttgggttgc gggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttgcggcg attcagcagg cggcaacctg    480
gcggccgtga ctagtattct ggcgaaagaa cgtggtggtc agcaattgc gtttcaactg    540
ctgatctatc cctttactgg ttatgatcca gcacatccac cagcaagtat ccttgagaat    600
gcggagggtt acctgttaac cggaggcatg atgctgtggt ttcgtgacca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caacccgtgc actggtacgt    900
attgccgaga aactgcgcga tgcgttggcg                                    930

<210> SEQ ID NO 52
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 52

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30
```

```
Gln Asn His Leu Phe Pro Pro Val Lys Lys Glu Pro Val Ala Glu Val
             35                   40                  45

Arg Glu Phe Asp Met Asp Leu Pro Gly Arg Thr Leu Lys Val Arg Met
     50                  55                  60

Tyr Arg Pro Glu Gly Val Glu Pro Pro Tyr Pro Ala Leu Val Tyr Tyr
 65                  70                  75                  80

His Gly Gly Gly Trp Val Ala Gly Asp Leu Glu Thr His Asp Pro Val
                 85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
        130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
                260                 265                 270

Glu Ile Glu Asn Phe Glu Asp Leu Ile His Gly Phe Ala Gln Phe Tyr
            275                 280                 285

Ser Leu Ser Pro Gly Ala Thr Arg Ala Leu Val Arg Ile Ala Glu Lys
        290                 295                 300

Leu Arg Asp Ala Leu Ala
305                 310

<210> SEQ ID NO 53
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 53
atgccattag atcctgtgat tcaatatgtc ctcgatcaac tgaaccgtat gccagcccct    60
gactacaagc acttaagcgc tcaacagttt cgttcacagc aacacctgtt tccaccagtt   120
aagaaagaac cggtcgcaga agttcgcgaa ttcgacatgg atctgccggg ccgtaccctg   180
aaagtccgta tgtaccgccc ggaaggtgtt gaaccaccat atccagcact ggtttactac   240
catggtggcg gttgggttgc gggtgacctg gaaacgcatg atccggtgtg tcgtgtgttg   300
gcgaaagatg gacgcgcagt ggtgtttagc gttgactacc gtctggcacc agaacacaag   360
```

-continued

```
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc agcaattgcg tttcaactg     540 ctgatctatc cctttactgg ttatgatcca gcacatccac cagcaagtat ccttgagaat    600
gcggagggtt acctgttaac cggaggcatg atgctgtggt tcgtgacca gtacctgaac     660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                     930
```

<210> SEQ ID NO 54
<211> LENGTH: 310
<212> TYPE: PRT
<213> ORGANISM: Artificial Sequence
<220> FEATURE:
<223> OTHER INFORMATION: Description of Artificial Sequence: Synthetic
    polypeptide sequence of a codon optimized
    carboxyesterase enzyme

<400> SEQUENCE: 54

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255
```

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 55
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 55
atgccattag atcctgtgat tcaatatgtc ctcgatcaac tgaaccgtat gccagcccct        60
gactacaagc acttaagcgc tcaacagttt cgttcacagc aacacctgtt tccaccagtt      120
aagaaagaac cggtcgcaga agttcgcgaa ttcgacatgg atctgccggg ccgtaccctg      180
aaagtccgta tgtaccgccc ggaaggtgtt gaaccaccat atccagcact ggtttactac      240
catggtggcg gttgggttgc gggtgacctg gaaacgcatg atccggtgtg tcgtgtgttg      300
gcgaaagatg gacgcgcagt ggtgtttagc gttgactacc gtctggcacc agaacacaag      360
tttccagcgg cagttgaaga cgcgtatgat gcactgcaat ggattgcaga acgtgcagcc      420
gatttccatc ttgatccagc acgcattgca gttggcggcg attcagcagg cggcaacctg      480
gcggccgtga ctagtattct ggcgaaagaa cgtggtggtc agcaattgc gtttcaactg      540 ctgatctatc cctttactgg ttatgatcca gcacatccac cagcaagtat ccttgagaat      600
gcggagggtt acctgttaac cggaggcatg atgctgtggt tcgtgacca gtacctgaac      660 agccttgagg aactgactca cccatggttt agtccagtgc tgtacccgga tcttagcggt      720
ttaccaccgg cgtacattgc aaccgcacag tacgatcccc tgcgcgatgt cggcaaactt      780
tacgctgaag ccctgaacaa agcgggcgtt aaggtggaga tcgagaactt cgaggatctg      840
attcatggct cgcgagtttt ctattctctg agcccaggcg caaccaaagc actggtacgt      900
attgccgaga aactgcgcga tgcgttggcg                                     930

<210> SEQ ID NO 56
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 56

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met

```
                  50                  55                  60
Tyr Arg Pro Glu Gly Val Glu Pro Pro Tyr Pro Ala Leu Val Tyr Tyr
 65                  70                  75                  80

His Gly Gly Gly Trp Val Ala Gly Asp Leu Glu Thr His Asp Pro Val
                 85                  90                  95

Cys Arg Val Leu Ala Lys Asp Gly Arg Ala Val Val Phe Ser Val Asp
             100                 105                 110

Tyr Arg Leu Ala Pro Glu His Lys Phe Pro Ala Val Glu Asp Ala
         115                 120                 125

Tyr Asp Ala Leu Gln Trp Ile Ala Glu Arg Ala Ala Asp Phe His Leu
     130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Ser Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 57
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 57
atgccattag atcctgtgat tcaatatgtc ctcgatcaac tgaaccgtat gccagcccct    60
gactacaagc acttaagcgc tcaacaggtt cgttcacagc aacacctgtt tccaccagtt   120
aagaaagaac cggtcgcaga agttcgcgaa ttcgacatgg atctgccggg ccgtaccctg   180
aaagtccgta tgtaccgccc ggaaggtgtt gaaccaccat atccagcact ggtttactac   240
catggtggcg gttgggttgc gggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc cagcaattgc gtttcaactg   540
```

-continued

```
ctgatctatc cctttactgg ttatgatcca gcacatccac cagcaagtat ccttgagaat    600
gcggagggtt acctgttaac cggaggcatg atgctgtggt ttcgtgacca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                    930
```

<210> SEQ ID NO 58
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 58

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Val Arg Ser
            20                  25                  30

Gln Gln His Leu Phe Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
```

```
              275                 280                 285
Ser Leu Ser Pro Gly Ala Thr Lys Ala Leu Val Arg Ile Ala Glu Lys
        290                 295                 300

Leu Arg Asp Ala Leu Ala
305                 310
```

<210> SEQ ID NO 59
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 59

```
atgccattag atcctgtgat tcaatatgtc ctcgatcaac tgaaccgtat gccagcccct    60
gactacaagc acttaagcgc tcaacagttt cgttcacagg aacacctgtt tccaccagtt   120
aagaaagaac cggtcgcaga agttcgcgaa ttcgacatgg atctgccggg ccgtaccctg   180
aaagtccgta tgtaccgccc ggaaggtgtt gaaccaccat atccagcact ggtttactac   240
catggtggcg gttgggttgc gggtgacctg aaaacgcatg atccggtgtg tcgtgtgttg   300
gcgaaagatg acgcgcagt ggtgtttagc gttgactacc gtctggcacc agaacacaag   360
tttccagcgg cagttgaaga gcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc agcaattgc gtttcaactg   540 ctgatctatc cctttactgg ttatgatcca gcacatccac cagcaagtat ccttgagaat   600
gcggagggtt acctgttaac cggaggcatg atgctgtggt ttcgtgacca gtacctgaac   660
agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctgaag ccctgaacaa agcgggcgtt aaggtggaga tcgagaactt cgaggatctg   840
attcatggct cgcgcagtt ctattctctg agcccaggcg caaccaaagc actggtacgt   900
attgccgaga aactgcgcga tgcgttggcg                                    930
```

<210> SEQ ID NO 60
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 60

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Glu His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80
```

```
His Gly Gly Gly Trp Val Ala Gly Asp Leu Glu Thr His Asp Pro Val
                 85                  90                  95
Cys Arg Val Leu Ala Lys Asp Gly Arg Ala Val Val Phe Ser Val Asp
            100                 105                 110
Tyr Arg Leu Ala Pro Glu His Lys Phe Pro Ala Ala Val Glu Asp Ala
        115                 120                 125
Tyr Asp Ala Leu Gln Trp Ile Ala Glu Arg Ala Ala Asp Phe His Leu
    130                 135                 140
Asp Pro Ala Arg Ile Ala Val Gly Gly Asp Ser Ala Gly Gly Asn Leu
145                 150                 155                 160
Ala Ala Val Thr Ser Ile Leu Ala Lys Glu Arg Gly Gly Pro Ala Ile
                165                 170                 175
Ala Phe Gln Leu Leu Ile Tyr Pro Phe Thr Gly Tyr Asp Pro Ala His
            180                 185                 190
Pro Pro Ala Ser Ile Leu Glu Asn Ala Glu Gly Tyr Leu Leu Thr Gly
        195                 200                 205
Gly Met Met Leu Trp Phe Arg Asp Gln Tyr Leu Asn Ser Leu Glu Glu
    210                 215                 220
Leu Thr His Pro Trp Phe Ser Pro Val Leu Tyr Pro Asp Leu Ser Gly
225                 230                 235                 240
Leu Pro Pro Ala Tyr Ile Ala Thr Ala Gln Tyr Asp Pro Leu Arg Asp
                245                 250                 255
Val Gly Lys Leu Tyr Ala Glu Ala Leu Asn Lys Ala Gly Val Lys Val
            260                 265                 270
Glu Ile Glu Asn Phe Gly Asp Leu Ile His Gly Phe Ala Gln Phe Tyr
        275                 280                 285
Ser Leu Ser Pro Gly Ala Thr Lys Ala Leu Val Arg Ile Ala Glu Lys
    290                 295                 300
Leu Arg Asp Ala Leu Ala
305                 310

<210> SEQ ID NO 61
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 61
atgccattag atcctgtgat tcaatatgtc ctcgatcaac tgaaccgtat gccagcccct    60
gactacaagc acttaagcgc tcaacagttt cgttcacagc aacacctgtt ccaccagtt   120 aagaaagaac cggtcgcaga agttcgcgaa ttcgacatgg atctgccggg ccgtaccctg   180
aaagtccgta tgtaccgccc ggaaggtgtt gaaccaccat atccagcact ggtttactac   240
catggtggcg gttgggttgc gggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttgcggcg attcagcagg cggcaacctg   480
gcggccgtga ctagtattct ggcgaaagaa cgtggtggtc cagcaattgc gtttcaactg   540
ctgatctatc cctttactgg ttttgatcca gcacatccac cagcaagtat ccttgagaat   600
gcggagggtt acctgttaac cggaggcatg atgctgtggt tcgtgaccca gtacctgaac   660
```

| | | | | |
|---|---|---|---|---|
| agccttgagg aactgactca cccatggttt agtccagtgc tgtacccgga tcttagcggt | | | | 720 |
| ttaccaccgg cgtacattgc aaccgcacag tacgatcccc tgcgcgatgt cggcaaactt | | | | 780 |
| tacgctgaag ccctgaacaa agcgggcgtt aaggtggaga tcgagaactt cgaggatctg | | | | 840 |
| attcatggct tcgcgcagtt ctattctctg agcccaggcg caaccaaagc actggtacgt | | | | 900 |
| attgccgaga aactgcgcga tgcgttggcg | | | | 930 |

<210> SEQ ID NO 62
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 62

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Phe Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300
```

Leu Arg Asp Ala Leu Ala
305                 310

<210> SEQ ID NO 63
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 63

```
atgccattag atcctgtgat tcaatatgtc ctcgatcaac tgaaccgtat gccagcccct    60
gactacaagc acttaagcgc tcaacagttt cgttcacagc aacacctgtt tccaccagtt   120
aagaaagaac cggtcgcaga agttcgcgaa ttcgacatgg atctgccggg ccgtaccctg   180
aaagtccgta tgtaccgccc ggaaggtgtt gaaccaccat atccagcact ggtttactac   240
catggtggcg gttgggttgc gggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc agcaattgc gtttcaactg   540
ctgatctatc cctttactgg ttatgatcca gcacatccac cagcaagtat ccttgagaat   600
gcggaggggtt acctgttaac cggaggcatg atgctgtggt ttcgtattca gtacctgaac   660
agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctgaag ccctgaacaa agcgggcgtt aaggtggaga tcgagaactt cgaggatctg   840
attcatggct cgcgcagtt ctattctctg agcccaggcg caaccaaagc actggtacgt   900
attgccgaga aactgcgcga tgcgttggcg                                    930
```

<210> SEQ ID NO 64
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 64

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

```
Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
        130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Ile Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 65
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 65
atgccattag atcctgtgat tcaatatgtc ctcgatcaac tgaaccgtat gccagccatt      60
gactacaagc acttaagcgc tcaacagttt cgttcacagc aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt tcgtgaccag gtacctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
```

```
attcatggct tcgcgcagtt ctattctctg agcccaggcg caaccaaagc actggtacgt    900
attgccgaga aactgcgcga tgcgttggcg                                     930
```

<210> SEQ ID NO 66
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 66

Met Pro Leu Asp Pro Val Ile Gln Tyr Val Leu Asp Gln Leu Asn Arg
1               5                   10                  15

Met Pro Ala Ile Asp Tyr Lys His Leu Ser Ala Gln Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 67

<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 67

```
atgccattag atcctgtgat tcaatatgtc ctcgatcaac tgaaccgtat gccagcccct      60
gactacaagc acttaagcgc tcaacagttt cgttcacagc aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc agcaattgc gtttcaactg      540
ctgatctatc cctttactgg ttatgatcca gcacatccac cagcaagtat ccttgagaat     600
gcggagggtt acctgttaac cggaggcatg atgctgtggt tcgtaatca gtacctgaac      660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct cgcgcagtt ctattctctg agcccaggcg caaccaaagc actggtacgt      900
attgccgaga aactgcgcga tgcgttggcg                                      930
```

<210> SEQ ID NO 68
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 68

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
```

```
                130                 135                 140
Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 69
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 69
atgccattag atcctgtgat tcaatatgtc ctcgatcaac tgaaccgtat gccagcccct      60
gactacaagc acttaagcgc tcaagatttt cgttcacagc aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga cgtgcagcc     420 gatttccatc ttgatccagc acgcattgca gttggcggcg attcagcagg cggcaacctg     480
gcggccgtga ctagtattct ggcgaaagaa cgtggtggtc agcaattgc gtttcaactg     540 ctgatctatc cctttactgg ttatgatcca gcacatccac cagcaagtat ccttgagaat     600
gcggagggtt acctgttaac cggaggcatg atgctgtggt tcgtgaccaa gtacctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct cgcgcagtt ctattctctg agcccaggcg caaccaaagc actggtacgt     900
attgccgaga aactgcgcga tgcgttggcg                                      930
```

<210> SEQ ID NO 70
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 70

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Asp Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 71
<211> LENGTH: 930
<212> TYPE: DNA
<213> ORGANISM: Artificial Sequence
<220> FEATURE:
<223> OTHER INFORMATION: Description of Artificial Sequence: Synthetic polynucleotide sequence encoding a codon optimized
carboxyesterase enzyme

<400> SEQUENCE: 71

```
atgccattag atcctgtgat tcaatatgtc ctcgatcaac tgaaccgtat gccagcccct      60
gactacaagc acttaagcgc tcaacagttt cgttcaggtc aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc agcaattgc gtttcaactg      540
ctgatctatc cctttactgg ttatgatcca gcacatccac cagcaagtat ccttgagaat     600
gcggagggtt acctgttaac cggaggcatg atgctgtggt tcgtgacca gtacctgaac      660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct tcgcgcagtt ctattctctg agcccaggcg caaccaaagc actggtacgt     900
attgccgaga aactgcgcga tgcgttggcg                                      930
```

<210> SEQ ID NO 72
<211> LENGTH: 310
<212> TYPE: PRT
<213> ORGANISM: Artificial Sequence
<220> FEATURE:
<223> OTHER INFORMATION: Description of Artificial Sequence: Synthetic
    polypeptide sequence of a codon optimized
    carboxyesterase enzyme

<400> SEQUENCE: 72

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gly Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

```
Ala Ala Val Thr Ser Ile Leu Ala Lys Glu Arg Gly Gly Pro Ala Ile
            165                 170                 175
Ala Phe Gln Leu Leu Ile Tyr Pro Phe Thr Gly Tyr Asp Pro Ala His
        180                 185                 190
Pro Pro Ala Ser Ile Leu Glu Asn Ala Glu Gly Tyr Leu Leu Thr Gly
            195                 200                 205
Gly Met Met Leu Trp Phe Arg Asp Gln Tyr Leu Asn Ser Leu Glu Glu
        210                 215                 220
Leu Thr His Pro Trp Phe Ser Pro Val Leu Tyr Pro Asp Leu Ser Gly
225                 230                 235                 240
Leu Pro Pro Ala Tyr Ile Ala Thr Ala Gln Tyr Asp Pro Leu Arg Asp
                245                 250                 255
Val Gly Lys Leu Tyr Ala Glu Ala Leu Asn Lys Ala Gly Val Lys Val
            260                 265                 270
Glu Ile Glu Asn Phe Glu Asp Leu Ile His Gly Phe Ala Gln Phe Tyr
        275                 280                 285
Ser Leu Ser Pro Gly Ala Thr Lys Ala Leu Val Arg Ile Ala Glu Lys
    290                 295                 300
Leu Arg Asp Ala Leu Ala
305                 310
```

```
<210> SEQ ID NO 73
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 73
atgccattag atcctgtgat tcaatatgtc ctcgatcaac tgaaccgtat gccagcccct      60
gactacaagc acttaagcgc tagtcagttt cgttcacagc aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg aaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt tcgtgacca gtacctgaac      660 agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct cgcgcagtt ctattctctg agcccaggcg caaccaaagc actggtacgt     900
attgccgaga aactgcgcga tgcgttggcg                                      930

<210> SEQ ID NO 74
<211> LENGTH: 310
<212> TYPE: PRT
<213> ORGANISM: Artificial Sequence
```

<220> FEATURE:
<223> OTHER INFORMATION: Description of Artificial Sequence: Synthetic
polypeptide sequence of a codon optimized
carboxyesterase enzyme

<400> SEQUENCE: 74

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Ser Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asp Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310
```

<210> SEQ ID NO 75
<211> LENGTH: 930
<212> TYPE: DNA
<213> ORGANISM: Artificial Sequence
<220> FEATURE:
<223> OTHER INFORMATION: Description of Artificial Sequence: Synthetic
polynucleotide sequence encoding a codon optimized
carboxyesterase enzyme

<400> SEQUENCE: 75

```
atgccattag atcctgtgat tcaatatgtg ctcgatcaac tgaaccgtat gccagcccct    60
gactacaagc acttaagcgc tcaacaggtt cgttcacaac aacacctgtt tccaccagtt   120
aagaaagaac cggtcgcaga agttcgcgaa ttcgacatgg atctgccggg ccgtaccctg   180
aaagtccgta tgtaccgccc ggaaggtgtt gaaccaccat atccagcact ggtttactac   240
catggtggcg gttgggttgc gggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc cagcaattgc gtttcaactg   540
ctgatctatc cctttactgg ttatgatcca gcacatccac cagcaagtct tcttgagaat   600
gcggagggtt acctgttaac cggaggcatg atgctgtggt tcgtaatca gtacctgaac    660 agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctgaag ccctgaacaa agcgggcgtt aaggtggaga tcgagaactt cgaggatctg   840
attcatggct tcgcgcagtt ctattctctg agcccaggcg caaccaaagc actggtacgt   900
attgccgaga aactgcgcga tgcgttggcg                                    930
```

<210> SEQ ID NO 76
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 76

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Val Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190
```

Pro Pro Ala Ser Leu Leu Glu Asn Ala Glu Gly Tyr Leu Leu Thr Gly
            195                 200                 205

Gly Met Met Leu Trp Phe Arg Asn Gln Tyr Leu Asn Ser Leu Glu Glu
        210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 77
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 77
atgccattag atcctgtgat tcaatatgtg ctcgatcaac tgaaccgtat gccagcccct      60
gactacaagc acttaagcgc tcaacagttt cgttcacagc aacacattgg tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttgcggcg attcagcagg cggcaacctg     480
gcggccgtga ctagtattct ggcgaaagaa cgtggtggtc agcaattgc gtttcaactg     540 ctgatctatc cctttactgg ttatgatcca gcacatccac cagcaagtat ccttgagaat     600
gcggagggtt acctgttaac cggaggcatg atgctgtggt tcgtaatca gtacctgaac     660 agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatacg     840
attcatggct cgcgcagtt ttattctatt agcccaggcg caaccaaagc actggtacgt     900
attgccgaga aactgcgcga tgcgttggcg                                       930

<210> SEQ ID NO 78
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 78

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Ile Gly Pro Pro Val Lys Lys Glu Pro Val Ala Glu Val
        35                  40                  45

Arg Glu Phe Asp Met Asp Leu Pro Gly Arg Thr Leu Lys Val Arg Met
50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Thr Ile His Gly Phe Ala Gln Phe Tyr
        275                 280                 285

Ser Ile Ser Pro Gly Ala Thr Lys Ala Leu Val Arg Ile Ala Glu Lys
290                 295                 300

Leu Arg Asp Ala Leu Ala
305                 310

<210> SEQ ID NO 79
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 79
atgccattag atcctgtgat tcaatatgtc ctcgatcaac tgaaccgtat gccagcccct      60
gactacaagc acttaagcgc tcaacagttt cgttcacagc aacacatggg tccaccagtt     120
aagaaagaac cggtcgcaga agttcgcgaa ttcgacatgg atctgccggg ccgtaccctg     180

-continued

```
aaagtccgta tgtaccgccc ggaaggtgtt gaaccaccat atccagcact ggtttactac    240
catggtggcg gttgggttgc gggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga cgtgcagcc     420 gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc cctttactgg ttatgatcca gcacatccac cagcaagtat ccttgagaat    600
gcggagggtt acctgttaac cggaggcatg atgctgtggt ttcgtaatca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatatg    840
attcatggct tcgcgcagtt ctattctatt agcccaggcg caaccaaagc actggtacgt    900
attgccgaga aactgcgcga tgcgttggcg                                     930
```

<210> SEQ ID NO 80
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 80

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Met Gly Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
        130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
```

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
            245                 250                 255

Val Gly Lys Leu Tyr Ala Glu Ala Leu Asn Lys Ala Gly Val Lys Val
        260                 265                 270

Glu Ile Glu Asn Phe Gly Asp Met Ile His Gly Phe Ala Gln Phe Tyr
    275                 280                 285

Ser Ile Ser Pro Gly Ala Thr Lys Ala Leu Val Arg Ile Ala Glu Lys
    290                 295                 300

Leu Arg Asp Ala Leu Ala
305                 310

<210> SEQ ID NO 81
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 81
atgccattag atcctgtgat tcaatatatg ctcgatcaac tgaaccgtat gccagcccct     60
gactacaagc acttaagcgc tcaacagttt cgttcacagc aacacttggg tccaccagtt    120
aagaaagaac cggtcgcaga agttcgcgaa ttcgacatgg atctgccggg ccgtaccctg    180
aaagtccgta tgtaccgccc ggaaggtgtt gaaccaccat atccagcact ggtttactac    240
catggtggcg gttgggttgc gggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga gcgtatgat gcactgcaat ggattgcaga cgtgcagcc     420 gatttccatc ttgatccagc acgcattgca gttggcggcg attcagcagg cggcaacctg    480
gcggccgtga ctagtattct ggcgaaagaa cgtggtggtc agcaattgc gtttcaactg     540 ctgatctatc cctttactgg ttatgatcca gcacatccac cagcaagtat ccttgagaat    600
gcggagggtt acctgttaac cggaggcatg atgctgtggt tcgtaatca gtacctgaac     660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatcta    840
attcatggct tcgcgcagtt ctattctctg agcccaggcg caaccaaagc actggtacgt    900
attgccgaga aactgcgcga tgcgttggcg                                      930

<210> SEQ ID NO 82
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 82

Met Pro Leu Asp Pro Val Ile Gln Tyr Met Leu Asp Gln Leu Asn Arg
1               5                   10                  15

Met Pro Ala Pro Asp Tyr Lys His Leu Ser Ala Gln Gln Phe Arg Ser
                20                  25                  30

Gln Gln His Leu Gly Pro Pro Val Lys Lys Glu Pro Val Ala Glu Val
            35                  40                  45

Arg Glu Phe Asp Met Asp Leu Pro Gly Arg Thr Leu Lys Val Arg Met
50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
            195                 200                 205

Gly Met Met Leu Trp Phe Arg Asn Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
            275                 280                 285

Ser Leu Ser Pro Gly Ala Thr Lys Ala Leu Val Arg Ile Ala Glu Lys
290                 295                 300

Leu Arg Asp Ala Leu Ala
305                 310

<210> SEQ ID NO 83
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 83
atgccattag atcctgtgat tcaatatgtc ctcgatcaac tgaaccgtat gccagcccct      60
gactacaagc acttaagcgc tagtcagttt cgttcacagc aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300

```
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc cctttactgg ttacgatcca gcacatccac cagcaagtat tcttgagaat    600
gcggagggtt acctgttaac cggaggcatg atgctgtggt ttcgtaatca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggtaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                     930
```

<210> SEQ ID NO 84
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 84

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Ser Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240
```

```
Leu Pro Pro Ala Tyr Ile Ala Thr Ala Gln Tyr Asp Pro Leu Arg Asp
            245                 250                 255

Val Gly Lys Leu Tyr Ala Glu Ala Leu Asn Lys Ala Gly Val Lys Val
        260                 265                 270

Glu Ile Glu Asn Phe Glu Asp Leu Ile His Gly Phe Ala Gln Phe Tyr
    275                 280                 285

Ser Leu Ser Pro Gly Ala Thr Lys Ala Leu Val Arg Ile Ala Glu Lys
290                 295                 300

Leu Arg Asp Ala Leu Ala
305                 310

<210> SEQ ID NO 85
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 85
atgccattag atcctgtgat tcaatatgtc ctcgatcaac tgaaccgtat gccagcccct      60
gactacaagc acttaagcgc tagtcagttt cgttcacagc aacatctgtt ccaccagtt     120
aagaaagaac cggtcgcaga agttcgcgaa ttcgacatgg atctgccggg ccgtaccctg    180
aaagtccgta tgtaccgccc ggaaggtgtt gaaccaccat atccagcact ggtttactac    240
catggtggcg gttgggttgc gggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga gcgtatgat gcactgcaat ggattgcaga cgtgcagcc     420
gatttccatc ttgatccagc acgcattgca gttgcggcg attcagcggg cggcaacctg    480
gcggccgtga ctagtattct ggcgaaagaa cgtggtggtc cagcaattgc gtttcaactg    540
ctgatctatc cctttactgg ttacgatcca gcacatccac cagcaagtct tcttgagaat    600
gcggagggtt acctgttaac cggaggcatg atgctgtggt ttcgtaatca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggtaaactt    780
tacgctgaag ccctgaccaa agcgggcgtt aaggtggaga tcgagaactt cgaggatctg    840
attcatggct cgcgcagtt ctattctctg agcccaggcg caaccaaagc actggtacgt    900
attgccgaga aactgcgcga tgcgttggcg                                     930

<210> SEQ ID NO 86
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 86

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Ser Gln Phe Arg Ser
            20                  25                  30

Gln Gln His Leu Phe Pro Pro Val Lys Lys Glu Pro Val Ala Glu Val
        35                  40                  45
```

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
                115                 120                 125

Tyr Asp Ala Leu Gln Trp Ile Ala Glu Arg Ala Ala Asp Phe His Leu
            130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
                180                 185                 190

Pro Pro Ala Ser Leu Leu Glu Asn Ala Glu Gly Tyr Leu Leu Thr Gly
                195                 200                 205

Gly Met Met Leu Trp Phe Arg Asn Gln Tyr Leu Asn Ser Leu Glu Glu
            210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Thr Lys Ala Gly Val Lys Val
                260                 265                 270

Glu Ile Glu Asn Phe Glu Asp Leu Ile His Gly Phe Ala Gln Phe Tyr
            275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 87
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 87
atgccattag atcctgtgat tcaatatgtc ctcgatcaac tgaaccgtat gccagcccct      60
gactacaagc acttaagcgc tagtcagttt cgttcacagc aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480

```
gcggccgtga ctagtattct ggcgaaagaa cgtggtggtc cagcaattgc gtttcaactg    540
ctgatctatc cctttactgg ttatgatcca gcacatccac cagcaagtct tcttgagaat    600
gcggagggtt acctgttaac cggaggcatg atgctgtggt ttcgtaatca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggtaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                     930
```

<210> SEQ ID NO 88
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 88

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Ser Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Leu Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270
```

Glu Ile Glu Asn Phe Glu Asp Leu Ile His Gly Phe Ala Gln Phe Tyr
              275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 89
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 89

```
atgccattag atcctgtgat tcaatatgtc ctcgatcaac tgaaccgtat gccagccccc    60
gactacaagc acttaagcgc tcaacaagtt cgttcatggc aacacctgtt tccaccagtt   120
aagaaagaac cggtcgcaga agttcgcgaa ttcgacatgg atctgccggg ccgtaccctg   180
aaagtccgta tgtaccgccc ggaaggtgtt gaaccaccat atcgggcact ggtttactac   240
catggtggcg gttgggttgc gggtgacctg gaaacgcatg atccggtgtg tcgtgtgttg   300
gcgaaatggg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc agcaattgc gtttcaactg   540
ctgatctatc cctttactgg atatgatcca gcacatccac cagcaagtat ccttgagaat   600
gcggagggtt acctgttaac cggaggcatg atgctgtggt ttcgtaatca gtacctgaac   660
agccttgagg aactgactca cccatggttt agtccagtgc tgtacccgga tcttagcggt   720
ttaccaccgg cgtacattgc aaccgcacag tacgatcccc tgcgcgatgt cggcaaactt   780
tacgctgaag ccctgaacaa gcgggcgtt aaagtggaga tcgagaactt cgaggatctg   840
attcatggct tcgcgcagtt ctattctctg agcccaggcg caaccaaagc actggtacgt   900
attgccgaga aactgcgcga tgcgttggcg                                    930
```

<210> SEQ ID NO 90
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 90

Met Pro Leu Asp Pro Val Ile Gln Tyr Val Leu Asp Gln Leu Asn Arg
1               5                  10                  15

Met Pro Ala Pro Asp Tyr Lys His Leu Ser Ala Gln Gln Val Arg Ser
              20                  25                  30

Trp Gln His Leu Phe Pro Pro Val Lys Lys Glu Pro Val Ala Glu Val
          35                  40                  45

Arg Glu Phe Asp Met Asp Leu Pro Gly Arg Thr Leu Lys Val Arg Met
      50                  55                  60

Tyr Arg Pro Glu Gly Val Glu Pro Pro Tyr Arg Ala Leu Val Tyr Tyr

```
                65                  70                  75                  80
His Gly Gly Gly Trp Val Ala Gly Asp Leu Glu Thr His Asp Pro Val
                    85                  90                  95
Cys Arg Val Leu Ala Lys Trp Gly Arg Ala Val Val Phe Ser Val Asp
                    100                 105                 110
Tyr Arg Leu Ala Pro Glu His Lys Phe Pro Ala Ala Val Glu Asp Ala
                    115                 120                 125
Tyr Asp Ala Leu Gln Trp Ile Ala Glu Arg Ala Ala Asp Phe His Leu
                130                 135                 140
Asp Pro Ala Arg Ile Ala Val Gly Gly Asp Ser Ala Gly Gly Asn Leu
145                 150                 155                 160
Ala Ala Val Thr Ser Ile Leu Ala Lys Glu Arg Gly Gly Pro Ala Ile
                    165                 170                 175
Ala Phe Gln Leu Leu Ile Tyr Pro Phe Thr Gly Tyr Asp Pro Ala His
                    180                 185                 190
Pro Pro Ala Ser Ile Leu Glu Asn Ala Glu Gly Tyr Leu Leu Thr Gly
                    195                 200                 205
Gly Met Met Leu Trp Phe Arg Asn Gln Tyr Leu Asn Ser Leu Glu Glu
                    210                 215                 220
Leu Thr His Pro Trp Phe Ser Pro Val Leu Tyr Pro Asp Leu Ser Gly
225                 230                 235                 240
Leu Pro Pro Ala Tyr Ile Ala Thr Ala Gln Tyr Asp Pro Leu Arg Asp
                    245                 250                 255
Val Gly Lys Leu Tyr Ala Glu Ala Leu Asn Lys Ala Gly Val Lys Val
                    260                 265                 270
Glu Ile Glu Asn Phe Glu Asp Leu Ile His Gly Phe Ala Gln Phe Tyr
                    275                 280                 285
Ser Leu Ser Pro Gly Ala Thr Lys Ala Leu Val Arg Ile Ala Glu Lys
                    290                 295                 300
Leu Arg Asp Ala Leu Ala
305                 310

<210> SEQ ID NO 91
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 91
atgccattag atcctgtgat tcaatatgtc ctcgatcaac tgaaccgtat gccagccatt      60
gactacaagc acttaagcgc tcaacaagtt cgttcatggc aacacctgtt tccaccagtt     120
aagaaagaac cggtccgcga agttcgcgaa ttcgacatgg atctgccggg ccgtaccctg     180
aaagtccgta tgtacacgcc ggaaggtgtt gaaccaccat atccagcact ggtttactac     240
catggtggcg gttgggttgc gggtgacctg gaaacgcatg atccggtgtg tcgtgtgttg     300
gcgaaatggg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttgcggcg attcagcagg cggcaacctg     480
gcggccgtga ctagtattct ggcgaaagaa cgtggtggtc cagcaattgc gtttcaactg     540
ctgatctatc cctttactgg atatgatcca gcacatccac cagcaagtat ccttgagaat     600
```

```
gcggagggtt acctgttaac cggaggcatg atgctgtggt ttcgtaatca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctagag ccctgaacaa agcgggcgtt aaagtggaga tcgagaactt cgaggatctg    840
attcatggct tcgcgcagtt ctattctctg agcccaggcg caaccaaagc actggtacgt    900
attgccgaga aactgcgcga tgcgttggcg                                     930
```

<210> SEQ ID NO 92
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 92

```
Met Pro Leu Asp Pro Val Ile Gln Tyr Val Leu Asp Gln Leu Asn Arg
1               5                   10                  15

Met Pro Ala Ile Asp Tyr Lys His Leu Ser Ala Gln Gln Val Arg Ser
            20                  25                  30

Trp Gln His Leu Phe Pro Pro Val Lys Lys Glu Pro Val Arg Glu Val
        35                  40                  45

Arg Glu Phe Asp Met Asp Leu Pro Gly Arg Thr Leu Lys Val Arg Met
    50                  55                  60

Tyr Thr Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Trp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Arg Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
```

Leu Arg Asp Ala Leu Ala
305              310

<210> SEQ ID NO 93
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 93

```
atgccattag atcctgtgat tcaatatgtc ctcgatcaac tgaaccgtat gccagcccct      60
gactggaagc acttaagcgc tcaacagttt cgttcacagc aacacctgtt tccaccagtt     120
aagaaagaac cggtcgcaga agttcgcgaa ttcgacatgg atctgccggg ccgtaccctg     180
aaagtccgta tgtaccgccc ggaaggtgtt gaaccaccat atcgggcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcggg cggcaacctg     480
gcggccgtga ctagtattct ggcgaaagaa cgtggtggtc agcaattgc gtttcaactg     540
ctgatctatc cctttactgg ttatgatcca gcacatccac cagcaagtat ccttgagaat     600
gcggagggtt acctgttaac cggaggcatg atgctgtggt ttcgtaatca gtacctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct tcgcgcagtt ctattctatt agcccaggcg caaccaaagc actggtacgt     900
attgccgaga aactgcgcga tgcgttggcg                                     930
```

<210> SEQ ID NO 94
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 94

Met Pro Leu Asp Pro Val Ile Gln Tyr Val Leu Asp Gln Leu Asn Arg
1               5                   10                  15

Met Pro Ala Pro Asp Trp Lys His Leu Ser Ala Gln Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Arg Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Val Glu Asp Ala
            115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
275                 280                 285

Ser Ile Ser Pro Gly Ala Thr Lys Ala Leu Val Arg Ile Ala Glu Lys
        290                 295                 300

Leu Arg Asp Ala Leu Ala
305                 310

<210> SEQ ID NO 95
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 95
atgccattag atcctgtgat tcaatatgtc ctcgatcaac tgaaccgtat gccagcccct    60
gactacaagc acttaagcgc tcaacagttt cgttcacagc aacacctgtt tccaccagtt   120
aagaaagaac cggtcaaaga agttcgcgaa ttcgacatgg atctgccggg ccgtaccctg   180
aaagtccgta tgtaccgccc ggaaggtgtt gaaccaccat atccagcact ggtttactac   240
catggtggcg gttgggttgc gggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacacc   480
gcggccgtga ctagtattct ggcgaaagaa cgtggtggtc cagcaattgc gtttcaactg   540
ctgatctatc cctttactgg ttatgatcca gcacatccac cagcaagtat ccttgagaat   600
gcggagggtt acctgttaac cggaggcatg atgctgtggt tcgtaatca gtacctgaac   660 agccttgagg aactgactca cccatggttt agtccagtgc tgtacccgga tcttagcggt   720
ttaccaccgg cgtacattgc aaccgcacag tacgatcccc tgcgcgatgt cggcaaactt   780

```
tacgctgaag ccctgaacaa agcgggcgtt aaggtggaga tcgagaactt cgaggatctg      840
attcatggct tcgcgaactt ctattctctg agcccaggcg caaccaaagc actggtacgt      900
attgccgaga aactgcgcga tgcgttggcg                                       930
```

<210> SEQ ID NO 96
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 96

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Pro Val Lys Lys Glu Pro Val Lys Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Thr
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Asn Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310
```

<210> SEQ ID NO 97
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 97

```
atgccattag atcctgtgat tcaatatgtc ctcgatcaac tgaaccgtat gccagcccct      60
gactacaagc acttaagcgc tcaacagttt cgttcacagc aacacctgtt tccaccagtt     120
aagaaagaac cggtcaaaga agttcgcgaa ttcgacatgg atctgccggg ccgtaccctg     180
aaagtccgta tgtaccgccc ggaaggtgtt gaaccaccat atccagcact ggtttactac     240
catggtggcg gttgggttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacacc     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt tcgtaatcag taccctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct tcgcgagctt ctattctctg agcccaggcg caaccaaagc actggtacgt     900
attgccgaga aactgcgcga tgcgttggcg                                      930
```

<210> SEQ ID NO 98
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 98

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln His Leu Phe Pro Pro Val Lys Lys Glu Pro Val Lys Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125
```

Tyr Asp Ala Leu Gln Trp Ile Ala Glu Arg Ala Ala Asp Phe His Leu
            130                 135                 140

Asp Pro Ala Arg Ile Ala Val Gly Gly Asp Ser Ala Gly Gly Asn Thr
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Gly Asp Leu Ile His Gly Phe Ala Ser Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 99
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 99
atgccattag atcctgtgat tcaatatgtc ctcgatcaac tgaaccgtat gccagcccct      60
gactacaagc acttaagcgc ttgccagttt cgttcacagc aacacctgtt tgaaccagtt     120
aagaaagaac cggtcgcaga agttcgcgaa ttcgacatgg atctgccggg ccgtaccctg     180
aaagtccgta tgtaccgccc ggaaggtgtt gaaccaccat atccagcact ggtttactac     240
catggtggcg gtggcgttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga gcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt tcgtaatca gtacctgaac     660 agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct tcgcgcagtt ctattctctg agcccaggcg caaccaaagc actggtacgt     900
attgccgaga aactgcgcga tgcgttggcg 930

<210> SEQ ID NO 100
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 100

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Leu Phe Glu Pro Val Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Val Ala Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 101
<211> LENGTH: 930
<212> TYPE: DNA
<213> ORGANISM: Artificial Sequence
<220> FEATURE:
<223> OTHER INFORMATION: Description of Artificial Sequence: Synthetic
    polynucleotide sequence encoding a codon optimized
    carboxyesterase enzyme

<400> SEQUENCE: 101

| | | | | | |
|---|---|---|---|---|---|
| atgccattag | atcctgtgat | tcaatatgtc | ctcgatcaac | tgaaccgtat | gccagcccct | 60 |
| gactacaagc | acttaagcgc | tcaacagttt | cgttcacagc | aaagcctgtt | tccaccagtt | 120 |
| aagaaagaac | cggtcgcaga | agttcgcgaa | ttcgacatgg | atctgccggg | ccgtaccctg | 180 |
| aaagtccgta | tgtacctgcc | ggaaggtgtt | gaaccaccat | atccagcact | ggtttactac | 240 |
| catggtggcg | gttggaccgc | gggtgacctg | gaaacgcatg | atccgatgtg | tcgtgtgttg | 300 |
| gcgaaagatg | gacgcgcagt | ggtgtttagc | gttgactacc | gtctggcacc | agaacacaag | 360 |
| tttccagcgg | cagttgaaga | cgcgtatgat | gcactgcaat | ggattgcaga | acgtgcagcc | 420 |
| gatttccatc | ttgatccagc | acgcattgca | gttggcggcg | attcagcagg | cggcaacccg | 480 |
| gcggccgtga | ctagtattct | ggcgaaagaa | cgtggtggtc | agcaattgc | gtttcaactg | 540 |
| ctgatccagc | cctttactgg | ttttgatcca | gcacatccac | cagcaagtat | ccttgagaat | 600 |
| gcggagggtt | acttttttaac | cggaggcatg | atggattgg | ttcgtaatca | gtacctgaac | 660 |
| agccttgagg | aactgactca | cccatggttt | agtccagtgc | tgtacccgga | tcttagcggt | 720 |
| ttaccaccgg | cgtacattgc | aaccgcacag | tacgatcccc | tgaacgatgt | cggcaaactt | 780 |
| tacgctgaag | ccctgaacaa | agcgggcctg | aaggtggaga | tcgagaactt | cgaggatctg | 840 |
| attcatggct | cgcgagcttc | ctattctctg | agcccaggcg | caaccaaagc | actggtacgt | 900 |
| attgccgaga | aactgcgcga | tgcgttggcg | | | 930 |

<210> SEQ ID NO 102
<211> LENGTH: 310
<212> TYPE: PRT
<213> ORGANISM: Artificial Sequence
<220> FEATURE:
<223> OTHER INFORMATION: Description of Artificial Sequence: Synthetic
    polypeptide sequence of a codon optimized
    carboxyesterase enzyme

<400> SEQUENCE: 102

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Leu Pro Glu Gly Val Glu Pro Pro Tyr Pro Ala Leu Val Tyr Tyr
65                  70                  75                  80

His Gly Gly Gly Trp Thr Ala Gly Asp Leu Glu Thr His Asp Pro Met
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Pro

```
            145                 150                 155                 160
Ala Ala Val Thr Ser Ile Leu Ala Lys Glu Arg Gly Gly Pro Ala Ile
                165                 170                 175

Ala Phe Gln Leu Leu Ile Gln Pro Phe Thr Gly Phe Asp Pro Ala His
                180                 185                 190

Pro Pro Ala Ser Ile Leu Glu Asn Ala Glu Gly Tyr Phe Leu Thr Gly
                195                 200                 205

Gly Met Met Asp Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Asn Asp
                245                 250                 255

Val Gly Lys Leu Tyr Ala Glu Ala Leu Asn Lys Ala Gly Leu Lys Val
                260                 265                 270

Glu Ile Glu Asn Phe Glu Asp Leu Ile His Gly Phe Ala Ser Phe Tyr
                275                 280                 285

Ser Leu Ser Pro Gly Ala Thr Lys Ala Leu Val Arg Ile Ala Glu Lys
                290                 295                 300

Leu Arg Asp Ala Leu Ala
305                 310

<210> SEQ ID NO 103
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 103
atgccattag atcctgtgat tcaatatgtc ctcgatcaac tgaaccgtat gccagcccct      60
gactacaagc acttaagcgc tcaacagttt cgttcacagc aaagcctgtt tccaccagtt     120
aagaaagaac cggtcgcaga agttcgcgaa ttcgacatgg atctgccggg ccgtaccctg     180
aaagtccgta tgtacctgcc ggaaggtgtt gaaccaccat atccagcact ggtttactac     240
catggtggcg gttggaccgc gggtgacctg gaaacgcatg atccgatgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt actttttaac cggaggcatg atgctgtggt ttcgtaatca gtacctgaac     660
agccttgagg aactgactca cccatggttt agtccagtgc tgtacccgga tcttagcggt     720
ttaccaccgg cgtacattgc aacctggcag tacgatcccc tgcgcgatgt cggcaaactt     780
tacgctgaag ccctgaacaa agcgggcgtt aaggtggaga tcgagaactt cgaggatctg     840
attcatggct tcgcgagctt ctattctctg agcccaggcg caaccaaagc actggtacgt     900
attgccgaga aactgcgcga tgcgttggcg                                      930

<210> SEQ ID NO 104
<211> LENGTH: 310
```

```
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 104

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Gln Gln Phe Arg Ser
            20                  25                  30

Gln Gln Ser Leu Phe Pro Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Leu Pro Glu Gly Val Glu Pro Pro Tyr Pro Ala Leu Val Tyr Tyr
65                  70                  75                  80

His Gly Gly Gly Trp Thr Ala Gly Asp Leu Glu Thr His Asp Pro Met
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Phe Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Trp Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Ser Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 105
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme
```

<400> SEQUENCE: 105

```
atgccattag atcctgtgat tcaatatgtc ctcgatcaac tgaaccgtat gccagcccct    60
gactacaagc acttaagcgc ttgccagttt cgttcacagc aacacctgtt ccaccagtt    120
aagaaagaac cggtcgcaga agttcgcgaa ttcgacatgc gtctgccggg ccgtaccctg   180
aaagtccgta tgtaccgccc ggaaggtgtt gaaccaccat atcgtgcact ggtttactac   240
catggtggcg gttgggttgc gggtgacctg gaaacgcatg atccggtgtg tcgtgtgttg   300
gcgaaagatg gacgcgcagt ggtgtttagc gttgactacc gtctggcacc agaacacaag   360
tttccagcgg cagttgaaga cgcgtatgat gcactgcaat ggattgcaga acgtgcagcc   420
gatttccatc ttgatccagc acgcattgca gttggcggcg attcagcagg cggcaacctg   480
gcggccgtga ctagtattct ggcgaaagaa cgtggtggtc cagcaatggc gtttcaactg   540
ctgatctatc cctttactgg ttatgatcca gcacatccac cagcaagtat ccttgagaat   600
gcggagggtt acttttttaac cggaggcatg atgctgtggt ttcgtaatca gtacctgaac   660
agccttgagg aactgactca cccatggttt agtccagtgc tgtacccgga tcttagcggt   720
ttaccaccgg cgtacattgc agtggcacag tacgatcccc tgcgcgatgt cggcaaactt   780
tacgctgaag ccctgaacaa agcgggcgtt aaggtggaga tcgagaactt cgaggatctg   840
attcatggct cgcgcagtt ctattctctg agcccaggcg caaccaaagc actggtacgt   900
attgccgaga aactgcgcga tgcgttggcg                                    930
```

<210> SEQ ID NO 106
<211> LENGTH: 310
<212> TYPE: PRT
<213> ORGANISM: Artificial Sequence
<220> FEATURE:
<223> OTHER INFORMATION: Description of Artificial Sequence: Synthetic
       polypeptide sequence of a codon optimized
       carboxyesterase enzyme

<400> SEQUENCE: 106

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Leu Phe Pro Pro Val Lys Lys Glu Pro Val Ala Glu Val
        35                  40                  45

Arg Glu Phe Asp Met Arg Leu Pro Gly Arg Thr Leu Lys Val Arg Met
    50                  55                  60

Tyr Arg Pro Glu Gly Val Glu Pro Pro Tyr Arg Ala Leu Val Tyr Tyr
65                  70                  75                  80

His Gly Gly Gly Trp Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Met
                165                 170                 175
```

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Phe Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Val Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 107
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 107
atgccattag atcctgtgct tcaatatgtg ctcgatcaac tgaaccgtat gccagcccct      60
gactacaagc acttaagcgc ttgccagttt cgttcacagc aacacctgtt tgaaccagtt     120
aagaaagaac cggtcgctga agttcgcgaa ttcgacatgg acctgccggg ccgtaccctg     180
aaagtccgta tgtaccgccc ggaaggtgtt gaaccaccat atccagcact ggtttactac     240
catggtggcg gtggcgttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctc     480
gcggccgtga ctagtattct ggcgaaagaa cgtggtggtc agcaattgc gtttcaactg     540 ctgatctatc cctttactgg ttatgatcca gcacatccac cagcaagtat cctggagaat     600
gcggagggtt acctgttaac cggaggcatg atgctgtggt tcgtaatca gtacctgaac     660 agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct cgcgcagtt ctattctctg agcccaggcg caaccaaagc actggtacgt     900
attgccgaga aactgcgcga tgcgttggcg                                      930

<210> SEQ ID NO 108
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized carboxyesterase enzyme

<400> SEQUENCE: 108

```
Met Pro Leu Asp Pro Val Leu Gln Tyr Val Leu Asp Gln Leu Asn Arg
1               5                   10                  15
Met Pro Ala Pro Asp Tyr Lys His Leu Ser Ala Cys Gln Phe Arg Ser
            20                  25                  30
Gln Gln His Leu Phe Glu Pro Val Lys Lys Glu Pro Val Ala Glu Val
        35                  40                  45
Arg Glu Phe Asp Met Asp Leu Pro Gly Arg Thr Leu Lys Val Arg Met
    50                  55                  60
Tyr Arg Pro Glu Gly Val Glu Pro Pro Tyr Pro Ala Leu Val Tyr Tyr
65                  70                  75                  80
His Gly Gly Gly Val Ala Gly Asp Leu Glu Thr His Asp Pro Val
                85                  90                  95
Cys Arg Val Leu Ala Lys Asp Gly Arg Ala Val Val Phe Ser Val Asp
            100                 105                 110
Tyr Arg Leu Ala Pro Glu His Lys Phe Pro Ala Ala Val Glu Asp Ala
        115                 120                 125
Tyr Asp Ala Leu Gln Trp Ile Ala Glu Arg Ala Ala Asp Phe His Leu
    130                 135                 140
Asp Pro Ala Arg Ile Ala Val Gly Gly Asp Ser Ala Gly Gly Asn Leu
145                 150                 155                 160
Ala Ala Val Thr Ser Ile Leu Ala Lys Glu Arg Gly Pro Ala Ile
                165                 170                 175
Ala Phe Gln Leu Leu Ile Tyr Pro Phe Thr Gly Tyr Asp Pro Ala His
            180                 185                 190
Pro Pro Ala Ser Ile Leu Glu Asn Ala Glu Gly Tyr Leu Leu Thr Gly
        195                 200                 205
Gly Met Met Leu Trp Phe Arg Asn Gln Tyr Leu Asn Ser Leu Glu Glu
    210                 215                 220
Leu Thr His Pro Trp Phe Ser Pro Val Leu Tyr Pro Asp Leu Ser Gly
225                 230                 235                 240
Leu Pro Pro Ala Tyr Ile Ala Thr Ala Gln Tyr Asp Pro Leu Arg Asp
                245                 250                 255
Val Gly Lys Leu Tyr Ala Glu Ala Leu Asn Lys Ala Gly Val Lys Val
            260                 265                 270
Glu Ile Glu Asn Phe Glu Asp Leu Ile His Gly Phe Ala Gln Phe Tyr
        275                 280                 285
Ser Leu Ser Pro Gly Ala Thr Lys Ala Leu Val Arg Ile Ala Glu Lys
    290                 295                 300
Leu Arg Asp Ala Leu Ala
305                 310
```

<210> SEQ ID NO 109
<211> LENGTH: 930
<212> TYPE: DNA
<213> ORGANISM: Artificial Sequence
<220> FEATURE:
<223> OTHER INFORMATION: Description of Artificial Sequence: Synthetic polynucleotide sequence encoding a codon optimized carboxyesterase enzyme

<400> SEQUENCE: 109
atgccattag atcctgtgat tcaatatgtg ctcgatcaac tgaaccgtat gccagcccct    60
gactacaagc acttaagcgc ttgccagttt cgttcacagc aacacctgtt tgaaccagtt    120

```
aagaaagaac cggtcaaaga agttcgcgaa ttcgacatgg acctgccggg ccgtaccctg     180
aaagtccgta tgtaccgccc ggaaggtgtt gaaccaccat atccagcact ggtttactac     240
catggtggcg gtggcgttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctc     480
gcggccgtga ctagtattct ggcgaaagaa cgtggtggtc agcaattgc gtttcaactg     540 ctgatctatc cctttactgg ttatgatcca gcacatccac cagcaagtat ccttgagaat     600
gcggagggtt acctgttaac cggaggcatg atgctgtggt tcgtaatca gtacctgaac     660 agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct tcgcgcagtt ctattctctg agcccaggcg caaccaaagc actggtacgt     900
attgccgaga aactgcgcga tgcgttggcg                                      930
```

<210> SEQ ID NO 110
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 110

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Leu Phe Glu Pro Val Lys Lys Glu Pro Val Lys Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Pro Ala Leu Val Tyr Tyr
65                  70                  75                  80

His Gly Gly Gly Val Ala Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
        130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205
```

```
Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 111
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 111
atgccattag atcctgtgat tcaatatgtc ctcgatcaac tgaaccgtat gccagcccct      60
gactacaagc acttaagcgc ttgccagttt cgttcacagc aacacacgtt ttggccagtt     120
aagaaagaac cggtcgcaga agttcgcgaa ttcgacatgc agctgccggg ccgtaccctg     180
aaagtccgta tgtacacgcc ggaaggtgtt gaaccaccat atccagcact ggtttactac     240
catggtggcg gtggcgttgc gggtgacctg aaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc agcaattgc gtttcaactg     540 ctgatctatc cctttactgg ttatgatcca gcacatccac cagcaagtat ccttgagaat     600
gcggagggtt acctgttaac cggaggcatg atgctgtggt ttcgtaatca gtacctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct tcgcgcagtt ctattctctg agcccaggcg caaccaaagc actggtacgt     900
attgccgaga aactgcgcga tgcgttggcg                                      930

<210> SEQ ID NO 112
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 112

Met Pro Leu Asp Pro Val Ile Gln Tyr Val Leu Asp Gln Leu Asn Arg
```

```
              1               5              10              15
Met Pro Ala Pro Asp Tyr Lys His Leu Ser Ala Cys Gln Phe Arg Ser
              20              25              30
Gln Gln His Thr Phe Trp Pro Val Lys Lys Glu Pro Val Ala Glu Val
              35              40              45
Arg Glu Phe Asp Met Gln Leu Pro Gly Arg Thr Leu Lys Val Arg Met
50                            55                            60
Tyr Thr Pro Glu Gly Val Glu Pro Pro Tyr Pro Ala Leu Val Tyr Tyr
65                            70              75                80
His Gly Gly Gly Val Ala Gly Asp Leu Glu Thr His Asp Pro Val
              85              90              95
Cys Arg Val Leu Ala Lys Asp Gly Arg Ala Val Val Phe Ser Val Asp
              100             105             110
Tyr Arg Leu Ala Pro Glu His Lys Phe Pro Ala Ala Val Glu Asp Ala
              115             120             125
Tyr Asp Ala Leu Gln Trp Ile Ala Glu Arg Ala Ala Asp Phe His Leu
              130             135             140
Asp Pro Ala Arg Ile Ala Val Gly Gly Asp Ser Ala Gly Gly Asn Leu
145                           150             155             160
Ala Ala Val Thr Ser Ile Leu Ala Lys Glu Arg Gly Gly Pro Ala Ile
              165             170             175
Ala Phe Gln Leu Leu Ile Tyr Pro Phe Thr Gly Tyr Asp Pro Ala His
              180             185             190
Pro Pro Ala Ser Ile Leu Glu Asn Ala Glu Gly Tyr Leu Leu Thr Gly
              195             200             205
Gly Met Met Leu Trp Phe Arg Asn Gln Tyr Leu Asn Ser Leu Glu Glu
              210             215             220
Leu Thr His Pro Trp Phe Ser Pro Val Leu Tyr Pro Asp Leu Ser Gly
225                           230             235             240
Leu Pro Pro Ala Tyr Ile Ala Thr Ala Gln Tyr Asp Pro Leu Arg Asp
              245             250             255
Val Gly Lys Leu Tyr Ala Glu Ala Leu Asn Lys Ala Gly Val Lys Val
              260             265             270
Glu Ile Glu Asn Phe Glu Asp Leu Ile His Gly Phe Ala Gln Phe Tyr
              275             280             285
Ser Leu Ser Pro Gly Ala Thr Lys Ala Leu Val Arg Ile Ala Glu Lys
              290             295             300
Leu Arg Asp Ala Leu Ala
305                 310
```

<210> SEQ ID NO 113
<211> LENGTH: 930
<212> TYPE: DNA
<213> ORGANISM: Artificial Sequence
<220> FEATURE:
<223> OTHER INFORMATION: Description of Artificial Sequence: Synthetic
    polynucleotide sequence encoding a codon optimized
    carboxyesterase enzyme

<400> SEQUENCE: 113
atgccattag atcctgtgat tcaatatgtc ctcgatcaac tgaaccgtat gccagcccct      60
gactacaagc acttaagcgc ttgccagttt cgttcacagc aacacacgtt ttggccagtt     120
aagaaagaac cggtcgcaga agttcgcgaa ttcgacatgg atctgccggg ccgtaccctg     180
aaagtccgta tgtaccgccc ggaaggtgtt gaaccaccat atccgcgcact ggtttactac     240

```
catggtggcg gtggcgttgc gggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc agcaattgc gtttcaactg     540
ctgatctatc cctttactgg ttatgatcca gcacatccac cagcaagtat ccttgagaat    600
gcggagggtt acctgttaac cggaggcatg atgctgtggt ttcgtaatca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                     930
```

<210> SEQ ID NO 114
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 114

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Thr Phe Trp Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Arg Ala Leu Val Tyr Tyr
65                  70                  75                  80

His Gly Gly Gly Val Ala Gly Asp Leu Glu Thr His Asp Pro Val
                85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Val Glu Asp Ala
            115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
```

```
                225                 230                 235                 240
Leu Pro Pro Ala Tyr Ile Ala Thr Ala Gln Tyr Asp Pro Leu Arg Asp
                    245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 115
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 115
atgccattag atcctgtgat tcaatatgtc ctcgatcaac tgaaccgtat gccagcccct     60
gactggaagc acttaagcgc ttgccagttt cgttcacagc aacacatgtt ttggccagtt    120
aagaaagaac cggtcgccga agttcgcgaa ttcgacatgg atctgccggg ccgtaccctg    180
aaagtccgta tgtaccgccc ggaaggtgtt gaaccaccat atcgcgcact ggtttactac    240
catggtggcg gtggcgttgc gggtgacctg gaaacgcatg atccggtgtg tcgtgtgttg    300
gcgaaagatg gacgcgcagt ggtgtttagc gttgactacc gtctggcacc agaacacaag    360
tttccagcgg cagttgaaga cgcgtatgat gcactgcaat ggattgcaga acgtgcagcc    420
gatttccatc ttgatccagc acgcattgca gttggcggcg attcagcagg cggcaacctg    480
gcggccgtga ctagtattct ggcgaaagaa cgtggtggtc agcaattgc gtttcaactg    540 ctgatctatc cctttactgg ttatgatcca gcacatccac cagcaagtat ccttgagaat    600
gcggagggtt acctgttaac cggaggcatg atgctgtggt tcgtaatca gtacctgaac    660 agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct cgcgcagtt ctattctctg agcccaggcg caaccaaagc actggtacgt    900
attgccgaga aactgcgcga tgcgttggcg                                    930

<210> SEQ ID NO 116
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 116

Met Pro Leu Asp Pro Val Ile Gln Tyr Val Leu Asp Gln Leu Asn Arg
1               5                   10                  15

Met Pro Ala Pro Asp Trp Lys His Leu Ser Ala Cys Gln Phe Arg Ser
            20                  25                  30
```

```
Gln Gln His Met Phe Trp Pro Val Lys Lys Glu Pro Val Ala Glu Val
         35                  40                  45

Arg Glu Phe Asp Met Asp Leu Pro Gly Arg Thr Leu Lys Val Arg Met
 50                  55                  60

Tyr Arg Pro Glu Gly Val Glu Pro Pro Tyr Arg Ala Leu Val Tyr Tyr
 65                  70                  75                  80

His Gly Gly Gly Val Ala Gly Asp Leu Glu Thr His Asp Pro Val
                 85                  90                  95

Cys Arg Val Leu Ala Lys Asp Gly Arg Ala Val Val Phe Ser Val Asp
                100                 105                 110

Tyr Arg Leu Ala Pro Glu His Lys Phe Pro Ala Ala Val Glu Asp Ala
                115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
                180                 185                 190

Pro Pro Ala Ser Ile Leu Glu Asn Ala Glu Gly Tyr Leu Leu Thr Gly
                195                 200                 205

Gly Met Met Leu Trp Phe Arg Asn Gln Tyr Leu Asn Ser Leu Glu Glu
                210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
                260                 265                 270

Glu Ile Glu Asn Phe Glu Asp Leu Ile His Gly Phe Ala Gln Phe Tyr
                275                 280                 285

Ser Leu Ser Pro Gly Ala Thr Lys Ala Leu Val Arg Ile Ala Glu Lys
                290                 295                 300

Leu Arg Asp Ala Leu Ala
305                 310

<210> SEQ ID NO 117
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 117
atgccattag atcctgtgat tcaatatgtc ctcgatcaac tgaaccgtat gccagcccct      60
gactacaagc acttaagcgc ttgccagttt cgttcacagc aacacacgtt ttggccagtt     120
aagaaagaac cggtcgcaga agttcgcgaa ttcgacatgg atctgccggg ccgtaccctg     180
aaagtccgta tgtaccgccc ggaaggtgtt gaaccaccat atatggcact ggtttactac     240
catggtggcg gtggcgttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
```

```
gatttccatc ttgatccagc acgcattgca gttggcggcg attcagcagg cggcaacctg    480
gcggccgtga ctagtattct ggcgaaagaa cgtggtggtc cagcaattgc gtttcaactg    540
ctgatctatc cctttactgg ttatgatcca gcacatccac cagcaagtat ccttgagaat    600
gcggagggtt acctgttaac cggaggcatg atgctgtggt ttcgtaatca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                      930
```

<210> SEQ ID NO 118
<211> LENGTH: 310
<212> TYPE: PRT
<213> ORGANISM: Artificial Sequence
<220> FEATURE:
<223> OTHER INFORMATION: Description of Artificial Sequence: Synthetic polypeptide sequence of a codon optimized carboxyesterase enzyme

<400> SEQUENCE: 118

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Thr Phe Trp Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Met Ala Leu Val Tyr Tyr
65                  70                  75                  80

His Gly Gly Gly Gly Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255
```

Val Gly Lys Leu Tyr Ala Glu Ala Leu Asn Lys Ala Gly Val Lys Val
            260                 265                 270

Glu Ile Glu Asn Phe Gly Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300

Leu Arg Asp Ala Leu Ala
305                 310

<210> SEQ ID NO 119
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 119
atgccattag atcctgtgat tcaatatgtc ctcgatcaac tgaaccgtat gccagcccct        60
gactacaagc acttaagcgc ttgccagttt cgttcacagc aacacctgtt tgaaccagtt       120
aagaaagaac cggtcgcaga agttcgcgaa ttcgacatgg atctgccggg ccgtaccctg       180
aaagtccgta tgtaccgccc ggaaggtgtt gaaccaccat atccagcact ggtttactac       240
catggtggcg gtggcgttgc gggtgacctg aaacgcatg atccggtgtg tcgtgtgttg       300
gcgaaagatg acgcgcagt ggtgtttagc gttgactacc gtctggcacc agaacacaag       360
tttccagcgg cagttgaaga gcgtatgat gcactgcaat ggattgcaga acgtgcagcc       420
gatttccatc ttgatccagc acgcattgca gttggcggcg attcagcagg cggcaacctg       480
gcggccgtga ctagtattct ggcgaaagaa cgtggtggtc agcaattgc gtttcaactg       540 ctgatctatc cctttactgg ttatgatcca gcacatccac cagcaagtat ccttgagaat       600
gcggagggtt acctgttaac cggaggcatg atgctgtggt tcgtaatca gtacctgaac       660 agccttgagg aactgactca cccatggttt agtccagtgc tgtacccgga tcttagcggt       720
ttaccaccgg cgtacattgc aaccgcacag tacgatcccc tgcgcgatgt cggcaaactt       780
tacgctgaag ccctgaacaa agcgggcgtt aaggtggaga tcgagaactt cgaggatctg       840
attcatggct cgcacagtt ctattctctg agcccaggcg caaccaaagc actggtacgt       900
attgccgaga aactgcgcga tgcgttggcg                                        930

<210> SEQ ID NO 120
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 120

Met Pro Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Leu Phe Glu Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Tyr Pro Ala Leu Val Tyr Tyr
65                  70                  75                  80

His Gly Gly Gly Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
            115                 120                 125

Tyr Asp Ala Leu Gln Trp Ile Ala Glu Arg Ala Ala Asp Phe His Leu
130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
            195                 200                 205

Gly Met Met Leu Trp Phe Arg Asn Gln Tyr Leu Asn Ser Leu Glu Glu
210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
            275                 280                 285

Ser Leu Ser Pro Gly Ala Thr Lys Ala Leu Val Arg Ile Ala Glu Lys
290                 295                 300

Leu Arg Asp Ala Leu Ala
305                 310

<210> SEQ ID NO 121
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 121
atgccattag atcctgtgat tcaatatgtc ctcgatcaac tgaaccgtat gccagcccct      60
gactacaagc acttaagcgc ttgccagttt cgttcacagc aacacacgtt ttggccagtt     120
aagaaagaac cggtcgcaga agttcgcgaa ttcgacatgg atctgccggg ccgtaccctg     180
aaagtccgta tgtaccgccc ggaaggtgtt gaaccaccat atcgcgcact ggtttactac     240
catggtggcg gtggcgttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540

```
ctgatctatc cctttactgg ttatgatcca gcacatccac cagcaagtat ccttgagaat    600
gcggagggtt acctgttaac cggaggcatg atgctgtggt ttcgtaatca gtacctgaac    660
agccttgagg aactgactca cccatggttt agtccagtgc tgtacccgga tcttagcggt    720
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgtgttt ctattctctg agcccaggcg caaccaaagc actggtacgt    900
attgccgaga aactgcgcga tgcgttggcg                                     930
```

<210> SEQ ID NO 122
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 122

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Thr Phe Trp Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Arg Ala Leu Val Tyr Tyr
65                  70                  75                  80

His Gly Gly Gly Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Leu Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Cys Phe Tyr
        275                 280                 285
```

Ser Leu Ser Pro Gly Ala Thr Lys Ala Leu Val Arg Ile Ala Glu Lys
        290                 295                 300

Leu Arg Asp Ala Leu Ala
305                 310

<210> SEQ ID NO 123
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 123
atgttgttag atcctgtgat tcaatatgtc ctcgatcaac tgaaccgtat gccagcccct      60
gactacaagc acttaagcgc ttgccagttt cgttcacagc aacacacgtt ttggccagtt     120
aagaaagaac cggtcgcaga agttcgcgaa ttcgacatgg atctgccggg ccgtaccctg     180
aaagtccgta tgtaccgccc ggaaggtgtt gaaccaccat atcgcgcact ggtttactac     240
catggtggcg gtggcgttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
ctgatctatc cctttactgg ttatgatcca gcacatccac cagcaagtat ccttgagaat     600
gcggagggtt acctgttaac cggaggcatg atgctgtggt ttcgtaatca gtacctgaac     660
agccttgagg aactgactca cccatggttt agtccagtgc tgtacccgga tcttagcggt     720
ttaccaccgg cgtacattgc aaccgcacag tacgatcccc tgcgcgatgt cggcaaactt     780
tacgctgaag ccctgaacaa agcgggcgtt aaggtggaga tcgagaactt cgaggatctg     840
attcatggct cgcgcagtt ctattctctg agcccaggcg caaccaaagc actggtacgt     900
attgccgaga aactgcgcga tgcgttggcg                                     930

<210> SEQ ID NO 124
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide sequence of a codon optimized
      carboxyesterase enzyme

<400> SEQUENCE: 124

Met Leu Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Thr Phe Trp Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Arg Ala Leu Val Tyr Tyr
65                  70                  75                  80

His Gly Gly Gly Gly Val Ala Gly Asp Leu Glu Thr His Asp Pro Val

```
                85                  90                  95
Cys Arg Val Leu Ala Lys Asp Gly Arg Ala Val Val Phe Ser Val Asp
            100                 105                 110
Tyr Arg Leu Ala Pro Glu His Lys Phe Pro Ala Ala Val Glu Asp Ala
            115                 120                 125
Tyr Asp Ala Leu Gln Trp Ile Ala Glu Arg Ala Ala Asp Phe His Leu
            130                 135                 140
Asp Pro Ala Arg Ile Ala Val Gly Gly Asp Ser Ala Gly Gly Asn Leu
145                 150                 155                 160
Ala Ala Val Thr Ser Ile Leu Ala Lys Glu Arg Gly Gly Pro Ala Ile
                165                 170                 175
Ala Phe Gln Leu Leu Ile Tyr Pro Phe Thr Gly Tyr Asp Pro Ala His
            180                 185                 190
Pro Pro Ala Ser Ile Leu Glu Asn Ala Glu Gly Tyr Leu Leu Thr Gly
            195                 200                 205
Gly Met Met Leu Trp Phe Arg Asn Gln Tyr Leu Asn Ser Leu Glu Glu
210                 215                 220
Leu Thr His Pro Trp Phe Ser Pro Val Leu Tyr Pro Asp Leu Ser Gly
225                 230                 235                 240
Leu Pro Pro Ala Tyr Ile Ala Thr Ala Gln Tyr Asp Pro Leu Arg Asp
                245                 250                 255
Val Gly Lys Leu Tyr Ala Glu Ala Leu Asn Lys Ala Gly Val Lys Val
            260                 265                 270
Glu Ile Glu Asn Phe Glu Asp Leu Ile His Gly Phe Ala Gln Phe Tyr
            275                 280                 285
Ser Leu Ser Pro Gly Ala Thr Lys Ala Leu Val Arg Ile Ala Glu Lys
            290                 295                 300
Leu Arg Asp Ala Leu Ala
305                 310

<210> SEQ ID NO 125
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide sequence encoding a codon optimized
      carboxyesterase enzyme

<400> SEQUENCE: 125
atgccattag atcctgtgat tcaatatgtc ctcgatcaac tgaaccgtat gccagcccct      60
gactacaagc acttaagcgc ttgccagttt cgttcacagc aacacacgtt ttggccagtt     120
aagaaagaac cggtcgcaga agttcgcgaa ttcgacatgg atctgccggg ccgtaccctg     180
aaagtccgta tgtaccgccc ggaaggtgtt gaaccaccat atcgcgcact ggtttactac     240
catggtggcg gtggcgttgc gggtgacctg gaaacgcatg atccggtgtg tcgtgtgttg     300
gcgaaagatg gacgcgcagt ggtgtttagc gttgactacc gtctggcacc agaacacaag     360
tttccagcgg cagttgaaga cgcgtatgat gcactgcaat ggattgcaga acgtgcagcc     420
gatttccatc ttgatccagc acgcattgca gttggcggcg attcagcagg cggcaacctg     480
gcggccgtga ctagtattct ggcgaaagaa cgtggtggtc cagcaattgc gtttcaactg     540
caaatctatc cctttactgg ttatgatcca gcacatccac cagcaagtat ccttgagaat     600
gcggagggtt acctgttaac cggaggcatg atgctgtggt tcgtaatca gtacctgaac      660 agccttgagg aactgactca cccatggttt agtccagtgc tgtacccgga tcttagcggt     720
```

```
ttaccaccgg cgtacattgc aaccgcacag tacgatcccc tgcgcgatgt cggcaaactt    780
tacgctgaag ccctgaacaa agcgggcgtt aaggtggaga tcgagaactt cgaggatctg    840
attcatggct tcgcgcagtt ctattctctg agcccaggcg caaccaaagc actggtacgt    900
attgccgaga aactgcgcga tgcgttggcg                                      930
```

<210> SEQ ID NO 126
<211> LENGTH: 310
<212> TYPE: PRT
<213> ORGANISM: Artificial Sequence
<220> FEATURE:
<223> OTHER INFORMATION: Description of Artificial Sequence: Synthetic
     polypeptide sequence of a codon optimized
     carboxyesterase enzyme

<400> SEQUENCE: 126

```
Met Pro Leu Asp Pro Val Ile Gln Tyr Val Leu Asp Gln Leu Asn Arg
1               5                   10                  15

Met Pro Ala Pro Asp Tyr Lys His Leu Ser Ala Cys Gln Phe Arg Ser
            20                  25                  30

Gln Gln His Thr Phe Trp Pro Val Lys Lys Glu Pro Val Ala Glu Val
        35                  40                  45

Arg Glu Phe Asp Met Asp Leu Pro Gly Arg Thr Leu Lys Val Arg Met
    50                  55                  60

Tyr Arg Pro Glu Gly Val Glu Pro Pro Tyr Arg Ala Leu Val Tyr Tyr
65                  70                  75                  80

His Gly Gly Gly Val Ala Gly Asp Leu Glu Thr His Asp Pro Val
                85                  90                  95

Cys Arg Val Leu Ala Lys Asp Gly Arg Ala Val Val Phe Ser Val Asp
            100                 105                 110

Tyr Arg Leu Ala Pro Glu His Lys Phe Pro Ala Ala Val Glu Asp Ala
        115                 120                 125

Tyr Asp Ala Leu Gln Trp Ile Ala Glu Arg Ala Ala Asp Phe His Leu
    130                 135                 140

Asp Pro Ala Arg Ile Ala Val Gly Gly Asp Ser Ala Gly Gly Asn Leu
145                 150                 155                 160

Ala Ala Val Thr Ser Ile Leu Ala Lys Glu Arg Gly Gly Pro Ala Ile
                165                 170                 175

Ala Phe Gln Leu Gln Ile Tyr Pro Phe Thr Gly Tyr Asp Pro Ala His
            180                 185                 190

Pro Pro Ala Ser Ile Leu Glu Asn Ala Glu Gly Tyr Leu Leu Thr Gly
        195                 200                 205

Gly Met Met Leu Trp Phe Arg Asn Gln Tyr Leu Asn Ser Leu Glu Glu
    210                 215                 220

Leu Thr His Pro Trp Phe Ser Pro Val Leu Tyr Pro Asp Leu Ser Gly
225                 230                 235                 240

Leu Pro Pro Ala Tyr Ile Ala Thr Ala Gln Tyr Asp Pro Leu Arg Asp
                245                 250                 255

Val Gly Lys Leu Tyr Ala Glu Ala Leu Asn Lys Ala Gly Val Lys Val
            260                 265                 270

Glu Ile Glu Asn Phe Glu Asp Leu Ile His Gly Phe Ala Gln Phe Tyr
        275                 280                 285

Ser Leu Ser Pro Gly Ala Thr Lys Ala Leu Val Arg Ile Ala Glu Lys
    290                 295                 300
```

```
Leu Arg Asp Ala Leu Ala
305                 310
```